US007638272B2

(12) United States Patent
Tai et al.

(10) Patent No.: US 7,638,272 B2
(45) Date of Patent: Dec. 29, 2009

(54) CANCER THERAPY SENSITIZER

(75) Inventors: Isabella T. Tai, Vancouver (CA); Lan Bo Chen, Lexington, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 11/181,115

(22) Filed: Jul. 14, 2005

(65) Prior Publication Data
US 2006/0088511 A1    Apr. 27, 2006

Related U.S. Application Data

(63) Continuation of application No. PCT/US2004/000901, filed on Jan. 14, 2004.

(60) Provisional application No. 60/440,009, filed on Jan. 14, 2003.

(51) Int. Cl.
C12Q 1/00 (2006.01)
C12Q 1/68 (2006.01)
G01N 33/53 (2006.01)
A61K 39/395 (2006.01)
A61K 39/385 (2006.01)

(52) U.S. Cl. .................. 435/4; 435/6; 435/7.1; 424/130.1; 424/193.1

(58) Field of Classification Search ............. 424/93.21, 424/130.1, 193.1; 435/4, 6, 7.1
See application file for complete search history.

(56) References Cited

U.S. PATENT DOCUMENTS

| 5,674,743 | A | 10/1997 | Ulmer | |
|---|---|---|---|---|
| 5,962,320 | A | 10/1999 | Robinson | |
| 6,187,307 | B1 | 2/2001 | Cohen | |
| 6,194,205 | B1 | 2/2001 | Staege et al. | |
| 6,239,326 | B1 | 5/2001 | Howe | |
| 6,316,193 | B1 | 11/2001 | He et al. | |
| 6,387,664 | B1 | 5/2002 | Ikemoto | |
| 6,406,693 | B1 * | 6/2002 | Thorpe et al. | 424/130.1 |
| 6,475,784 | B1 | 11/2002 | Papkoff | 435/325 |
| 2002/0169121 | A1 * | 11/2002 | Ronai | 514/12 |
| 2003/0082228 | A1 | 5/2003 | Flowers et al. | 424/450 |
| 2003/0180306 | A1 | 9/2003 | Hill et al. | |
| 2004/0229338 | A1 | 11/2004 | King | |

FOREIGN PATENT DOCUMENTS

| WO | WO 98/29138 | 7/1998 |
|---|---|---|
| WO | WO 00/72679 | 12/2000 |
| WO | WO 01/20989 A1 | 3/2001 |
| WO | WO 01/25397 A2 | 4/2001 |
| WO | WO 01/81631 A1 | 11/2001 |
| WO | WO 02/02771 A2 | 1/2002 |
| WO | WO 02/089772 A1 | 11/2002 |
| WO | WO 2004/005883 A2 | 1/2004 |
| WO | WO 2004/016758 A2 | 2/2004 |
| WO | WO 2005/026357 A1 * | 3/2005 |

OTHER PUBLICATIONS

Lankat-Buttgereit et al (FEBS Letters, Aug. 1988, 236:352-356).*
Nair et al. (J. Immunol 2000 165(12): 6949-6955).*
Hebbes et al. (Mol Immunol, 1989, 26(9):865-73).*
Schwartz et al. (J. Immunol (1985) 135(4):2598-608).*
Stites and Terr Eds (Basic and Clinical Immunology, Seventh Edition, 1991, Appleton and Lange, East Norwalk, Connecticut).*
Tockman et al (Cancer Res., 1992, 52:2711s-2718s).*
Chilenski, et al., Sparc is a key Schwanian-derived inhibitor controlling neuroblastoma tumor angionesis, Cancer Res., Dec. 15, 2002, vol. 62, pp. 7357-7363.
Yiu et al., SPARC (Secreted protein acidic and rich in cysteine) induces apoptosis in ovarian cancer cells, Am. J. Pathol., Aug. 2001, vol. 159, No. 2, pp. 609-622.
International Search Report, Jul. 15, 2005, PCT/US04/00901.
Bellahcene et al., "Increased expression of osteonectin and osteopontin, two bone matrix proteins, in human breast cancer," *Am. J. Pathol.* 146, 95-100 (Jan. 1995).
Bornstein, "Diversity of function is inherent in matricellular proteins: an appraisal of thrombospondin 1," *J. Cell Biol.* 130, 503-506 (1995).
Bradshaw et al., "SPARC, a matricellular protein that functions in cellular differentiation and tissue response to injury," *J. of Clinical Investigation*, 107(9), 1049-1054 (May 2001).
Bradshaw et al., "SPARC-null mice exhibit increased adiposity without significant differences in overall body weight," *PNAS*, 100(10), 6045-6050 (May 13, 2003).
Dhanesuan et al., "Doxycycline-inducible expression of SPARC/Osteonectin/BM40 in MDA-MB-231 human breast cancer cells results in gorwth inhibition," *Breast Cancer Research and Treatment*, 75, 73-85 (2002).
Folkman, "Clinical applications of research on angiogenesis," *N. Engl. J. Med.*, 333(26), 1757-1763 (1995).
Georgiou et al., "Expression of correctly folded proteins in *Escherichia coli*," *Curr. Opn. in Biotechnology*, 7, 190-197 (1996).
Gilbert et al., "SPARC gene expression is reduced in early diabetes-related kidney growth," *Kidney International*, 48, 1216-1225 (1995).
Hasselaar et al., "SPARC antagonizes the effect of basic fibroblast growth factor on the migration of bovine aortic endothelial cells," *J. Cell. Biochem.* 49, 272-283 (1992).
Hasselaar et al., "SPARC induces the expression of type 1 plasminogen activator inhibitor in cultured bovine aortic endothelial cells," *J. of Biological Chemistry*, 266(20), 13178-13184 (Jul. 15, 1991).

(Continued)

*Primary Examiner*—Sean E Aeder
(74) *Attorney, Agent, or Firm*—Leydig, Voit & Mayer, Ltd.

(57) ABSTRACT

The present invention relates to compositions and methods for sensitizing cancer therapy. The invention provides such compositions comprising a SPARC family polypeptide or polynucleotide, as well as recombinant cells containing a SPARC family polypeptide or polynucleotide. The compositions and methods of the invention are useful in in vitro study of cancer therapy resistance, as well as ex vivo and in vivo therapy of cancer.

18 Claims, 198 Drawing Sheets

OTHER PUBLICATIONS

Hohenadl et al., "Two adjacent N-terminal glutamines of BM-40 (osteonectin, SPARC) act as amine acceptor sites in transglutaminaseC-catalyzed modification," *J. Biological Chemistry*, 270(40), 23415-23420 (Oct. 6, 1995).

Jendraschak et al., "Regulation of angiogenesis by SPARC and angiostatin: implications for tumor cell biology," *Sem. Can. Biol.* 7, 139-146 (1996).

Kim et al., "Expression of osteopontin and osteonectin in breast cancer," *J. Korean Med. Sci.*, 13, 652-657 (1998).

Lane et al., "SPARC is a source of copper-binding peptides that stimulate angiogenesis," *J. Cell. Biol.*, 125(4), 929-943 (May 1994).

Lane et al., "The biology of SPARC, a protein that modulates cell-matrix interactions," *FASEB J.*, 8, 163-173 (Feb. 1994).

Lane et al., "Regulation of gene expression by SPARC during angiogenesis in vitro. Changes in fibronectin, thrombospondin-1, and plasminogen activator imhibitor-1," *J. Biol. Chem.* 267(23), 16736-16745 (Aug. 15, 1992).

Mason et al., "Evidence from molecular cloning that SPARC, a major product of mouse embryo parietal endoderm, is related to an endothelial cell 'culture shock' glycoprotein of Mr 43,000," *EMBO J.*, 5(7), 1465-1472 (1986).

Parikh et al., "Random mutagenesis by whole-plasmid PCR amplification," *Biotechniques*, 24, 428-431 (Mar. 1998).

Pichler et al., "SPARC is expressed by mesangial cells in experimental mesangial proliferative nephritis and inhibits platelet-derived-growth-factor-medicated mesangial cell proliferation in vitro," *Am. J. of Pathology*, 148(4), 1153-1167 (Apr. 1996).

Porter et al, "Distribution of SPARC in Normal and neoplastic human tissue," *J. Histochemistry and Cytochemistry*, 43(8), 791-800 (1995).

Qi et al, "L-RCA (ligation-rolling circle amplification): a general method for genotyping of single nucleotide polymorphisms (SNPs)," *Nucleic Acids Research*, 29(22) e116 (2001).

Raines et al., "The extracellular glycoprotein SPARC interacts with platelets-derived growth factor (PDGF)-AB and -BB and inhibits the binding of PDGF to its receptors," *Proc. Natl. Acad. Sci. USA*, 89, 1281-1285 (Feb. 1992).

Rempel et al., "SPARC: a potential diagnostic marker of invasive meningiomas," *Clinical Cancer Research*, 5, 237-241 (Feb. 1999).

Sage et al., "Extracellular proteins that modulate cell-matrix interactions. SPARC, tenascin, and thrombospondin," *J. Biol. Chem.*, 266 (23), 14831-14834 (Aug. 15, 1991).

Sage et al., "Inhibition of endothelial cell proliferation by SPARC is mediated through a Ca(2+)-binding EF-hand sequence," *J. Cellular Biochemistry*, 57, 127-140 (1995).

Sage et al., "Cleavage of the matricellular protein SPARC by matrix metalloproteinase 3 produces polypeptides that influence angiogenesis," *J. Biological Chemistry*, 278(39) 37849-37857 (Sep. 26, 2003).

Swaroop et al., "Molecular analysis of the cDNA for human SPARC/osteonectin/BM-40: sequence, expression, and localization of the gene to chromosome 5q310q33," *Genomics*, 2, 37-47 (1988).

Takahashi et al., "The expression of SPARC in adipose tissue and its increased plasma concentration in patients with coronary artery disease," *Obesity Res.*, 9(7) 388-393 (Jul. 2001).

Werb, "ECM and cell surface proteolysis: regulating cellular ecology," *Cell*, 91, 439-442 (Nov. 14, 1997).

Wolfsberg et al., "ADAM, a novel family of membrane proteins containing A Disintegrin And Metalloprotease domain: multipotential functions in cell-cell and cell-matrix interactions," *J. Cell Biology*, 131(2) 275-278 (Oct. 1995).

Yamanaka et al., "Analysis of the gene expression of SPARC and its prognostic value for bladder cancer," *J. Urology*, 166, 2495-2499 (Dec. 2001).

Yan et al., "SPARC, a matricellular glycoprotein with important biological functions," *J. Histochem. Cytochem.* 47 (12), 1495-1505 (1999).

Cree et al., *Curr. Opn. Invest. Drugs*, 3 (4), 641-647 (2002).
Stein et al., *J. Natl. Cancer Inst.*, 88 (19), 1383-1392 (Oct. 2, 1996).
European Search Report for EP 04 70 2173 (Sep. 2, 2008).
Alliel et al., *Eur. J. Biochem*, 214, 347-350 (1993).
Arber et al., *Gastroenterology*, 118, 1 045-1 050 (2000).
Bendik et al., *Cancer Res.*, 58(4), 626-629 (Feb. 15, 1998).
Brown et al., *Gyn. Oncol.*, 75, 25-33 (1999).
Carmichael et al., *Cancer Res.*, 47, 936-942 (Feb. 15, 1987).
de las Alas et al., *J. Natl. Cancer. Inst.*, 89 (20), 1537-1541 (Oct. 15, 1997).
Eltabbakh, Gamal H., *J. Surg. Oncol.*, 73, 148-152 (2000).
Filipits et al., *Br. J. Cancer*, 75(2), 208-212 (1997).
Guermah et al., *Proc Natl. Acad. Sci. USA*, 88, 4503-4507 (May 1991) 1.
Kelm et al., *J. Biol. Chem.*, 269 (48), 30147-30153 (Dec. 2, 1994).
Iruela-Arispe et al., *Mol. Biol. Cell*, 6, 327-343 (Mar. 1995).
Johnston et al., *Neuron*, 2, 165-176 (Jan. 1990).
Johnstone et al., *Cell*, 108, 153-164 (Jan. 25, 2002).
Kelm et al., *J. Biol. Chem.*, 269 (48), 30147-30153 (1994).
Kamesaki, H., *Int J. Hematology.*, 68, 29-43 (1998).
Kupprion et al., *J. Biol. Chem.*, 273 (45), 29635-29640 (1998).
Latvala et al., *Exp. Eye. Res.*, 63, 579-584 (1996).
Le Bail et al., *J. Pathol.*, 189, 46-52 (1999).
Ledda et al., *Nat. Med.*, 3 (2), 171-176 (Feb. 1997).
Lehnert Manfred, *Anticancer Res.*, 18, 2225-2226 (1998).
Li et al., *Clin & Exp. Metastasis*, 17, 423-429 (1999),.
Lin et al., *Mol. Pharm.*, 56, 390-395 (1999).
Lussier et al., *J. Cell. Biochem.*, 81, 463-476 (2001).
Ma et al., *Antisense & Nuc. Acid Drug Dev.*, 8, 415-426 (1998).
Maillard et al., *Bone*, 13, 257-264 (1992).
Makin, Guy, *Expert Opn. Ther. Targets*, 6 (1), 73-84 (2002).
Mason et al., *Embo J.*, 5 (8), 1831-1837 (1986).
Paley et al., *Gyn. Oncol.*, 78, 336-341 (2000).
Porte et al, *Int. J. Cancer*, 64, 70-75 (1995).
Porte et al., *Clin. Cancer Res.*, 4, 1375-1382 (Jun. 1998).
Porter et al., *J. Histochem. And Cytochem.*, 43 (8), 791-800 (1995).
Ringborg et al., *Acta Oncol.*, 76-80 (1996).
Sage E. Helene, *Biochem. Cell Biol.*, 70, 579-592 (1992).
Schulz et al., *Am. J. Path.*, 132 (2), 233-238 (Aug. 1988).
Shea et al., *Cancer Res.*, 48, 527-533 (Feb. 1, 1988).
Shibanuma et al., *Eur. J. Biochem.*, 217, 13-19 (1993).
Skoudy et al., *Biochem. J.*, 317, 279-284 (1996).
St. Croix et al, *Nat. Med.*, 2(11), 1204-1210 (Nov. 1996).
Strandjord et al., *Am. J. Respir. Cell Mol. Biol.*, 13, 279-287 (1995).
Tanigawa et al., *Cancer Res.*, 42, 2159-2164 (Jun. 1982).
Termine et al., *Cell*, 26, 99-105 (Oct. 1981).
Thomas et al., *Clin. Cancer Res.*, 6, 1140-1149 (Mar. 2000).
Vannahme et al. *J. Biol. Chem.*, 277 (41), 37977-37986 (Oct. 11, 2002).
Vial et al., *Oncogene*, 19, 1772-1782 (2000).
Waldman et al., *Nature*, 381, 713-716 (Jun. 20, 1996).
Weisenthal et al., *Recent Results in Cancer Research*, 94, 161-173 (1984).
Weisenthal et al., *Cancer Treatment Reports*, 69(6), 615-632 (Jun. 1985).
Weisenthal, L.M., "Cell Culture Drug Resistance Assays in Hematologic Neoplasms Based on the Concept of a Total Tumor Cell Kill," *Drug Resistance in Leukemia and Lymphoma: The Clinical Value of Laboratory Studies*, Harwood Academic Publishers,. pp. 415-432 (1993).
Weisenthal, Larry M., *Contrib. Gynecol. Obstet.*, 19, 82-90 (1994).
Weisenthal, Larry M.; "Clinical Correlations for Cell Culture Assays Based on the Concept of Total Tumor Cell Kill," *Chemosensitivity Testing in Gynecologic Malignancies and Breast Cancer*, v. 19, pp. 82-90, Basel, Karger (1994).
Yiu et al., *Am. J. Path.*, 159 (2), 609-622 (Aug. 2001).

\* cited by examiner

TUNEL ASSAY

MIP-S-Rx5FU    MIP(5FU-R)      MIP(5FU-R)
               + Rx5FU         + SPARC
                               +Rx5FU

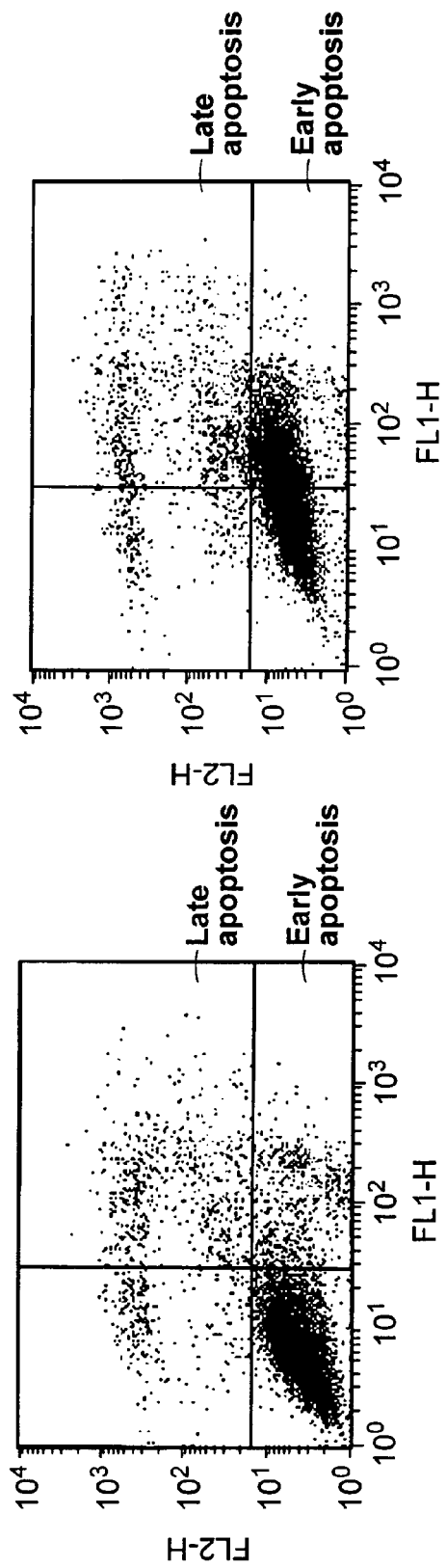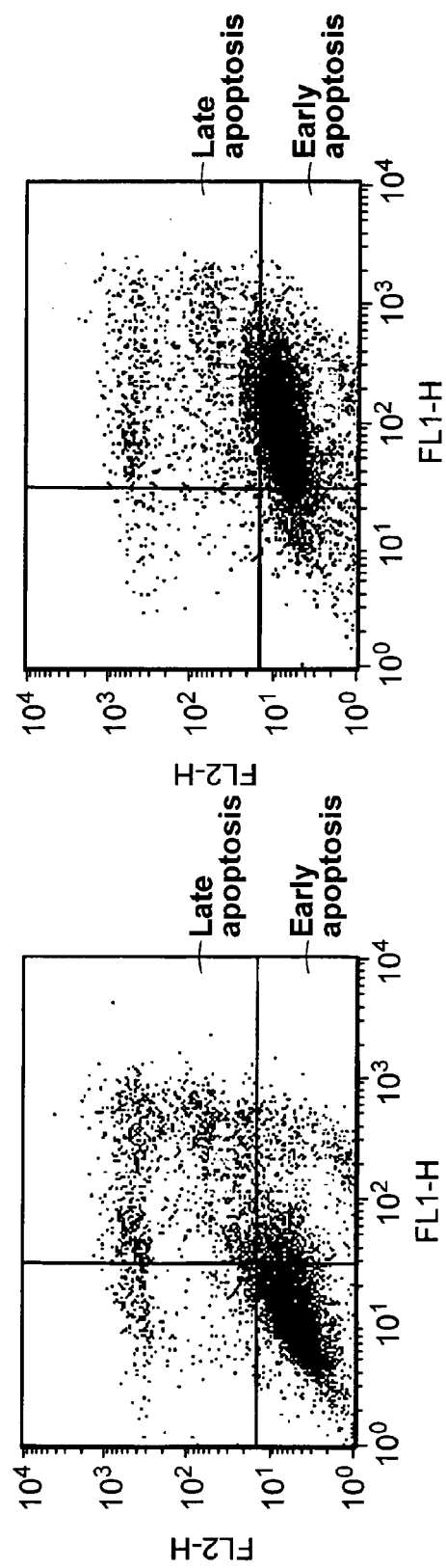

| NCBI | | | | | | Nucleotide | | |
|---|---|---|---|---|---|---|---|---|
| PubMed | Nucleotide | Protein | Genome | Structure | PMC | Taxonomy | OMIM | Boo |

Search Nucleotide ▽ for [_____] Go  Clear

Limits  Preview/Index  History  Clipboard  Details

Display default ▽ Show: 20 ▽ Send to File ▽  Get Subsequence  Links

☐ 1: NM_003118. Homo sapiens secr...[gi:4507170]

```
LOCUS       SPARC                   2133 bp    mRNA    linear   PRI 05-NOV-2002
DEFINITION  Homo sapiens secreted protein, acidic, cysteine-rich (osteonectin)
            (SPARC), mRNA.
ACCESSION   NM_003118
VERSION     NM_003118.1  GI:4507170
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2133)
  AUTHORS   Termine,J.D., Kleinman,H.K., Whitson,S.W., Conn,K.M., McGarvey,M.L.
            and Martin,G.R.
  TITLE     Osteonectin, a bone-specific protein linking mineral to collagen
  JOURNAL   Cell 26 (1 Pt 1), 99-105 (1981)
```

FIG. 12-1

```
MEDLINE     82115304
PUBMED      7034958
REFERENCE   2  (bases 1 to 2133)
AUTHORS     Swaroop,A., Hogan,B.L. and Francke,U.
TITLE       Molecular analysis of the cDNA for human SPARC/osteonectin/BM-40:
            sequence, expression, and localization of the gene to chromosome
            5q31-q33
JOURNAL     Genomics 2 (1), 37-47 (1988)
MEDLINE     88256150
PUBMED      2838412
REFERENCE   3  (bases 1 to 2133)
AUTHORS     Lankat-Buttgereit,B., Mann,K., Deutzmann,R., Timpl,R. and Krieg,T.
TITLE       Cloning and complete amino acid sequences of human and murine
            basement membrane protein BM-40 (SPARC, osteonectin)
JOURNAL     FEBS Lett. 236 (2), 352-356 (1988)
MEDLINE     88312997
PUBMED      3410046
REFERENCE   4  (bases 1 to 2133)
AUTHORS     Le Beau,M.M., Espinosa,R. III, Neuman,W.L., Stock,W., Roulston,D.,
            Larson,R.A., Keinanen,M. and Westbrook,C.A.
TITLE       Cytogenetic and molecular delineation of the smallest commonly
            deleted region of chromosome 5 in malignant myeloid diseases
JOURNAL     Proc. Natl. Acad. Sci. U.S.A. 90 (12), 5484-5488 (1993)
MEDLINE     93296163
PUBMED      8516290
REFERENCE   5  (bases 1 to 2133)
```

FIG. 12-2

```
AUTHORS    Kato,Y., Lewalle,J.M., Baba,Y., Tsukuda,M., Sakai,N., Baba,M.,
           Kobayashi,K., Koshika,S., Nagashima,Y., Frankenne,F., Noel,A.,
           Foidart,J.M. and Hata,R.I.
TITLE      Induction of SPARC by VEGF in human vascular endothelial cells
JOURNAL    Biochem. Biophys. Res. Commun. 287 (2), 422-426 (2001)
MEDLINE    21438978
PUBMED     11554745
COMMENT    PROVISIONAL REFSEQ: This record has not yet been subject to final
           NCBI review. The reference sequence was derived from J03040.1.
FEATURES             Location/Qualifiers
     source          1..2133
                     /organism="Homo sapiens"
                     /db_xref="taxon:9606"
                     /chromosome="5"
                     /map="5q31.3-q32"
     gene            1..2133
                     /gene="SPARC"
                     /note="synonym: ON"
                     /db_xref="LocusID:6678"
                     /db_xref="MIM:182120"
     CDS             58..969
                     /gene="SPARC"
                     /note="Osteonectin (secreted protein, acidic,
                     cysteine-rich)"
                     /codon_start=1
                     /product="secreted protein, acidic, cysteine-rich
                     (osteonectin)"
                     /protein_id="NP_003109.1"
```

FIG. 12-3

```
             /db_xref="GI:4507171"
             /db_xref="LocusID:6678"
             /db_xref="MIM:182120"
             /translation="MRAWIFFLLCLAGRALAAPQQEALPDETEVVEETVAEVTEVSVG
             ANPVQVEVGEEDDGAEETEEVVAENPCQNHHCKHGKVCELDENNTPMCVCQDPTSCP
             APIGEFEKVCSNDNKTFDSSCHFFATKCTLEGTKKGHKLHLDYIGPCKYIPPCLDSEL
             TEFPLRMRDWLKNVLVTLYERDEDNNLLTEKQKLRVKKIHENEKRLEAGDHPVELLAR
             DFEKNYNMYIFPVHWQFGQLDQHPIDGYLSHTELAPLRAPLIPMEHCTTRFFETCDLD
             NDKYIALDEWAGCFGIKQKDIDKDLVI"   SEQ ID NO. 1
misc_feature 268..339
             /gene="SPARC"
             /note="FOLN; Region: Follistatin-N-terminal domain-like"
             /db_xref="CDD:smart00274"
misc_feature 340..504
             /gene="SPARC"
             /note="kazal; Region: Kazal-type serine protease inhibitor
             domain. Usually indicative of serine protease inhibitors.
             However, kazal-like domains are also seen in the
             extracellular part of agrins, which are not known to be
             protease inhibitors. Kazal domains often occur in tandem
             arrays. Small alpha+beta fold containing three
             disulphides. Alignment also includes a single domain from
             transporters in the OATP/PGT family"
             /db_xref="CDD:pfam00050"
misc_feature 349..504
             /gene="SPARC"
             /note="KAZAL; Region: Kazal type serine protease
             inhibitors"
```

FIG. 12-4

```
variation        /db_xref="CDD:smart00280"
                 559
                 /gene="SPARC"
                 /allele="G"
                 /allele="C"
                 /db_xref="dbSNP:1053296"
variation        562
                 /gene="SPARC"
                 /allele="T"
                 /allele="G"
                 /allele="A"
                 /db_xref="dbSNP:707157"
variation        complement(570)
                 /allele="G"
                 /allele="C"
                 /db_xref="dbSNP:2304049"
variation        998
                 /gene="SPARC"
                 /allele="G"
                 /allele="C"
                 /db_xref="dbSNP:1053411"
variation        1117
                 /gene="SPARC"
                 /allele="T"
                 /allele="A"
                 /db_xref="dbSNP:1060151"
variation        1451
                 /gene="SPARC"
                 /allele="T"
                 /allele="G"
                 /db_xref="dbSNP:1053660"
variation        1509
                 /gene="SPARC"
                 /allele="T"
                 /allele="G"
                 /db_xref="dbSNP:3194455"
variation        1551
                 /gene="SPARC"
                 /allele="G"
                 /allele="C"
                 /db_xref="dbSNP:1054204"
variation        1655
                 /gene="SPARC"
                 /allele="T"
                 /allele="G"
```

FIG. 12-5

```
variation    /db_xref="dbSNP:1055210"
             1724
             /gene="SPARC"
             /allele="T"
             /allele="C"
             /db_xref="dbSNP:1804455"
variation    1862
             /gene="SPARC"
             /allele="T"
             /allele="C"
             /db_xref="dbSNP:1804456"
variation    complement(1922)
             /allele="C"
             /allele="A"
             /db_xref="dbSNP:1059279"
variation    2045
             /gene="SPARC"
             /allele="C"
             /allele="A"
             /db_xref="dbSNP:1064799"
variation    2072
             /gene="SPARC"
             /allele="T"
             /allele="C"
             /db_xref="dbSNP:1059829"
variation    2104
             /gene="SPARC"
             /allele="C"
             /allele="A"
             /db_xref="dbSNP:1804458"
```

FIG. 12-6

BASE COUNT    543 a    533 c    521 g    536 t
ORIGIN
    1 cgggagagcg cgctctgcct gccgcctgcc tgcctgccac tgagggttcc cagcaccatg
   61 agggcctgga tcttctttct cctttgcctg gccggaggg cctggcagc ccctcagcaa
  121 gaagccctgc ctgatgagac agaggtggtg gaagaaactg tggcagaggt gactgaggta
  181 tctgtgggag ctaatcctgt ccaggtggaa gtaggagaat ttgatgatgg tgcagaggaa
  241 accgaagagg agttggtggc ggaaaatccc tgccagaacc accactgcaa acacggcaag
  301 gtgtgcgagc tggatgagaa caacaccccc atgtgcgtgt gccaggaccc caccagctgc
  361 ccagccccca ttggcgagtt tgagaaggtg tgcagcaatg acaacaagac cttcgactct
  421 tcctgccact tctttgccac ctgagggca ctggagggca ccaagaaggg ccacaagctc
  481 cacctggact acatcgggcc ttgcaaatac acatccccctt gcctggactc tgagctgacc
  541 gaattccccc tgcgcatgcg ggactggctc aagaacgtcc tggtcaccct gtatgagagg
  601 gatgagagca acaaccttct gactgagaag cagaagctgc gggtgaagaa gatccatgag
  661 aatgagaagc gcctggaggc ctggttccac gagaccccac ccgtggagc tgctggcccg ggacttcgag
  721 aagaactata acatgtacat cttccctgta cactgccagt tcgtgctctc ggaccagcac
  781 cccattgacg ggtacctctc ccacacgag ctggctccac acctgtgacc tgcgtgctcc cctcatcccc
  841 atgagcatt gcaccaccgg ctttttcgag acctgtgacc tggacaatga caagatatct
  901 gccctggatg agtgggccgg ctgcttcggc atcaagcaga aggatatcga tttaaccctc caaggatctt
  961 gtgatctaaa tccactcctt ccacagtacc ggatttctctc tttaaccctc cccttcgtgt
 1021 ttcccccaat gtttaaaatg tttggatggt ttgttgttct gcctggagac aaggtgctaa
 1081 catagattta agtgaatca ttaacgtggtgc taaaaatgaa aattctaacc caagacatga
 1141 cattcttagc tgtaacttaa ctattaaggc cttttccaca cgcattaata gtcccatttt
 1201 tctcttgcca tttgtagctt tgcccattgt cttattggca catggtgga cacggatctg
 1261 ctgggctctg ccttaaacac acattgtgt ttcaactttt ctctttagtg ttctgttga
 1321 aactaatact taccgagtca gactttgtgt tcatttcatt tcaggtctt ggctgcctgt
 1381 gggcttcccc agtggcctg gaggtgggca aaggaagta acagacacac gatgttgtca
 1441 aggatggttt tgggactaga ggctcagtgg cctgcagaa tgggagagat cccctgagag tccaccaacc
 1501 agaacgtggt ttgcctgagg ctgtaactga gagaaagatt ctgggctgt cttatgaaaa

FIG. 12-7

```
1561  tatagacatt ctcacataag cccagttcat caccatttcc tcctttacct ttcagtgcag
1621  tttctttttca cattaggctg ttggttcaaa cttttgggag cacggactgt cagttctctg
1681  ggaagtggtc agcgcatcct gcaggcttc gcctcctctg tcttttggag aaccagggct
1741  cttctcaggg gctctaggga ctgccaggct gtttcagcca ggaagccaa aatcaagagt
1801  gagatgtaga aagttgtaaa atagaaaaag tggagttggt gaatcggttg ttctttcctc
1861  acatttggat gattgtcata aggtttttag oatgttcctc cttctttcct ccctcccctt
1921  tgttcttcta ttaatcaaga gaaacttcaa agttaatggg atggtcggat ctcacaggct
1981  gagaactcgt tcacctccaa gcatttcatg aaaaagctgc ttcttattaa tcatacaaac
2041  tctccaccatg atgtgaagag tttcacaaat ctttcaaaat aaaaagtaat gacttagaaa
2101  ctgaaaaaaa aaaaaaaaaa aaa SEQ ID NO. 18
//
```

Revised July 5, 2002

Disclaimer | Write to the Help Desk
NCBI | NLM | NIH

FIG. 12-8

NCBI
PubMed  Nucleotide  Protein  Genome  Structure  PMC  Taxonomy  OMIM  Boo

Nucleotide

Search Nucleotide ▽ for [                    ] Go  Clear
Limits  Preview/Index  History  Clipboard  Details Display default ▽ Show: 20 ▽ Send to File ▽  Get Subsequence ☐ 1: NM_009242. Mus musculus secr...[gi:6678076]                Links LOCUS        Sparc                     2079 bp    mRNA    linear   ROD 07-JAN-2002
DEFINITION   Mus musculus secreted acidic cysteine rich glycoprotein (Sparc),
             mRNA.
ACCESSION    NM_009242
VERSION      NM_009242.1  GI:6678076
KEYWORDS     .
SOURCE       Mus musculus (house mouse)
ORGANISM     Mus musculus
             Eukaryota; Metazoa; Chordata; Craniata; Vertebrata; Euteleostomi;
             Mammalia; Eutheria; Rodentia; Sciurognathi; Muridae; Murinae; Mus.
REFERENCE    1  (bases 1 to 2079)
AUTHORS      Mason,I.J., Taylor,A., Williams,J.G., Sage,H. and Hogan,B.L.
TITLE        Evidence from molecular cloning that SPARC, a major product of
             mouse embryo parietal endoderm, is related to an endothelial cell
             'culture shock' glycoprotein of Mr 43,000
JOURNAL      EMBO J. 5 (7), 1465-1472 (1986)

FIG. 12-9

```
MEDLINE    86300644
PUBMED     3755680
REFERENCE  2  (bases 1 to 2079)
AUTHORS    McVey,J.H., Nomura,S., Kelly,P., Mason,I.J. and Hogan,B.L.
TITLE      Characterization of the mouse SPARC/osteonectin gene. Intron/exon
           organization and an unusual promoter region
JOURNAL    J. Biol. Chem. 263 (23), 11111-11116 (1988)
MEDLINE    88298750
PUBMED     3165375
REFERENCE  3  (bases 1 to 2079)
AUTHORS    Howe,C.C., Overton,G.C., Sawicki,J., Solter,D., Stein,P. and
           Strickland,S.
TITLE      Expression of SPARC/osteonectin transcript in murine embryos and
           gonads
JOURNAL    Differentiation 37 (1), 20-25 (1988)
MEDLINE    88255622
PUBMED     3384223
REFERENCE  4  (bases 1 to 2079)
AUTHORS    Carninci,P., Shibata,Y., Hayatsu,N., Sugahara,Y., Shibata,K.,
           Itoh,M., Konno,H., Okazaki,Y., Muramatsu,M. and Hayashizaki,Y.
TITLE      Normalization and subtraction of cap-trapper-selected cDNAs to
           prepare full-length cDNA libraries for rapid discovery of new genes
JOURNAL    Genome Res. 10 (10), 1617-1630 (2000)
MEDLINE    20499374
PUBMED     11042159
REFERENCE  5  (bases 1 to 2079)
AUTHORS    Shibata,K., Itoh,M., Aizawa,K., Nagaoka,S., Sasaki,N., Carninci,P.,
           Konno,H., Akiyama,J., Nishi,K., Kitsunai,T., Tashiro,H., Itoh,M.,
```

FIG. 12-10

```
            Sumi,N., Ishii,Y., Nakamura,S., Hazama,M., Nishine,T., Harada,A.,
            Yamamoto,R., Matsumoto,H., Sakaguchi,S., Ikegami,T., Kashiwagi,K.,
            Fujiwake,S., Inoue,K. and Togawa,Y.
  TITLE     RIKEN integrated sequence analysis (RISA) system--384-format
            sequencing pipeline with 384 multicapillary sequencer
  JOURNAL   Genome Res. 10 (11), 1757-1771 (2000)
  MEDLINE   20530913
   PUBMED   11076861
COMMENT     PROVISIONAL REFSEQ: This record has not yet been subject to final
            NCBI review. The reference sequence was derived from X04017.1.
FEATURES             Location/Qualifiers
     source          1..2079
                     /organism="Mus musculus"
                     /db_xref="taxon:10090"
                     /chromosome="11"
                     /map="11 29.9 cM"
     gene            1..2079
                     /gene="Sparc"
                     /note="synonym: BM-40"
                     /db_xref="LocusID:20692"
                     /db_xref="MGD:98373"
     CDS             90..998
                     /gene="Sparc"
                     /note="osteonectin"
                     /codon_start=1
                     /product="secreted acidic cysteine rich glycoprotein"
                     /protein_id="NP_033268.1"
                     /db_xref="GI:6678077"
```

FIG. 12-11

```
                 /db_xref="LocusID:20692"
                 /db_xref="MGD:98373"
                 /translation="MRAWIFFLLCLAGRALAAPQQTEVAEEIVEETVVEETGVPVGA
                 NPVQVEMGEFEDGAEETVEEVVADNPCQNHHCKHGKVCELDESNTPMCVCQDPTSCPA
                 PIGEFEKVCSNDNKTFDSSCHFFATKCTLEGTKKGHKLHLDYIGPCKYIAPCLDSELT
                 EFPLRMRDWLKNVLVTLYERDEGNNLLTEKQKLRVKKIHENEKRLEAGDHPVELLARD
                 FEKNYNMYIFPVHWQFGQLDQHPIDGYLSHTELAPLRAPLIPMEHCTTRFFETCDLDN
                 DKYIALEEWAGCFGIKEQDINKDLVI" SEQ ID NO. 2
     misc_feature    297..368
                 /gene="Sparc"
                 /note="FOLN; Region: Follistatin-N-terminal domain-like"
                 /db_xref="CDD:smart00274"
     misc_feature    369..533
                 /gene="Sparc"
                 /note="kazal; Region: Kazal-type S protease inhibitor
                 domain"
                 /db_xref="CDD:pfam00050"
     misc_feature    378..533
                 /gene="Sparc"
                 /note="KAZAL; Region: Kazal type serine protease
                 inhibitors"
                 /db_xref="CDD:smart00280"
     misc_feature    432..434
                 /gene="Sparc"
                 /note="put. glycosylation signal (aa 115)"
     misc_feature    2054..2059
                 /gene="Sparc"
                 /note="polyA signal"
```

FIG. 12-12

```
BASE COUNT      526 a     552 c     518 g     483 t
ORIGIN
   1 gcattcctgc agcccttcag accgccagaa ctcttctgcc gcctgcctgc ctgcctgcct
  61 gcctgcctgt gccgagagtt cccagcatca tgagggcctg gatcttcttt ctcctttgcc
 121 tggccgggag ggccctggca gccctcagc agactgaagt tgctgaggag atagtggagg
 181 aggaaaccgt ggtggaggag acaggggtac ctgtgggtgc caacccagtc caggtggaaa
 241 tgggagaatt tgaggacggt gcagaggaaa cggtcgagga ggtggtggct gacaacccct
 301 gccagaacca tcattgcaaa catgcgcaagg tgtgtgagct ggacgagagc aacaccccca
 361 tgtgtgtgtg ccaggaccccc accagctgcc ctgctcccat tggcgagttt gagaaggtat
 421 gcagcaatga caacaagacc ttcgactctt cctgccactt cctcgcacc aagtgcaccc
 481 tggagggcac caagaaggg cacaagctca acctgactc atcggacca catcggacca
 541 tcgcccccctg cctggattcc gagctgaccg aattccctct gcgcatgcgt gactggctca
 601 aaaatgtcct ggtcaccttg tacgagagag atgagggcaa caacctcctc actgagaagc
 661 agaagctgcg tgtgaagaag atccatgaga atgagaagcg cctggaggct ggagaccacc
 721 ccgtgagct gttggcccga gactttgaga agaactacaa tatgtacatc ttccctgtcc
 781 actggcagtt tggccagctg gatcagcacc ctattgatgg gtacctgtcc cacactgagc
 841 tgcccccact gcgtgctccc ctcatcccca tggaacattg caccacacgt ttctttgaga
 901 cctgtgacct agacaacgac aagtacactg ccctggagga atggccggc tgctttggca
 961 tcaaggagca ggacatcaac aaggatctgg tgatctaagt tcacgcctcc tgctgcagtc
1021 ctgaactctc tccctctgat gtgtcacccc tcccattacc ccctttgttta aatgttttgg
1081 atgttggct gttccgcctg gggataaggt gctaacatag atttaactga atacattaac
1141 ggtgctaaaa aaaaaaaaaa actctgaggc catgccccat gaaagaaact agaacccaag
1201 ttcccacata actctgact gaaacggagt tgcataagct ccactccct gcactaccca
1261 gtgtctcact ggctgtgttg tttcattca atttgcatt tgactcttaa caccgtccac
1321 tatctctagc tttcattca atttgcatt tgactcttaa cactcaccca agcactgaga
1381 ttatttcatt ttggggatg tggcttttt cccctggtgg tttggagtta ggcagaggga
1441 agttacagac acaggtacaa aatttgggta aagatactgt gagacctgag gaccaccag
1501 tcagaaccca catgcaagt cttagtagcc taggtcaagg aaagacagaa taatccagag
```

FIG. 12-13

```
1561  ctgtggcaca  catgacagac  tcccagcagc  ccgggacctt  gctgtcttct  cgactcttcg
1621  ggcgttctt   tccatgtttg  gctgttggtt  ttagtttttgg tgagccatgg  gtgggccaga
1681  acatcactca  actgcaattg  ggctttcagg  ttcttgccgg  gagctctagg  cactgggagg
1741  ctgtttcagg  aaagtgagac  tcaagaggaa  gacagaaaag  gttgtaacgt  agaggaagtg
1801  agactggtga  attgtttga   ttttttttcac atctagatgg  ctgtcataaa  gtttctagca
1861  tgttcccct   cacctctccc  cacccctgc   cacttgaaac  cttctactaa  tcaagagaaa
1921  cttccaagcc  aacggaatgg  tcagatctca  caggctgaga  aattgttccc  ctccaagcat
1981  ttcatgaaaa  agctgcttct  cattaaccat  gcaaactctc  acagcgatgt  gaagagcttg
2041  acaagtcttt  caaaataaaa  agtaacaact  tagaaacgg              SEQ ID NO. 19
```

FIG. 12-14

```
PubMed    Nucleotide    Protein    Genome    Structure    PMC    Taxonomy    OMIM    Boo Nucleotide Search Nucleotide ▽ for [                    ]  Go   Clear                Details Limits       Preview/Index    History           Clipboard
Display default ▽ Show: 20 ▽ Send to File ▽        Get Subsequence         Links
```

☐ 1: AB088113. Homo sapiens SC1,...[gi:27544421]

```
LOCUS       AB088113               14468 bp    DNA     linear   PRI 08-JAN-2003
DEFINITION  Homo sapiens SC1, OTF3 genes for transcription factor 19, POU
            domain class 5 transcription factor 1, complete cds.
ACCESSION   AB088113
VERSION     AB088113.1  GI:27544421
KEYWORDS    
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1
  AUTHORS   Shiina,T., Ota,M., Katsuyama,Y., Hashimoto,N. and Inoko,H.
  TITLE     Genome diversity in HLA: A new strategy for detection of genetic
            polymorphisms in expressed genes within the HLA class III and class
            I regions
```

FIG. 12-15

```
JOURNAL      Unpublished
REFERENCE    2  (bases 1 to 14468)
AUTHORS      Shiina,T.
TITLE        Direct Submission
JOURNAL      Submitted (08-JUL-2002) Takashi Shiina, Tokai University School of
             Medicine, Molecular Life Sciense 2; Bohseidai, Isehara, Kanagawa
             259-1193, Japan (E-mail:tshiina@is.icc.u-tokai.ac.jp,
             Tel:81-463-93-1121, Fax:81-463-94-8884)
FEATURES             Location/Qualifiers
     source          1..14468
                     /organism="Homo sapiens"
                     /db_xref="taxon:9606"
                     /chromosome="6"
                     /map="6p21.31"
                     /cell_line="LKT3"
                     /cell_type="B cell"
     exon            1066..1680
                     /number=1
     gene            join(1443..1680,3384..3942,4414..4654)
                     /gene="SC1"
     CDS             join(1443..1680,3384..3942,4414..4654)
                     /gene="SC1"
                     /note="DNA binding protein required for late cell cycle
                     progression"
                     /codon_start=1
                     /product="transcription factor 19"
                     /protein_id="BAC54945.1"
                     /db_xref="GI:27544422"
```

FIG. 12-16

```
             /translation="MLPCFQLLRIGGGRGGDLYTEHPPAGAGCTYRLGHRADLCDVAL
             RPQQEPGLISGIHAELHAEPRGDDWRVSLEDHSSQGTLVNNVRLPRGHRLELSDGDLL
             TFGPEGPPGTSPSEFYFMFQQVRVKPQDFAAITIPRSRGEARVGAGFRPMLPSQGAPQ
             RPLSTFSPAPKATLILNSIGSLSKLRPQPLTFSPSWGGPKSLPVPAPPGEVGTTPSAP
             PQRNRRKSVHRVLAELDDESEPPENPPPVLMEPRKKLRVDKAPLTPTGNRRGRPRKYP
             VSAPMAPPAVGGEPCAAPCCCLPQEETVAWVQCDGCDWFHVACVGCSIQAAREADF
             RCPGCRAGIQT" SEQ ID NO. 3
   exon      3384..3942
             /gene="SC1"
             /number=2
   exon      4414..5723
             /gene="OTF3"
             /number=3
   exon      6283..6805
             /number=4
   gene      complement(join(6539..6805,7068..7226,7511..7641,
             7875..8115))
             /gene="OTF3"
   CDS       complement(join(6539..6805,7068..7226,7511..7641,
             7875..8115))
             /gene="OTF3"
             /note="POU-type homeodomain-containing DNA-binding
             protein"
             /codon_start=1
             /product="POU domain, class 5, transcription factor 1"
             /protein_id="BAC54946.1"
             /db_xref="GI:27544423"
             /translation="MHFYRLFLGATRRFLNPEWKGEIDNWCVYVLTSLLPFKIQSQDI
             KALQKELEQFAKLLKQKRITLGYTQADVGLTLGVLFGKVFSQTTICRFEALQLSFKNM
```

FIG. 12-17

```
exon            CKLRPLLQKWVEEADNNENLQEICKAETLVQARKRKRTSIENRVRGNLENLFLQCPKP
                TLQQISHIAQQLGLEKDVVRVWFCNRRQKGKRSSSDYAQREDFEAAGSPFSGGPVSFP
                LAPGPHFGTPGYGSPHFTALYSSVPFPEGEAFPPVSVTTLGSPMHSN"
                7068..7226 SEQ ID NO. 35
                /number=3
exon            7511..7641
                /number=2
exon            7875..8216
                /number=1

BASE COUNT    3555 a    3859 c    3746 g    3308 t
ORIGIN
    1 tctaaggctg ttctgatctc ttcatctgtc ccttcacctg gccctgtac ccccttcccc
   61 tttggacccc ttgaaccctc ccaggaccc cgctcagcc gcccctact gcgctttgc ccaaccgact
  121 cttcccgaac gtcccttacc cccggcccg aaccgcgaga gcccctact gcgctttgc cacacccct
  181 acgcctcgct cccgccccg ctctctgccc tgaccgcgc tgcgcaaggc gggcgccta
  241 aagtcctatt tcactctgtt gggagaggg ggaaagtgt acgcaggcgc agtggcgtct
  301 aaatttgggc ccactaaatg cgtcggagca tctccgcgcc caggcggctc ctcctcactg
  361 cggcaacccg ggaaaacttg tgaactaatc agaaaaagtg gaagcggga gatcttgggg
  421 cgctgtccaa tggcgcggaa gagaacaaat gagctggcca atcgggaacg gcacggggc
  481 gggctcgctc ggcgcgaagt tcgggcccgg gaattccgaa ggaggggtag gcgctgcccg
  541 cgcgcagagg ccgcgcccct cctgccccg gcttcttggc tgtcaaacag atgcagcaac
  601 gtcggctcct gccgaggagc ccaaggggtc ccggatccg ccgcacaggc tggcactgct
  661 tgaagaggag gctactcgga gactgcgccg cgcgggtaga tccgaaacgg ggctggggcg
  721 gagtgggaaa aggccgggta tgccttgcat gatcgcgggg agctccttcc tgttttatc
  781 ccacctagag aagccgggaa gtaggggttt agtgacagt ggattcattg cccctcgagg ttcaaccagt
  841 cgttgcact ttctttttgg ggatgacagt ggattcattg cccctcgagg ttcaaccagt
  901 tatgagtgag ggattggcca gaagatcggg gcgcaggcaa gcaggagtgc tctattagga
```

FIG. 12-18

```
 961 taagcaagtt tgacaggaag aagctgctct tctccgaatt acacagaggt gatgtgttcg
1021 tattgcacgt agacgtgtgt ataacaggac ctccttcccc gcgcccgcc acccgacac
1081 acacaggagc tgcctaaagt atccttgcct tgcagattgg aggctcccca aatatttgt
1141 gatctgagga tccagctcaa gtgaggtgcc ataggacgtg ttcctgagtt tgcattgcac
1201 ggagaccttc ctgaatttt tcatttgcaa gtcggcttaa ccaattttgc attgagtcct
1261 aggctgcttg cacctgctgt ttggctatt caggtagtgt gctcaaagtt gaaaccgcat
1321 acagcacaac tcaagtttgc atcagactgg gaagcgaact taagccagcg gtgcgtggcc
1381 caggagtggg aaaggaaatg gatgcctgaa gtggaagagg tggtgcagag gggcaccgc
1441 ccatgctgcc ctgcttccaa ctgctgcgca tagggcgcgg caggggcggt gatctctaca
1501 ccttccaccc ccccgccggg gctggctgca cctatcgctt gggccacagg gccgacctgt
1561 gtgatgtggc cctgcgccc cagcaggagc ctggcctcat ctctggatc cacgccgaac
1621 tgcatgccga gccccggggt gatgactgga gggtcagcct ggaagaccac agcagccaag
1681 gtgagcatta agcaggcag ctttgcccct gggtgttga agcgccaggc tggaatgagt
1741 aaggtctcca caagaccctg ctgcctgcct cccatactcc catcagattg gatgatagt
1801 cgtggtccag accttcatct tccaccaga agtgtgcaca gtcagaagct ctctgccaga
1861 ctgaccctt ttggtcccgt ttagctcata caggacctgg gatatcatca gaaagatatc
1921 acagtgggga tgttctgagg ccactagagg ccaagtttag acttgattca gtttccagct
1981 ttgctgaggc actctgttcc tgggttaggg cagttctatg ttgaataatg ttttttaataa
2041 tctgggcatg tctttctccg tgacttgagg cagttagcct cagaaagcct agattcacat
2101 ttgagttttg ccactgcctc ttggtaaagt cagctgtagg agtgttatgg ttattagact
2161 atagtagcca acattcatct agtgcttact gttatgagcc aggccctatt ttaagtgtat
2221 tgaatgtagg tggtactaat attatcctca tttacagtaa aggaaaatga ggcacaaaga
2281 ggttaaggaa cttgtccagg gctggcatg cctgagct gtggtttaca cctataatcc agcactttgg
2341 gaggctaagg cagggtggat cacttgagct caggagttcg caggagtcct agaccagcct ggcaacatg
2401 gtgaaaacct gtctctacca aaaaattaat taattttta aaaaaaagcct gggcgcggtg
2461 gctcacgcct gtaatcccag cactttggga ggccgagatg ggcagatcac gaggtcagga
2521 gttcgagacc atccgtgacca acatgttgaa acatgttgaa acccatcctg tgctgaaaa aaaatacaaa
2581 aattagccag gtgtggtggc gtgcacctgt aacccagct actcaggagg ctgaagcagc
```

FIG. 12-19

```
2641 agaatcactt gaacccggga ggcggaggtt gcagtgagct gagatcgcac cactgcactc
2701 cagcttgggc gacagagcga gactccatct caaacaaaca aacaaaccaa aagcttgccc
2761 agggtcacat aactggtaag tgtagagct aggatctgaa cgagctggag ctggggaga
2821 gtgagcatgt ttgaaaactg gaccttaggg cggggcacgg tggctcacgc ctgtaatccc
2881 agcactttgg gaggctgagg cgggcagatc aggaggtcag gagtatgaga ccagcctggc
2941 caacatggta aaaccctgtc tctgctaaaa ataaaaaaat tagccagacg tggtggcaca
3001 tgcctgtaat cccagctact caggaggctg aggcaggaga attgcttgaa cctgggaggc
3061 ggttcaagct tgggcaatag agcaaaactc catctcaaaa aaaaaaaaag aagaaaaaa
3121 aaagaagaaa gaagaaaaat tggaccttag gacagtgagg gcaggatcc tttgtaggaa
3181 agcacaagaa acacagactt gttcctagct gacaaggagt gtactgcctg gtacctgtca
3241 cctgctgagg ggcttaggat gtgagggaga atctgactac agtttcatat tcttcccag
3301 aaatcataca gatttctcca ctcctgactc tggtcatttc tgttttttgtc ctccatattt
3361 gcctggtgcc ccaccatcaa caggtactt gtcgactcc caagaggtca
3421 caggctggaa ttgagtgatg gagacctcct gaccttggc cctgaagggc cccaggaac
3481 cagcccctcg gagttctact tcatgttcca acaagtacga gtcaagcctc aggactttgc
3541 tgccattacc atcccacgt ctaggggaga agcccgggtt gggctggtt tccggcctat
3601 gctgccctcc cagggggctc cacacgggcc tctcagcacc ttctcccctg cccccaaggc
3661 cacactgatc ctaaactcca taggcagcct cagcaagctc cggccccagc ccctcacctt
3721 ctcccctagt tgggtggac caaagagcct gcctgttccc gccccacctg gggaagtggg
3781 gaccacgcct tctgctccaa cccaacgcaa tcggaggaaa tctgttcacc gagtgttggc
3841 ggaactggat gatgagagtg agcctcctga gaacccgcca ccgtccttta tggagcccag
3901 gaagaaactc cgtgtagaca aagccccact gactcccact gggtaagtgg agtcctcact
3961 tgccctctc agtgttttac tgcttttcga ttccttgtat cctaggctg tgaggggtc
4021 ccctgcctg ggggatggg cacgggaggt ggaatagatg ggaacatga gaatggcaag acctggtta
4081 gctctgatag gaaaagaaaa atatgtgcag gagaacatga gaggtggggt gggcagtgc
4141 ttataaaaca accggagtga gcatgtcctg cttttacat tcatatgct ttaaccccat
4201 tcttctagtg cctaaggatg gggaactttc aggctcacac tagaggtttt taggcccacc
4261 ctatgtgttt ttaaggacag agtccaggct cacccttagtt ctcagaccac tgtgcctctg
```

FIG. 12-20

```
4321 tggcctcacc ctatgaccag ccataggtg gcaaggtcta ggccttctcc tacagtttc
4381 cggtgaccct tgtgtctgtg tcacttcctt cagaaatcga cgtggccgtc ctcggaagta
4441 cccagtgagc gctcccatgg ctcccctgc agttgggggc gggagccct gtgcagctcc
4501 ttgttgctgc ctgcccagg aagagacagt ggcctgggtt cagtgtgatg gctgtgacgt
4561 ctgttccat gtggcctgtg ttggctgcag catccaggct gccagggag ccgacttccg
4621 atgcccaggg tgccgggctg gcattcagac ctaaggtcca cgccaaggc accatcggac
4681 acacctgccc atgagtagac acagcagcga gcaaataggt ctgataaata ccccccttcc
4741 cttccctccc caagaggga tgactacagg gaagaaggat ggattgatgt ggactcattc
4801 agggcctgga gcagaccctg gtggccaaga cagaagagat ggtttcctgc caaagatatt
4861 gccacctcca ggaaattgcc agtgagctgg aagttccac tattacaagc cataaggcca
4921 tgttgccatg gacaccagaa tatctgtagt cagagcacct atcagttgca aaagccatgc
4981 ctgcaaccga tggaaaatgt aagagggagt tcttaaggtt cttggtgca tcacccaagg
5041 cattctggaa aaacctaggg cctgccccca aaacttccct actctgtggc tagtcctgct
5101 gccaacaaaa tcgtagcgac ctggcttttc acagctttgc tttatttcc aagtcaagga
5161 caagccgctt cattcactcc tggcattta ctcttcttgt gggtctgtga tattccttgc
5221 tttccaggga gaatgtgctt ggcaaggtct ggagaactaa ttcagaatct tagggaagg
5281 ggagagatgg aaatacaaac ctgcttactg gaaaggtgca aatatatggg ttgagctgga
5341 ggtaggaata caggtaatta aggtttctag tttaagggaa aacagatcta ttgccattta
5401 aataaggtaa ctgggatttg gttaagttca caaagatagc agaagattta tttacaggct
5461 tcacctgtac tgtcagggca agagaaagcc tggtaaacca gctacagcag tttaccagtg
5521 tgatggctgt gacacagctc cactccacgg gtggacacag cagagggcaa ctggctggc
5581 ctggttcagt gtgaatcaaa ccgcttaaacc cacacatgt acatgtgatt ttcttttgtg
5641 agccttacac caagccaaac tattgtcaaa gcatcatttc tatagaaata aagccttatc
5701 ttgacctgtt ctattaaaac ctgccacatc cgccctttcc tacctagatt taatgagccc
5761 aagtttttt acatgaaga aatgactctg gggcaaagac ccctaatgaa ctagtggcag
5821 agccaggaat aaaacttgag taactaatga gtcacttatg ggcagagtat gcaaaacct
5881 taagtggaaa ccaaatagac cctggtatca agaaagcaca agtattaat agaagttct
5941 ggttggggtg atctaggttc aacagaaata agatgatttc taagtataaa gccatttaag
```

FIG. 12-21

```
6001  aattccagag  tagggtggga  aagcaaaaag  ccagctctga  acaggtaaca  gctacatggt
6061  gactgagtct  atggcaaaa   gttcttgcat  cacaggcttt  tgggaactag  cctatcacag
6121  ggccctgtac  aaataaactt  ggctgcaatc  ccagctctcc  ctctgatgtt  gtgtgacctt
6181  aggagtgta   aatgcaccct  tagtttcagg  gtcacttggg  tatgagcatt  ggatattccc
6241  atcccacct   cagtaactga  aggacaaacc  aagataagtg  tgtctatcta  ctgtgtccca
6301  agcttcttta  tttaagaaaa  aagtgataca  tgatgtggga  ttaaaatcaa  gagcatcatt
6361  gaacttcacc  ttccctccaa  ccagttgccc  caaactcccc  tgcccccacc  ctttgtgttc
6421  ccaattcctt  ccttagtgaa  tgaagaactt  aatcccaaaa  accctgcac   aaactccagg
6481  tttctttcc   ctagctcctc  cctctcccc   gtccccatt   cctagaaggg  caggcacctc
6541  agtttgaatg  catgggagag  cccagagtgg  tgacagagac  aggggaaag   gcttcccct
6601  cagggaaagg  gaccgaggag  tacagtgcag  tgaagtgagg  gctcccatag  cctggggtac
6661  caaatgggg   ccctgggcc   agaggaaagg  acactgtcc   cctgagaaa   ggagaccag
6721  cagcctcaaa  atcctctcgt  tgtgcatagt  cgctgcttga  tcgcttgccc  ttctggcgcc
6781  ggttacagaa  ccacactcgg  accacctgcc  agtgaatgac  agaaaggaga  atgacattag
6841  acaatgagct  gagagacggg  cctgactctg  cttgacatt   ctatccaaag  ccaacagccc
6901  tagagcagtt  agagagagac  attagagaat  gagctgagac  aggcctgact  gcttggacat
6961  tctgtccaaa  gccaacagcc  ctagacagt   tggaggagcc  tggagctagg  aaagcgaggt
7021  ggtgacaggg  gaaagagatg  gagcccgcag  agagacatgg  cactcacatc  cttctcgagc
7081  ccaagctgct  gggcgatgtg  gctgatctgc  tgcagtgtgg  gtttcgggca  ctgcaggaac
7141  aaattctcca  ggttgcctct  cactcggttc  tcgatactgg  ttcgctttct  ctttcgggcc
7201  tgcacgaggg  tttctgcttt  gcatatctgt  gcaggtggga  aggggtgac   aaggcaagc
7261  tttggacttg  ctgagtaaca  gcatcacagg  gttctgtgac  tagatgtgtc  agcagagcca
7321  ggtggtggtg  tgaaaaggca  ggatcctgga  agggttggct  ctgaccta    tccagcaga
7381  actgaggaat  ttcactccat  cccactgaga  accactgcac  caaagacgga  gagctacgag
7441  ccagtgatgg  aagcaatgaa  aattaggcca  agaaagggaa  ggtcccgg    tatcccctc
7501  ccacccttac  ctccctgaaga ttttcattgt  ttcttgaagc  tgtcagcttc  ctccacccac
7561  agggccgcag  cttacacatg  ttcttgaagc  taagctgcag  agcctcaaag  cggcagatgg
7621  tcgtttggct  gaatacctc   ctggggag    gccagtcaaa  agagaagcaa  aatgagggag
```

FIG. 12-22

```
7681  cacgcagggc ccttgtgacc ctgagatcca agcttaccac ctcttcccag agggagctca
7741  aagcccaagc atcttctccc tctccctact cctcttcatg ggtgagggta gagtctgccc
7801  ctgcccctcc ccactaggtt cagggatact ccttagaggg gagatgcggt cagaatctgc
7861  agaggggaac ccaccaaata gaaccccccag ggtgagcccc acatcggcct gtgtatatcc
7921  cagggtgatc ctcttctgct tcaggagctt ggcaaattgc tcgagttctt tctgcagagc
7981  tttgatgtcc tgggactgga ttttaaaagg cagaagactt gtaagaacat aaacacacca
8041  gttatcaatc tccccttttcc attcggatt caagaaccta cgtgtgccc caaggaatag
8101  tctgtagaag tgcatctgcc ttccaagctg cccacctaac ttctagaaat aacctaccca
8161  caaatgtcat tcaccattc cctgttcact gactcatgca tgtaacaaag gactactctt
8221  ccccagaaa ctggcacatc caaggatgc agagcatggt gaaaggacag aaagagagac
8281  cctggcctcg aggagaacac ctgtcaggtt atgaaggtta gaagttcttt gctggcgcg
8341  gtggctcatg cctataattc cagcactttg ggaggccgag gtgggcagat cacgaggtca
8401  ggagttcaag accagcatgg ccaacatggt gaaaccccgt ctctactaaa aacacaaaaa
8461  ttagctgggc acggtggcac gcacctgtaa tcccagctac caggagggct gaggcaggag
8521  aatcacttga acccggagg cgagggttgc agtgagctga gatcacgcca ctgcactcca
8581  gcctgggtga cagagcaaga ctctgtctca aagaaaaaaa aaaagaagat agttcattta
8641  atacctgcaa aattctctca ctcaagtatc accccccagtt taaggatgtt ttgagattag
8701  agaaatagat aagctgctaa gttctggggtt aattaaaaag gaagagcatc atgtctcaga
8761  agctaaattc agtatatact ctccccagct tgctttgagg gtcccacaaa ctataacatg
8821  gcatgcatac acacaaacac agcaaaaaag taacaggtgt cataagaatg gataaagtgc
8881  tttgtgtgta cttactcctc atttttaaa ttgattatcc ctcatctttta ctgtatcttt
8941  ttcactatag agcatccta attgatttt aaattcaaga gatttatcga gcaccttcta
9001  taagccagcg gctatacaaa gtggacaaag agccctgaca tccagcatga cagaagtgct
9061  attcggcact tgttcttcaa gttgcccact tggatctctt ccaagtgcac tttccttttt
9121  tccctgccct ataactttt aataataaac ttccactcct gctctgaaaa ataaaaaagt
9181  aaataaaata aaaatgcc aggcacagtg gctcatgtct gtaaatccta gcactttggg
9241  aggccaggt gggcagactg cttgagccca agagttagaa agcagcctgg gtaacatagt
9301  gagacccgtg ccgcccctt tcccacccct gctgcctcta tttaaaaat atatatatat
```

FIG. 12-23

| | | | | | |
|---|---|---|---|---|---|
| 9361 | tatgaaaaa | agcaaagcag | tccggggcgca | gtggtcatgc | ctgtaatccc | ttcactttgg |
| 9421 | gaggccaagg | tgggtagatc | acttgaggtc | aggagttcaa | gactagcctg | gtcaacatag |
| 9481 | tgagactctg | tctctactaa | aaatacaaaa | attagctggg | catcatgcg | ctccctata |
| 9541 | atcccagcta | ctcaggaggc | tgggcagga | gaattgcttg | aacctaggag | gtggagtttg |
| 9601 | cagtgagcca | agatcgcacc | actgcactcc | agcctgaggg | acagagtgag | actccatctc |
| 9661 | aaaaattaaa | aaaaaaataa | agcagtctat | aggagtaggg | taaaggaggg | aaggagatta |
| 9721 | tggaggaggg | tgcactttt | aaagacagag | aaggtgattg | tttgagcaaa | ggacaagagt |
| 9781 | ctaatgtggc | aagccctga | agtgggcctt | ccagagccca | aagctggtct | ggtggctagg |
| 9841 | tagatcctgt | tgcagacata | gtgactttgt | tttagtccaa | gtgaaatgat | ctctcacct |
| 9901 | ttttctcccc | cccaagacg | gaatctcgtt | ctatcgccca | ggctggagtg | ctgtggcgtg |
| 9961 | atccttgctc | actgcaatct | ccgccttctg | gttcaagct | attctgcctc | agccgcctga |
| 10021 | gtagctggga | ctacaggcac | ccaccaccat | gcccggctaa | ttttgtatt | tttagtagat |
| 10081 | atgggtttc | accatgttgg | ccaggctggt | caggagacct | caagtgatct | gtccaccttg |
| 10141 | gcttcccaaa | gtgctgggat | tacaggtgtg | aaccaccgca | cctagcctca | ccttttttt |
| 10201 | tttttttttg | agagtttcgc | ttttgttgcc | taggctggag | tgcactcggc | cgatctcggc |
| 10261 | tcaccgcaac | ctacatctcc | caggttcaag | cgattctcct | gcctcagctt | cctgagtagc |
| 10321 | tgagattaca | ggcatgcgtc | accacgccca | gctaattttg | tatttttagt | agagatgggg |
| 10381 | tttcgccatg | ttggtcaggc | tggactcgaa | ctcccaacct | caggtgattc | gcctgcctcg |
| 10441 | gcctcccaaa | gtgcctggcc | acaccttta | aaacactgac | tctagttgac | gtgttggcca |
| 10501 | cagacagtag | ggaggaagca | gtataatttg | agaagctact | gcggtaatcc | cagcagagat |
| 10561 | gatgtggct | gaggccaggg | ttaggtttgtg | attgattcag | gatgttcctt | aaggatagga |
| 10621 | tgtaggacgt | gaaagaaact | gaggatgact | gggttttggcc | ttgagcaact | gggtgatcag |
| 10681 | ggtgagcag | ttcagggagc | catcacaaga | gacagaaaac | gcggtagtca | tctggtgtct |
| 10741 | aaatggcatt | taagccttga | gggtgggtga | gaggaaggaa | gggtagatag | agcagaggtt |
| 10801 | gaagactga | gccctggggc | atgccatatg | aggctgccgg | cggacagagg | tgcacagcta |
| 10861 | gtgagaaaa | aacaaggcct | ttttgtagtc | ctgaagcctc | aaggaagtgt | ttcaatggtg |
| 10921 | cttgatcata | tcaatttcaa | ataggctgtt | ttcatcccca | acttctgctc | agccaataac |
| 10981 | tcaaactgat | aaatgccctc | tgctatcctg | gatttccaa | attctgtttt | ggggtttttgg |

FIG. 12-24

```
11041  aataaacact ggtccaaatc ctcgcttcat cattagcag ttaaacccg ttaaatagga
11101  taataatacc tccccctagg agattttgtg ctggttaatg ttaaaacccg gtataaacgg
11161  agcacacagc caggcactta ggaagtggac cacaattgcc agccattatc attcaaggct
11221  cagcagtgac ctcctgcgaa gaggttgggg cttctcggtc actccagaaa ccagtcacac
11281  cttctctgtga ggtctcaagg cttagtattt aatctctaat tgcttacact tgtcgccttg
11341  gaggactgga agatacatct ttaatagtcc tcagcagggc tggatgcctt caatcccgca
11401  gcagctctat atttgcaaat ggcctggaga aatctctcac cattttctt gtttacaact
11461  ttggaactga ggctgaagtc aatcaaaatc cagctttcta caagggtgc caggtgtgc
11521  accttaacac agtggccagt cattggcctg aggcagagat ccggggaaga caagcctat
11581  acttgactgg aggtaaaccc agctcacaac gcgcacacac acagcccaaa caggagatcc
11641  tatcagaaac gagtcacacc ctagactttc aggaacaata atcctggaat gagcactgtt
11701  tttaccctca ggctatgctt aaccctaagg ccaaatctt ggtctgata agggtcaaat
11761  tttcaagcag gactaagggt gggaaagggg gctcaaacca accccaagct gggtctggtg
11821  ctgggccagt aatgagtgac cagacccctg gcaggcctag gagatgtgag agaccctgac
11881  aagggctggg ccagacagag caaaggccag cctgggccag cttccgactc tcccaggccg
11941  ctctgcccct acctgcagtt gtctcttga aatccagctt ccagtcccca cctggcccct
12001  gcctgccagg gctgcctgca gttgatacac ccctcccct ggccagggca gctgaccctg
12061  cctgctcctc tcctgggtgc caggtctggg cagtctgcagg cccatcagc gcctcctccg
12121  tgccctgtca tgaccacctc cccacaccc aacccgtcg aagctcactt gcctcctccg
12181  ggtttgtc cagcttctcc ttctccagct tcacggcacc aggggtgacg gtgcaggct
12241  ccggggagc cccatcggag ttgctctcca cccgactcc tgcttcgccc tcaggctgag
12301  aggtctccaa gccgccttgg ggcactagcc ccactccaac ctgggccca cagtacgcca
12361  tcccccaca gaactcatac ggcgggggc cggccctc ccccacacc ttgaagctt agccaggtcc
12421  gccaaccca cggcccgatt cctgccctc caggaggcc ctgcccatc acctccacca cctggagggg
12481  gaggatcaac ccagcccggc tccggcccc gccaggtgtc ctgccatggg gaagaaggc gccccaagcc
12541  gcgagaaggc aaaatctgaa gccagtgtc ccgcactca ggactactca acccctctct cctcccccag
12601  gggggcctgg tgaaatgagg gcttgcgaag ggactactca
```

FIG. 12-25

```
12661  tcccacccac  tagccttgac  ctctgcccc   gcccctgga   tgggtggagg  agagggaggt
12721  gggggagaa   actgaggcga  aggatgtttg  cctaatggtg  gtgcaatgg   tgtctgtgga
12781  agggaaaac   cgggagacac  aactgcgcc   cctccaggac  ctcagtgcag  gtccccaca
12841  gaaactttt   ttattttat   ttttaagac   agggtctcac  tttgttgccc  agactggagt
12901  gcagtggagt  acaatgatgg  ctcaatgtag  cctcgatcta  ctggccaaa   gcaatccttc
12961  tgctccagcc  tcctaagtgg  ctggactac   aggcttggac  cactgtgccc  tgttagtttt
13021  tttatttta   gtagagatgg  ggccttgcta  tgttacccag  gctggtcttg  aattcctgtc
13081  ctcaagaaat  cctcccgcct  ctgccgccca  gtgtcatgat  taaaggcgtg  agccaccaca
13141  cccaactttc  aactcccaac  ccgctccctg  gcactctctc  aggctctgca  catcccagct
13201  gtctgaatc   actccacac   ctccatgttc  ttcaggaacc  caggtgcttg  acccctctc
13261  cacagacctc  tgcactgtg   ccttcaggg   ccagtcaccc  tctcagctcc  tcaaatttat
13321  tgaatgtgtg  tgtggcgcta  tccctcaatg  catcaacagc  cataagcaca  atggccagct
13381  gctccctat   gccttccccc  gatccatcca  gaatcctagg  catcccatc   ccgatactgg
13441  ccaaatccag  ccaccccgca  gcctgggtgc  ctggcaccat  ctgccagcc   tgccaaattt
13501  caccccatct  tcaagagtag  actgccagac  aaggcctccg  tgctatatcc  cccacccccc
13561  catccccca   cccctccgtc  ttccagaatc  agactccaga  ctctcctcat  ctaacagact
13621  aagggtttgg  ccctacttc   cccttcaagg  gaccagactt  tggactgatt  gggcctcagt
13681  ttcccaacct  ttgctgaaac  agagtgataa  gacaccccgct ttggcccccc  tccactatgg
13741  aacctgcaca  tcaggttcct  tgctccccte  tcaaccaaaa  ctcagacatc  taataccacg
13801  gtaggcccg   ttctccctcc  cccacctccc  tgccccagge  ctccagccct  aggccctggg
13861  tgggaaaac   caggggtgg   ggggtgtgga  gaaaaaatat  ctgacttcag  gttcaaagaa
13921  gcctgggagg  gactgggga   agggggcagg  acaatggcct  tggctggaca  atcccggtcc
13981  ccagaggggg  cagctctaac  cctaaacaag  tgctcaaccc  ttgaatgggc  ctggatggct
14041  cccctggga   ctgcttcctg  ctcccaaacc  cccagtcccc  aatcccctca  cacagaatcc
14101  ccttcagaga  cgctaaaagg  agctccagca  acccccctct  gcaatcccct  caaagactga
14161  gcctcagacg  ggcaccaagg  gccccctaca  gggacctagg  tatctagttc  ctccttcctc
14221  tgggggactc  aggcgtccag  cttcatcgtg  catccctccc  cgagcccgga  agattgaggg
14281  atgtgctttg  tttagtgggg  ctggctggca  gaaagacgca  gaggaggtgg  cgagtgattt
```

FIG. 12-26

```
14341 gtggaggggt gcaggaaggc tgccctaagc tccccttcag ggtctgtttt tctgggcctg
14401 gcctgagtat cctgaggctc atgctgctgg tctagtgctt gattctgttt gcaagagaat
14461 agccaacg SEQ ID NO. 20
//
```

Revised July 5, 2002

Disclaimer | Write to the Help Desk
NCBI | NLM | NIH

FIG. 12-27

```
                    PubMed  Nucleotide  Protein  Genome  Structure   PMC   Taxonomy  OMIM   Boo
          NCBI                               Nucleotide
          Search  Nucleotide ▽ for                                                           Details Limits           Preview/Index      History      Clipboard
          Display  default ▽ Show: 20 ▽ Send to File ▽              Get Subsequence          Links
```

☐ 1: BC033086. Homo sapiens, Sim...[gi:21620013]

```
LOCUS       BC033086                3021 bp    mRNA    linear   PRI 27-JUN-2002
DEFINITION  Homo sapiens, Similar to transcription factor 19 (SC1);
            transcription factor like #, clone MGC:45652 IMAGE:3160434, mRNA,
            complete cds.
ACCESSION   BC033086
VERSION     BC033086.1  GI:21620013
KEYWORDS    MGC
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 3021)
  AUTHORS   Strausberg,R.
  TITLE     Direct Submission
```

FIG. 12-28

JOURNAL    Submitted (25-JUN-2002) National Institutes of Health, Mammalian
           Gene Collection (MGC), Cancer Genomics Office, National Cancer
           Institute, 31 Center Drive, Room 11A03, Bethesda, MD 20892-2590,
           USA REMARK     NIH-MGC Project URL: http://mgc.nci.nih.gov
COMMENT    Contact: MGC help desk
           Email: cgapbs-r@mail.nih.gov
           Tissue Procurement: ATCC
           cDNA Library Preparation: Rubin Laboratory
           cDNA Library Arrayed by: The I.M.A.G.E. Consortium (LLNL)
           DNA Sequencing by: Genome Sequence Centre,
           BC Cancer Agency, Vancouver, BC, Canada
           info@bcgsc.bc.ca
           Steven Jones, Jennifer Asano, Ian Bosdet, Yaron Butterfield,
           Susanna Chan, Readman Chiu, Chris Fjell, Erin Garland, Ran Guin,
           Letticia Hsiao, Martin Krzywinski, Reta Kutsche, Oliver Lee, Soo
           Sen Lee, Victor Ling, Carrie Mathewson, Candice McLeavy, Steven
           Ness, Pawan Pandoh, Anna-Liisa Prabhu, Parvaneh Saeedi, Jacqueline
           Schein, Duane Smailus, Michael Smith, Lorraine Spence, Jeff Stott,
           Michael Thorne, Miranada Tsai, Natasja van den Bosch, Jill Vardy,
           George Yang, Scott Zuyderduyn, Marco Marra.

Clone distribution: MGC clone distribution information can be found
           through the I.M.A.G.E. Consortium/LLNL at: http://image.llnl.gov
           Series: IRAL Plate: 43 Row: a Column: 8
           This clone was selected for full length sequencing because it
           passed the following selection criteria: matched mRNA gi: 6005891.

FIG. 12-29

```
FEATURES         Location/Qualifiers
     source      1..3021
                 /organism="Homo sapiens"
                 /db_xref="taxon:9606"
                 /clone="MGC:45652 IMAGE:3160434"
                 /tissue_type="Brain, neuroblastoma"
                 /clone_lib="NIH_MGC_19"
                 /lab_host="DH10B-R"
                 /note="Vector: pOTB7"
     CDS         422..1459
                 /codon_start=1
                 /product="Similar to transcription factor 19 (SC1);
                 transcription factor like #"
                 /protein_id="AAH33086.1"
                 /db_xref="GI:21620014"
                 /translation="MLPCFQLLRIGGGRGGDLYTFHPPAGAGCTYRLGHRADLCDVAL
                 RPQQEPGLISGIHAELHAEPRGDDWRVSLEDHSSQGTLVNNVRLPRGHRLELSDGDLL
                 TFGPEGPPGTSPSEFYFMFQQVRVKPQDFAAITIPRSRGEARVGAGFRPMLPSQGAPQ
                 RPLSTFSPAPKATLILNSIGSLSKLRPQPLTFSPSWGGPKSLPVPAPPGEVGTTPSAP
                 PQRNRRKKSVHRVLAELDDESEPLENPPPVLMEPRKKLRVDKAPLTPTGNRRGRPRKYP
                 VSAPMAPPAVGGGEPCAAPCCCLPQEETVAWVQCDGCDVWFHVACVGCSIQAAREADF
                 RCPGCRAGIQT" SEQ ID NO. 4
BASE COUNT      795 a      774 c      791 g      661 t
ORIGIN
    1 tcgtctcctg ccgaggagcc caagggtcc cggatccgc cgcacaggct ggcactgctt
   61 gaagaggagg ctactcggag actgcgccgc gcggattgga ggctcccaa atattttgcg
```

FIG. 12-30

```
 121 atctgaggat ccagctcaag tgaggtgcca taggacgtgt tcctgagttt gcattgcacg
 181 gagaccttcc tggaatttt catttgcaag tcggcttaac caatttgca ttgagtccta
 241 ggctgcttgc actctgaatt tgggctattc aggtagtgtg ctcaaagttg aaaccgcata
 301 cagcacaact caagtttgca tcagactggg aagcgaactt aagccagcgg tgcgtggccc
 361 aggagtggga aaggaaatgg atgcctgaag tggaagaggt ggtgcagagg gggcaccgcc
 421 catgctgccc tgcttccaac tgctgcgcat aggggcggc agggcggtg atctctacac
 481 cttccacccc ccgcgcgggg ctgctgcac ctatcgcttg ggccacagg ccgacctgtg
 541 tgatgtgcc ctgcggcccc agcaggagcc tgccctcatc tctgggatcc acgccgaact
 601 gcatgccgag ccccggggtg atgactggag ggtcagcctg gaagaccaca gcagccaagg
 661 tactttggtc aataatgtcc gactcccaag aggtcacagg ctggaattga gtgatggaga
 721 cctcctgacc tttggccctg aagggccccc aggaaccagc cctcgagt tctacttcat
 781 gttccaacaa gtacgagtca agcctcagga ctttgctgcc attaccatcc cacggtctag
 841 gggagaagcc cgggttgggg ctggtttccg gcctatgctg ccctccagg gggctccaca
 901 gcggcctctc agcacccttct cccctgcccc caaggccaca ctgatcctaa actccatagg
 961 cagcctcagc aagctccggc ccccagcccc caccctctcc cctagttggg gtggaccaaa
1021 gagcctgcct gttcccgccc cacctgggga agtggggacc acgccttctg ctccaccca
1081 acgcaatcgg aggaaatctg ttcaccgagt gttggcggaa ctggatgatg agagtgagcc
1141 tcttgagaac ccgccaccgg tcctttatgga gcccaggaag aaactccgtg tagacaaagc
1201 cccactgact cccactggaa atcgacgtgg ccgtcctcgg aagtacccag tgagcgctcc
1261 catgctgctcc cctgcagttg ggggcgggga gccctgtgca gctccttgtt gctgctgcc
1321 ccaggaagag acagtggcct gggttcagtg tgatgctgt gacgtctgt tccatgtggc
1381 ctgtgttggc tgcagcatcc aggctgccag ggaggccgac aaggcaccat ttccgatgcc cagggtgccg
1441 ggctggcatt cagacctaag gtccaccgcc aaggcaccat cggacacacc tgccaccc
1501 tagacacagc agcgagcaaa taggtctgat aaataccccc cttccctcc ctccccagga
1561 gggaatgact acaggaaga aggatggatt gatgtggact cattcaggc ctgagcaga
1621 cctgtgtggc caagacagaa gagatggttt cctgccaaag atattgccac ctccaggaaa
```

FIG. 12-31

```
1681 ttgccagtga gctggaagtt cccactatta caagccataa ggccatgttg ccatggacac
1741 cagaatatct gtagtcagag cacctatcag ttgcaaaagc catgcctgca accgatggaa
1801 aatgtaagag ggagttctta aggttccttga tggcatcacc caaggcattc tggaaaacc
1861 tagggcctgg cccaaaact tccctactct gtggctagtc ctgctgccaa caaatcgta
1921 gcgaccctgg ttttcacagc tttgctttta tttccaagtc aaggacaagc cgcttcattc
1981 actcctgggc atttactctt cttgtgggtc tgtgatattc cttgctttcc agggagaatg
2041 tgcttggcaa ggtctggaga actaattcag tgtgatattc aatcttaggg gaaggggaga gatgaaata
2101 caaacctgct tactggaaag gtgcaaatat atggggttgag ctggaggtag gaatacaggt
2161 aattaaggtt tctgtttttaa gggaaaacag atctattgcc atttaaataa ggtaactggg
2221 atttggttaa gttcacaaag ttagcagaag atctatttac aggcttcacc tgtactgtca
2281 gggcaagaga aagcctggta aaccagctac agcagtttac cagtgtgatg gctgtgacac
2341 agctccactc cacgggtgga cacagcagag ggcaactggg ctggcctggt tcagtgtgaa
2401 tcaaaccgct taaccacac atggtacatg tgatttttctt ttgtgagcct tacaccaagc
2461 caaactattg tcaaagcatc atttctatag aaataaagcc ttatcttgac ctgttctatt
2521 aaaacctgcc acatccgccc tttcctacct agatttaatg agcccaagtt tttttacatg
2581 gaagaaatga ctctgggca aagaccccta atgaactagt ggcagagcca ggaataaaac
2641 ttgagtaact aatgagtcac ttatgggcag agtatgcaaa aacccttaagt ggaaaccaaa
2701 tagaccctgg tatcaagaaa gcacaaagta ttaatagaag tttctggttg gggtgatcta
2761 ggttcaacag aaataagatg atttctaagt ataaagccat tttagaattc cagagtaggg
2821 tgggaaagca aaaagccagc tctgaacagg taacagctac atggtgactg agtctatggg
2881 caaaagttct tgcatcacag gcttttggga actagcctat cacagggccc tgtacaaata
2941 aacttggctg caatcccaaa aaaaaaaaaa aaaaaaaaaa aaaaaaaa
3001 aaaaaaaaaa aaaaaaaaa a SEQ ID NO. 21
```

FIG. 12-32

```
PUBMED      1868030
REFERENCE   2  (bases 1 to 1080)
AUTHORS     Krishnan,B.R., Jamry,I. and Chaplin,D.D.
TITLE       Feature mapping of the HLA class I region: localization of the
            POU5F1 and TCF19 genes
JOURNAL     Genomics 30 (1), 53-58 (1995)
MEDLINE     96129301
PUBMED      8595903
REFERENCE   3  (bases 1 to 1080)
AUTHORS     Krishnan,R.
TITLE       Molecular mapping by transposon-based nested deletion sequencing:
            the SC1 gene maps near the HLA-C locus
JOURNAL     Unpublished
COMMENT     PROVISIONAL REFSEQ: This record has not yet been subject to final
            NCBI review. The reference sequence was derived from U25826.1.
FEATURES         Location/Qualifiers
     source      1..1080
                 /organism="Homo sapiens"
                 /db_xref="taxon:9606"
                 /chromosome="6"
                 /map="6p21.3"
                 /clone="YAC B209D7, Cosmid 52, pDEL5.5"
                 /haplotype="A3 B8 C- DR3 DQw2 DRw52 and A29 Bw65 C- DR7
                 DQw2 DP4"
                 /sex="male"
                 /cell_line="B lymphoblastoid"
                 /tissue_type="blood"
                 /clone_lib="CGM1 library from the Washington University
                 School of Medicine"
```

FIG. 12-34

```
gene            1..1080
                /gene="TCF19"
                /dev_stage="adult"
                /note="synonym: SC1"
                /db_xref="LocusID:6941"
                /db_xref="MIM:600912"
CDS             1..1080
                /gene="TCF19"
                /note="transcription factor like #"
                /codon_start=1
                /product="transcription factor 19 (SC1)"
                /protein_id="NP_009040.1"
                /db_xref="GI:6005892"
                /db_xref="LocusID:6941"
                /db_xref="MIM:600912"
                /translation="MLPCFQLLRIGGGRGGDLYTFHPPAGVGCTYRLGHRADLCDVAL
                RPQQEPGLISGIHAELHAEPRGDDWRVSLEDHSSQGTLVNNVRLPRGHRLELSDGDLL
                TFGPEGPPGTSPSEFYFMFQQVRVKPQDFAAITIPRSRGEARVGAGFRPMLPSQGAPQ
                RPLSTFSPAPKATLILNSIGSLSKLRPQPLTFSPSWGGPKSLPVPAPPGEVGTTPSAP
                PQRNRRKSVHRVLAELDDESEPPENPPPVLMEPRKKLRVDKAPLTPTGNARGRPRKYP
                VSAPMAPPAVGAGSPVQLLVAACPRKRQWPGFSVMAVTSGSMWPVLAAASRLPGRPTS
                DAQGAGLAFSLRSTAKAPSDTPAHE" SEQ ID NO. 5
misc_feature    88..264
                /gene="TCF19"
                /note="FHA; Region: Forkhead associated domain"
                /db_xref="CDD:smart00240"
misc_feature    91..306
                /gene="TCF19"
```

FIG. 12-35

```
          /note="FHA; Region: FHA domain. The FHA
          (Forkhead-associated) domain is a phosphopeptide binding
          motif"
          /db_xref="CDD:pfam00498"
   80
          /gene="TCF19"
          /citation=[1]
          /replace="c"
conflict   80
          /gene="TCF19"
          /note="WARNING: map location ambiguous"
          /allele="T"
          /allele="C"
          /db_xref="dbSNP:1065459"
variation  367..369
          /gene="TCF19"
          /citation=[1]
          /replace="aac"
conflict   577
          /gene="TCF19"
          /citation=[1]
          /replace="a"
conflict   631
          /gene="TCF19"
          /note="WARNING: map location ambiguous"
          /allele="G"
          /allele="A"
variation  /db_xref="dbSNP:2073721"
```

FIG. 12-36

```
variation    657
             /gene="TCF19"
             /note="WARNING: map location ambiguous"
             /allele="C"
             /allele="A"
             /db_xref="dbSNP:2073722"
variation    722
             /gene="TCF19"
             /note="WARNING: map location ambiguous"
             /allele="T"
             /allele="C"
             /db_xref="dbSNP:2073724"
conflict     802..803
             /gene="TCF19"
             /citation=[1]
             /replace="cg"
conflict     869..871
             /gene="TCF19"
             /citation=[1]
             /replace=""
variation    1042
             /gene="TCF19"
             /note="WARNING: map location ambiguous"
             /allele="G"
             /allele="A"
             /db_xref="dbSNP:1065460"
conflict     1045..1046
             /gene="TCF19"
```

FIG. 12-37

/citation=[1]
/replace="cg"

BASE COUNT    200 a    361 c    315 g    204 t
ORIGIN
   1 atgctgccct gcttccaact gctgcgcata ggggcggca gggcggtga tctctacacc
  61 ttccacccc cgcccgggt tggctgcacc tatcgcttgg gccacaggc cgacctgtgt
 121 gatgtggccc tgcggcccca gcaggagcct ggcctcatct ctgggatcca cgccgaactg
 181 catgccgagc cccggggtga tgactggagg gtcagcctgg aagaccacag cagccaaggt
 241 actttggtca ataatgtccg actcccaaga ggtcacaggc tggaattgag tgatggagac
 301 ctcctgacct ttggccctga agggccccca ggaaccagcc cctcggagtt ctacttcatg
 361 ttccaacaag tacgagtcaa gcctcaggac tttgctgcca ttaccatccc acgtgtctagg
 421 ggagaagccc gggttggggc tggtttccgg cctatgctgc cctcccaggg ggctccacag
 481 cggcctctca gcaccttctc ccctgccccc aaggccacac tgatcctaaa ctccataggc
 541 agcctcagca agctccgggc ccagcccctc accttctccc acttctgggg tggaccaaag
 601 agcctgcctg ttcccgcccc acctggggaa gtggggacca cgccttctgc tccacccaa
 661 cgcaatcgga ggaaatctgt tcaccgagtg ttggcggaac tggatgatga gagtgagcct
 721 cctgagaacc cgccaccggt ccttatggag cccaggaaga aactccgtgt agacaaagcc
 781 ccactgactc ccactggaaa tgcacgtggc cgtcctcgga agtaccagt gagcgctccc
 841 atggctcccc ctgcagttgg gcggggagc cctgtgcagc tccttgttgc tgcctgcccc
 901 aggaagagac agtggcctgg gttcagtgtg atggctgtga cgtctggttc catgtggcct
 961 gtgttggctg cagcatccag gctgccaggg agccgactt ccgatgccca gggtgccggg
1021 ctggcattca gcctaaggtc cacccgccaag gcaccatcgg gcacacctgc ccatgagtag

SEQ ID NO. 22

FIG. 12-38

| NCBI | PubMed | Nucleotide | Protein | Genome | Structure | PMC | Taxonomy | OMIM | Boo |

Nucleotide

Search Nucleotide ▽ for [                    ] Go  Clear

Limits    Preview/Index    History    Clipboard                    Details

Display default ▽  Show: 20 ▽  Send to File ▽   Get Subsequence

Links

☐ 1: AB029519. Homo sapiens SC1(...[gi:5420470]

```
LOCUS       AB029519               4651 bp    DNA     linear   PRI 29-APR-2000
DEFINITION  Homo sapiens SC1(TCF19)-7 gene, complete cds.
ACCESSION   AB029519
VERSION     AB029519.1  GI:5420470
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1 (sites)
  AUTHORS   Teraoka,Y., Naruse,T.K., Oka,A., Matsuzawa,Y., Shiina,T.,
            Iizuka,M., Iwashita,K., Ozawa,A. and Inoko,H.
  TITLE     Genetic polymorphisms in the cell growth regulated gene, SC1
            telomeric of the HLA-C gene and lack of association of psoriasis
            vulgaris
  JOURNAL   Tissue Antigens 55 (3), 206-211 (2000)
```

FIG. 12-39

```
MEDLINE     20236853
REFERENCE   2  (bases 1 to 4651)
AUTHORS     Teraoka,Y. and Inoko,H.
TITLE       Direct Submission
JOURNAL     Submitted (02-JUL-1999) Yoshika Teraoka, Tokai University School of
            Medicine, Molecular Life Science; Bohseidai, Isehara, Kanagawa
            259-1193, Japan (E-mail:yoshika@is.icc.u-tokai.ac.jp,
            Tel:81-463-93-1121(ex.2653), Fax:81-463-94-8884)
FEATURES             Location/Qualifiers
     source          1..4651
                     /organism="Homo sapiens"
                     /db_xref="taxon:9606"
     gene            join(378..615,2320..2878,3346..3586)
                     /gene="SC1(TCF19)-7"
     CDS             join(378..615,2320..2878,3346..3586)
                     /gene="SC1(TCF19)-7"
                     /codon_start=1
                     /protein_id="BAA82327.1"
                     /db_xref="GI:5420471"
                     /translation="MLPCFQLLRIGGGRGGDLYTFHPPAGAGCTYRLGHRADLCDVAL
                     RPQQEPGLISGIHAELHAEPRGDDWRVSLEDHSSQGTLVNNVRLPRGHRLELSDGDLL
                     TFGPEGPPGTSPSEFYFMFQQVRVKPQDFAAITIPRSRGEARVGAGFRPMLPSQGAPQ
                     RPLSTFSPAPKATLILNSIGSLSKLRPQPLTFSPSWGGPKSLPVPAPPGEVGTTPSAP
                     PQRNRRKSVHRVLAELDDESEPPENPPPVLMEPRKKLRVDKAPLTPTGNRRGRPRKYP
                     VSAPMAPPAVGGGEPCAAPCCCLPQEETVAWVOCDGCDVWFHVACVGCSIQAAREADF
                     RCPGCRAGIQT" SEQ ID NO. 6
BASE COUNT   1160 a    1163 c    1244 g    1084 t
```

FIG. 12-40

```
ORIGIN
    1 cgccacccc gacacacaca ggagctgcct aagtatcct tgccttgcag attggaggct
   61 cccaaatat tttgtgatct gaggatccag ctcaagtgag gtgccatagg acgtgttcct
  121 gagtttgcat tgcacggaga cctccctga attttcatt tgcaagtcgg cttaaccaat
  181 tttgcattga gtcctaggct gcttgcactc tgaatttggg ctattcaggt agtgtgctca
  241 aagttgaaac cgcatacagc acaactcaag tttgcatcag actgggaagc gaacttaagc
  301 cagcggtgcg tggcccagga gtgggaaagg aaatgatgc ctgaagtgga agaggtgtg
  361 cagaggggc accgcccatg ctgccctgct tccaactgct gcgcataggg ggcggcaggg
  421 gcggtgatct ctacaccttc caccccccg ccgggctgg ctgcacctat cgcttgggcc
  481 acagccgga cctgtgtgat gtggccctgc ggcccagca ggccctggc ctcatctctg
  541 ggatccacgc cgaactgcat gccagcccc gggtgatga ctggagggtc agcctggaag
  601 accacagcag ccaaggtgag cattaagcag ggcagcttg ccctgggtg gttgaagcgc
  661 caggctggaa tgagtaaggt ctccacaaga ggcagcttc cctgctgcc actcccatca
  721 gattggatgg atagtcgtgg tccagacctt tcctttggt ggcagcttgt gcacagtcag
  781 aagctctctg ccagactgac ccttttggt gggatgttc ccgttttagc tcatacagga cctggatat
  841 catcagaaag atatcacagt ccagaacctt gggatgttc agaggccaag tttagacttg
  901 attcagtttc cagcttgct gagcactct gttcctgggt tagggcagtt ctatgttgaa
  961 taatgttttt aataatctgg gcatgtctt ctccgtgact ctccgtgact tgaggcagtt agcctcagaa
 1021 agcctagatt cacatttgag ttttgccact gcctcttggt aaagtcagct gtaggagtgt
 1081 tatgttatt agactatagt agccaacatt catctagtgc ttactgttat gagccaggcc
 1141 ctatttttaag tgtattgaat gtaggtggta ctaatattat cctcatttac agtaaaggaa
 1201 aatgaggcac aaagaggtta aggaacttgt ccagggctgg gcatgtggt ttacacctat
 1261 aatccagcac tttgggaggc taaggcaggg tggatcactt gagctcagga gttcgagacc
 1321 agcctgggca acatggtgaa aacctgtctc taccaaaaaa ccagcactt ttaattaatt tttaaaaaa
 1381 agcctgggcg cggtggctca cgcctgtaat cccagcactt tgggaggccg agatgggcag
 1441 atcacgaggt caggagttcg agaccatcct gaccaacatg ttgaaacccc atctgtgctg
 1501 aaaaaaaat acaaaaatta gccaggtgtg gtgcgtgca cctgtaacc cctgtaacc cagctactca
 1561 ggaggctgaa gcagcagaat cacttgaacc cggagggcgg aggttgcagt gagctgagat
```

FIG. 12-41

```
1621  cgcaccactg cactccagct tgggcgacag agcgagactc catctcaaac aaacaaacaa
1681  accaaaagct tgcccaggt cacataactg gtaagtggta gagctaggat ctgaacgagc
1741  tggagctggg ggagagtgag catgtttgaa aactggacct taggcgggg cacggtggct
1801  cacgcctgta atcccagcac tttgggaggc tgaggcgggc agatcaggag gtcaggagta
1861  tgagaccagc ctggccaaca ctgtccaaacc ctgtctctgc taaaaataaa aaaattagcc
1921  agacgtggtg gcacatgcct gtaatcccag ctactcagga ggctgaggca ggagaattgc
1981  ttgaacctgg gaggcggttc aagcttgggc aatagagcaa aactccatct caaaaaaaaa
2041  aaaagaaag aaaaaaaag aagaaagaaa gaaaattgga ccttaggaca gtgaggcag
2101  ggatccttg taggaaagca caagaaacac agacttgttc ctagctgaca aggagtgtac
2161  tgcctggtac ctgtcacctg ctgagggct taggatgtga gggagaatct gactacagtt
2221  tcatattctt cccagaaat catacagatt tctccactcc tgactctgt catttctgtt
2281  tttgtcctcc atatttgcct ggtgcccac tacttttggtc aataatgtcc
2341  gactccaag aggtcacagg ctggaattga gtgatggaga cctcctgacc tttggccctg
2401  aagggcccc aggaaccagc ccctcggagt tctacttcat gttccaacaa gtacgagtca
2461  agcctcagga ctttgctgcc attaccatcc cacggtctag gggagaagcc cgggttgggg
2521  ctggtttccg gcctatgctg ccctccagg gggcctccaca gcggcctctc agcacctict
2581  cccctgcccc caaggccaca ctgatcctaa actccatagg cagcctcagc aagctccggc
2641  cccagcccct cacccttctcc cctagtggg gtggaccaaa gagcctgcct gttcccgccc
2701  cacctgggga agtgggaccc acgcctctg ctccaccca acgcaatcgg aggaaatctg
2761  ttcaccgagt gttggcagc ctgatgatg agagtgagcc tcctgagaac ccgccaccgg
2821  tccttatgga gcccaggaag aaactccgtg tagacaaagc ccactgact cccactggt
2881  aagtggagtc ctcacttggc cctctcagtg tttactgct tttcgattcc ttgtatccct
2941  aggctgtgag gaggtcccc tgcctggggg gatgggcacg ggaggtggaa tagatggaat
3001  ggcaagacct gggttagctc tgataggaa agaaaaatat gtgcaggaga acatgagagg
3061  tggggtgggg cagtgcttat aaaacaaccg gagtgagcat gtcctgcttt ttacattcat
3121  atggctttaa ccccattctt ctagtgccta aggatgggga actttcaggc tcacactaga
3181  ggttttttagg cccaccctat gtgttttttaa ggacagagtc caggctcacc ttagttctca
3241  gaccactgtg cctctgtggc ctcacccat gaccagccat agggtggcaa ggtctaggcc
```

FIG. 12-42

```
3301  ttctcctaca ggtttccggt gacccttgtg tctgtgtcac ttcagaaatc gacgtgccg
3361  tcctcggaag tacccagtga gcgctcccat ggctccccct gcagttgggg gcggggagcc
3421  ctgtgcagct ccttgttgct gcctgcccca ggaagagaca gtggcctggg ttcagtgtga
3481  tggctgtgac gtctgghtcc atgtggcctg tgttggctgc agcatccagg ctgccaggga
3541  ggccgacttc cgatgccagg ggtgccggge tggcattcag acctaaggtc caccgccaag
3601  gcaccatcgg acacacctgc ccatgagtag acacagcagc gagcaaatag gtctgataaa
3661  tacccccctt cccttccctc cccaagaggg aatgactaca gggaagaagg atggattgat
3721  gtggactcat tcagggcctg gagcagaccc tggtggccaa gacagagag atggtttcct
3781  gccaaagata ttgccacctc caggaaattg ccagtgagct ggaagttccc actattacaa
3841  gccataaggc catgttgcca tggacaccag aatatctgta gtcagagcac ctatcagttg
3901  caaaagccat gcctgcaacc gatgaaaat gtaagaggga gttcttaagg ttcttggtgg
3961  catcacccaa ggcattctgg gaaaacctag ggcctgcccc caaaacttcc ctactctgtg
4021  gctagtcctg ctgccaacaa aatcgtagcg acctggcttt tcacagcttt gcttttattt
4081  ccaagtcaag gacaagccgc ttcattcact cctgggcatt tactctcttt gtgggtctgt
4141  gatattcctt gctttccagg gagaatgtgc ttgcaaggt ctggagaact aattcagaat
4201  cttaggggaa ggggagagat ggaaatacaa acctgcttac tggaaaggtg caaatatatg
4261  ggttgagctg gaggtaggaa tacaggtaat taaggttct agtttaaggg aaaacagatc
4321  tattgccatt taaataaggt aactgggatt tggttaagtt cacaaagata gcagaagatt
4381  tatttacagg cttcacctgt actgtcaggg caagagaaag cctggtaaac cagctacagc
4441  agtttaccag tgtgatggct gtgacacagc tccactccac gggtggacac agcagagggc
4501  aactgggctg gcctggttca gtgtgaatca accgcttaa cccacacatg gtacatgtga
4561  ttttctttg tgagccttac tgagccttac actattgtca aagcatcatt tctatagaaa
4621  taaagcctta tcttgacctg ttctattaaa a          SEQ ID NO. 23
```

FIG. 12-43

```
NCBI                                                              Nucleotide
   PubMed  Nucleotide  Protein  Genome  Structure  PMC  Taxonomy  OMIM      Boo
   Search  Nucleotide ▽  for                                 Go  Clear     Details
        Limits          Preview/Index    History        Clipboard
   Display default ▽ Show: 20 ▽          Send to File ▽  Get Subsequence    Links
```

☐ 1: U25826. Human transcripti...[gi:833832]

```
LOCUS       HSU25826                5522 bp    DNA     linear   PRI 27-MAY-1995
DEFINITION  Human transcription factor (SC1) gene, complete cds.
ACCESSION   U25826
VERSION     U25826.1  GI:833832
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 5522)
  AUTHORS   Krishnan,R.
  TITLE     Molecular mapping by transposon-based nested deletion sequencing:
            the SC1 gene maps near the HLA-C locus
  JOURNAL   Unpublished
REFERENCE   2  (sites)
```

FIG. 12-44

```
AUTHORS    Ku,D.H., Chang,C.D., Koniecki,J., Cannizzaro,L.A.,
           Boghosian-Sell,L., Alder,H. and Baserga,R.
TITLE      A new growth-regulated complementary DNA with the sequence of a
           putative trans-activating factor
JOURNAL    Cell Growth Differ. 2 (4), 179-186 (1991)
MEDLINE    91329275
PUBMED     1868030
REFERENCE  3 (bases 1 to 5522)
AUTHORS    Krishnan,R.
TITLE      Direct Submission
JOURNAL    Submitted (27-APR-1995) Rajendra Krishnan, Dept. of Internal
           Medicine, Washington University School of Medicine, Div. Allergy &
           Immun., 660 South Euclid Avenue, St. Louis, MO 63110, USA
FEATURES             Location/Qualifiers
     source          1..5522
                     /organism="Homo sapiens"
                     /db_xref="taxon:9606"
                     /chromosome="6"
                     /map="6p23.1"
                     /clone="YAC B209D7, Cosmid 52, pDEL5.5"
                     /haplotype="A3 B8 C- DR3 DQw2 DRw52 and A29 Bw65 C- DR7
                     DQw2 DP4"
                     /sex="male"
                     /cell_line="B lymphoblastoid"
                     /tissue_type="blood"
                     /clone_lib="CGM1 library from the Washington University
                     School of Medicine"
                     /dev_stage="adult"
```

FIG. 12-45

```
gene            join(933..1170,2905..3463,3929..4211)
                /gene="SC1"
CDS             join(933..1170,2905..3463,3929..4211)
                /gene="SC1"
                /codon_start=1
                /product="transcription factor SC1"
                /protein_id="AAB60363.1"
                /db_xref="GI:833833"
                /translation="MLPCFQLLRIGGGRGGDLYTFHPPAGVGCTYRLGHRADLCDVAL
                RPQQEPGLISGIHAELHAEPRGDDWRVSLEDHSSQGTLVNNVRLPRGHRLELSDGDLL
                TFGPEGPPGTSPSEFYFMFQQVRVKPQDFAAITIPRSRGEARVGAGFRPMLPSQGAPQ
                RPLSTFSPAPKATLILNSIGSLSKLRPQPLTFSPSWGGPKSLPVPAPPGEVGTTPSAP
                PQRNRRKSVHRVLAELDDESEPPENPPPVLMEPRKKLRVDKAPLTPTGNARGRPRKYP
                VSAPMAPPAVGAGSPVQLLVAACPRKRQWPGFSVMAVTSGSMWPVLAAASRLPGRPTS
                DAQGAGLAFSLRSTAKAPSDTPAHE"       SEQ ID NO. 7
exon            <933..1170
                /gene="SC1"
conflict        1012
                /gene="SC1"
                /citation=[2]
                /replace="c"
intron          1171..2904
                /gene="SC1"
repeat_region   1937..2238
                /rpt_family="Alu"
exon            2906..3463
                /gene="SC1"
```

FIG. 12-46

```
conflict        3033..3035
                /gene="SC1"
                /citation=[2]
                /replace="aac"
                3243
conflict        /gene="SC1"
                /citation=[2]
                /replace="a"
                3464..3928
intron          3929..>4211
exon            /gene="SC1"
                3933..3934
conflict        /gene="SC1"
                /citation=[2]
                /replace="cg"
                4000..4002
conflict        /gene="SC1"
                /citation=[2]
                /replace=""
                4176..4177
conflict        /gene="SC1"
                /citation=[2]
                /replace="cg"

BASE COUNT     1376 a    1368 c    1497 g    1281 t
ORIGIN
    1 gaattccgaa ggaggggtag gcgctgcccg cgcgcagagg ccgcgcccct cctgcccccg
   61 gcttcttggc tgtcaaacag tagcagcaac gtcggctcct gccgaggagc ccaagggtc
```

FIG. 12-47

```
121  ccgggatccg ccgcacaggc tgcactgct tgaagaggag gctactcgga gactgcgccg
181  cgcgggtaga tccgaaacgg ggctggggcg gagtgggaaa aggccgggta tgccttgcat
241  gatcgcgggg agctccttcc tgtttttatc ccacctagag aagccgggaa gtagggtttt
301  aggtccaatt tgttggagta cttaaggact cgtttgcact ttctttttggg ggatgacagt
361  ggattcattg ccctcggagg ttcaaccagt tatgagtgag ggattggcca gaagatcggg
421  gcgcaggcaa gcacagagtgc tctattagga taagcaagtt tgacaggaag aagctgctct
481  tctccgaatt acacagaggt gatgtgttcg tattgcacgt agacgtgtgt ataacaggac
541  ctccttcccc gcgccccgcc accccgacac acacaggagc tgcctaaagt atccttgcct
601  tgaagattgg aggctcccca aatatttggt gatctgagga tccagctcaa gtgaggtgcc
661  ataggacgtg ttcctgagtt tgcattgcac ggagaccttc ctggaatttt tcatttgcaa
721  gtcggcttaa ccaatttggc attgagtcct aggctgcttg cactctgaat ttggctatt
781  caggtagtgt gctcaaagtt gagaccgcat acagaacaac tcaagtttgc atcagactgg
841  gaagcgaact taagccagcg gtgcgtggcc caggagtggg aaaggaaatg gatgcctgaa
901  gtggaagagg tggtgcagag gggcaccgc ccatgctgcc ctgcttccaa ctgctgcgca
961  tagggggcgg caggggcggt gatctctaca cctccaccc cccgccggg gttggctgca
1021 cctatcgctt gggccacagg gccgacctgt gtgatgtgcc cctgcgggcc cagcaggagc
1081 ctgccctcat ctctgggatc cacgccgaac tgcatgccga gccccgggt gatgactgga
1141 gggtcagcct ggaagaccac agcagccaag gtgagcatta agcaggcag ctttgcccct
1201 gggtgtttga agcgccagcc tggaatgagt aaggtctcca caagacctg ctgtctgcct
1261 cccatactcc catcagattg gatggatagt cgtggtccag accttcatct tccaccaga
1321 agtgtgcaca gtcagaagct ctctgccaga ctgacccttt ttgtccccgt ttagctcata
1381 caggacctgg gatatcatca gaaagatatc acagtgggga tgtttctgagg ccactagagg
1441 ccaagtttag acttgattca gtttccagct ttgctgaggc actctgttcc tgggttaggg
1501 cagttctatg ttgaataatg ttttttaataa tctgggcatg tcttttctccg tgacttgagg
1561 cagttagcct cagaaagcct agattcacat ttgagtttgg ccactgcctc ttggtaaagt
1621 cagctgtagg agtgttatgg ttattagact atagtagcca acattcatct agtgcttact
1681 gttatgagcc aggccctatt ttaagtgtat tgaatgtagg tggtactaat attatcctca
1741 tttacagaaa aggaaaatga ggcacaaaga aggttaaggaa cttgtccagg gctggcatg
```

FIG. 12-48

```
1801  gtggtttaca cctataatcc agcactttgg gaggctaagg caggtgat caggtgagct cacttgagct
1861  caggagttcg agaccagcct gggcaacatg gtgaaaacct gtctctacca aaaaattaat
1921  tagttttttta aaaaaagcct gggcgcggtg ggtcacgcct gtaatcccag cactttggga
1981  ggccgagatg ggcagatcac gaggtcagga gttcgagacc atcctgacca acatgttgaa
2041  acccatctg tgctgaaaaa aaaaaaccca aattaaccag gtgtggtggc gtgcacctgt
2101  aacccagct actcaggagg ctgaagcagc agaatcactt gaacccggga ggcggaggtt
2161  ggagtgagct gagatcgcac cactgcactc cagcttggc gacagagcga gactccatct
2221  caaacaaaca aacaaaccaa aagcttgccc agggtcacat aactggtaag tggtagagct
2281  agtactgaa cgagctggag ctgggggaga gtgagcatgt ttgaaaactg gacttaggg
2341  cggggcacgg tccgtcacgc ctgtaatccc agcactttgg gaggctgagg cgggcagatc
2401  aggaggtcag gagtatgaga ccagcctggc caacatggta aaaccctgtc tctcgtaaaa
2461  ataaaaaaat tagccagaca tgctggcaca tgcctgtaat cccagctact caggaggctg
2521  aggcaggaga attgcttgaa cctgggaggc ggagtgcagt gagctgagat tgcactactg
2581  cactccagct tgggcaatag agcaaatctc catctcaaaa aaaaaaaaaa gaaagaaaaa
2641  aaaagaagaa agaaaagaatt ttgccctta ggacagtgag ggcagggttc ctttgtggga
2701  aagcacaaga aacacagatt tgttcctagc tgacaaggag tgtactgcct ggtacctgtc
2761  acctgctgag gggcttagga tgtgaggag aatctgacca cagtttcata ttcttcccca
2821  gaaatcatac agattctctc actcctgact ctggtcaatt ctgtttttgt cctccatatt
2881  tgcctggtgc cccaccatca acaggtactt tgtcaataa tgtccgactc ccaagaggtc
2941  acaggctgga attgagtgat ggagacctcc tgacctttgg ccctgaaggg cccccaggaa
3001  ccagcccctc ggagttctac ttcatgttcc aacaagtacg agtcaagcct caggactttg
3061  ctgccattac catcccacgg tctagggag aagcccgggt tgggctggt ttccggccta
3121  tgctgccctc ccaggggct ccacagcggc ctctcagcac cttctcccct gccccaagg
3181  ccacactgat cctaaactcc ataggcagcc tcagcaagct ccgcccac cccctccacct
3241  tctccctag ttggggtgga ccaaagagcc tgcctgttcc cgccccacct ggggaagtgg
3301  ggaccacgcc ttctgctcca cccccaacgca atcggaggaa atctgttcac cgagtgttgg
3361  cggaactgga tgatgagagt gagcctcctg agaacccgcc agaacccgcc acccggtccttt atggagccca
3421  ggaagaaact ccgtgtagac aaagcccccac tgactcccac tgggtaagtg gagtcctcac
```

FIG. 12-49

```
3481 ttgccctct cagtgtttta ctgcttttcg attccttgta tccctaggct gtgaggaggt
3541 cccctgcct gggggatgg gcacgggagg tgaatgcaa ggaatgcaa gacctggtt
3601 agctctgata gggaaagaaa aatatgtgca ggagaacatg agaggtgggg tgggcagtg
3661 ctataaaaca accggagtga gcatgtcctg ctttttacat tcatatggct ttaacccac
3721 tttctagtgc ctaaggatgg ggaactttca ggctcacact agaggttttt aggccacct
3781 catgtgtttt taaggacaga gtccagctc acctagttc tcagaccact gtgcctctgt
3841 ggcctcaccc tatgaccagc cataggtgg caaggtctag gccttctcag atttccggtg
3901 accctgtgt ctctctcact tccttcagaa atgcacgtgg cgtcctcgg aagtaccag
3961 tgagcgctcc catgctccc cctgcagttg gggcggggag cctgtgcag ctccttgttg
4021 ctgcctgccc caggaagaga cagtggcctg ggttcagtgt gatggctgtg acgtctgtt
4081 ccatgtggcc tgtgttggct gcagcatcca ggctgccagg gaggccgact tcgatgcc
4141 agggtgccgg gctgcattc agcctaaggt ccaccgccaa ggcaccatcg gacacacctg
4201 cccatgagta gacacagcag cgagcaaata ggtctgataa atacccccct tcccttcct
4261 cccaagagg gaatgactac agggaagaag gatggattga tgtggactca ttcaggcct
4321 ggagcagacc ctggtggcca ctgcctccc agacagaaga gatggttcc ttccaaagat attgccacct
4381 ccagaaatt gccagtgagc tggaagttcc cactattaca agccataagg ccatgtcgcc
4441 atggacacca gaatatctgt agtcagagca cctatcagtt gcaaaagcca tgcctgcaac
4501 cgatggaaaa tgtaagaggg agttcttaag gttcttggtg gaatcaccca aggtattctg
4561 ggaaaaccta gggcctgcc ccaaaacttc cctactctgt ggctagtcct gctgccaaca
4621 aaatcgtagc gacctggctt ttcacagctt tgcttttatt tccaagtcaa ggacaagccg
4681 cttcattcac tcctgggcat ttactctttct tgtgggtctg tgatattcct tgctttccag
4741 ggagaatgtg cttgcaagg tctggagaac taattcagaa tcttagggga aggggagaga
4801 tggaaataca aacctgctta ctggaaaggt ctgaaatatg gttgagctg gaggtaggaa
4861 tacagtaat taaggttct agtttaaggg aaaacagatc tatttgccat ttaaatatgg
4921 taactgggat ttggttaagt tcaccagat agcagaagat ttatttacag gcttcacctg
4981 tactgtcagg gacaagagaa aagcctggta accagcaga gggcacctgg gctgcctgg
5041 ggctctcaca cagctccacc ccccgggtgg acacagcaga gggcacctgg gctgcctgg
5101 ttcagtgtga atcaaaccgc ttaacccaca catggtacat gtgattttct tttgtgagcc
```

FIG. 12-50

```
5161 ttacaccaag ccaaactatt gtcaaagcat catttctata gaaataaagc cttatcttga
5221 cctgttctat taaaacctgc cacatccgcc ctttcctacc tagatttaat gagcccaagt
5281 tttttacat ggaagaaatg actctggggc aaagaccct aatgaactag tggcagagcc
5341 aggaataaaa cttgagtaac taatgagtca cttatgggca gagtatgcaa aaaccttaag
5401 tggaaaccaa atagaccctg gtatcaagaa agcacaaagt attaatagaa gtttctggtt
5461 ggggtgatct aggttcaaca gaaataagat gatttctaag tataaagctc aaaattgaat
5521 tc  SEQ ID NO. 24
```

FIG. 12-51

Disclaimer | Write to the Help Desk
NCBI | NLM | NIH

Revised July 5, 2002

≋ NCBI                                    Nucleotide

PubMed    Nucleotide    Protein    Genome    Structure    PMC    Taxonomy    OMIM    Boo Search  Nucleotide ▽ for [                                    ]

Limits                Preview/Index        History        Clipboard        Details Display default ▽ Show: 20 ▽ Send to File ▽                    Get Subsequence ☐ 1: NM_010097. Mus musculus SPAR...[gi:6753707]                                    Links LOCUS         Sparcl1                  2713 bp    mRNA         linear   ROD 19-SEP-2002
DEFINITION    Mus musculus SPARC-like 1 (mast9, hevin) (Sparcl1), mRNA.
ACCESSION     NM_010097
VERSION       NM_010097.1  GI:6753707
KEYWORDS      .
SOURCE        Mus musculus (house mouse)
  ORGANISM    Mus musculus
              Eukaryota; Metazoa; Chordata; Craniata; Vertebrata; Euteleostomi;
              Mammalia; Eutheria; Rodentia; Sciurognathi; Muridae; Murinae; Mus.
REFERENCE     1  (bases 1 to 2713)
  AUTHORS     McKinnon,P.J., Kapsetaki,M. and Margolskee,R.F.
  TITLE       The exon structure of the mouse Sc1 gene is very similar to the
              mouse Sparc gene
  JOURNAL     Genome Res. 6 (11), 1077-1083 (1996)
  MEDLINE     97092869
   PUBMED     8938431

FIG. 12-52

```
REFERENCE   2  (bases 1 to 2713)
AUTHORS     Soderling,J.A., Reed,M.J., Corsa,A. and Sage,E.H.
TITLE       Cloning and expression of murine SC1, a gene product homologous to
            SPARC
JOURNAL     J. Histochem. Cytochem. 45 (6), 823-835 (1997)
MEDLINE     97343039
 PUBMED     9199668
COMMENT     PROVISIONAL REFSEQ: This record has not yet been subject to final
            NCBI review. The reference sequence was derived from U66166.1.
FEATURES             Location/Qualifiers
     source          1..2713
                     /organism="Mus musculus"
                     /db_xref="taxon:10090"
                     /chromosome="5"
                     /map="5 55.0 cM"
     gene            1..2713
                     /gene="Sparcl1"
                     /note="synonyms: Sc1, hevin, mast9"
                     /db_xref="LocusID:13602"
                     /db_xref="MGD:108110"
     CDS             322..2274
                     /gene="Sparcl1"
                     /note="similar to to Mus musculus Sparc and human hevin;
                     secreted glycoprotein; extracellular matrix protein 2"
                     /codon_start=1
                     /product="SPARC-like 1 (mast9, hevin)"
                     /protein_id="NP_034227.1"
                     /db_xref="GI:6753708"
```

FIG. 12-53

```
/db_xref="LocusID:13602"
/db_xref="MGD:108110"
/translation="MKAVLLLCALGTAVAIPTSTRFLSDHSNPTTATLVTPEDATVP
IAGVEATADIENHPNDKAEKPSALNSEEETHEQSTEQDKTYSFEVDLKDEEDGDGDLS
VDPTEGTLTLDLQEGTSEPQQKSLPENGDFPATVSTSYVDPNQRANITKGKESQEQPV
SDSHQQPNESSKQTQDLKAEESQTQDPDIPNEEEEEEEEPEDIGAPSDNQ
EEGKEPLEEQPTSKWEGNREQSDDTLEESSQPTQISKTEKHQSEQGNQGQESDSEAEG
EDKASGSKEHIPHTEQQDQEGKAGLEAIGNQKDTDEKAVSTEPTDAAVVPRSHGGAGD
NGGGDDSKHGAGDDYFIPSQEFLEAERMHSLSYILKYGGGETTGESENQREAADNQ
EAKKAESSPNAEPSDEGNSREHSAGSCTNFQCKRGHICKTDPQGKPHCVCQDPETCPP
AKILDQACGTDNQTYASSCHLFATKCRLEGTKKGHQLQLDYFGACKSIPACTDFEVAQ
FPLRMRDWLKNILMQLYEPNPKHGGYLNEKQRSKVKKIYLDEKRLLAGDHPIELLIRD
FKKNYIHMYVYPVHWQFNELDQHPADRILTHSELAPLRASLVPMEHCITRFFEECDPNK
DKHITLKEWGHCFGIKEEDIDENLLF" SEQ ID NO. 8 misc_feature    1573..1644
                /gene="Sparcl1"
                /note="FOLN; Region: Follistatin-N-terminal domain-like"
                /db_xref="CDD:smart00274"

misc_feature    1645..1806
                /gene="Sparcl1"
                /note="kazal; Region: Kazal-type serine protease inhibitor
                domain. Usually indicative of serine protease inhibitors.
                However, kazal-like domains are also seen in the
                extracellular part of agrins, which are not known to be
                protease inhibitors. Kazal domains often occur in tandem
                arrays. Small alpha+beta fold containing three
                disulphides. Alignment also includes a single domain from
                transporters in the OATP/PGT family"
```

FIG. 12-54

```
misc_feature      /db_xref="CDD:pfam00050"
                  1654..1806
                  /gene="Sparcl1"
                  /note="KAZAL; Region: Kazal type serine protease
                  inhibitors"
                  /db_xref="CDD:smart00280"

BASE COUNT    862 a    642 c    661 g    548 t
ORIGIN
    1 cagcacggag ggagcgagat ccaggaatct gcaacagaaa ccatgacagc ctgaaacacc
   61 ctgtggtgcc aacctccaaa ttctcatctg tcacttcaga ccctgactgg ctgacagagc
  121 agcagaattt caactccaat aaacgtgaat gtgcttctag gcaaagcagc caagctgacg
  181 agggaggggg gtggaagagc tagctcctct tgggcatttg tcaaactttt acctcctggc
  241 tgtgtgcaag gagggactc aacttcggct tcaagctacc aaggctctgg atccagccac
  301 ctctccgcag atctagccag catgaaggct gtgcttctcc tcctgtgcgc cttgggaacc
  361 gctgtgcaa tcccgacaag tacaaggttt ctctctgacc actccaaccc aactactgca
  421 acactggtga caccggaaga cgctacagtc cccattgccg gggttgaagc tacagcagac
  481 atagaaaacc atcccaatga caaggctgaa aaaccttcag cacttaattc agaagaggaa
  541 actcatgaac agtcaacaga gcaggacaaa acctacagct tcgaggtgga cctgaaggat
  601 gaggaggatg gagatgggga tttaagtgta gatccaacgg aggaacact aacactggat
  661 ctacaagaag gtacaagtga gcctcaacag aaaagtctcc cggagaacgg cgatttcccc
  721 gcgaccgtgt ccacttccta tgtggatcct aaccaacgcg caaacatcac aaaggaaag
  781 gagagtcagg agcaacctgt aagtgactca caccagcaac cgaatgaaag cagcaagcaa
  841 acccaagact taaagctga agaaagccag acacaagatc cagacattcc caatgaagaa
  901 gaggaagaag aagagaaga agagaggaa gaagaggaag cctctggagg agccggaaga
  961 cccagtgata accaagagga gggaaaagaa tgatgacacc ttagaagagt agcagcctac
 1021 gaaggaaaca gagagcaatc tgatgacacc ggaaaccaag ccagtcagcc cactcagata
 1081 agcaagacag agaagcatca atctgagcaa aggaacacag gcaggagag tgactctgag
 1141 gcagaaggag aggacaaggc ttcaggcagc aaggaacaca ttccacatac agagcagcag
```

FIG. 12-55

```
1201 gaccaagaag ggaaagctgg ccttgaagct attggcaacc agaaggacac tgatgagaag
1261 gccgtttcca cagaacctac cgatgctgcc gtggtgccta ggagtcacgg aggagctggt
1321 gataacgggg gcggggatga ctctaagcat ggtgcaggcg atgactactt catccccagc
1381 caggaattcc tagaggccga aaggatgcat tccctctcct attacctcaa atatggcggc
1441 ggcgaggaga caacgactgg cgagagtgag cgagagaggg aacccaaga aggctgcaga caaccaagag
1501 gccaagaaag ctgagagctc accaaatgct gaacctttcag atgagggcaa ctcaaggag
1561 cacagtgctg gtccttgcac gaacttccaa tgtaaaaggg gacacatttg caaaaccgat
1621 ccacaaggga aacctcactg tgtttgccaa gatccagaga cttgtccccc tgcaaaaatc
1681 ctagatcagg cttgtggcac tgacaaccaa acctacgcca gctcctgtca cctgtttgct
1741 accaagtgca ggctggaggg gaccaaaaag ggacaccaac tgcagctgga ttacttcgga
1801 gcttgcaaat ctattcctgc ttgtacggac tttgaagtgg ctcagtttcc cctgcggatg
1861 agagactggc tcaaaaacat cctcatgcag ctttatgaac caaatcccaa acatggcggc
1921 tatctcaatg aaaagcaaag agcaaagtc aaaaaaattt acctggatga gaagagactc
1981 ttggctggag accatcccat tgaactctc ttgagggact ttaagaaaaa ctaccacatg
2041 tatgtgtatc ctgtcactg gcagtttaat gaactggacc agcatcctgc agacaggatc
2101 ttgacacact ctgaacttgc tcctctgcga tcctcccgg gcttccctgg tgccatgga acactgcata
2161 actcgcttct ttgaggagtg tgacccccaac aaggataagc acatcaccttt gaaggaatgg
2221 ggccactgct ttggaattaa agaggaggat atagatgaaa acctcctctt ttgaattaag
2281 atttgagaga atcggaactt tccatccacc tcacctgctt taaccgcttc agaaatacga
2341 gcagccatga cactatacat tcatatgtag caaaacattt gtttggcatg tgagagaaga
2401 caatggtagt aattacttct tggtgatata tatatgagcc aggcacttaa tattaactta
2461 ggaaatgaaa ctttaaaatt aagtagagtc aatgtctata aaagactgtc ctgtctgggg
2521 acagttagcc accatggcaa tgtcactctg tgcatctgcg tttataattg ataattataa
2581 actattaaaa aaacaatgtt catattgtcc ataatacctt atgcatgctg aggaagtgag
2641 atactgctct tttgagataa atatgcctcc ttttcagtgt cttgatgtcc taataaaaaa
2701 tctataaaac ccc    SEQ ID NO. 25
```

FIG. 12-56

```
NCBI          Nucleotide

PubMed   Nucleotide   Protein   Genome   Structure   PMC   Taxonomy   OMIM

Search [Nucleotide ▽] for [                              ]  [Go] [Clear]                    Boo Limits    Preview/Index    History    Clipboard                                     Details Display [default ▽] Show: [20 ▽] Send to [File ▽]   [Get Subsequence]                        Links
```

☐ 1: U64827. Mus musculus extr...[gi:1546922]

```
LOCUS         MMU64827                2734 bp    mRNA    linear   ROD 30-NOV-2000
DEFINITION    Mus musculus extracellular matrix associated protein (Sc1) mRNA,
              complete cds.
ACCESSION     U64827
VERSION       U64827.1  GI:1546922
KEYWORDS      .
SOURCE        Mus musculus (house mouse)
  ORGANISM    Mus musculus
              Eukaryota; Metazoa; Chordata; Craniata; Vertebrata; Euteleostomi;
              Mammalia; Eutheria; Rodentia; Sciurognathi; Muridae; Murinae; Mus.
REFERENCE     1  (bases 1 to 2734)
  AUTHORS     McKinnon,P.J., Kapsetaki,M. and Margolskee,R.F.
  TITLE       The exon structure of the mouse Sc1 gene is very similar to the
              mouse Sparc gene
  JOURNAL     Genome Res. 6 (11), 1077-1083 (1996)
  MEDLINE     97092869
```

FIG. 12-57

```
PUBMED       8938431
REFERENCE    2  (bases 1 to 2734)
AUTHORS      McKinnon,P.J.
TITLE        Direct Submission
JOURNAL      Submitted (22-JUL-1996) Genetics, St. Jude Children's Research
             Hospital, 332 North Lauderdale, Memphis, TN 38101, USA
FEATURES             Location/Qualifiers
     source          1..2734
                     /organism="Mus musculus"
                     /db_xref="taxon:10090"
                     /chromosome="5"
                     /map="5E4"
     gene            1..2734
                     /gene="Scl"
     CDS             322..2274
                     /gene="Scl"
                     /note="similar to to Mus musculus Sparc and human hevin;
                     secreted glycoprotein"
                     /codon_start=1
                     /product="extracellular matrix associated protein"
                     /protein_id="AAB08451.1"
                     /db_xref="GI:1546923"
                     /translation="MKAVLLLCALGTAVAIPTSTRFLSDHSNPTTATLVTPEDATVP
                     IAGVEATADIENHHPNDKAEKPSALNSEEETHEQSTEQDKTYSFEVDLKDEEDGDGDLS
                     VDPTEGTLTLDLQEGTSEPQQKSLPENGDFPATVSTSYVDPNQRANITKGKESQEQPV
                     SDSHQQPNESSKQTQDLKAEESQTQDPDIPNEEEEEEEEEEEPEDIGAPSDNQ
                     EEGKEPLEEQPTSKWEGNREQSDDTLEESSQPTQISKTEKHQSEQGNQGQESDSEAEG
                     EDKASGSKEHIPHTEQQDQEGKAGLEAIGNQKDTDEKAVSTEPTDAAVVPRSHGGAGD
```

FIG. 12-58

"NGGGDDSKHGAGDDYFIPSQEFLEAERMHSLSYYLKYGGGETTTGESENQREAADNQ
EAKKAESSPNAEPSDEGNSREHSAGSCTNFQCKRGHICKTDPQGKPHCVCQDPETCPP
AKILDQACGTDNQTYASSCHLFATKCRLEGTKKGHQLQLDYFGACKSIPACTDFEVAQ
FPLRMRDWLKNILMQLYEPNPKHGGYLNEKQRSKVKKIYLDEKRLLAGDHPIELLLRD
FKKNYHMYVYPVHWQFNELDQHPADRILTHSELAPLRASLVPMEHCITRFFEECDPNK
DKHITLKEWGHCFGIKEEDIDENLLF" SEQ ID NO. 9

BASE COUNT      882 a      641 c      663 g      548 t
ORIGIN
    1 cagcacggag ggagcgagat ccaggaatct gcaacagaaa ccatgacagc ctgaaacacc
   61 ctgtgtgcc aacctccaaa ttctcatctg tcacttcaga ccctgactgg ctgacagagc
  121 agcagaattt caactcccaat aacgtgaat gtgcttctag gcaaagcagc caagctgacg
  181 agggaggggg gtggaagagc aacttcggct tgggcatttg tcaaactttt acctcctggc
  241 tgtgtgcaag gagggactc atctagccag catgaaggct tcaagctacc aaggctctgg atccagccac
  301 ctctccgcca atctagccag tacaaggttt ctctctgacc actccaaccc cttgggaacc
  361 gctgtggcaa tcccgacaga cgctacagtc cccattgccg gggttgaagc tacagcagac
  421 acactggtga caccggaaga caaggctgaa aaacctttcag cacttaattc agaagagaaa
  481 atagaaaaacc atcccaatga gcaggacaga tttaagtgta acctacagct tcgaggtgga cctgaaggat
  541 actcatgaac agtcaacaga gagatgggga gcaggacaaa acctacagct tcgaggtgga cctgaaggat
  601 gaggaggatg gagatgggga tttaagtgta gatccaaacgg aaggaacact aacactggat
  661 ctacaagaag gtacaagtga gcctcaacag aaaagtctcc cggaaaaacgg ggatttcccc
  721 gcgaccgtgt ccacttccta tgtggatcct aaccaaagcg caaacatcac aaaggaaag
  781 gagagtcagg agcaacctgt aagtgactca agaagaggaa caccagcaag cgaatgaaag cagcaagcaa
  841 acccaagact taaaggctga agaagagga acacaagatc cagacattcc caatgaagaa
  901 gaggagaag aagagaggaa gggaaaagaa gaagaggaag cctctggagg agcagcctac cattggtgcc
  961 cccagtgata accaagagaa gggaaaagaa tgatgacacc ttagaagagt ccagtcagcc cagcaagtgg
 1021 gaaggaaaaca gagagcaatc tgatgacacc atctgagcaa ggaaaaccaag cactcagata
 1081 agcagagaca agaagcatca atctgagcaa ggaaaccaag ggcaggagag tgactctgag
 1141 gcagaaggag aggacaaggc ttcaggcagc aaggaacaca ttccacatac agagcagcag

FIG. 12-59"

```
1201 gaccaagaag ggaaagctgg ccttgaagct attggcaacc agaaggacac tgatgagaag
1261 gccgtttcca cagaacctac cgatgctgcc gtggtgccta ggagtcacgg aggagctggt
1321 gataacgggg gcgggatga ctctaagcat ggtgcaggcg atgactactt catcccagc
1381 caggaattcc tagaggccga aggatgcat tccctctcct attacctcaa atatggcggg
1441 ggcgaggaga caacgactgg cgagagtgag aaccagaggg aggctgcaga caaccaagag
1501 gccaagaaag ctgagagctc accaaatgct gaaccttcag atgagggcaa ctcaaggag
1561 cacagtgctg gttcttgcac gaacttccaa tgtaaaaggg gacacatttg caaaaccgat
1621 ccacaaggga aacctcactg tgtttgccaa gatccagaga cttgtccccc tgcaaaaatc
1681 ctagatcagg cttgtggcac tgacaaccaa acctacgcca gctcctgtca cctgttttgct
1741 accaagtgca ggctggaggg gaccaaaaag ggacaccaac tgcagctgga ttacttcga
1801 gcttgcaaat ctattcctgc ttgtacggac tttgaagtgg ctcagtttcc cctgcggatg
1861 agagactgc ctaaaaacat cctcatgcag ctttatgaac caatcccaa acatggcggc
1921 tatctcaatg aaaagcaaag aagcaaagtc aaaaaatt acctggatga gaagagactc
1981 ttggctggag accatcccat tgaacttctc tgagggact ttaagaaaaa ctaccacatg
2041 tatgtgtatc ctgtgcactg gcagtttaat gaactggacc agcatcctgc agacaggatc
2101 ttgacacact ctgaacttgc tcctctgcga gcttccctgg tgcccatgga acactgcata
2161 actcgcttct ttgaggagtg tgacccaaac aagataagc acatcacctt gaaggaatgg
2221 ggccactgct ttggaattaa agaggaggat atagatgaaa acctcctctt ttgaattaag
2281 atttgagaga atcggaactt tccatccacc tcacctgctt taaccgcttc agaaatacga
2341 gcagccatga cactatacat tcatatgtag caaaacattt gtttggcatg tgagagaaga
2401 caatggtagt aattacttct tggtgatata tatatgagcc agcacttaa tattaactta
2461 ggaaatgaaa ctttaaaatt aagtagagtc aatgtctata aaagactgtc ctgtctgggg
2521 acagttagcc accatggcaa tgtcactctg tgcatctgcg tttataattg ataattataa
2581 actattaaaa aaacaatgtt catattgtcc ataatacctt atgcatgctg aggaagtgag
2641 atactgctct tttgagataa atatgcctcc ttttcagtgt cttggatgtc ctaataaaa
2701 atctataaaa ccccaaaaa aaaaaaaaa aaaa  SEQ ID NO. 26
```

FIG. 12-60

```
NCBI                                                              Nucleotide
  PubMed   Nucleotide   Protein   Genome   Structure   PMC   Taxonomy   OMIM   Boo
Search [Nucleotide ▼] for [                                    ]                Details
         Limits       Preview/Index       History         Clipboard        Links
Display [default ▼] Show: [20 ▼]  [Send to ▼]    [Go] [Clear]
                                                 [Get Subsequence]
```

▣ 1: M58460. Human 75-kD autoa...[gi:179286]

```
LOCUS       HUMAUTOANT              1542 bp    mRNA    linear   PRI 31-DEC-1994
DEFINITION  Human 75-kD autoantigen (PM-Scl) mRNA, complete cds.
ACCESSION   M58460
VERSION     M58460.1  GI:179286
KEYWORDS    autoantigen; nucleolar protein.
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1542)
  AUTHORS   Alderuccio,F., Chan,E.K. and Tan,E.M.
  TITLE     Molecular characterization of an autoantigen of PM-Scl in the
            polymyositis/scleroderma overlap syndrome: a unique and complete
            human cDNA encoding an apparent 75-kD acidic protein of the
            nucleolar complex
  JOURNAL   J. Exp. Med. 173 (4), 941-952 (1991)
```

FIG. 12-61

MEDLINE    91178455
PUBMED     2007859
COMMENT    Original source text: Homo sapiens (tissue library: lambda gt11)
           lymphoblastoma cDNA to mRNA.
FEATURES          Location/Qualifiers
    source        1..1542
                  /organism="Homo sapiens"
                  /db_xref="taxon:9606"
                  /cell_line="MOLT-4"
                  /cell_type="T-cell"
                  /tissue_type="lymphoblastoma"
                  /tissue_lib="lambda gt11"
    gene          1..1542
                  /gene="PM-Scl"
    CDS           420..1487
                  /gene="PM-Scl"
                  /note="75-kD"
                  /codon_start=1
                  /product="autoantigen"
                  /protein_id="AAA58384.1"
                  /db_xref="GI:179287"
                  /translation="MAAPAFEPGRQSDLLVKLNRLMERCLRNSKCIDTESLCVVAGEK
                  VWQIRVDLHLLNHDGNIIDAASIAAIVALCHFRRPDVSVQGDEVTLYTPEERDPVPLS
                  IHHMPICVSFAFFQQGTYLLVDPNEREERVMDGLLVIAMNKHREICTIQSSGGIMLLK
                  DQVLRCSKIAGVKVAEITELILKALENDQKVRKEGGKFGFAESIANQRITAFKMEKAP
                  IDTSDVEEKAEEIIAEAEPPSEVVSTPVLWTPGTAQIGEGVENSWGDLEDSEKEDDEG
                  GGDQAIILDGIKMDTGVEVSDIGSQDAPIILSDSEEEMILEPDKNPKKIRTQTTSA
                  KQEKAPSKKPVKRRKKRAAN" SEQ ID NO. 10

```
BASE COUNT    494 a    283 c    355 g    410 t
ORIGIN
    1 cgaccggcac gttcacccca tccctcaggc tttattatt ttttttcgac aggttctttt
   61 caaggctcca gtcaccgcag cagttgtcca tgctgtagtt tccactttcc tgtatgggcg
  121 ggctggttag gattccactt tcccccaagt gcttagccca gggcagaca aaaagtagtt
  181 gcttaagaaa tacttgttga aggaataaat taatgaatga atttgtgctt acagcggctg
  241 gatggcagac aaacctatga ttataggaac atcagatct cattggaac agattacga
  301 tgctgcattg tggaacttgg aaaaacaaga gttcttggac aggtttcctg tgaacttgtg
  361 tctccaaaac tcaatcgggc aacagaaggt attcttttt taaccttgaa ctctctcaga
  421 tggccgctcc agctttcgaa cctggcaggc agtcagatct cttggtgaag ttgaatcgac
  481 tcatggaaag atgtctaaga aattcgaagt gtatagacac tgagtctctc tgtgttgttg
  541 ctgtgaaaa ggtttggcaa atacgtgtag acctacatt attaaatcat gatgaaata
  601 ttattgatgc tgccagcatt gctgcaatcg tggccttatg tcatttccga agacctgatg
  661 tctctgtcca aggagatgaa gtaacactgt atacacctga agagcgtgat cctgtaccat
  721 taagtatcca ccacatgccc atttgtgtca gttttgcctt tttccagcaa ggaacatatt
  781 tattggtgga tcccaatgaa cgagaagaac gtgtgatgga tggcttgctg gtgattgcca
  841 tgaacaaaca tcgagagatt tgtactatcc agtccagtgg tgggataatg ctactaaag
  901 atcaagttct gagatgcagt aaaatcgctg gtgtgaaagt agcagaaatt acagagctaa
  961 tattgaaagc tttggagaat gaccaaaaag taagaaaga aggtggaaag tttgttttg
 1021 cagagtctat agcaaatcaa aggatcacag catttaaaat ggaaaaggcc cctattgata
 1081 cctcggatgt agaagaaaaa gcagaagaaa tcattgctga agcagaacct ccttcagaag
 1141 ttgtttctac acctgtgcta tggactcctg gaactgccca aattggagag ggagtagaaa
 1201 actcctgggg tgatcttgaa gactctgaga aggaagatga tgaaggcggt ggtgatcaag
 1261 ctatcattct tgatggtata aaatggaaca ctggagtaga agtctctgat attggaagcc
 1321 aagatgctcc cataatactc tcagatagtg aagaagaaga aatgatcatt ttgaaccaga
 1381 acaagaatcc aaagaaaata agaacacaga ccaccagtgc aaaacaagaa aaagcaccaa
 1441 gtaaaaagcc agtgaaaaga agaaaaaaga agagctgc caattaaagc taacagttgt
 1501 atatctgtat atataactat taaagggat atttattcca tt    SEQ ID NO. 27
```

```
NCBI                                                                              Boo
PubMed    Nucleotide   Protein   Genome   Structure   PMC   Taxonomy   OMIM Search Nucleotide ▽ for [                              ]

Nucleotide

Limits         Preview/Index    History    Clipboard         Details
Display default ▽ Show: 20 ▽ Send to File ▽   Go  Clear ☐ 1: NM_004684. Homo sapiens SPAR...[gi:21359870]                      Links Get Subsequence LOCUS         SPARCL1                2808 bp    mRNA    linear   PRI 23-DEC-2002
DEFINITION    Homo sapiens SPARC-like 1 (mast9, hevin) (SPARCL1), mRNA.
ACCESSION     NM_004684
VERSION       NM_004684.2  GI:21359870
KEYWORDS      .
SOURCE        Homo sapiens (human)
  ORGANISM    Homo sapiens
              Eukaryota; Metazoa; Chordata; Craniata; Vertebrata; Euteleostomi;
              Mammalia; Eutheria; Primates; Catarrhini; Hominidae; Homo.
REFERENCE     1  (bases 1 to 2808)
  AUTHORS     Girard,J.P. and Springer,T.A.
  TITLE       Cloning from purified high endothelial venule cells of hevin, a
              close relative of the antiadhesive extracellular matrix protein
              SPARC
  JOURNAL     Immunity 2 (1), 113-123 (1995)
  MEDLINE     95323677
```

FIG. 12-64

```
PUBMED     7600298
REFERENCE  2
AUTHORS    Schraml,P., Shipman,R. and Ludwig,C.U.
TITLE      An alternative PCR-based method for the direct isolation of cDNA
           ends (DICE)
JOURNAL    Unpublished
COMMENT    PROVISIONAL REFSEQ: This record has not yet been subject to final
           NCBI review. The reference sequence was derived from X86693.1.
           On Jun 9, 2002 this sequence version replaced gi:4758521.
FEATURES          Location/Qualifiers
     source       1..2808
                  /organism="Homo sapiens"
                  /db_xref="taxon:9606"
                  /chromosome="4"
                  /map="4q22.1"
                  /tissue_type="lung"
                  /clone_lib="human fetal lung 5'-stretch cDNA in lambda
                  gt10(Clontech)"
     gene         1..2808
                  /gene="SPARCL1"
                  /note="synonyms: HEVIN, MAST9"
                  /db_xref="LocusID:8404"
                  /db_xref="MIM:606041"
     variation    complement(139)
                  /allele="T"
                  /allele="A"
                  /db_xref="dbSNP:2615483"
     variation    161
```

FIG. 12-65

```
variation        /gene="SPARCL1"
                 /allele="G"
                 /allele="A"
                 /db_xref="dbSNP:1049539"
                 291
variation        /gene="SPARCL1"
                 /allele="G"
                 /allele="A"
                 /db_xref="dbSNP:1130639"
                 291
CDS              323..2317
                 /gene="SPARCL1"
                 /note="mast9; hevin"
                 /codon_start=1
                 /product="SPARC-like 1"
                 /protein_id="NP_004675.2"
                 /db_xref="GI:21359871"
                 /db_xref="LocusID:8404"
                 /db_xref="MIM:606041"
                 /translation="MKTGPFFLCLLGTAAAIPTNARLLSDHSKPTAETVAPDNTAIPS
                 LWAEAEENEKETAVSTEDDSHHKAEKSSVLKSKEESHEQSAEQGKSSSQELGLKDQED
                 SDGHLSVNLEYAPTEGTLDIKEDMIEPQEKLSENTDFLAPGVSSFTDSNQQESITKR
                 EENQEQPRNYSHQLNRSSKHSQGLRDQGNQEQDPNISNGEEEEKEPGEVGTHNDNQ
                 ERKTELPREHANSKQEEDNTQSDDILEESDQPTQVSKMQEDEFDQGNQEQEDNSNAEM
                 EEENASNVNKHIQETEWQSQEGKTGLEAISNHKETEEKTVSEALLMEPTDDGNTTPRN
                 HGVDDDGDDDGDDGGTDGPRHSASDDYFIPSQAFLEAERAQSIAYHLKIEEQREKVHE
                 NENIGTTEPGEHQEAKKAENSSNEEETSSEGNMRVHAVDSCMSFQCKRGHICKADQQG
```

FIG. 12-66

```
              KPHCVCQDPVTCPPTKPLDQVCGTDNQTYASSCHLFATKCRLEGTKKGHQLQLDYFGA
              CKSIPTCTDFEVIQFPLRMRDWLKNIILMQLYEANSEHAGYLNEKQRNKVKKIYLDEKR
              LLAGDHPIDLLLRDFKKNYHMYVYPVHWQFSELDQHPMDRVLTHSELAPLRASLVPME
              HCITRFFEECDPNKDKHITLKEWGHCFGIKEEDIDENLLF" SEQ ID NO. 11
misc feature  1616..1687
              /gene="SPARCL1"
              /note="FOLN; Region: Follistatin-N-terminal domain-like"
              /db_xref="CDD:smart00274"
misc feature  1688..1849
              /gene="SPARCL1"
              /note="kazal; Region: Kazal-type serine protease inhibitor
              domain. Usually indicative of serine protease inhibitors.
              However, kazal-like domains are also seen in the
              extracellular part of agrins, which are not known to be
              protease inhibitors. Kazal domains often occur in tandem
              arrays. Small alpha+beta fold containing three
              disulphides. Alignment also includes a single domain from
              transporters in the OATP/PGT family"
              /db_xref="CDD:pfam00050"
misc feature  1697..1849
              /gene="SPARCL1"
              /note="KAZAL; Region: Kazal type serine protease
              inhibitors"
              /db_xref="CDD:smart00280"
variation     336
              /gene="SPARCL1"
variation     433
              /gene="SPARCL1"
```

FIG. 12-67

```
                    /allele="T"
                    /allele="C"
                    /db_xref="dbSNP:8342"
variation           433
                    /gene="SPARCL1"
variation           458
                    /gene="SPARCL1"
variation           468
                    /gene="SPARCL1"
                    /allele="C"
                    /allele="A"
                    /db_xref="dbSNP:13051"
variation           468
                    /gene="SPARCL1"
variation           638
                    /gene="SPARCL1"
                    /allele="G"
                    /allele="C"
                    /db_xref="dbSNP:1049544"
variation           638
                    /gene="SPARCL1"
variation           668
                    /gene="SPARCL1"
variation           702
                    /gene="SPARCL1"
variation           1577
                    /gene="SPARCL1"
                    /allele="G"
                    /allele="A"
                    /db_xref="dbSNP:3189727"
variation           1957
                    /gene="SPARCL1"
variation           2047
                    /gene="SPARCL1"
                    /allele="T"
                    /allele="C"
                    /db_xref="dbSNP:9933"
variation           2047
                    /gene="SPARCL1"
variation           2327
                    /gene="SPARCL1"
                    /allele="T"
                    /allele="A"
                    /db_xref="dbSNP:10626"
BASE COUNT      996 a    554 c    606 g    652 t
```

FIG. 12-68

ORIGIN
```
   1 cggcatgaga ggccagcctg ccaggaaat  ccaggaatct gcaacaaaaa cgatgacagt
  61 ctgaaatact ctctggtgcc aacctccaaa ttctcgtctg tcacttcaga ccccactag
 121 ttgacagagc agcagaatat caactccagt agacttgaat gtgcctctgg gcaaagaagc
 181 agagctaacg aggaaaggga tttaaagagt ttttcttggg tgtttgtcaa actttattc
 241 cctgtctgtg tgcagagggg attcaacttc aattttctgc agtggctctg ggtccagccc
 301 cttacttaaa gatctggaaa gcatgaagac tgggcctttt ttcctatgtc tcttgggaac
 361 tgcagctgca atcccgacaa atgcaaagatt attatctgat cattccaaac caactgctga
 421 aacggtagca cctgacaaca ctgcaatccc cagtttatgg gctgaagctg aagaaaatga
 481 aaaagaaaca gcagtatcca cagaagacga ttcccaccat aaggctgaaa aatcatcagt
 541 actaaagtca aaagaggaaa gccatgaaca gtcagcagaa caggcaaga ttaagtgtga gttctagcca
 601 agagctggga ttgaaggatc tggacataaa agaagatatg attgagcctc ttaagtgtga atttggagta
 661 tgcaccaact gaagtacat tggacataaa agaagatatg attgagcctc tccttcacag aggagaaaaa
 721 actctcagag aacactgatt ttttggctcc tgtgttagt tccttcacag cctagaaatt attctaacca
 781 acaagaaagt atcacacaga gagagaaaca ccaagaacaa aggcctaagg gatcaaggaa accaagagca
 841 tcagttgaac aggagcagta atttccaatg gagaagagga agaagaaaa agccccagg aagttggtac
 901 ggatccaaat aaccaagatg aaagacaga attgcccagg gagcatgcta acagcaagca
 961 ccacaatgat aatacccaat ctgatgatat tttgaagag tctgatcaac caactcaagt
1021 ggaggaagac cagcggaagt aatttgatca gggtaaccaa gaacaagaag ataactccaa
1081 aagcaagatg caggaggatg atgcatcgaa cgtcaataag cacattcaag aaactgaatg
1141 tgcagaaatg gaagagaaa atgcacttca tctgcctaga agctatcagc aaccacaaag agacagaaga
1201 gcaagtcaa gagggctc tgctcatgga acctactgga atggtaata ccacgcccag
1261 aaagactgtt tctgaggctc gttgatgatg atggcgat gatggcggca ctgatggccc
1321 aaatcatgga gttgatgatg atggcgatga actacctcat cccaagccag gccttctgg aggccgagag
1381 caggcacagt gcaagtgatg actacctcat acctcaaaat tgaggagcaa agagaaaaag tacatgaaaa
1441 agctcaatcc attgcctatc acctcaaaat tgaggagcaa gcaccaagag gccaagaaag cagagaactc
1501 tgaaatata ggtaccactg agcctggaga gcaccaagag gccaagaaag cagagaactc
1561 atcaaatgag gaggaaacgt caagtgaagg caacatgagg caacatgagg gtgcatgctg tgattcttg
```

FIG. 12-69

```
1621 catgagcttc cagtgtaaaa gaggccacat ctgtaaggca gaccaacagg gaaaacctca
1681 ctgtgtctgc caggatccag tgacttgtcc tccaacaaaa cccctttgatc aagtttgtgg
1741 cactgacaat cagacctatg ctagttcctg tcatctattc gctactaaat gcagactgga
1801 ggggaccaaa aagggcatc aactccagct ggattatttt ggagcctgca aatctattcc
1861 tacttgtacg gactttgaag tgattcagtt tcctctacgg atgagagact ggctcaagaa
1921 tatcctcatg cagctttatg aagccaactc tgaacatgct ggttatctaa atgagaagca
1981 gagaaataaa gtcaagaaaa tttacctgga tgaaaagagg cttttggctg gggaccatcc
2041 cattgatctt ctcttaaggg acttaagaa aaactaccac atgtatgtgt atcctgtgca
2101 ctggcagttt agtgaacttg accaacaccc tatggataga gtcttgacac attotgaact
2161 tgctcctctg cgagcatctc tggtgcccat ggaacactgc ataaccgtt tctttgagga
2221 gtgtgacccc aacaaggata agcacatcac cctgaaggag tggggccact gctttgaat
2281 taaagaagag gacatagatg aaaatctctt gttttgaacg aagattttaa agaactcaac
2341 tttccagcat cctcctctgt tctaaccact tcagaaatat atgcagctgt gatacttgta
2401 gatttatatt tagcaaaatg ttagcatgta tgacaagaca atgagagtaa ttgcttgaca
2461 acaacctatg caccaggtat ttaacattaa ctttgaaac ttaattcata gtaatttcac
2521 agtcaacata tgcaaaatac tgtacattgt gaacagaagt ttaattcata gtaatttcac
2581 tctctgcatt gacttatgag ataattaatg attaaactat taatgataaa aataatgcat
2641 ttgtattgtt catatatca tgtgcacttc aagaaaatgg aatgctactc ttttgtggtt
2701 tacgtgtatt attttcaata tcttaatacc ctaataaaga gtccataaaa atccaaaaaa
2761 aaaaaaaaaa aaaaaaaa          SEQ ID NO. 28
```

FIG. 12-70

```
NCBI                                                    Nucleotide

PubMed    Nucleotide    Protein    Genome    Structure    PMC    Taxonomy    OMIM    Boo Search  Nucleotide  ▽  for [                              ]    Go   Clear                Details Limits         Preview/Index      History           Clipboard
Display default ▽  Show: 20 ▽   Send to  File ▽                Get Subsequence ☐ 1: X82157. H.sapiens mRNA fo...[gi:758065]                                              Links LOCUS         HSHEVIN                 2645 bp    mRNA     linear   PRI 31-MAR-1995
DEFINITION    H.sapiens mRNA for high endothelial venule.
ACCESSION     X82157
VERSION       X82157.1  GI:758065
KEYWORDS      hevin gene.
SOURCE        Homo sapiens (human)
  ORGANISM    Homo sapiens
              Eukaryota; Metazoa; Chordata; Craniata; Vertebrata; Euteleostomi;
              Mammalia; Eutheria; Primates; Catarrhini; Hominidae; Homo.
REFERENCE     1
  AUTHORS     Girard,J.P. and Springer,T.A.
  TITLE       Cloning from purified high endothelial venule cells of hevin, a
              close relative of the antiadhesive extracellular matrix protein
              SPARC
  JOURNAL     Immunity 2 (1), 113-123 (1995)
```

FIG. 12-71

```
MEDLINE     95323677
REFERENCE   2  (bases 1 to 2645)
AUTHORS     Girard,J.
TITLE       Direct Submission
JOURNAL     Submitted (10-OCT-1994) J. Girard, Center for Blood Research and
            Dept. of Pathology, Harvard Medical School, 200 Longwoode Avenue,
            Boston, MA 02115, USA
FEATURES             Location/Qualifiers
     source          1..2645
                     /organism="Homo sapiens"
                     /db_xref="taxon:9606"
                     /clone="HEC25"
                     /cell_line="purified high endothelial cells"
                     /cell_type="high endothelial cells"
                     /tissue_type="tonsil"
     gene            1..2645
                     /gene="hevin"
     CDS             198..2192
                     /gene="hevin"
                     /codon_start=1
                     /protein_id="CAA57650.1"
                     /db_xref="GI:758066"
                     /db_xref="SPTREMBL:Q14515"
                     /translation="MKTGLFFLCLLGTAAAIPTNARLLSDHSKPTAETVAPDNTAIPS
                     LRAEDEENEKETAVSTEDDSHHKAEKSSVLKSKEESHEQSAEQGKSSSQELGLKDQED
                     SDGDLSVNLEYAPSEGTLDIKEDMSEPQEKKLSENTDFLAPGVSSFTDSNQQESITKR
                     EENQEQPRNYSHHQLNRSSKHSQGLRDQGNQEQDPNISNGEEEEKEPGEVGTHNDNQ
```

FIG. 12-72

ERKTELPREHANSKQEEDNTQSDDILEESDQPTQVSKMQEDEFDQGNQEQEDNSNAEM
EEENASNVNKHIQETEWQSQEGKTGLEAISNHKETEEKTVSEALLMEPTDDGNTTPRN
HGVDDDGDDDGDDGGTDGPRHSASDDYFIPSQAFLEAERAQSIAYHLKIEEQREKVHE
NENIGTTEPGEHQEAKKAENSSNEEETSSEGNMRVHAVDSCMSFQCKRGHICKADQQG
KPHCVCQDPVTCPPTKPLDQVCGTDNQTYASSCHLFATKCRLEGTKKGHQLDYFGA
CKSIPTCTDFEVIQFPLRMRDWLKNILMQLYEANSEHAGYLNEKQRNKVKKIYLDEKR
LLAGDHPIDLLLRDFKKNYHMYVYPVHWQFSELDQHPMDRVLTHSELAPLRASLVPME
HCITRFFEECDPNKDKHITLKEWGHCFGIKEEDIDENLLF" SEQ ID NO. 12 sig_peptide    198..260
               /gene="hevin"
polyA_signal   2608..2613
               /gene="hevin"

BASE COUNT     923 a    516 c    580 g    626 t
ORIGIN
         1 gagcagcaga atttcaactc cagtagactt gaatatgcct ctgggcaaag aagcagagct
        61 aacgaggaaa gggatttaaa gagtttttct cttcaattta tctgcagtgg ctctgagtcc agcccctgtc
       121 tgtgtgcaga ggggattcaa cttcaatttt tctgcagtgg cttttttcct atgtctcttg ggaactgcag
       181 ttaaagatct ggaaagcatg aagactggc agattattat ctgatcattc caaccaact gctgaaacgg
       241 ctgcaatccc gacaaatgca caacactgca atccccagtt taagggctga agatgaagaa aatgaaaaag
       301 tagcaccega caacagtgca tccacagaa gacgattccc accataaggc cagaacaggg caagagttct agccaagagc
       361 aaacagcagt atccacagaa ggaaagccat gaacagtcag cagaacaggg caagagttct agccaagagc
       421 agtcaaaaga ggatcaagag gacagtgatg gtgacttaag tgtgaattg gagtatgcac
       481 tgggattgaa tacattggac ataaaagaag atatgagtga gcctcaggag aaaaaactct
       541 catctgaagg cagagaacac tgatttttg gctcctggtg ttagttcctt cacagattct aaccacaag
       601 cagagaacac aaagagagag gaaaaccaag aaaaccaag aaattattca catcatcagt
       661 aagtatcac cagtaaacat agccaaggcc taagggatca aggaaaccaa gagcaggatc
       721 tgaacaggag

FIG. 12-73

```
 781 caaatatttc caatggagaa gaggaagaag aaaaagagcc aggtgaagtt ggtacccaca
 841 atgataacca agaaagaaag acagaattgc ccagggagca tgctaacagc aagcaggagg
 901 aagacaatac ccaatctgat gatattttgg aagagtctga tcaaccaact caagtaagca
 961 agatgcagga ggatgaattt gatcagggta accaagaaca agaagataac tccaatgcag
1021 aaatggaaga ggaaaatgca tcgaacgtca ataagcacat tcaagaaact gaatgcgaga
1081 gtcaagaggg taaaactggc ctagaagcta tcagcaacca caaagagaca gaagaaaaga
1141 ctgtttctga ggctctgctc atgaaccta  ctgatgatgg taataccacg cccagaaatc
1201 atggagttga tgatgatggc gatgatgatg gcgcagaagg cggcactgat ggccccaggc
1261 acagtgcaag tgatgactac ttcatcccaa gccaggcctt tctggaggcc gagagagctc
1321 aatccattgc ctatcacctc aaaattgagg agcaaagaga aaaagtacat gaaaatgaaa
1381 atataggtac cactgagcct ggagagcacc aagagcagag aaagcagag  aactcatcaa
1441 atgaggaga  aacgtcaagt gaaggcaaca tgagggtgca tgctgtggat cctcactgtg
1501 gcttccagtg taaaagaggc cacatctgta acaggacca  acagggaaaa ccctcactgt
1561 tctgccagga tccagtgact tgtcctccaa caaaacccct tgatcaagtt tgtggcactg
1621 acaatcagac ctatgctagt tcctgtcatc tattcgctac taaatgcaga ctggagggga
1681 ccaaaaaggg gcatcaactc cagctggatt attttggagc ctgcaaatct attcctactt
1741 gtacggactt tgaagtgatt tgaagtcctc tacgatgag agactggctc aagaatatcc
1801 tcatgcagct ttatgaagcc aactctgaac acgctggtta tctaaatgag aagcagagaa
1861 ataaagtcaa gaaaatttac ctggatgaaa agaggctttt ggctggggac catcccattg
1921 accttctctt aagggacttt aagaaaaact accacatgta tgtgtatcct gtgcactggc
1981 agtttagtga acttgaccaa cacctatgg  atagagtctt gacacattct gaacttgctc
2041 ctctgcgagc atctctggtg cccatggaac actgcataac ccgttctctt gaggagtgtg
2101 acccaacaa  ggataagcac atcaccctga aggagtgggg ccactgcttt ggaattaaag
2161 aagaggacat agatgaaaat ctcttgtttt gaacgaagat tttaaagaac tcaactttcc
2221 agcatcctcc tctgttctaa ccacttcaga aatatatgca gctgtgatac ttgtagattt
2281 atatttagca aatgttagc  atgtatgaca agacaatgag agtaattgct tgacaacaac
2341 ctatgcacca ggtatttaac attaactttg gaaacaaaaa tgtacaatta agtaaagtca
```

FIG. 12-74

```
2401 acatatgcaa aatactgtac attgtgaaca gaagtttaat tcatagtaat ttcactctct
2461 gcattgactt atgagataat taatgattaa actattaatg ataaaaataa tgcatttgta
2521 ttgttcataa tatcatgtgc acttcaagaa aatggaatgc tactctttg tggtttacgt
2581 gtattatttt caatatccta ataccctaat aaagagtcca taaaaatcca aaaaaaaaa
2641 aaaaa SEQ ID NO. 29
//
```

Revised July 5, 2002

Disclaimer | Write to the Help Desk
NCBI | NLM | NIH

FIG. 12-75

| | | | | | | | |
|---|---|---|---|---|---|---|---|
| NCBI | PubMed | Nucleotide | Protein | Genome | Structure | PMC | Taxonomy | OMIM | Boo |

Nucleotide

Search Nucleotide ▽ for [                    ] Go  Clear

Limits    Preview/Index    History    Clipboard    Details

Display default ▽  Show: 20 ▽  Send to File ▽    Get Subsequence    Links

☐ 1: X86693. H.sapiens mRNA fo...[gi:809026]

```
LOCUS       HSMAST9                 2808 bp    mRNA    linear   PRI 08-SEP-1995
DEFINITION  H.sapiens mRNA for hevin like protein.
ACCESSION   X86693
VERSION     X86693.1  GI:809026
KEYWORDS    Hevin-like protein; MAST 9 gene.
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1
  AUTHORS   Schraml,P., Shipman,R. and Ludwig,C.U.
  TITLE     An alternative PCR-based method for the direct isolation of cDNA
            ends (DICE)
  JOURNAL   Unpublished
REFERENCE   2  (bases 1 to 2808)
  AUTHORS   Schraml,P.H.
```

FIG. 12-76

```
TITLE      Direct Submission
JOURNAL    Submitted (26-APR-1995) P.H. Schraml, Zentrum fuer Lehre und
           Forschung (ZLF), Molecular Oncology, Laboratory 405, Kantonsspital
           Basel, Hebelstrasse 20, CH-4031 Basel, SWITZERLAND
COMMENT    Related sequences X82157 and S73397.
FEATURES          Location/Qualifiers
     source       1..2808
                  /organism="Homo sapiens"
                  /db_xref="taxon:9606"
                  /tissue_type="lung"
                  /clone_lib="human fetal lung 5'-stretch cDNA in lambda
                  gt10(Clontech)"
     gene         1..2808
                  /gene="MAST-9"
     mRNA         <1..>2808
                  /gene="MAST-9"
     variation    291
                  /gene="MAST-9"
     gene         323..2317
                  /gene="MAST 9"
     CDS          323..2317
                  /gene="MAST 9"
                  /codon_start=1
                  /product="Hevin-like protein"
                  /protein_id="CAA60386.1"
                  /db_xref="GI:809027"
                  /db_xref="SPTREMBL:Q14800"
                  /translation="MKTGPFFLCLLGTAAAIPTNARLLSDHSKPTAETVAPDNTAIPS
```

FIG. 12-77

LWAEAEENEKETAVSTEDDSHHKAEKSSVLKSKEESHEQSAEQGKSSSQELGLKDQED
SDGHLSVNLEYAPTEGTLDIKEDMIEPQEKKLSENTDFLAPGVSSFTDSNQQESITKR
EENQEQPRNYSHHQLNRSSKHSQGLRDQGNQEQDPNISNGEEEEKEPGEVGTHNDNQ
ERKTELPREHANSKQEEDNTQSDDILEESDQPTQVSKMQEDEFDQGNQEQEDNSNAEM
EEENASNVNKHIQETEWQSQEGKTGLEAISNHKETEEKTVSEALLMEPTDDGNTTPRN
HGVDDDGDDDGDDGGTDGPRHSASDDYFIPSQAFLEAERAQSIAYHLKIEEQREKVHE
NENIGTTEPGEHQEAKKAENSSNEEETSSEGNMRVHAVDSCMSFQCKRGHICKADQQG
KPHCVCQDPVTCPTKPLDQVCGTDNQTYASSCHLFATKCRLEGTKKGHQLQLDYFGA
CKSIPTCTDFEVIQFPLRMRDWLKNILMQLYEANSEHAGYLNEKQRNKVKKIYLDEKR
LLAGDHPIDLLLRDFKKNYHMYVYPVHWQFSELDQHPMDRVLTHSELAPIRASLVPME
HCITRFFEECDPNKDKHITLKEWGHCFGIKEEDIDENLLF"   SEQ ID NO. 13 variation    336  /gene="MAST 9"
variation    433  /gene="MAST 9"
variation    458  /gene="MAST 9"
variation    468  /gene="MAST 9"
variation    638  /gene="MAST 9"
variation    668  /gene="MAST 9"
variation    702  /gene="MAST 9"
variation   1957  /gene="MAST 9"
variation   2047  /gene="MAST 9"

FIG. 12-78

```
BASE COUNT      996 a      554 c      606 g      652 t
ORIGIN                /gene="MAST 9"
    1 cggcatgaga ggccagcctg ccagggaaat ccagggatct gcaacaaaaa cgatgacagt
   61 ctgaaatact ctctggtgcc aacctccaaa ttctcgtctg tcacttcaga ccccactag
  121 ttgacagagc agcagaatat caactccagt agacttgaat gtgcctctgg gcaaagaagc
  181 agagctaacg aggaaaggga tttaaagagt ttttcttggg tgtttgtcaa actttattc
  241 cctgtctgtg tgcagagggg attcaacttc aattttctgc agtggctctg ggtccagccc
  301 cttacttaaa gatctggaaa gcatgaagac tgggcctttt ttcctatgtc tcttgggaac
  361 tgcagctgca atcccgacaa atgcaagatt attatctgat cattccaaac caactgctga
  421 aacggtagca cctgacaaca ctgcaatccc cagtttatgg gctgaagctg aagaaaatga
  481 aaaagaaaca gcagtatcca cagaagacga ttcccaccat aaggctgaaa aatcatcagt
  541 actaaagtca aaagaggaaa gccatgaaca gtcagcagaa caggcaagaa gttctagcca
  601 agagctggga ttgaaggatc aagagacag ttaagtgtca ttaagtgtga atttggagta
  661 tgcaccaact gaaggtacat tggacataaa agaagatatg attgagcctc aggagaaaaa
  721 actctcagag aacactgatt tttggctcc tggtgttagt tccttcacag attctaacca
  781 acaagaaagt atcacaaaga gagagaacaa ccaagaacaa cctagaaatt attcacatca
  841 tcagttgaac aggagcagta aacatagcca aggcctaagg gatcaaggaa accaagagca
  901 ggatccaaat atttccaatg gagaagagga gaaagacaga attgcccagg gagccaggtg aagttggtac
  961 ccacaatgat aaccaagaaa aatacccaat ctgatgatat tttggaagag tctgatcaac acagcaagca
 1021 ggaggaagac caggaggatg aatttgatca gggtaaccaa gaacaagaag caactccaa
 1081 aagcaagatg cagagaaatg gaagaggaaa atgcatcgaa cgtcaattaag cacattcaag ataactgaatg
 1141 tgcagagagc gagagtaaa ctgcctaga agctatcagc aaccacaaag agacagaga
 1201 gcagagtaa gagggtaaa tctgagggctc tgctcatgga agctatctgat gatggtaata ccacgcccag
 1261 aaagactgtt tctgagcct atgggcgat gatgcgat gatggcggca ctgatgcccc
 1321 aaatcatgga gttgatgatg actacttcat cccaagccag gcctttctgg aggccgagag
 1381 caggcacagt gcaagtgatg actacttcat cccaagccag gcctttctgg aggccgagag
 1441 agctcaatcc attgcctatc acctcaaaat tgaggagcaa agagaaaaag tacatgaaaa
```

FIG. 12-79

```
1501 tgaaatata ggtaccactg agcctggaga gccaagaaag gccaagaaag cagagaactc
1561 atcaaatgag gaggaaacgt caagtgaagg caacatgagg gtgcatgctg tggattcttg
1621 catgagcttc cagtgtaaaa gaggccacat ctgtaaggca gaccaacagg gaaaacctca
1681 ctgtgtctgc caggatccag tgacttgtcc tccaacaaaa cccttgatc aagtttgtgg
1741 cactgacaat cagacctatg ctagttcctg tcatctattc gctactaaat gcagactgga
1801 ggggaccaaa aagggcatc aactccagct ggattatttt ggagcctgca aatctattcc
1861 tacttgtacg gactttgaag tgattcagtt tcctctacgg atgagagact ggctcaagaa
1921 tatcctcatg cagctttatg aagccaactc tgaacatgct ggttatctaa atgagaagca
1981 gagaaataaa gtcaagaaaa tttacctgga tgaaaagagg cttttggctg gggaccatcc
2041 cattgatctt ctcttaaggg acttttaaga aaactaccac atgtatgtgt atcctgtgca
2101 ctggcagttt agtgaacttg accaacaccc tatggataga gtcttgacac attctgaact
2161 tgctcctctg cgagcatctc tggtgcccat agcacatcac ataacccgtt tcttttgagga
2221 gtgtgacccc aacaaggata gacataagatg aaaatctctt gggcactt agaactcaac
2281 taaagaagag cctcctctgt tctaaccact gttttgaacg aagattttaa atgcagctgt gatacttgta
2341 tttccagcat cctcctctgt tctaaccact gttttgaacg aagattttaa atgcagctgt gatacttgta
2401 gatttatatt tagcaaaatg ttagcatgta tcagaaatat tcagaaatat atgcagagta ttgcttgaca
2461 acaacctatg caccaggtat ttaacattaa ctttggaaac aaaaatgtac aattaagtaa
2521 agtcaacata tgcaaaatac tgtacattgt gaacagaagt ttaattcata gtaatttcac
2581 tctctgcatt gacttatgag ataattaatg attaaactat taatgataaa aataatgcat
2641 ttgtattgtt cataatatca tgtgcacttc aagaaaatgg aatgctactc tttgtggtt
2701 tacgtgtatt attttcaata tcttaatacc ctaataaaga gtccataaaa atccaaaaaa
2761 aaaaaaaaaa aaaaaaaaaa aaaaaaaaaa aaaaaaaa    SEQ ID NO. 30
```

FIG. 12-80

```
NCBI                                              Nucleotide

PubMed    Nucleotide   Protein   Genome   Structure   PMC   Taxonomy   OMIM      Boo
Search Nucleotide ▽ for [                              ]  Go  Clear                Details
           Limits                                                                  Links
Display ▽     Show: 20 ▽   Preview/Index   History   Clipboard
                           Send to  File ▽           Get Subsequence ☐ 1: M61908. C.coturnix japoni...[gi:213614]

LOCUS       QULQR1        2678 bp    mRNA    linear   VRT 28-APR-1993
DEFINITION  C.coturnix japonica QR1 gene, complete cds.
ACCESSION   M61908
VERSION     M61908.1  GI:213614
KEYWORDS
SOURCE      Coturnix coturnix (common quail)
  ORGANISM  Coturnix coturnix
            Eukaryota; Metazoa; Chordata; Craniata; Vertebrata; Euteleostomi;
            Archosauria; Aves; Neognathae; Galliformes; Phasianidae;
            Phasianinae; Coturnix.
REFERENCE   1  (bases 1 to 2678)
  AUTHORS   Guermah,M., Crisanti,P., Laugier,D., Dezelee,P., Bidou,L.,
            Pessac,B. and Calothy,G.
  TITLE     Transcription of a quail gene expressed in embryonic retinal cells
            is shut off sharply at hatching
  JOURNAL   Proc. Natl. Acad. Sci. U.S.A. 88 (10), 4503-4507 (1991)
```

FIG. 12-81

```
MEDLINE    91239596
PUBMED     2034690
COMMENT    Original source text: Coturnix coturnix RNA.
           From EMBL entry CCQR1; dated 23-JUN-1991.
FEATURES        Location/Qualifiers
     source     1..2678
                /organism="Coturnix coturnix"
                /db_xref="taxon:9091"
     gene       220..2250
                /gene="QR1"
     CDS        220..2250
                /gene="QR1"
                /codon_start=1
                /protein_id="AAA49499.1"
                /db_xref="GI:213615"
                /translation="MKTVLLICLLGSAFTTPTDPLNYQFGAHGQKTAEKHKYTHSEM
                PEEENTGFVNKGDVLSGHRTIKAEVPVLDTQKDEPWASRRQGQGDGEHQTKNSLRSIN
                FLTLHSNPGLASDNQESNSGSSREQHSSEHHQPRRHRKHGNMAGQWALRGESPVDALG
                LVRERNTWKYNKNTVGLDENNNGSEEEAGEEEDEEWGEETDYRDMKHRARGTSHGRE
                YRRWQNENSRPSGEFLRDSSLPVRITKRHGEKFSMEEESQEKLYKEGKLPLSKKNHNE
                DQGEKRQSEESKEHFQVVNQRKHRAVTKRQDKEGSNAEEDDNDSGDDGEEDLGNVWRE
                AVYEEEERMQSNDQDSITNKQKEEITAGDDSGVYREMQDYKGDKIKDVTHSEDNHYHH
                EPPNSSSKQQLQTSSSVESMNSTEHEDEVKTTGGSYHEESARNSTGKALPDLCRNFHC
                KRGKVCQADKQGKPSCICQDPAACPSTKDYKRVCGTDNKTYDGTCQLFGTKCQLEGTK
                MGRQLHLDYMGACKHIPHCTDYEVNQFPLRMRDWLKNILMQYYERDQDTSAFLTEKQR
                NKVKKIYLNEKRLVSGEHPVELLLHDFEKNYHMYLYPVHWQFYQLDQHPVDRSLTHSE
                LAPLRASLVPMEHCITRFFQECDGDQDKLITLKEWCHCFAIKEEDINENLLF"
```

FIG. 12-82

```
sig_peptide    220..270         SEQ ID NO. 14
               /gene="QR1"
mat_peptide    271..2247
               /gene="QR1"
               /product="unnamed"
CDS            220..2250
               /gene="QR1"
               /codon_start=1
               /protein_id="AAA49500.1"
               /db_xref="GI:213616"
               /translation="MKTVLLLICLLGSAFTTPTDPLNYQFGAHGQKTAEKHKYTHSEM
               PEEENTGFVNKGDVLSGHRTIKAEVPVLDTQKDEPWASRRQGQGDGEHQTKNSLRSIN
               FLTLHSNPGLASDNQESNSGSSREQHSSEHHQPRRHRKHGNMAGQWALRGESPVDALG
               LVRERNTWKYNKNTVGLDENNNGSEEEAGEEEDEEWGEETDYRDMKHRARGTSHGRE
               YRRWQNENSRPSGEFLRDSSLPVRITKRHGEKFSMEEESQEKLYKEGKLPLSKKNHNE
               DQGEKRQSEESKEHFQVVNQRKHRAVTKRQDKEGSNAEEDDNDSGDDGEEDLGNVWRE
               AVYEEERMQSNDQDSITNKQKEEITAGDDSGVYREMQDYKGDKIKDVTHSEDNHYHH
               EPPNSSSKQQLQTSSSVESMNSTEHEDEVKTTGGSYHEESARNSTGKALPDLCRNFHC
               KRGKVCQADKQGKPSCICQDPAACPSTKDYKRVCGTDNKTYDGTCQLFGTKCQLEGTK
               MGRQLHLDYMGACKHIPHCTDYEVNQFPLRMRDWLKNILMQYYERDQDTSAFLTEKQR
               NKVKKIYLNEKRLVSGEHPVELLLHDFEKNYHMYLYPVHWQFYQLDQHPVDRSLTHSE
               LAPLRASLVPMEHCITRFFQECDGDQDKLITLKEWCHCFAIKEEDINENLLF"

BASE COUNT    898 a     570 c     619 g     591 t   SEQ ID NO. 36
ORIGIN
        1 gtcagacctt cctcctcaga agctcacaga aaaacacgct ttctgaaaga ttccacactc
       61 aatgccaaaa tataccacag gaaaattttg caaggctcac ggatttccag tgcaccactg
      121 gctaaccaag taggagcacc tcttctactg ccatgaaagg aaaccttcaa accctaccac
      181 tgagccatta actaccatcc tgtttaagat ctgaaaaaca tgaagactgt attgctcctg
```

FIG. 12-83

```
 241 atttgtcttc taggatctgc tttcaccact ccaaccgatc cattgaacta ccaatttggg
 301 gcccatggac agaaaactgc agagaagcat aaatatactc attctgaaat gccagaggaa
 361 gagaacacag ggtttgtaaa caaggtgat gtgctgtctg gccacaggac cataaaagca
 421 gaggtaccgg tactggatac acagaaggat gagccctggg cttccagaag acaaggacaa
 481 ggtgatggtg agcatcaaac aaaaaacagc ctgaggagca ttaacttcct tactctgcac
 541 agtaatccag ggttggcttc tgataaccag gaaagcaact ctggcagcag cagggaacag
 601 cacagctctg agcaccacca gcccaggagg cacaggaaac acggcaacat ggctggccag
 661 tgggctctga gaggagaaag tccagtggat gctcttggtc tggttcgtga gcgcaacaca
 721 tggaaataca ataaaaacac agttggccta gatgaaaaca acaatggaag tgaagaagag
 781 gaagctgggg aggaagaaga tgaggaatgg ggtgaagaaa ctgattacag ggatatgaaa
 841 cacagagccc gtgggacaag ccatgaaga gaatacagaa gatggcaaaa tgaaaacagc
 901 cggccatctg gtgaattctt gagagattcc agtctgccag tacgtataac caagagacac
 961 ggtgagaaat tcagcatgga ggaggaaagt caggaaaaagc tctacaagga aggaaaactc
1021 cctctctcaa agaaaaatca taatgaggat caagtgaaa aaagacaaag tgaagaaagt
1081 aaagagcatt ttcaagtagt caatcagcgc aaacacagag cagtgacgaa aagcaggat
1141 aaggagggca gcaatgctga ggagatgat aatgatagtg gtgatgatgg gtgatgatgg aaggcaggat
1201 cttggcaatg tctggaggga agcagtctac gaggagaagg aaagaatgca aagcaatgac tgtagaaac
1261 caggacagta tcactaacaa gcaaaaaga agaaattaaa ctggagatga cagtggagtt
1321 tataggaga tgcaggatta caaaggttca ccctaattcc aacagattata atgttactca ctctgaagac
1381 aatcattacc accatgagcc ccctaattcc agcagcaagc aacaactgca aacaagtagc
1441 tctgttgaga gcatgaattc aacagagcat gaggatgagg ttaagaccac aggaggttca
1501 tatcatgagg aaagtgcaag gaacagcact gggaaggctc tcccggatct ttgtagaaac
1561 ttccactgca aaagaggaaa agtctgccaa gcagacaagc aggaaaaacc cagctgtatt
1621 tgccaagatc ctgctgcttg cccttccacc aaagattata agcgtgtttg tggcactgat
1681 aataagactt acgatggtac gtgccacca tttggcacca aatgtcaact tgaaggaca
1741 aaaatgggac gccagctgca cctgactat atgggtgcct gcaaacacat acccactgt
1801 actgattacg aagtgaatca gttccctctc cgtatgagag actggctcaa aaacatccta
1861 atgcaatatt atgaacgtga tcaggatacg tcaggatacg tctgcatttc taaccgaaaa gcaaaggaat
```

FIG. 12-84

```
1921 aaggtcaaaa agatatacct gaatgagaag cgtctcgtct ctggtgagca cccagttgag
1981 cttctcctgc atgactttga gaaaactac cacatgtatc tctatcctgt gcactggcaa
2041 ttttatcagc ttgaccagca cccagttgac agatcactga ctcattcaga gctcgctcct
2101 ttgagagcct ccctcgttcc catggaaccc gtttcttcca ggagtgtgat
2161 ggagaccaag acaaacttat cactttgaaa gagtggtgcc actgctttgc gattaaggaa
2221 gaagacataa atgaaaatct cctgttctga gcccacctga gcagaatccc catgcagcgc
2281 tacagcttgt caaacatgca atgcccattt atgactgcaa ttaacagctc tgttaatttt
2341 caggaataag ttggcataag attcttggag gcagaacaag tcgctcttgg ataacacaag
2401 tgcctaattg ttacaaattc attaacagca gtagtgttta agagctctaa gtagctcata
2461 cttaaagagt gtttccctct gcacgtacca ataatctctt agtaagacga ctaacttgat
2521 gactgagttg ttcacaaaac ccttccgtag ccttttcttt tgtggatttt ataatacacc
2581 gataaaaact actttgaaat aggtttttctt ttcctgtcgt ttactgtcag tagctctctg
2641 catagaaatg tcaaataaac agatcttgtt ttggtttc   SEQ ID NO. 31
```

FIG. 12-85

```
NCBI                                                    Nucleotide

PubMed    Nucleotide    Protein    Genome    Structure    PMC    Taxonomy    OMIM    Boo Search  Nucleotide  for                                            Go   Clear           Details Limits      Preview/Index    History     Clipboard
Display default    Show: 20    Send to  File                Get Subsequence              Links □ 1: NM_008047. Mus musculus foll...[gi:6679870]

LOCUS       Fstl                   2823 bp    mRNA    linear   ROD 19-SEP-2002
DEFINITION  Mus musculus follistatin-like (Fstl), mRNA.
ACCESSION   NM_008047
VERSION     NM_008047.1  GI:6679870
KEYWORDS    .
SOURCE      Mus musculus (house mouse)
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus.
REFERENCE   1  (bases 1 to 2823)
  AUTHORS   Shibanuma,M., Mashimo,J., Mita,A., Kuroki,T. and Nose,K.
  TITLE     Cloning from a mouse osteoblastic cell line of a set of
            transforming-growth-factor-beta 1-regulated genes, one of which
            seems to encode a follistatin-related polypeptide
  JOURNAL   Eur. J. Biochem. 217 (1), 13-19 (1993)
  MEDLINE   94039028
```

FIG. 12-86

```
PUBMED      7901004
COMMENT     PROVISIONAL REFSEQ: This record has not yet been subject to final
            NCBI review. The reference sequence was derived from M91380.1.
FEATURES            Location/Qualifiers
     source         1..2823
                    /organism="Mus musculus"
                    /db_xref="taxon:10090"
                    /chromosome="16"
                    /map="16 27.3 cM"
                    /cell_line="MC3T3-E1"
                    /cell_type="osteoblast"
     gene           1..2823
                    /gene="Fstl"
                    /note="synonyms: TSC-36, AI316791, AW107808"
                    /db_xref="LocusID:14314"
                    /db_xref="MGD:102793"
     CDS            80..1000
                    /gene="Fstl"
                    /codon_start=1
                    /product="follistatin-like"
                    /protein_id="NP_032073.1"
                    /db_xref="GI:6679871"
                    /db_xref="LocusID:14314"
                    /db_xref="MGD:102793"
                    /translation="MWKRWLALSLVTIALVHGEEPRSKSKICANVFCGAGRECAVTE
                    KGEPTCLCIEQCKPHKRPVCGSNGKTYLNHCELHRDACLTGSKIQVDYDGHCKEKKSA
                    SPSASPVVCYQANRDELRRRLIQWLEAEIIPDGWFSKGSNYSEILDKYFKSFDNGDSH
                    LDSSEFLKFVEQNETAINITTYADQENNKLLRSLCVDALIELSDENADWKLSFQEFLK
```

FIG. 12-87

```
                CLNPSFNPPEKKCALEVETYADGAETEVDCNRCVCSCGHWVCTAMTCDGKNQKGVQTH
                TEEEKTGYVQELQKHQGTAEKTKKVNTKEI" SEQ ID NO. 15
                233..367
misc feature   /gene="Fst1"
                /note="KAZAL; Region: Kazal type serine protease
                inhibitors"
                /db_xref="CDD:smart00280"
                239..367
misc feature   /gene="Fst1"
                /note="kazal; Region: Kazal-type serine protease inhibitor
                domain. Usually indicative of serine protease inhibitors.
                However, kazal-like domains are also seen in the
                extracellular part of agrins, which are not known to be
                protease inhibitors. Kazal domains often occur in tandem
                arrays. Small alpha+beta fold containing three
                disulphides. Alignment also includes a single domain from
                transporters in the OATP/PGT family"
                /db_xref="CDD:pfam00050"
                770..913
misc feature   /gene="Fst1"
                /note="VWC_out, Region: von Willebrand factor (vWF) type C
                domain"
                /db_xref="CDD:smart00215"
                1362
variation      /gene="Fst1"
                /allele="A"
                /allele="C"
                /db_xref="dbSNP:3023433"
```

FIG. 12-88

BASE COUNT    762 a    663 c    697 g    701 t
ORIGIN
   1 aagcgacgct cccaccttcg cctctaactc gctgccgcca ccctgcccag tgtcctccgg
  61 agtcccggac ccgagcacga tgtggaaacg atggctggcg ctctcgctgg tgaccatcgc
 121 cctggtccac ggcgaggagg aacctagaag caaatccaag atctgcgcca atgtgttttg
 181 tggagctggc agggaatgtg ccgtcacaga gcctgtgtg cccacgtgcc tctgcattga
 241 gcaatgcaaa cctcacaaga ggcctgcctcac tggcagtaat ggcaagacct acctcaacca
 301 ctgtgaactt catagagatg cctgcctcac tggatccaag atccaggttg attatgatgg
 361 gcactgcaaa gaaaagaagt ctgcgagtcc atctgccagc ccagttgtct gctatcaagc
 421 taaccgcgat gagctccgac ggcgcctcat ccagtggctg gaagctgaga tcattccaga
 481 tggctggttc tctaaaggca gtaactacag tgagatccta gacaagtact ttaagagctt
 541 tgataatggc gactctcacc tggactccag tgaattcctg aaattcgtgg agcagaatga
 601 aacagccatc aacatcacca cttatgcaga tcaggagaac aacaaactgc tcagaagcct
 661 ctgtgttgac gcccctcattg aactgtctga tgagaacgct gactgaaaac tcagcttcca
 721 agagttcctc aagtgcctca accctccctt caacccctct gagaagaagt gtgccctgga
 781 ggtcgaaacc tatgcagatg gagctgagac agctgagct tgcaatcgct gtgtctgttc
 841 ctgtggccac tgggtctgca cagcaatgac ctgtgatgga aagaatcaga agggtgtcca
 901 gacccacaca gaggaggaga agagagata tgtccaggaa ctccagaaagc accaggcac
 961 agcagaaaag accaagaaag tgaacaccaa agagatctaa gaagaggcac agagcaccgt
1021 gtccggagcc cagcgcctcc tcttcagcgc tgagcccagt acacacagag tctgcagcaa
1081 tcaccaaatc actagtattt gcttgtatgg cagcgaatct tattttgttt gttttgcaat
1141 aaaggaaatg agggtggcca gcctagcgag ggaaggccac aacctttcacc tgtaggaatg
1201 ctttaagaga aactaaagga cacccttggga cgagaggcaa ctaaggaaac agcatcgggt
1261 tggcagagga gcagaggcag gtttgaatga agcctttctg gggtcacagc agctgcgagg
1321 agaatacagg aaaagcatag agaaacattg aactagccct gctggaggaa gtggggggag
1381 ctttgtaggg aggaaccctg ctgctttgac ccttgtcacc actgtcagca tgacagacct
1441 gcagcaagtc tgcttctcct tttggtccca acaatcacct gaacacacag ccgcccaact
1501 agttacctgt gtcctcagcc ttgcatggag tttcctggag gaggtgttta aatgatgcag

FIG. 12-89

```
1561 acacttatgt acttcaagcg catggagact aaccaaattt ttaaaataca ttttctttt
1621 tttttttttt ttgttaacca aagtgctat ttctctgtaa aagacttttt tccaagctga
1681 cttcattcct cagttattac cgttatatta ttgttgtttt ttaatatttc atttttgac
1741 tagatattaa gcttttgtaa ttattttca ttagtcctac tatttcgaga agtgaaggtg
1801 aaggggttt gggcattttt ccaggtaca gggaactctg taacacaaac agcccatacc
1861 ctgtcacata ttagaccggt tgcagttcgg agcatgcacc ccaacccaga gcttctagaa
1921 aatcagctcc atgccacgaa ggcacaagag gcccctcagc agaagccaca ggacaaagca
1981 tcttcataga cagctgttga gatccaaaca gttaatttgc ttttgtttct tgtaagaagt
2041 tccaaggatg gacgctcagg ctatcccagc ctgccagcct gctgtgatct gtggctaact
2101 ggcagagtca gccactgtgg tccttagctg ctcctgtttc taggtgtcag tttacttagt
2161 aaactggtaa gaatgaatct tggaatttaa taaatggtag tttgtggttt agccaactgg
2221 tccagaggga gctaccttct ccttaggata gatgaatcta ctcccataaga aaaaccagcc
2281 aggaatagca tggatgggtt ttgctttggt tgaaatgatc ctagcaggtg actgggtatg
2341 aggacttcat ggtcactctg cccaggaaga gagcgtgaag gacaactagc agcttccta
2401 gggatggtac acatgtgtgt gatctctgga gatcagaggt tgccccacac acatgatgat
2461 aaaacttttc agatttagag cggttaaaac tggagatcga atctgattg agaatcagca
2521 ctgggggcag aaactgttat tgaaagtcaa tccttttcttt gagacactcc gaataaacta
2581 tggagatttt cctgcatagg aaagtgtgga atgttgagct attgagatgg gagtggaatt
2641 cgtcctaaat agttttttcc tggtctcatc tgaacaagac aatttgctct gcctagtgtt
2701 ctgtgccctc cctttcaaaa gctctgagcc ccgctcatgc agtccagatt tcatccccct
2761 ctccaagtgc cttggagagc tcacgacagc aatgccatca tcaaaagttt tgctgctggg
2821 aag    SEQ ID NO. 32
```

```
source          1..3484
                /organism="Homo sapiens"
                /db_xref="taxon:9606"
                /clone_lib="lambda gt11"
CDS             435..1754
                /codon_start=1
                /product="testican"
                /protein_id="CAA51999.1"
                /db_xref="GI:793845"
                /db_xref="SPTREMBL:Q08629"
                /translation="MPAIAVLAAAAAWCFLQVESRHLDALAGGAGPNHGNFLDNDQW
                LSTVSQYDRDKYWNRFRDDDYFRNWNPNKPFDQALDPSKDPCLKVKCSPHKVCVTQDY
                QTALCVSRKHLLPRQKKGNVAQKHWVGPSNLVKCKPCPVAQSAMVCGSDGHSYTSKCK
                LEFHACSTGKSLATLCDGPCPCLPEPEPPKHKAERSACTDKELRNLASRLKDWFGALH
                EDANRVIKPTSSNTAQGRFDTSILPICKDSLGWMFNKLDMNYDLLLDPSEINAIYLDK
                YEPCIKPLFNSCDSFKDGKLSNNEWCYCFQKPGGLPCQNEMNRIQKLSKGKSLLGAFI
                PRCNEEGYYKATQCHGSTGQCWCVDKYGNELAGSRKQGAVSCEEEQETSGDFGSGGSV
                VLLDDLEYERELGPKDKEGKLRVHTRAVTEDDEDEDDDKEDEVGYIW" SEQ ID NO. 16
BASE COUNT       894 a       910 c       808 g       872 t
ORIGIN
    1 cactctctgt tgtccaatgg acacacctgt cgtgttttga gccagcgaga gatgcagtgg
   61 aagtgaaaag catggttaca gactcccat gcgacagtac actccttga agtagcggac
  121 gcctggttag cttgacattc tatgcaaaga tccataatgt ggttcctgca gatgcacag
  181 ttatcaacca caatatccca ggcccagagg gctactgcat tccactttt cacttcaaag
  241 cgcttcttgc ccgcgcgct gttggtgccg ctcgggtat ccacatccat cgctgcgggc
  301 tcacaaagcg gccagacgct cgcggcgggc cgtgtggcag agcgcagggg cgcgagcccgg
  361 cgatcagcct tccggcgac cgtgcgcgg gagctcgagc aactcggact agggaccccg
  421 ggccggcccc caagatgccg gcgatcgcg tgttggcggc tgttcctgca ggccgcccgc gcgtggtgct
```

```
 481 tcctccaagt cgagagccgg cacctggacg cgctcgccgg aggcgcgggc cccaaccacg
 541 gcaatttcct agacaatgac cagtggctga gcaccgtctc ccagtacgac cggacaagt
 601 actggaaccg ctttcgagac gatgattatt tcagaaactg gaatcccaac aagcccttg
 661 accagccct ggacccatcc aaggacccct gcctgaaggt aaaatgcagc cctcacaaag
 721 tgtgtgtgac ccaggactac cagaccgccc tgtgtgtcag ccgcaagcac ctgctcccca
 781 ggcaaaagaa ggggaacgtg gcccagaaac actgggttgg accttcgaat ttggtcaagt
 841 gcaagccctg tcccgtggca cagtcagcca tggtctgcgg ctcagatggc cactcctaca
 901 catccaagtg caaattggag ttccatgctt gttctactgg caaaagcctc gccacctct
 961 gtgatgggcc ctgtccctgt ctcccagagc ctgagccacc aaagcacaag gcagaaagga
1021 gtgcctgcac agacaaggag ttgcggaaac ttgcctcccg gctgaaggat tggtttggag
1081 ctctccacga ggatgcgaac agagtcatca agcccaccag ctccaacaca gcccaaggca
1141 ggtttgacac tagcatcctg cccatctgca aggactccct gggctggatg ttcaacaagt
1201 tggacatgaa ctatgacctc ctgcttgacc cttcagagat caatgccatc tacctggata
1261 agtacgagcc ctgtatcaag cctcttttca actcgtgtga ctccttcaag gatggcaagc
1321 tttctaacaa tgagtggtgc tactgcttcc agaagcctgg agtctcccct tgccagaatg
1381 aaatgaacag aattcagaag ctgagtaagg ggaaaagcct gttggggcc ttcatacctc
1441 ggtgtaatga ggagggctat tacaaagcca cacagtgcca cggcagcacg gggcagtgct
1501 ggtgtgtgga caaatatggg aatgagttgg ctggctccag gaaacaggt gctgtgagct
1561 gtgaagagga gcaggaaaacc tcaggggatt ttggcagtgg tgggtccgtg gtcctgctgg
1621 atgacctaga atatgaacgg gagctgggac caaaggacaa agaggggaag ctgagggtgc
1681 acaccccgagc cgtgacagag gatgatgagg atgaggatga gacacaagtt tgacaaagag gatgaggtcg
1741 ggtacatatg gtagtgccca caagaaagag gacacaagtt ttgcacaaaa ttgcaagtca
1801 cttcctattc ctgcatttgt atctaagact ccaaggcacc aaggtctctt ctccattgtt
1861 gctctctata cccgacctaa ggtttggaag acaactgctt gttcccagag gattctgatt
1921 ttgcatatgt ttgtatggga gaaaggggtgt tgtgttttt ttttggttgt tgttttattt
1981 ttggataggg aagtcattgg cttaattaga aattctgaca gcctccttcc tttctgtgag attttccaa
2041 caagcatgtg atttacgtgg aattctgaca gtgcaggag ccccaccct cttaaatgtc
2101 aaagaccctt tttgattacc cacactggtg gttattacag catggttccc agccttacag
```

FIG. 12-93

```
2161 tgtctaagtg cttctcttgt gtcctgtaga tgttgtgaaa aagaaaaaaa caaaaatac
2221 accacactgt actttttccc cctgccccg ttactgccgg tgattattat taaaaattag
2281 ttttttcac atcattctat ctggcttcct ataaacaaca gccttaattc agtcaagact
2341 cccttggga attcatttta ttaaaaattg gtgtctggat acttccctgt acatgcataa
2401 atatgcatgc atgtacagaa agactgtatg tgtgtgcctt gcacacacac ccatacctct
2461 cagaaaaagt gtttgggtat cttaaaaact cgaaaaacaa tgataaattt ctcagcttgt
2521 ccagacctgg aacaaaattt ctggaataag aaatttgtat taaagtcctt ttttgcacta
2581 acagttggct cttgtagcct gcaggctgag gaagtctctt ctctgtgcat cagcagagtt
2641 actgaaagcc tctgattgag aaaaaacctc cgtctgccta aatcacttttt ctcgcagaag
2701 ccatgcgact cccacacgac acgggcagct tcacaagcca tctctttcat ttctgcttga
2761 agcccttgg ctgcagcaat cctgtctgcc ataggtttct tccttcctta cctactcaag
2821 ggcttttttct aaggcatgca cacatatctc ctgttctctg agagtaccat ggtgttcctt
2881 aaaagaagaa aatttctaat tctgaactca atgttttgct tttactccct ttctactgac
2941 aaatcatgat aagggcacaa aagctgtaca gatttttttt tttaaccact caatcccaaa
3001 tggaggccta caaagaacat cgtaataaca catggaagca catgaaagac ttttaagagc
3061 aaattctgtc cccccctcac tccccccaagt gacaagatac taatgaagaa agttcttcac
3121 catagtgttt gtttaacta aactcattgg agtctagttc caaatttggt agggtcatca
3181 tctctacatt ccttaggatt tctctcccta ttcctttcagt accagtctat ccagatacaa gtaccaaaca
3241 gtagtctctg aagttcccat ccagggtgtc ctaatcagaa tcagccaccc aagctactgt ccgccactga
3301 ttttcatcta tcaggggtgc ctaatcagaa tcagccaccc aagcaagcct ctctggccca
3361 catatctatc tcttgccttc cccatgaac ttcagcctgt ccacacaaaa gccacataaa
3421 ctcaagcaag aaatatgttc agccaaaaca tgattatagt ggcagctgac caatacccca
3481 cccc SEQ ID NO. 33
```

FIG. 12-94

Nucleotide

PubMed  Nucleotide  Protein  Genome  Structure  PMC  Taxonomy  OMIM  Boo

Search Nucleotide ▽ for [                    ]  Go  Clear

Limits  Preview/Index  History  Clipboard  Details

Display default ▽  Show: 20 ▽  Send to File ▽  Get Subsequence  Links

☐ 1: NM_022137. Homo sapiens secr...[gi:24475656]

```
LOCUS       SMOC1                   3669 bp    mRNA    linear   PRI 05-NOV-2002
DEFINITION  Homo sapiens secreted modular calcium-binding protein 1 (SMOC1),
            mRNA.
ACCESSION   NM_022137
VERSION     NM_022137.2  GI:24475656
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1
  AUTHORS   Vannahme,C., Smyth,N., Miosge,N., Gosling,S., Frie,C., Paulsson,M.,
            Maurer,P. and Hartmann,U.
  TITLE     Characterization of SMOC-1, a Novel Modular Calcium-binding Protein
            in Basement Membranes
```

FIG. 12-95

| | | |
|---|---|---|
| JOURNAL | J. Biol. Chem. 277 (41), 37977-37986 (2002) | |
| MEDLINE | 22254804 | |
| COMMENT | PROVISIONAL REFSEQ: This record has not yet been subject to final NCBI review. The reference sequence was derived from AJ249900.1. On Nov 2, 2002 this sequence version replaced gi:11545872. | |
| FEATURES | Location/Qualifiers | |
| source | 1..3669 | |
| | /organism="Homo sapiens" | |
| | /db_xref="taxon:9606" | |
| | /chromosome="14" | |
| | /map="14q24.1" | |
| | /tissue_type="brain" | |
| | /dev_stage="fetal" | |
| | /tissue_lib="stretch cDNA library Clontech" | |
| gene | 1..3669 | |
| | /gene="SMOC1" | |
| | /db_xref="LocusID:64093" | |
| CDS | 255..1559 | |
| | /gene="SMOC1" | |
| | /codon_start=1 | |
| | /product="secreted modular calcium-binding protein 1" | |
| | /protein_id="NP_071420.1" | |
| | /db_xref="GI:11545873" | |
| | /db_xref="LocusID:64093" | |
| | /translation="MLPARCARLLTPHLLLVLVQLSPARGHRTTGPRFLISDRDPQCN LHCSRTQPKPICASDGRSYESMCEYQRAKCRDPTLGVHRGRCKDAGQSKCRLERAQA LEQAKKPQEAVFVPECGEDGSFTQVQCHTYTGYCWCVTPDGKPISGSSVQNKTPVCSG | |

FIG. 12-96

```
              SVTDKPLSQGNSGRKDDGSKPTPTMETQPVFDGDEITAPTLWIKHLVIKDSKLNNTNI
              RNSEKVYSCDQERQSALEEAQQNPREGIVIPECAPGGLYKPVQCHQSTGYCWCVLVDT
              GRPLPGTSTRYVMPSCESDARAKTEADDPFKDRELPGCPEGKKMEFITSLLDALTTD
              MVQAINSAAPTGGGRFSEPDSHTLEERVVHWYFSQLDSNSSNDINKREMKPFKRYVK
              KKAKPKKCARRFTDYCDLNKDKVISLPELKGCLGVSKEGRLV" SEQ ID NO.37
sig peptide   255..332
              /gene="SMOC1"
mat peptide   333..1556
              /gene="SMOC1"
              /product="smoc-1"
misc feature  375..515
              /gene="SMOC1"
              /note="kazal; Region: Kazal-type serine protease inhibitor
              domain. Usually indicative of serine protease inhibitors.
              However, kazal-like domains are also seen in the
              extracellular part of agrins, which are not known to be
              protease inhibitors. Kazal domains often occur in tandem
              arrays. Small alpha+beta fold containing three
              disulphides. Alignment also includes a single domain from
              transporters in the OATP/PGT family"
              /db_xref="CDD:pfam00050"
misc feature  378..515
              /gene="SMOC1"
              /note="KAZAL; Region: Kazal type serine protease
              inhibitors"
              /db_xref="CDD:smart00280"
misc feature  537..728
```

FIG. 12-97

```
misc_feature    /gene="SMOC1"
                /note="thyroglobulin_1; Region: Thyroglobulin type-1
                repeat. Thyroglobulin type 1 repeats are thought to be
                involved in the control of proteolytic degradation. The
                domain usually contains six conserved cysteines. These
                form three disulphide bridges. Cysteines 1 pairs with 2, 3
                with 4 and 5 with 6"
                /db_xref="CDD:pfam00086"
                597..737
misc_feature    /gene="SMOC1"
                /note="TY; Region: Thyroglobulin type I repeats"
                /db_xref="CDD:smart00211"
                933..1130
                /gene="SMOC1"
misc_feature    /gene="SMOC1"
                /note="thyroglobulin_1; Region: Thyroglobulin type-1
                repeat. Thyroglobulin type 1 repeats are thought to be
                involved in the control of proteolytic degradation. The
                domain usually contains six conserved cysteines. These
                form three disulphide bridges. Cysteines 1 pairs with 2, 3
                with 4 and 5 with 6"
                /db_xref="CDD:pfam00086"
                996..1136
misc_feature    /gene="SMOC1"
                /note="TY; Region: Thyroglobulin type I repeats"
                /db_xref="CDD:smart00211"
                956
variation
```

FIG. 12-98 variation       /gene="SMOC1"
                     /allele="T"
                     /allele="C"
                     /db_xref="dbSNP:3825739"
                     complement(2487)
                     /allele="T"
                     /allele="C"
                     /db_xref="dbSNP:2273780"
                     2939
     variation       /gene="SMOC1"
                     /allele="G"
                     /allele="A"
                     /db_xref="dbSNP:3742912"
                     2968
     variation       /gene="SMOC1"
                     /allele="G"
                     /allele="A"
                     /db_xref="dbSNP:3742913"
                     2993
     variation       /gene="SMOC1"
                     /allele="T"
                     /allele="C"
                     /db_xref="dbSNP:3742914"
                     3648..3653
     polyA_signal    /gene="SMOC1"

BASE COUNT     842 a    988 c    1026 g    813 t
ORIGIN

FIG. 12-99

```
   1 gcctgctgcc gcctgggccc cgccgagcgg agctagcgcc gcgcgcagag cacacgctcg
  61 cgctccagct cccctcctgc gcggttcatg actgtgtccc ctgaccgcag cctctgcgag
 121 cccccgcgc  aggaccacgg cccgctcccc gccgcgcgga gggccccgag cgaaggaagg
 181 aagggaggcg cgctgtcgc  cccgcggagc ccgcgaaccc cgctcgctgc cggctgccca
 241 gcctggctgg caccatgctg cccgcgcgct gcgcccgcct gctcacgccc cacttgctgc
 301 tggtgttggt gcagctgtcc cctgctcgcg gccaccgcac cacaggcccc aggtttctaa
 361 taagtgaccg tgacccacag tgcaacctcc actgctccag gactcaaccc aaaccatct
 421 gtgcctctga tggcaggtcc tacgagtcca tgtgtgagta ccagcgagcc aagtgccgag
 481 acccgaccct gggcgtggtg catcgagtta gatgcaaaga ccaggccag  tgctggccag agcaagtgtc
 541 gcctggagcg ggctcaagcc ctggagcaag ccaagaagcc tcaggaagct gtgtttgtcc
 601 cagagtgtgg cgaggatggc tcctttaccc aggtgcagtg ccatacttac actgggtact
 661 gctgtgtgt  cacccccgat gggaagccca tcagtggctc ttctgtgcag aataaaactc
 721 ctgtatgttc aggttcagtc accgacaagc ccttgagcca gggtaactca ggaaggaaag
 781 atgacgggtc taagccgaca cccacgatgg agacccagcc ggtgttcgat ggagatgaaa
 841 tcacagcccc aactctatgg attaaacact tggtgatcaa ggactccaaa ctgaacaaca
 901 ccaacataag aaattcagag aaagtctatt cgtgtgacca ggagaggcag agtgccctgg
 961 aagaggccca gcagaatccc cgtgagggta ttgtcatccc tgaatgtgcc cctggggac
1021 tctataagcc agtgcaatgc caccagtcca ctggctactg ctgtgtgtg  ctggtggaca
1081 cagggcgccc gctgcctggg acctccacac gctacgtgat gccagttgt  gagagcgacg
1141 ccagggccaa gactacagag gcggatgacc ccttcaagga ccttcaagct caggagcta  ccaggctgtc
1201 cagagggaa  gaaaatggag tttatcacca gcctactgga tgctctcacc actgacatgg
1261 ttcaggccat taactcagca gcgcccactg gaggtgggag gttctcagag ccagacccca
1321 gccacaccct ggaggagcgg gtagtgcact ggtatttcag ccagctggac agcaatagca
1381 gcaacgacat taacaagcgg gagatgaagc cctttcaagg ctactgtgaa cctgaacaaa aagaaagcca
1441 agcccaagaa atggcccgg  cgtttcaccg actactgtga cctgaacaaa gacaaggtca
1501 tttcactgcc tgagctgaag ggctgcctgg gtgttagcaa agaaggacgc ctcgtctaag
1561 gagcagaaaa cccaagggca ggtggagagt ccagggaggc aggatggatc accagacacc
```

FIG. 12-100

```
1621 taaccttcag cgttgccat ggccctgcca catcccgtgt aacataagtg gtgccacca
1681 tgtttgcact tttaataact cttacttgcg tgttttgttt ttggtttcat tttaaaacac
1741 caatatctaa taccacagtg ggaaaggaa actatattgc gactttattc tctctcttat
1801 tgtaagtttt tggatctgct actgacaact tttagagggt tttggggggg tgggggaggg
1861 tgttgttggg gcctgagaag aaagagattt atatgctgta tataaatata tatgtaaatt
1921 gtatagttct tttgtacagg cattgcatt gctgtttgtt tattctctc cctctgcctg
1981 ctgtgggtgg tgggcactct ggacacatag tccagctttc taaaatccag gactctatcc
2041 tgggcctact aaacttctgt ttggagactg acccctgtgt ataaagacgg gagtcctgca
2101 attgtactgc ggactccacg agttctttc tgtgggagg actatattgc cccatgccat
2161 tagttgtcaa aattgataag tcacttggct ctcggccttg tccagggagg ttgggctaag
2221 gagagatgga aactgccctg ggagaggaag ggagtccaga tcccatgaat agcccacaca
2281 ggtaccggct ctcagagggt ccgtgcattc ctgctctccg gacccccaaa gggcccagca
2341 ttggtgggtg caccagtatc ttagtgaccc tcggagcaaa ttatccaca aggatttgca
2401 ttacgtcact cgaaacgttt tcatccatgc ttagcatcta ctctgtataa cgcatgagag
2461 gggagcaaa gaagaaaagg acacacggaa gggcctttaa aaaagtagat atttaatatc
2521 taagcagggg aggggacagg acagaaagcc tgcactgagg ggtgcggtgc caacaggaa
2581 actcttcacc tccctgcaaa cctaccagtg aggctcccag agacgcagct gtctcagtgc
2641 ccaggggcag attgggtgtg accctctcac tcctccatct cctgctgttg tcctagtggc
2701 tatcacaggc ctgggtgggt gggttggggg aagtgtcagt caccttgttg gtaacactaa
2761 agttgttttg ttggttttt aaaaacccaa tactgaggtt cttcctgttc cctcaagttt
2821 tcttatgggc ttccaggctt taagctaatt ccagaagtaa aactgatctt gggtttccta
2881 ttctgcctcc cctagaaggg cagggtgat aacccagcta caggaaatc ccggcccagc
2941 tttccacagg catcacaggc atcctccgcg gattctaggg tgggctgccc agccttctgg
3001 tctgaggcgc agctccctct gcccagtgc tgtgcctatt caagtggcct tcaggcagag
3061 cagcaagtgg cccttagcgc cccttcccat aagcagctgt ggtggcagtg agggaggttg
3121 ggtagccctg gactggtccc ctcctcagat caccctttgca aatctggcct catcttgtat
3181 tccaacccga catcccctaa agtacctcca cccgttccgg gtctggaagg cgttggcacc
```

FIG. 12-101

```
3241 acaagcactg tccctgtggg aggagcacaa ccttctcggg acaggatctg atggggtctt
3301 gggctaaagg agtccctgc tgtcctggag aaagtcctag aggttatctc aggaatgact
3361 ggtggccctg cccaacgtg gaaggtggg aaggaagcct tctcccatta gccccaatga
3421 gagaactcaa cgtgccggag ctgagtgggc cttgcacgag acactgcccc cactttcagg
3481 cctggaggaa gcatgcacac atggagacgg cgcctgcctg tagatgtttg gatcttcgag
3541 atctccccag gcatcttgtc tcccacagga tcgtgtgtgt aggtggtgtt gtgtgtttt
3601 cctttgtgaa ggagagaggg aaactattg tagcttgttt tataaaaat aaaaaatggg
3661 taaatccttg SEQ ID NO. 38
```

FIG. 12-102

```
NCBI                                                  Nucleotide

PubMed    Nucleotide   Protein   Genome   Structure   PMC   Taxonomy   OMIM   Boo Search  Nucleotide ▽  for                                    Go  Clear       Details Limits     Preview/Index   History     Clipboard
Display default ▽  Show: 20 ▽  Send to File ▽    Get Subsequence ☐ 1: BC004617. Mus musculus, Sim...[gi:13435493]                              Links LOCUS        BC004617              1611 bp     mRNA     linear  ROD 20-SEP-2002
DEFINITION   Mus musculus, Similar to transcription factor 19 (SC1), clone
             MGC:6711 IMAGE:3585301, mRNA, complete cds.
ACCESSION    BC004617
VERSION      BC004617.1  GI:13435493
KEYWORDS     MGC.
SOURCE       Mus musculus (house mouse)
  ORGANISM   Mus musculus
             Eukaryota; Metazoa; Chordata; Craniata; Vertebrata; Euteleostomi;
             Mammalia; Eutheria; Rodentia; Sciurognathi; Muridae; Murinae; Mus.
REFERENCE    1  (bases 1 to 1611)
  AUTHORS    Strausberg,R..
  TITLE      Direct Submission
  JOURNAL    Submitted (21-MAR-2001) National Institutes of Health, Mammalian
             Gene Collection (MGC), Cancer Genomics Office, National Cancer
```

FIG. 12-103

```
REMARK       Institute, 31 Center Drive, Room 11A03, Bethesda, MD 20892-2590,
             USA
             NIH-MGC Project URL: http://mgc.nci.nih.gov
COMMENT      Contact: MGC help desk
             Email: cgapbs-r@mail.nih.gov
             Tissue Procurement: Gilbert Smith, Ph.D.
             cDNA Library Preparation: Life Technologies, Inc.
             cDNA Library Arrayed by: The I.M.A.G.E. Consortium (LLNL)
             DNA Sequencing by: Baylor College of Medicine Human Genome
             Sequencing Center
             Center code: BCM-HGSC
             Web site: http://www.hgsc.bcm.tmc.edu/cdna/
             Contact: amg@bcm.tmc.edu
             Gunaratne, P.H., Garcia, A.M., Lu, X., Hulyk, S.W., Hale, S.M.,
             Yoon, V.S., Kowis, C.R., Lawrence, S., Martin, R.G., Muzny, D.M.,
             Richards, S., Gibbs, R.A.

Clone distribution: MGC clone distribution information can be found
             through the I.M.A.G.E. Consortium/LLNL at: http://image.llnl.gov
             Series: IRAK Plate: 10 Row: 1 Column: 11
             This clone was selected for full length sequencing because it
             passed the following selection criteria: GenomeScan gene
             prediction, Similarity but not identity to protein.
FEATURES          Location/Qualifiers
     source       1..1611
                  /organism="Mus musculus"
                  /strain="FVB/N"
                  /db_xref="taxon:10090"
```

FIG. 12-104

```
      /clone="MGC:6711 IMAGE:3585301"
      /tissue_type="Mammary tumor. Metallothionien-TGF alpha
      model. 10 month old virgin mouse. Taken by biopsy."
      /clone_lib="NCI_CGAP_Mam1"
      /lab_host="DH10B"
      /note="Vector: pCMV-SPORT6"
CDS   360..1151
      /codon_start=1
      /product="Similar to transcription factor 19 (SC1)"
      /protein_id="AAH04617.1"
      /db_xref="GI:13435494"
      /translation="MLPCFQLLRIGGGRGGDLYTFHPPSKSGCTYGLGCRADLCDVAL
      RPQQEPGLISGVHAELHAELQGDDWRVSLEDHSSQGTLVNNVRLPRGHRLELSDGDLL
      TFGPQGQAGTSSSSEFYMFQQVRVKPQDFAAITVPRSKGEAGGFQPMLPPQGAPQR
      PLSTLSSAPKATLILNSIGSLSKLQAQPLTFSRGGRPQGLAIPSQHGEAQVSPAPPT
      RNRRKSAHKVLAELDDEVSPGPLSVLTEPRKRLRVEKAALIASGE" SEQ ID NO. 17
BASE COUNT   393 a     456 c     417 g     345 t
ORIGIN
  1 ggaatccctt cctcagttta cccgcgagc gaaaaaaga aaggattgtc ggaggctccc
 61 ggatgttgag ccgcctgagg atccggcttc actgaggtgc cacaagacgt cttcctgtt
121 ttgcatcgca tcaggacttt actggaattg cttttaaac ctcatcttga cagcctctgt
181 cttgtgcat atccaggcct ctggcgctct gaatctgcac tgcttaagtt ggcattaggc
241 acaatactta gctgttgaca tcagagagaa ctgaattgaa gcccacggtg catgacccag
301 gagtaggaga gggaatggac ttctgaggtg ggcgaagtgg ggggcggcag tgcagagggg gcaccccca
361 tgctgccctg tttccagctg ctgcgtatag gcgcacct atggattggg ctgcagggcc ctctacacct
421 tccacccccc gtccaagtct ggctgcact caggagcccg gcctcatctc tggagtccat gacctgtgtg
481 atgtggccct gcggcccct caggagcccg caggagcccg gcctcatctc tggagtccat gcgaattgc
541 atgctgaact ccaagggggac gactggaggg tcagcctgga ggatcacaga agccaaggga
```

FIG. 12-105

```
 601 ctttggtcaa taatgtccga cttccaagag gccacagact ggagttgagt gatggtgacc
 661 ttctgacctt tggcccccaa ggtcaagcag gaaccagctc ctccctcagag ttctacttca
 721 tgtttcaaca agtccgggtt aaacctcagg actttgcagc ctccctcagc cctcgtcta
 781 agggagaagc tggggcggt ttccaaccta tgctgccccc ccaagggca cctcagaggc
 841 cactcagcac tctctcctct gcccccaagg cctctcacct tctcaattcc atcggcagcc
 901 tcagcaaact ccaggcccaa gggaaagcgc tctcccgtgg tggtggcagg ccacagggcc
 961 tggctattcc ctctcagcat ctctcagcat aagtttcgcc tgctccaccc acaagaaacc
1021 ggaggaaatc agctcataaa gtgttggcag agctagatga cgaggtctcc ccaggcccccc
1081 tgtccgtcct gacggagccc tccggggtgga agaagagcc aggaagaggc gaaagctgct ctgatagcca
1141 gtggggaatg accacaggga aggtccatt gctaaagact gactcaaggc tggagaatgc
1201 ttgcaaatga agtgacagaa agatggtttt cctgccaaag atgttgcagc ctccaagttt
1261 ccagtgagct acaagcccag tcacaaggaa cctgccatga ggtatggttt tgccaggata
1321 cctgcagtta gagcaccggt cccagaaacc attcctagaa taaccctact tatttttgctg
1381 aagccatcg ataccaggca agtgctctgc cacaataccc ttcccaaggc catgttcttg
1441 aatggcatcg gctaaagcat cctgaaggac ccagagcaca ttcccaaggc atcctcatgc
1501 caccgctagc tagtatcacc accagctgag tctctgggac tagcttttca gagcttagtc
1561 tttattccca aataaagaat aaactgtttc atccaaaaaa aaaaaaaaaa a SEQ ID NO. 34
```

```
                                                    Majority
TGG - - - AGAGTGTAT - TGAACTTGAATT - TC - -
                    |         |         |
                   210       220

206  TGG - - - - - - AAGTAGGA - - GAATTTGA - - - - -   4507170-SPARC.seq
221  TGA T - - - AGACTGTAT - TGCTCCTGATTTGTC - - -     213614-QR-1.seq
251  TGC - - - - - AGAGGGGAT - TCAACTTCAAATTTC - - -   21359870-Hevin.seq
401  CAG CCCTCACAAAGTGTGTGACCCAGGACTACCAGACC            15451924-SPOCK.seq
158  TG - - - - - - - - - - - - - - - - - - - T - - -  13242264-FRP.seq Majority
- TTCTGTGGATCTGG - TCCAGCACCT - -
          |         |
         230

225  - - - - - - - - - - - - - - - CA - - -            4507170-SPARC.seq
248  - - TTCTA - GGATCTGCTTTCACCACTC - -                213614-QR-1.seq
278  - - TGCAGTGCTCTGGGTCCAGCCCCT - - -                 21359870-Hevin.seq
441  GCCCTGTGTCAGCCGCAAGCACCTGCTCCCCAGGCAAA             15451924-SPOCK.seq
160  - TTTTGTGGAGCTGG - - - - - - - - - -               13242264-FRP.seq
```

```
                GCACAAACTGAGAGATG---AACCCCAGCCCCCA-CAGAA  Majority
                                    |      |
                       350         360    370
350  CCACCAGCTG----------------------CCCAGCCCCCA-TTGG--GCA  4507170-SPARC.seq
435  GGATACACAGAAGGATG---AGCCCTGGCTTC--CAGAA-----TCA  213614-QR-1.seq
470  GAAGAAAATGAAAAAGA---AACAGCAGTCCA-CAGAA-----ATC  21359870-Hevin.seq
721  GCACAGACAAGGAGTTGCGGAACCTTGCCTCCCGGCTGAA-----GTC  15451924-SPOCK.seq
220  -----------ATTGAGCAATG---------CAAACCTCA-CAAGA  13242264-FRP.seq GG-----CGAGTCTGAGCGTGAGGGTGAGCA-----GTC  Majority
                        |       |
                       380     390
375  ----------CGAGTTTGA----GAAGGTGTGCA-----GCA  4507170-SPARC.seq
470  GA-----CAAGGACAAG-GTGATGGTGAGCA-----TCA  213614-QR-1.seq
506  GA-----CGATTCCACCATAAGCTGAAAA-----ATC  21359870-Hevin.seq
761  GGATTGGTTTGGAGCTCTCCACGAGGATGCGAACAGAGTC  15451924-SPOCK.seq
245  GG-----C-------CTGTGTGG--------  13242264-FRP.seq
```

```
                              ATCTTTGCCACA------GTGAGG-TCACT  Majority
                                         |
                                        440
     431  -TCTTTGCCACA------------        4507170-SPARC.seq
     578  ACTCTGGCAGCA---------           213614-QR-1.seq
     618  ATCAAGAGGACA------GTGATGGTCACT  21359870-Hevin.seq
     961  AGCCCTGTATCAAGCCTCTTTCAACTCGTGTGACTCCTT  15451924-SPOCK.seq
     275  ACCTCAACCATT------GTGA------ACT  13242264-FRP.seq TAAGTACAGC---TCTG---GAGTA-TGC-ACCAC  Majority
                                             |            |
                                            450          460
     442  -AAGTGCA-C------CCTG----GAGG--GC-ACCAA  4507170-SPARC.seq
     600  ---GCACAGC-----TCTG---AGCA-C--C-ACCAG  213614-QR-1.seq
     642  TAAGTGTGAA----TTTG---GAGTA-TGC-ACCAA  21359870-Hevin.seq
    1001  CAAGGATGGCAAGCTTTCTAAACAAATGAGTGGTGCTACTGC  15451924-SPOCK.seq
     294  T----CACA-------------GAG-A-CGC--CTGC  13242264-FRP.seq

|  |  | Majority |
|--|--|--|
| ...CGAGTGGTGA---AGGAGAAT | | Majority |

| | | | |
|--|--|--|--|
| 640 | ...AGATCCAT | 4507170-SPARC.seq |
| 857 | ...AAGAGAAT | 213614-QR-1.seq |
| 915 | ...AGAGGAAG | 21359870-Hevin.seq |
| 1361 GAAGCTGAGGGTGCACACCCGAGCCGTGACAGAGGATGAT | 15451924-SPOCK.seq |
| 470 | . | 13242264-FRP.seq |

| | | Majority |
|--|--|--|
| GAGGATGAGGGTCATG...TGAAGTCAGT-ACC | | Majority |

| | | | |
|--|--|--|--|
| 658 GAGAATGAGAAGCGCC...TGGAGGCAGGAGAC | 4507170-SPARC.seq |
| 875 ACAGAAGATGGCAAAA...TGAAAACAGCCGGC | 213614-QR-1.seq |
| 933 AAGAAAAAGAGCCAGG...TGAAGTTGGT-ACC | 21359870-Hevin.seq |
| 1401 GAGGATGAGGATGATGACAAAGAGGAGGTCGGGTACA | 15451924-SPOCK.seq |
| 470 - - - - - - - - - GGTTCTC - - - - - TAAAGGCAGT-AAC | 13242264-FRP.seq |

FIG. 13-18

```
                    CACCGTGGTGACCAC-AGAGAGA------TAC Majority
                           |          |
                          690        700

688   CACCCCG-TG-------------GAGC----TGC  4507170-SPARC.seq
905   CATC-TGGTGAATTCTTGAGAGA---------TTC  213614-QR-1.seq
962   CACAATGATAACCAAGAAAAGAAA--------GAC  21359870-Hevin.seq
1441  TATGGTAGTGCCCACAAAGAGGACACAAGTTTGCAC 15451924-SPOCK.seq
490   TACAGTG----------AGA------------TCC  13242264-FRP.seq ---CCAGTACTTATA-CTAA Majority
                              |
                             710

704   TG---GC-------CCGGGACTT----CGA  4507170-SPARC.seq
930   CAGTCTGC------C-AGTACGTATAACCAA 213614-QR-1.seq
988   AGAATTGC-----CCAGGGAGCATG-CTAA  21359870-Hevin.seq
1481  AAAATTGCAAGTCACTTCCTATTCCTGTATCTAA 15451924-SPOCK.seq
503   TAGA-----------CAAGTACTT----TAA 13242264-FRP.seq
```

FIG. 13-19

```
                    Majority
        GA-----GGCACCATGA----------------------------------------
               |  720  |  730
    720 GA-----AGAACTATAA----------------------------------------  4507170-SPARC.seq
    954 GA-----GACACGGTGA----------------------------------------  213614-QR-1.seq
   1012 CA----AGCAAGCAGGA----------------------------------------  21359870-Hevin.seq
   1521 GACTCCAAGGCACCAAGGTCTCTTCTCCATTGTTGCTCTC-----------------  15451924-SPOCK.seq
    519 GA-----GC---------------------------------------------TC-  13242264-FRP.seq Majority
        -----GGAATACAAACT-----------------------------------TCC
             |   740    |
    732 -----CATGTACATCT-------------------------------------TC-  4507170-SPARC.seq
    966 -----GAAATTCAGCA-------------------------------------TGG  213614-QR-1.seq
   1024 -----GGAAGACAATA-------------------------------------CCC  21359870-Hevin.seq
   1561 TATACCCGACCTAAGGTTTGGAAGACAACTGCTTGTTCCC----------------  15451924-SPOCK.seq
    523 -----------------------------------------------------t--  13242264-FRP.seq
```

```
                    ACCGAGCAG---------------------------------AAAGA- Majority 805   -ACCGAGC---------------------------------------- 4507170-SPARC.seq
1052  -A--AGGTGA--------------------------AAAAA-       213614-QR-1.seq
1116  -ACCAAGAAC--------------------------AAGAA-       21359870-Hevin.seq
1761  GACAGTGCAGGGAGCCCCACCCTCTAAATGTCAAAGAC           15451924-SPOCK.seq
571   -GTGGAGCAG--------------------------AATGA-       13242264-FRP.seq GATAACTC-CACTG-CAGTAA---ACAGCAT-GT Majority 812   ---------TGGCTC-CACTG-C------------C----------   4507170-SPARC.seq
1064  ---GACAAGT-GAAGA-AAGTAA---AGAGCATTT-          213614-QR-1.seq
1130  ---GATAACTC-CAATG-CAG-AA---ATGGAAGAGG         21359870-Hevin.seq
1801  CCTTTTGATTACCACACTGGTGGTTATTACAGCATGGT        15451924-SPOCK.seq
595   -AACAGCC------------------GTCA--ACA           13242264-FRP.seq
```

```
                      ---GACAACA-------------CTGGTCAAGA--- Majority

847   ----CATTGCA-------------CCACCC--------- 4507170-SPARC.seq
1147  ---GGCAGCA-------------ATGCTGAGGA------ 213614-QR-1.seq
1214  ---GGTAAAA-------------CTGGCCTAGA------ 21359870-Hevin.seq
2001  TCCTATAAACAAACAGCCTAATTCAGTCAAGACTCCTTT 15451924-SPOCK.seq
622   ----AACAACA---------------------------- 1324264-FRP.seq -GGA----TATTAA-AAT-------------------- Majority 860   --------------------------------------- 4507170-SPARC.seq
1164  -GGA---TGATAATGAT---------------------- 213614-QR-1.seq
1231  -AGC---TATCAGCAAC---------------------- 21359870-Hevin.seq
2041  GGGAATTCATTTATTAAAAATTGGTGTCTGGATACTTCC 15451924-SPOCK.seq
629   --------------------------------------- 1324264-FRP.seq
```

```
                                                                              Majority    
                                                                                          4507170-SPARC.seq
- A - A G - - - - - - - - - - - - - - - - - - - - - - - - - - - - - - - - -              213614-QR-1.seq
                              -       -                                                   21359870-Hevin.seq
1036 - - - - - - - - - - - - - - - - - - - - - - - - - - - - - - - - - - - -
1419 - G C A - - - - - - - - - - - - - - - - - - - - - - - - - - - - - - - -
1481 - A G A G - - - - - - - - - - - - - - - - - - - - - - - - - - - - - - -
2481 C A T A G G T T T C T T C C T T C C T A C C T C A A G G C T T T T C     15451924-SPOCK.seq
746  - - A G - - - - - - - - - - - - - - - - - - - - - - - - - - - - - - - - 13242264-TRP.seq

- A A G A A G T G C A X A C A - A T T T G C T G T T C T - - - - G G T A G C A   Majority
                              |              |              |
                            1040           1050           1060
1036 - - A A T G T T T G G A T G - G T T T G T T C T - - - - - - G - - C C      4507170-SPARC.seq
1422 - - A C A A C T G C A A A C A - A G T A G C C T C T G T T - - - - -        213614-QR-1.seq
1485 - - A A A A G T A C A T G A A - A A T G A A A A T A T A - - - - - - -      21359870-Hevin.seq
2521 T A A G G C A T G C A C A C A T C C T G T T C T C T G A G A G C A          15451924-SPOCK.seq
748  - - A A G A A G T G C G - - - - - - - - - - - - - - - - - - - G G - A G G A 13242264-TRP.seq
```

```
                                                                    Majority
      -GTGCTGGTCTCTGC-CAACT-TTCGCCACTAAAT---GT
                  |         |              |
                 1260      1270           1280

1260 ---GCTGGGCTCTGC------C--------TTAAAC----AC  4507170-SPARC.seq
1691 -ACGGATGGTACGTGC--CAACTCTTTGGCAACCAAAT---GT  213614-QR-1.seq
1758 -ATGCTAGTTCCTGT-CATCTATTCGCTACTAAAT----GC  21359870-Hevin.seq
2961 AGTACCAGTCTATAAGCTACTGTCCGCACTGATTTCAT  15451924-SPOCK.seq
857  -GTGATGG----------------------------  13242264-FRP.seq Majority
      CXATT-GAG-----------GGGATCAG-----AAGGGGG
                                    |
                                   1281

1281 ACATT----------------------GCAG  4507170-SPARC.seq
1726 CAACTTGAA--------GGGACAAA---AATGGGA  213614-QR-1.seq
1793 AGACTGGAG--------GGGACCAA---AAAGGGG  21359870-Hevin.seq
3001 CTATCAGGGTGTCCTAATCAGAATCAGCCACCCAAGCAAG  15451924-SPOCK.seq
864  ----AA-----------AGAATCAG---AAGGGGG  13242264-FRP.seq
```

```
                                              TACTTA-CCTGTACA-GATTTTGG----AGTG Majority 1327  -------------------------------------------------TG  4507170-SPARC.seq
1790  ----TACTTA-CCGAGTCA-GACTTTG-------------------TG  213614-QR-1.seq
1857  ----TACCCC-ACTGTACT-GATTACGA------------AGTG  21359870-Hevin.seq
3121  ---TTCCTA-CTTGTACG-GACTTGA------------AGTG  15451924-SPOCK.seq
891   AAGAAATATGTTCAGCCAAAACATGATTATAGTGGCAGCT  13242264-FRP.seq
      ---CAC------------A GA----A G------GG----AG-----

ATTCAGTTTTCCT-TTCCGGAT-----GAGAGACTG Majority

1350  -TTCA-TTTCAT-TTCAGGGT-------------CTTGG-CTG  4507170-SPARC.seq
1816  AATCAGTTCCCT-CTCCGTAT-------------GAGACTG  213614-QR-1.seq
1883  ATTCAGTTTCCT-CTACGGAT-------------GAGACTG  21359870-Hevin.seq
3161  GACCAAATCCCCATCCCAAATTGACCATTAGATGTACCA  15451924-SPOCK.seq
901   ------------------------------------t-----GAGA-TG  13242264-FRP.seq
```

FIG. 13-40

```
                                                 Majority
       ---AGGATATCCC------CAGGCGGCATTA           Majority
GCTCA                 |              |
                    1380           1390
1376  ----CCTG---------------CAGGTGGCCT---       4507170-SPARC.seq
1845  GCTCA---------------TGGGCTTGCCC-----       213614-QR-1.seq
1912  GCTCA------AAACATCCT---AATGCAATATA---      21359870-Hevin.seq
3201  ACTCACCCTAAATTAGCATG--AGATATCCT------CATGCAGCTTTA---  15451924-SPOCK.seq
907   AC----------------------TTCCAATCCAGTCGGCATTG---   13242264-FRP.seq
                                                  GAGATATGCC---CAGG Majority
       --TGAA----GGTAACTCCGGAC--ATA-CTGGTTTT      Majority
                |              |
              1400           1410
1400  ----GGA---GGT------AAA---GGG                4507170-SPARC.seq
1872  ----TGAA----CGTGA-TCAGGAT--ACGTCTGCATTT     213614-QR-1.seq
1939  ----TGAA----GCCAACTCTGAAC--ATG-CTGGTTAT     21359870-Hevin.seq
3241  CCTGAATACAGTAGCATACCTATAGTTGGTCTTAGAT       15451924-SPOCK.seq
923   -------------AACTCCAGAA--GCACCAGG           13242264-FRP.seq
```

```
                    EDGDGHLSVNLLYAP-SEGTLDIKEDMIEP-QEKKLSEST Majority

101  EDSDGHLSVNLEYAP-TEGTLDIKEDMIEP-QEKKLSENT  SPARC.pro
 53  TQGRF---DTSILPICKDSLGWMFNK1DMN-YDLLDHSE   TESTICAN.pro
101  EDSDGHLSVNLEYAP-TEGTLDIKEDMIEP-QEKKLSENT  HEVIN.pro
 54  SRGGY---SVTLRPS-SVGVPW-FTKVTLQREFVRTTPE   FRP.pro
 93  QTKNSLRSINFLTLH-SNPGLASDNQE9NS-GSSREQHSS  QR1.pro D-------------FLA-------------------- Majority 139  D-------------FLAP SPARC.pro
 89  INAIYLDKYEPCIKPLENSCDSFKDGKLSNNEWCYCFQ- TESTICAN.pro
139  D-------------FLAP HEVIN.pro
 89  D-------------LE-- FRP.pro
131  E-------------MHQ- QR1.pro

FIG. 13-63
```

```
                                ----FTDSNQQESIT-----KREENQEQPRNYSHHQL-NRS Majority
                                       |              |              |
                                      150            160            170

144 G V S G F T D S N Q Q E S I T - - - - - K R E E N Q E Q P R N Y S H H Q L - N R S  SPARC.pro
   127 - - - - - - - - - - - - - - - - - - - - - - - - - - - - - - - - - - - - - - - -   TESTICAN.pro
   144 G V S S F T D S N Q Q E S I T - - - - - K R E E N Q E Q P R N Y S H H Q L - N R S  HEVIN.pro
    92 - - - - - - - - - - - - - - - - - - - - - - - - - - - - - - - - - - - - - - - -   FRP.pro
   135 - - - P R R K H G N M A G Q W A L R G E S P V D A L G L V R E R N T W K Y         QR1.pro SKHSQG---LREQGNIEQ----ISNGEEEEKEPGEVGTHND Majority
                                       |              |              |
                                      180            190            200            210

179 S K H S Q G - - - L R D Q G N Q E Q D P N I S N G E E E E K E P G E V G T H N D  SPARC.pro
   127 - K P G G L P C Q N E M N R I Q K - - L S K G - - - - - - - - - - - - - - - -  TESTICAN.pro
   179 S K H S Q G - - - L R D Q G N Q E Q D P N I S N G E E E E K E P G E V G T H N D  HEVIN.pro
    92 - R S V T L - - E K E I E Q I E D - - - S I Q A - - - - - - - - - - - - - - -  FRP.pro
   171 N K N T V G - - L D E N N G S E - - E E E A G E E E D E E W G E E T D Y R D    QR1.pro
```

FIG. 13-64

```
                                      - - - - - - - - - - - - - - - RATELPGEHA - - - - - - G S  Majority
                                                                    |        |              |
                                                                    220                     230

217 N Q E - - - - - - - - - - - - - - - RKTELPREHA - - - - - - - N S  SPARC.pro
147 - - KSLLGAFIPRCNEEGYYKATQCHGSTGQCWCVDKYGN  TESTICAN.pro
227 N Q E - - - - - - - - - - - - - - - RKTELPREHA - - - - - - - N S  HEVIN.pro
110 - - - - - - - - - - - - - - - - - - NAAAIAGEAE - - - - - - - G N  FRP.pro
206 M K H - - - - - - - - - - - - - - - RARGTSHGRE - - - - - - - Y R  QR1.pro

- E Q E E - - - N T Q S D D I L E E S D Q P T Q V S K M Q E D E F D Q G N E E  Majority
                |              |              |              |
                240            250            260

232 - KQEE - - - DNTQSDDILEESDQPTQVSKMQEDEFDQGNQE  SPARC.pro
184 - ELAG - - - SRKQGTV - - - - - - - - - - - - SCEE  TESTICAN.pro
232 - KQEE - - - DNTQSDDILEESDQPTQVSKMQEDEFDQGNQE  HEVIN.pro
122 - ELGGTWTSQKRSTAL - - - - - - - - - - - - SKTK  FRP.pro
221 RWQNE - - - NBRPSGEEFIRDSSLPVRITKRHGEKFSNEEES  QR1.pro
```

FIG. 13-65

```
                           330              340               350
                            |                |                 |
    : PTDDGNTTPRNAGVDDDGDDDGDDDGGTDGPRHSASD--  Majority 322 MEPTDDGNTTPRNHGVDDDGDDDGDDDGGTDGPRHSASD--  SPARC.pro
229 ---KEGKLRVHTRAVREDDEDDDDKEDEVGLCFIGNTPL   TESTICAN.pro
322 MEPTDDGNTTPRNHGVDDDGDDDGDDDGGTDGPRHSASD--  HEVIN.pro
170 --QA-----MAYARALVVGFELD--------YMDDL---   FRP.pro
337 --YEEERMQSNDQDSITNKQKEEITAGDDSGVYREMQ--   QR1.pro 360             370                380
                             |                |                  |
    ---D--I--PG--QAFLEAERAQ-SIAYHL--KIEEQK     Majority 360 ---DYFI-PS--QAFLEAERAQ-SIAYHL--KIEEQR     SPARC.pro
266 LIKMSPL--GFFPGFHSFQQHKMSST-LSYALI--FCEIGK  TESTICAN.pro
360 ---DYFI-PS--QAFLEAERAQ-SIAYHL--KIEEQR     HEVIN.pro
191 ---F---SFAD--AFGASRLREACVNF-VD--LCKRKN    FRP.pro
373 ---D--Y-KG--DKIKDVTHSE-DNHYHHEPPNSSK      QR1.pro
```

FIG. 13-67

```
                    E K V Q E N E V - - - - - - - I G T T E P G E H Q E A K K A E N S S N E  Majority
                           |                     |                       |
                          390                   400                     410

388  E K V H E N E N - - - - - - - - - - I G T T E P G E H Q E A K K A E N S S N E  SPARC.pro
301  E - - Q N A R V S S G W K E V A N T R E A M A S - - - - - - - - - - - - - -   TESTICAN.pro
388  E K V H E N E N - - - - - - - - - - I G T T E P G E H Q E A K K A E N S S N E  HEVIN.pro
218  E - - D R M N V - - - - - - - - - - D Q I T A - - - - - - - - - - - - - - -   FRP.pro
401  Q Q L Q T S S S - - - - - - - - - - V E S M N S T E H E D E V K T T G G S Y H  QR1.pro E E T S S E G N M R V H - V D S C M S F Q C K R G H I C K A D Q Q G K P H C V C  Majority
                           |                     |                       |
                          420                   430                     440                     450

417  E E T S S E G N M R V H - V D S C M S F Q C K R G H I C K A D Q Q G K P H C V C  SPARC.pro
323  - - - - - - - - - - - - V N K L I - D K                                         TESTICAN.pro
417  E E T S S E G N M R V H A V D S C M S F Q C K R G H I C K A D Q Q G K P H C V C  HEVIN.pro
229  - - - - - - - M Q A F P - R P                                                   FRP.pro
430  E E S A R N S T G K A L - P D L C R N F H C K R G K V C Q A D K Q G K P S C I C  QR1.pro
```

FIG. 13-68

```
                    QDPVTCPPTKPLDQVCGTDNQTYASSCHLFATKCRLEGTK  Majority
                              |              |              |
                             460            470            480            490

457   QDPVTCPPTKPLDQVCGTDNQTYASSCHLFATKCRLEGTK  SPARC.pro
329   QDPVTCPPTKPLDQVCGTDNQTYASSCHLFATKCRLEGTK  TESTICAN.pro
457   QDPVTCPPTKPLDQVCGTDNQTYASSCHLFATKCRLEGTK  HEVIN.pro
235   QDEAACPSTKDYKRVCGTDNKTYDGTCQLFEGTK         FRP.pro
469   QDEAACPSTKDYKRVCGTDNKTYDGTCQLEGTKCQLEGTK  QR1.pro KGHQLQLDYFGACKSIPTCTDFEVIQFPLRMRDWLKNILM  Majority
                              |              |              |
                             500            510            520            530

497   KGHQLQLDYFGACKSIPTCTDFEVIQFPLRMRDWLKNILM  SPARC.pro
329   KGHQLQLDYFGACKSIPTCTDFEVIQFPLRMRDWLKNILM  TESTICAN.pro
497   KGHQLQLDYFGACKSIPTCTDFEVIQFPLRMRDWLKNILM  HEVIN.pro
235   KGHQLQLDYFGACKSIPTCTDFEVIQFPLRMRDWLKNILM  FRP.pro
509   MGRQLHLDYMGACKHIPHCTDYEVNQFPLRMRDWLKNILM  QR1.pro
```

FIG. 13-69

```
            QLYEANSEHAGYLNEKQRNKVKKIYLDEKRLLAGDHPIDL Majority
                         |         |         |
                        540       550       560       570

537  QLYEANSEHAGYLNEKQRNKVKKIYLDEKRLLAGDHPIDL  SPARC.pro
329                                            TESTICAN.pro
537  QLYEANSEHAGYLNEKQRNKVKKIYLDEKRLLAGDHPIDL  NEVIN.pro
235                                            FRP.pro
549  QYYERDQDTSAFLTEKQRNKVKKIYLNEKRLVSGEHPVEL  QR1.pro LLRDEKKNYHMYVYPVHWQFSELDQHPMDRVLTHSELAPL Majority
                         |         |         |
                        580       590       600       610

577  LLRDEKKNYHMYVYPVHWQFSELDQHPMDRVLTHSELAPL  SPARC.pro
329                                            TESTICAN.pro
577  LLRDEKKNYHMYVYPVHWQFSELDQHPMDRVLTHSELAPL  NEVIN.pro
235                                            FRP.pro
589  LLHDFEKNYHMYLYPVHWQFYQLDQHPVDRSLTHSELAPL  QR1.pro
```

FIG. 13-70

NORMAL COLON

ADENOCARCINOMA

MUCINOUS ADENOCARCINOMA

MIVER METASTASIS

CANCER THERAPY SENSITIZER

RELATED APPLICATION(S)

This application is a continuation of Application No. PCT/US04/000901, filed Jan. 14, 2004, which claims the benefit of U.S. Provisional Application No. 60/440,009, filed on Jan. 14, 2003. The entire teachings of the above applications are incorporated herein by reference.

FIELD OF THE INVENTION

The invention relates to cancer therapy sensitizing compositions and methods.

BACKGROUND

The reason for cancer treatment failures following induction with chemotherapy or radiation therapy is still unclear. Many factors have been implicated in therapeutic resistance, such as upregulation of efflux pumps from multidrug resistance family (MDR) p-glycoprotein and other non-classical MDR proteins (multidrug resistance-associated protein, MRP; lung resistance protein, LRP) have been described in a variety of cancers (Lehnert, M. Anticancer Res 1998; 18:2225-2226; Ringborg, U. and Platz, A. Acta Oncol 1996; 5:76-80; Shea, T. C., Kelley, S. L., and Henner, W. D. Cancer Res 1998; 48:527-533). Unfortunately, many tumors that are intrinsically resistant to chemotherapy, such as the gastrointestinal malignancies, have relatively low levels of expression of the MDR genes. For example, only 23% of primary colorectal tumors express MRP and 65% express p-glycoprotein (Filipits M, Suchomel R W, Dekan G, Stigilbauer W, Haider K, Depisch D, Pirker R. Br. J. Cancer 1997; 75: 208-212). Therefore, resistance to therapeutic agents cannot be explained solely on the basis of activation and up-regulation of known MDR genes. Studies have also shown that genetic mutations responsible for tumorigenesis may also contribute to drug resistance. For example, loss of DNA mismatch repair (MMR) genes found in hereditary non-polyposis colorectal cancer (HNPCC), have been associated with a more rapid emergence of clinical drug resistance (de las Alas M M, S Aebi, D Fink, S B Howell, G Los. J Natl Canc Inst 1997; 89:1537-41; Lin X, Howell S B (1999). Mol Pharmacol 56:390-5). Mutations in the K-ras gene, detected in approximately 40% of adenomatous polyps and adenocarcinomas, are associated with an increased relapse rate, mortality and a poor chemotherapeutic response (Arber N, I. Shapira, J. Ratan et al. Gastroenterology 2000; 118:1045-1050). Genes involved in cell cycle regulation, such as p21 and p27, have been shown to protect tumors from undergoing apoptosis elicited by various anticancer agents (Waldman T, Lengauer C, Kinzler K W, Vogelstein B. Nature 1996, 381:713-716; St. Croix B, Florenes V A, Rak J W, Flanagan M, Bhattacharya N, slingerland J M, Kerbel R S. Nature Med 1996, 2:1204-1210). In addition, cell adhesion molecules, such as E-cadherin, confer resistance to cells when exposed to chemotherapeutic agents (Skoudy A, Llosas M D, Garcia de Herreros A. Biochem J 1996).

The mechanisms involved in therapeutic resistance therefore appear to be very complex. Recent evidence suggests that the selectivity of chemotherapy for the relatively few tumors ever cured by drugs depends, to a large extent, upon their easy susceptibility to undergo apoptosis, i.e., to kill themselves (Makin G, Expert Opin Ther Targets. 2002 6(1):73-84; Johnstone R W, Ruefli A A, Lowe S W, Cell. 2002 108(2): 153-64; Kamesaki H, Int J Hematol. 1998 68(1):29-43).

Secreted protein acidic and rich in cystein (SPARC) belongs to a family of extracellular proteins, called matricellular proteins. Since its identification and cloning, the functional role of SPARC remains unclear. Its high evolutionary conservation suggests an important physiological role for this protein (Iruela-Arispe M L, Lane T F, Redmond D, Reilly M, Bolender R P, Kavanagh T J, Sage E H. Mol Biol Cell. 1995 March; 6(3):327-43). Initial studies showed that SPARC is important in bone mineralization (Termine J D, Kleinman H K, Whitson S W, Conn K M, McGarvey M L, Martin G R. Cell. 1981 October; 26(1 Pt 1):99-105). While SPARC is expressed at high levels in bone tissue, it is also distributed widely in other tissues and cell types (Maillard, C., et al., Bone, 13:257-264 (1992)). Its role has been expanded to include tissue remodeling (Latvala T, Puolakkainen P, Vesaluoma M, Tervo T. Exp Eye Res. 1996 November;63(5):579-84; Kelm R J Jr, Swords N A, Orfeo T, Mann K G. J Biol. Chem. 1994 Dec. 2;269(48):30147-53); endothelial cell migration (Hasselaar P, Sage E H. J Cell Biochem. 1992 July;49(3):272-83), morphogenesis (Mason I J, Murphy D, Munke M, Francke U, Elliott R W, Hogan B L. EMBO J. 1986 August; 5(8):1831-7; Strandjord T P, Sage E H, Clark J G. Am J Respir Cell Mol. Biol. 1995 September; 13(3):279-87), and angiogenesis (Kupprion C, Motamed K, Sage E H. J Biol. Chem. 1998 Nov. 6; 273(45):29635-40; Lane T F, Iruela-Arispe M L, Johnson R S, Sage E H. J Cell Biol. 1994 May; 125(4):929-43). SPARC has also been shown to have an antiproliferative effect on endothelial cells, mesangial cells, fibroblasts and smooth muscle cells (Sage E H. Biochem Cell Biol. 1992 July; 70(7):579-92).

Experiments in vitro have also identified SPARC in tumors (Schulz, A., et al., Am. J. Pathol., 132:233-238 (1988); Porter, P. L., et al., J. Histochem. Cytochem., 43:791-800 (1995)). There is conflicting evidence that SPARC can function either as an oncogene, as suggested by studies in melanoma (Ledda M F, Adris S, Bravo A T, Kairiyama C, Bover L, Chernajovsky Y, Mordoh J, Podhajcer O L. Nat Med. 1997 February; 3(2):171-6) or as a tumor suppressor, as demonstrated by its strong inhibition of growth in vJun-ml and v-Src-transformed chicken embryo fibroblasts (Vial E, Castellazzi M. Oncogene. 2000 Mar. 30; 19(14):1772-82). Although the growth inhibitory properties of SPARC have been mainly shown in primary cells, such as endothelial, fibroblast, mesangial and smooth muscle cells, this may also contribute to the role of SPARC in tumorigenesis. SPARC has also been shown to have tumor invasive properties. Variable SPARC expression has been observed in a variety of cancers. Higher levels of expression have been detected in breast cancer (Bellahcene A, Castronovo V. Am J Pathol. 1995 January; 146(1):95-100), esophageal cancer (Porte H, Triboulet J P, Kotelevets L, Carrat F, Prevot S, Nordlinger B, DiGioia Y, Wurtz A, Comoglio P, Gespach C, Chastre E. Clin Cancer Res. 1998 June; 4(6): 1375-82), hepatocellular carcinoma (Le Bail B, Faouzi S, Boussarie L, Guirouilh J, Blanc J F, Carles J, Bioulac-Sage P, Balabaud C, Rosenbaum J. J Pathol. 1999 September; 189 (1):46-52), and prostate (Thomas R, True L D, Bassuk J A, Lange P H, Vessella R L. Clin Cancer Res 2000; 6:1140-1149). However, conflicting results have been seen with ovarian cancers (Brown T J, Shaw P A, Karp X, Huynh M H, Begley, Ringuette M J. Gynecol Oncol 1999; 75: 25-33; Paley P J, Goff B A, Gown A M, Greer B E, Sage E H. Gynecol Oncol 2000; 78: 336-341; Yiu G K, Chan W Y, Ng S W, Chan P S, Cheung K K, Berkowitz R S, Mok S C. Am J Pathol 2001; 159:609-622), and colorectal cancers (Porte H, Chastre E, Prevot 5, Nordlinger B, Empereur S, Basset P, Chambon P, Gespach C. Int J Cancer 1995; 64: 70-75; Lussier C, Sodek J, Beaulieu J F. J Cell Biochem. 2001;81(3):463-76).

Recently, SPARC has been suggested to be involved in inducing apoptosis of ovarian cancer cells (Yiu G K, Chan W Y, Ng S W, Chan P S, Cheung K K, Berkowitz R S, Mok S C. Am J Pathol 2001; 159:609-622). Yiu et al. (2001, supra) has showed that there was downregulation of SPARC expression following malignant transformation, and that there were antiproliferative properties of SPARC on both normal ovarian and cancer cells. Yiu et al. (2001, supra) further provided additional evidence that exogenous exposure to SPARC alone was capable of inducing apoptosis in ovarian cancer cells. However, human pathological specimens of tumors with high SPARC expression levels have not been shown to have higher number of apoptotic cells.

WO0202771 discloses a novel hSPARC-h1 polypeptide and its potential applications in tissue remodeling, tissue repair and general modulation of various growth factor activities.

U.S. Pat. No. 6,387,664 provides a SPARC fusion protein obtainable by fusing SPARC to thioredoxin which can be used for basic research in neurobiology and/or for treating various neuropathologies.

U.S. Pat. No. 6,239,326 provides a SPARC-deficient transgenic mouse model for testing drugs in promoting or retarding wound healing and treating or preventing cataracts, diabetes mellitus or osteoporosis.

All references cited herein above and throughout the specification, including patents, patent applications, are hereby incorporated by reference in their entirety.

SUMMARY OF THE INVENTION

The invention is based on the discovery that SPARC sentitizes cancer therapy.

The present invention provides compositions and methods for sensitizing cancer therapeutic treatment.

The present invention provides a composition comprising a SPARC family polypeptide and a chemotherapy agent.

The present invention provides a composition comprising a SPARC family polypeptide and a chemotherapy-resistant cell.

The present invention provides a chemotherapy-resistant cell comprising a recombinant SPARC family polynucleotide.

The present invention provides a recombinant cell comprising a heterologous transcription control region operatively associated with a SPARC family polynucleotide.

In another aspect, the present invention provides a method for in vivo sensitizing a mammal to a therapeutic treatment, the method comprising administrating to the mammal diagnosed with cancer an effective amount of a SPARC family polypeptide or a polynucleotide encoding a SPARC polypeptide.

The present invention provides a method for ex vivo sensitizing a mammal diagnosed with cancer to a therapeutic treatment, the method comprising: administering to a mammal an effective amount of a cell comprising a SPARC family polypeptide or a polynucleotide encoding a SPARC family polypeptide; wherein the cell produces an increased amount of the SPARC polypeptide.

The present invention also provides a method for ex vivo sensitizing a mammal diagnosed with cancer to a therapeutic treatment, the method comprising: (1) Obtaining a cancer sample from the mammal; (2) contacting the cancer sample with an effective amount of a composition comprising a SPARC family polypeptide or a polynucleotide encoding a SPARC polypeptide; and (3) returning the cancer sample after the contacting of (2) to the mammal.

The present invention further provides a method for sensitizing a cancer sample to a therapeutic treatment, the method comprising contacting the cancer sample with an effective amount of a composition comprising a SPARC family polypeptide or a polynucleotide encoding a SPARC polypeptide.

In one embodiment of the invention, the cancer sample is a cell or tissue sample.

In another embodiment of the invention, the cancer sample is transfected or infected with the polynucleotide of (e)-(f).

The present invention provides a method for evaluating a first cancer cell for its resistance to a therapeutic treatment, comprising: (a) measuring the expression level of a SPARC family mRNA or polypeptide, or the extracellular level of a SPARC family polypeptide in the first cancer cell; and (b) comparing the expression level or the extracellular level obtained in (a) with the expression level of the SPARC family mRNA or polypeptide, or the extracellular level of the SPARC family polypeptide in a second cancer cell which does not exhibit resistance to the therapeutic treatment; wherein a lower level of expression or extracellular level in (a) is indicative of the first cancer cell being resistant to the therapeutic treatment.

The present invention provides a method for evaluating a first cancer cell for its resistance to a therapeutic treatment, comprising: (a) measuring expression level of a SPARC family mRNA or polypeptide, or extracellular level of a SPARC family polypeptide in the first cancer sample; (b) measuring expression level of the SPARC family mRNA or polypeptide, or extracellular level of the SPARC family polypeptide in a second cancer sample which does not exhibit resistance to the therapeutic treatment; (c) comparing the expression levels or the extracellular levels obtained in (a) and (b), where a lower level of expression or extracellular level in (a) is indicative of the first cancer sample being resistant to the therapeutic treatment.

In one embodiment, the first sample is from a first mammal and the lower level of expression or extracellular level in (a) is further indicative of the first mammal being resistant to the therapeutic treatment.

In another embodiment, the second cancer sample is from a first mammal who provides the first cancer sample.

In yet another embodiment, the second cancer sample is from a second mammal who is different from the first mammal providing the first cancer sample.

Preferably, the first mammal and the second mammal are diagnosed with the same cancer.

In one embodiment, the expression level of the SPARC family mRNA is measured by polymerase chain reaction, DNA microarray or northern blot.

In one embodiment, the expression or extracellular level of the SPARC family polypeptide is measured by Immuno Blotting or Enzyme-Linked Immunosorbent Assay (Elisa).

The present invention provides a method for identifying an agent which modulates a SPARC family mRNA or polypeptide expression, or a SPARC family polypeptide secretion, comprising: (a) measuring expression level of the SPARC family mRNA or polypeptide, or extracellular level of the SPARC family polypeptide in a sample; (b) contacting a candidate agent with the sample; (c) after the contacting of (b), measuring expression or extracellular level of the SPARC family mRNA or polypeptide, or extracellular level of the SPARC family polypeptide in the sample of (b); (d) comparing the expression levels or the extracellular levels in (a) and (c), where a differential level of expression or extracellular level in (a) and (c) indicates the candidate agent being an agent which modulates the SPARC family mRNA or polypeptide expression, or the SPARC family polypeptide secretion.

The present invention also provides a method for identifying an agent which sensitizes a cancer sample to a therapeutic treatment, comprising: (a) measuring expression level of a SPARC family mRNA or polypeptide, or extracellular level of a SPARC family polypeptide in the cancer sample; (b) contacting a candidate agent with the cancer sample; (c) after the contacting of (b), measuring expression level of the SPARC family mRNA or polypeptide, or extracellular level of the SPARC family polypeptide in the cancer sample of (b); (d) comparing the expression levels or the extracellular levels obtained in (a) and (c), where an increased level of expression or extracellular level in (c) indicates the candidate agent being an agent which sensitizes a cancer sample to a therapeutic treatment.

In one embodiment, the cancer sample of the subject method is from a mammal diagnosed with cancer, and the increased level of expression or extracellular level is further indicative of the candidate agent being an agent which sensitizes the mammal to a therapeutic treatment.

The present invention provides a method for determining a therapeutic treatment protocol for a first mammal diagnosed with cancer, comprising: (a) determining if expression of a SPARC family mRNA or polypeptide or extracellular level of a SPARC family polypeptide is lower in a first sample from the first mammal than a second sample which does not exhibit resistance to the therapeutic treatment; and (b) if (a) is positive, increasing the strength of the therapeutic treatment to the first mammal so as to increase the response to the treatment.

Preferably, the polynucleotide of (e) or (f) of the subject composition and method is an expression vector.

More preferably, the expression vector is a plasmid or a viral vector.

In one embodiment, the plasmid vector is pcDNA3.1.

The SPARC family polypeptide or a polynucleotide encoding a SPARC family polypeptide of the present invention include: (a) a SPARC polypeptide which is selected from the group consisting of SEQ ID Nos. 1-17; (b) a polypeptide having an amino acid sequence of at least 60% homology to the SPARC family polypeptide in (a); (c) a polypeptide fragment of (a)-(b) where the fragment is at least 50 amino acids in length; (d) a fusion polypeptide comprising the polypeptide of (a), (b), or (c); (e) a polynucleotide encoding the polypeptide of (a), (b), (c) or the fusion polypeptide of (d); or (f) a polynucleotide hybridizing to the polynucleotide of (e) under a stringent hybridization condition.

Preferably, the SPARC family polypeptide or polynucleotide of the present invention is selected from: SMOC-1, SPARC, hevin, SC1, QR-1, follistatin-like proteins (TSC-36), testican.

Preferably, the therapeutic agent of the subject composition and method is a chemotherapy agent or a radiation therapy agent.

More preferably, the therapeutic agent is selected from the group consisting of the agents listed in Table 1.

In one embodiment, the mammal of the subject method exhibits resistance to the therapeutic treatment.

In one embodiment, the therapeutic treatment is chemotherapy or radiation therapy.

In one embodiment, the cancer sample of the subject method is a cell or a tissue sample.

Preferably, the cell or tissue sample is lysed before the measuring of the expression or extracellular level of a SPARC family polypeptide or polynucleotide (e.g., mRNA).

More preferably, a polynucleotide or polypeptide extract is obtained from the cell or tissue sample before the measuring of the expression or extracellular level of a SPARC family polypeptide or polynucleotide (e.g., mRNA).

BRIEF DESCRIPTION OF THE DRAWINGS

The foregoing features of the invention will be more readily understood by reference to the following detailed description, taken with reference to the accompanying drawings:

FIG. 8 is a FACS analysis showing cell populations induced to undergo apoptosis following exposure to chemotherapeutic agents according to one embodiment of the invention.

DETAILED DESCRIPTION

Figure 1:
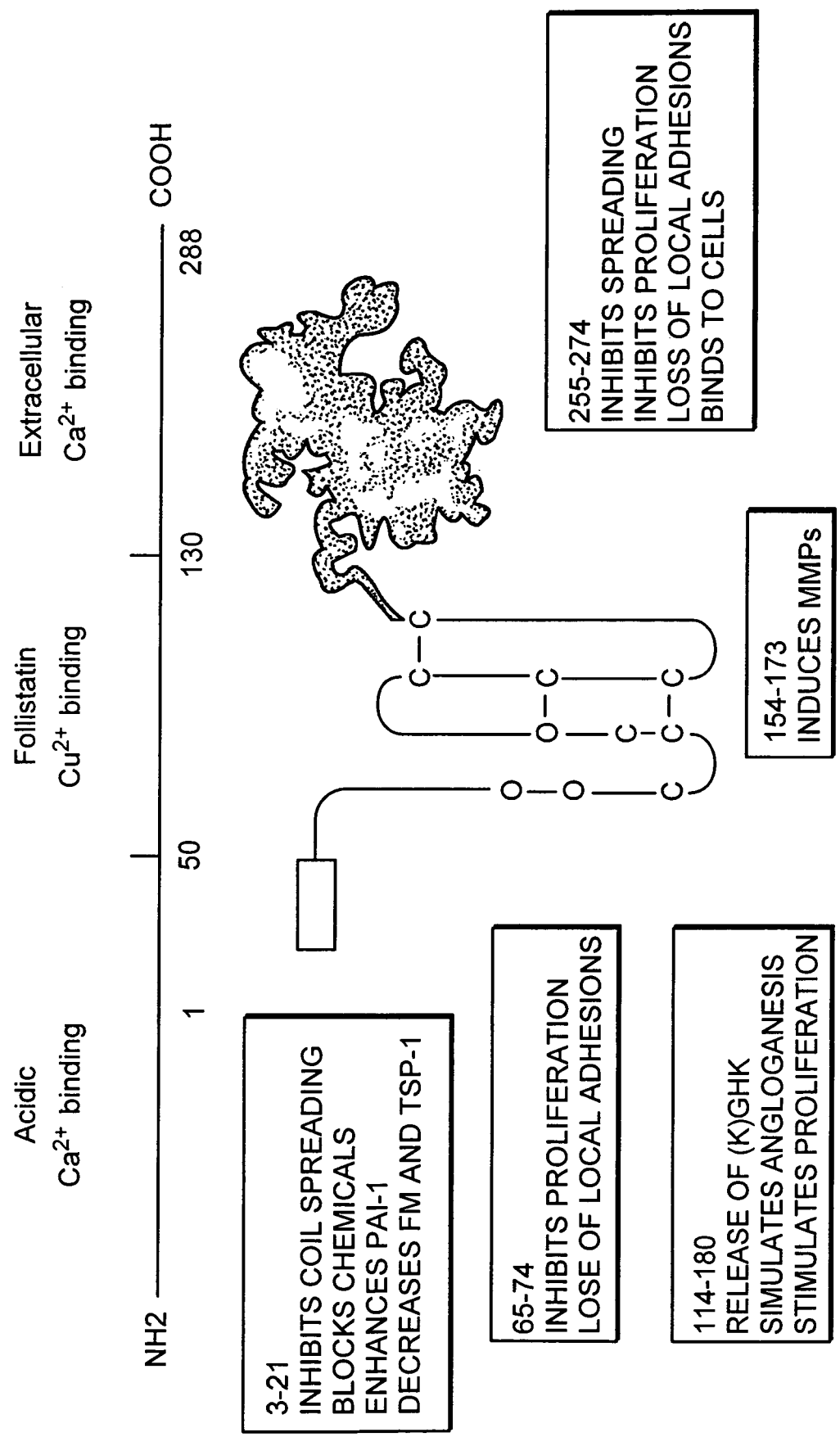
FIG. 1 is a modular structure of human SPARC and the location and functions of synthetic peptides. Three domains and their residue numbers are shown as described in Yan and Sage, 1999, J. Histochem. & Cytochem. 47(12):1495-1505.
Figure 2:
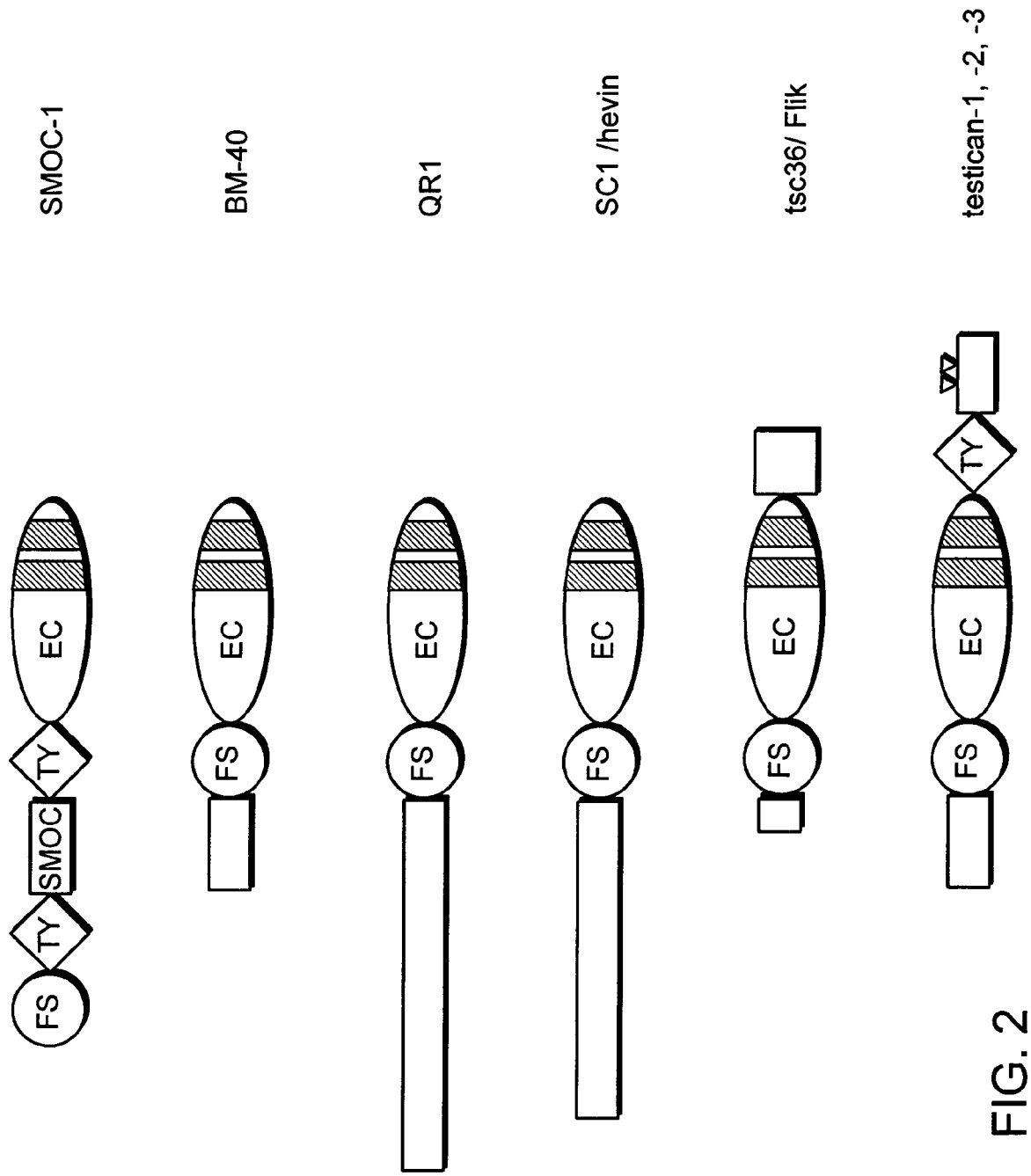
FIG. 2 is a domain organization of various SPARC family proteins. FS represents the follistatin-like domain, TY the thyroglobulin-like domain, EC the extracellular calcium-binding domain as described in Vannahme et al., 2002, J. Biol. Chem. 277(41):37977-37986. Domains with no homology to other proteins are shown as open boxes. Signal peptides are not shown.

The invention is based on the SPARC family and sensitization to cancer therapy.

Definitions

As used herein, a "SPARC family polypeptide" refers to a polypeptide (including a fragment or variant thereof) of a family of extracellular proteins. This family of extracellular proteins include SPARC and other members of the family, such as SMOC-1, hevin, SC1, QR-1, follistatin-like proteins (TSC-36) and testican (see for example, Vannahme et al., (2002), J. Biol. Chem. 277(41): 37977-37986; Johnston, I. G., Paladino, T., Gurd, J. W., and Brown, I. R. (1990) Neuron 2, 165-176; Guermah, M., Crisanti, P., Laugier, D., Dezelee, P., Bidou, L., Pessac, B., and Calothy, G. (1991) Proc. Natl. Acad. Sci. U.S.A. 88, 4503-4507; Shibanuma, M., Mashimo, J., Mita, A., Kuroki, T., and Nose, K. (1993) Eur. J. Biochem. 217, 13-19; Alliel, P. M., Perin, J. P., Jolles, P., and Bonnet, F. J. (1993) Eur. J. Biochem. 214, 347-350, hereby incorporated by reference.) A SPARC family polypeptide is typically composed of three independently folded domains (Yan and Sage, 1999, J. Histochem. & Cytochem., 47(12):1495-1505, hereby incorporated by reference). The N-terminal domain (e.g., two adjacent N-terminal $Glu_3$ and $Glu_4$ in SPARC) is negatively charged, the second domain (e.g., residues 53-137 in SPARC) is homologous to follistatin (FS)1 with 10 cysteines in a typical pattern, the C-terminal extracellular calcium-binding (EC) domain (e.g., residues 138-286 in SPARC) has two EF-hand calcium-binding motifs, each with a bound calcium ion in the x-ray structure (Maurer, P., Hohenadl, C., Hohenester, E., Gohring, W., Timpl, R., and Engel, J. (1995) J. Mol. Biol. 253, 347-357; Hohenester, E., Maurer, P., Hohenadl, C., Timpl, R., Jansonius, J. N., and Engel, J. (1996) Nat. Struct. Biol. 3, 67-73).

The term "SPARC family polypeptide", according to the present invention, includes the full length polypeptide or a fragment thereof, a wild-type polypeptide or any variant thereof. A "SPARC family polynucleotide" is a polynucleotide (e.g., DNA or mRNA) molecule encoding a SPARC polypeptide, or a fragment thereof. (a) a SPARC family polypeptide or gene selected from the group consisting of SEQ ID Nos. 1-17; (b) a polypeptide having an amino acid sequence of at least 60% homology to the SPARC family polypeptide in (a) or a gene encoding the polypeptide of at least 60% homology; (c) a polypeptide fragment of (a)-(b) wherein the fragment is at least 50 amino acids in length; (d) a fusion polypeptide comprising the polypeptide of (a), (b), or (c); (e) a polynucleotide encoding the polypeptide of (a), (b), (c) or the fusion polypeptide of (d); or (f) a polynucleotide hybridizing to the polynucleotide of (e) under a stringent hybridization condition.

The term "SPARC" polypeptide refers to SEQ ID Nos. 1-17, and the term "SPARC gene" to SEQ ID Nos. 18-34, the corresponding nucleotide sequences of SEQ ID Nos. 1-17. It is contemplated that variations of these sequences which retain the biological activity of SPARC are equivalents of these sequences. The biological activity of the SPARC gene is that it is downregulated in chemotherapy resistant cells. The gene also may be overexpressed in cells that are sensitive to chemotherapy. The biological activity of the SPARC polypeptide is that it sensitizes chemotherapy resistant cells to chemotherapy.

With respect to a SPARC family polypeptide member, it is contemplated that variations of their sequences which retain the biological activity of the family member are equivalents of these sequences. The biological activity of a SPARC gene family member is that the gene is downregulated in chemotherapy resistant cells, i.e., expression decreased by at least 25%, for example, 30%, 40%, 50%, 75%, 100% (1-fold), 2-fold, 4-fold, or 5-fold or more, compared to chemotherapy sensitive cells. The gene also may be overexpressed in cells that are sensitive to chemotherapy. The biological activity of the SPARC family polypeptide member is that it sensitizes chemotherapy resistant cells to chemotherapy, i.e., increase the response to chemotherapy by at least 25%, for example, 30%, 40%, 50%, 60%, 70%, 80%, or more, to 2-fold, 3-fold, 4-fold, 5-fold, 10-fold, 15-fold, 20-fold or more, compared to treatment sensitivity in the absence of the SPARC family polypeptide.

As defined herein, a "tissue" is an aggregate of cells that perform a particular function in an organism. The term "tissue" as used herein refers to cellular material from a particular physiological region. The cells in a particular tissue may comprise several different cell types. A non-limiting example of this would be brain cells that further comprise neurons and glial cells, as well as capillary endothelial cells and blood cells.

The term "cell type" or "tissue type" refers to the tissue of origin, for example, from which a tumor develops. Such tissues (cells types) include, for example, without limitation, blood, colorectal, breast, esophageal, hepatocellular, prostate, ovarian, thyroid, pancreas, uterus, testis, pituitary, kidney, stomach, esophagus and rectum.

As used herein, the term "cancer" refers to a proliferative disorder disease caused or characterized by the proliferation of cells which have lost susceptibility to normal growth control. The term "cancer," as used in the present application, includes tumors and any other proliferative disorders. Cancers of the same tissue type originate in the same tissue, and may be divided into different subtypes based on their biological characteristics. The cancer may be selected from one or more from the group consisting of: melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum.

As used herein, the term "sensitizing" refers to an increased sensitivity or reduce the resistance of a cancer sample or a mammal responding to a therapeutic treatment. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, PA: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician.

As used herein, the term "administer" or "administering" refers to introduce by any means a composition (e.g., a therapeutic agent) into the body of a mammal in order to prevent or treat a disease or condition (e.g., cancer).

As used herein, the terms "treating", "treatment", "therapy" and "therapeutic treatment" as used herein refer to curative therapy, prophylactic therapy, or preventative therapy. An example of "preventative therapy" is the prevention or lessening of a targeted disease (e.g., cancer) or related condition thereto. Those in need of treatment include those already with the disease or condition as well as those prone to have the disease or condition to be prevented. The terms "treating", "treatment", "therapy" and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

By "therapeutically effective amount" is meant an amount that relieves (to some extent, as judged by a skilled medical practitioner) one or more symptoms of the disease or condition in a mammal. Additionally, by "therapeutically effective amount" is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. The determination of amount of a composition that must be administered to be therapeutically effective is routine in the art and within the skill of an ordinarily skilled clinician.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified. An "agent", according to the present invention, also includes a radiation therapy agent.

As used herein, "modulation" or "modulating" means that a desired/selected response is more efficient (e.g., at least 10%, 20%, 40%, 60% or more), more rapid (e.g., at least 10%, 20%, 40%, 60% or more), greater in magnitude (e.g., at least 10%, 20%, 40%, 60% or greater), and/or more easily induced (e.g., at least 10%, 20%, 40%, 60% or more) in the presence of an agent than in the absence of the agent.

As used herein, the term "resistance to a therapeutic treatment" refers to an acquired or natural resistance of a cancer sample or a mammal to a therapy, i.e., being nonresponsive to or having reduced or limited response to the therapeutic treatment, e.g., having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response is measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi drug-resistant microorganism or a combination of microorganisms. The determination of resistance to a therapeutic treatment is routine in the art and within the skill of an ordinarily skilled clinician, for example, can be measured by cell proliferative assays and cell death assays as described herein above under "sensitizing".

As used herein, the term "chemotherapy" refers to the use of drugs to destroy cancer cells (including leukaemias and lymphomas). There are over 50 different chemotherapy drugs and some are given on their own, but often several drugs may be combined (known as combination chemotherapy). Chemotherapy may be used alone to treat some types of cancer. Sometimes it can be used together with other types of treatment such as surgery, radiotherapy, immunotherapy, or a combination thereof.

As used herein, "radiotherapy", also called "radiation therapy", refers to the treatment of cancer and other diseases with ionizing radiation. Ionizing radiation deposits energy that injures or destroys cells in the area being treated (the "target tissue") by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or uterine cervix. It can also be used to treat leukemia and lymphoma (cancers of the blood-forming cells and lymphatic system, respectively)

As used herein, the term "treatment protocol" refers to the process of informing the decision making for the treatment of a disease. As used herein, treatment protocol is based on the comparative levels of one or more cell growth-related polypeptides in a patient's tissue sample relative to the levels of the same polypeptide(s) in a plurality of normal and diseased tissue samples from mammals for whom patient information, including treatment approaches and outcomes is available.

As used herein, the term "biological characteristics" refers to the phenotype and/or genotype of one or more cells or tissues, which can include cell type, and/or tissue type from which the cell was obtained, morphological features of the cell(s)/tissue(s), and the expression of biological molecules within the cell(s)/tissue(s).

As used herein, the term "sample" refers to material derived from the body of a mammal, including, but not limited to, blood, serum, plasma, urine, nipple aspirate, cerebrospinal fluid, liver, kidney, breast, bone, bone marrow, testes or ovaries and brain, colon, and lung. A "sample," according to the present invention, may also be cultured cells and tissues.

As used herein, a "cancer sample" refers to a sample which originates from a cancer, i.e., from a new growth of different or abnormal tissue. A "cancer sample" may be a cell or tissue sample. The cancer cells may exist as part of the cancer tissue, or may exist as free-floating cells detached from the cancer tissue from which they originate. A cancer sample, according to the present invention, may be used for in vitro or ex vivo testing of cancers.

As used herein, the term "non-cancer sample" refers to cell or tissue sample obtained from a normal tissue. A sample may be judged a non-tumor sample by one of skill in the art on the basis of morphology and other diagnostic tests.

As used herein, the term "mammal" refers to a human or other animal, such as farm animals or laboratory animals (e.g. guinea pig or mice).

As used herein, "specific hybridization" or "selective hybridization" or "hybridization under a stringent condition" refers to hybridization which occurs when two polynucleotide sequences are substantially complementary, i.e., there is at least about 60% and preferably, at least about 80% or 90% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). Typically, stringent conditions will be those in which the salt concentration is at least about 0.01 to 1.0 M Na ion concentration (or other salts) at pH 7.0 to 8.3 and the temperature is at least about 30° C. for short probes (e.g., about 6 to 50 nucleotides). Stringent conditions may also be achieved with the addition of destabilizing agents such as formamide. Generally, stringent conditions are selected to be about 5° C. lower than the thermal melting point (Tm) for the specific sequence at a defined ionic strength and pH, as calculated using methods routine in the art.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue. A "homology of 60% or higher" includes a homology of, for example, 60%, 70%, 75%, 80%, 85%, 90%, 95%, and up to 100% (identical) between two or more nucleotide or amino acid sequences.

As used herein, the term "polynucleotide" includes RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

As used herein, the term "mutation" refers to a change in nucleotide sequence within a gene, or outside the gene in a regulatory sequence compared to wild type. The change may be a deletion, substitution, point mutation, mutation of multiple nucleotides, transposition, inversion, frame shift, nonsense mutation or other forms of aberration that differentiate the polynucleotide or protein sequence from that of a normally expressed gene in a functional cell where expression and functionality are within the normally occurring range.

"Polypeptide" and "protein" are used interchangeably herein to refer to a polymer of amino acid residues. The term "recombinant protein" refers to a protein that is produced by expression of a recombinant DNA molecule that encodes the amino acid sequence of the protein. Polynucleotides and recombinantly produced polypeptide, and fragments or analogs thereof, may be prepared according to methods known in the art and described in Maniatis et al., Molecular Cloning: A Laboratory Manual, 2nd Ed., (1989), Cold Spring Harbor, N.Y., and Berger and Kimmel, Methods in Enzymology, Volume 152, Guide to Molecular Cloning Techniques (1987), Academic Press, Inc., San Diego, Calif., which are incorporated herein by reference.

As used herein, the term "fragment" when in reference to a polypeptide (as in "a fragment of a given protein") refers to a shorter portion of the polypeptide. The fragment may range in size from four amino acid residues to the entire amino acid sequence minus one amino acid. In one embodiment, the present invention contemplates "functional fragments" of a polypeptide. Such fragments, according to the present invention, are "functional" in that they retain the ability to sensitize a cancer sample or cancer mammal to a therapeutic treatment, albeit with perhaps lower sensitizing activity than that observed for the full-length polypeptide. Such "fragment" of a polypeptide is preferably greater than 10 amino acids in length, and more preferably greater than 50 amino acids in length, and even more preferably greater than 100 amino acids in length. A "fragment" of a SPARC family polypeptide, according to the present invention, may contain one or more of the three conserved domains of the SPARC family members, i.e., the Acidic N-terminal domain, the follistatin-like domain, and the extracellular calcium-binding EC domain.

As used herein, a "variant" of a specific polypeptide refers to a polypeptide substantially similar to either the entire specific peptide or a fragment thereof. By "substantially similar", it means that the variant is made to arrive at a final construct which possesses the desired function, i.e., sensitizing a cancer sample or a mammal to a therapeutic treatment, albeit with perhaps lower sensitizing activity of the variant than that observed for the wild-type polypeptide. Such variants include, for example, deletions, insertions, or substitutions of residues within the amino-acid sequence of the specific polypeptide. In addition, a "variant" may also be a fusion polypeptide between a SPARC family polypeptide and a second polypeptide. Any combination of deletion, insertion, substitution, and fusion may also be made.

As used herein, "isolated" or "purified" when used in reference to a polynucleotide or a polypeptide means that a naturally occurring nucleotide or amino acid sequence has been removed from its normal cellular environment or is synthesized in a non-natural environment (e.g., artificially synthesized). Thus, an "isolated" or "purified" sequence may be in a cell-free solution or placed in a different cellular environment. The term "purified" does not imply that the nucleotide or amino acid sequence is the only polynucleotide or polypeptide present, but that it is essentially free (about 90-95%, up to 99-100% pure) of non-polynucleotide or polypeptide material naturally associated with it.

As used herein the term "encoding" refers to the inherent property of specific sequences of nucleotides in a polynucleotide, such as a gene in a chromosome or an mRNA, to serve as templates for synthesis of other polymers and macromolecules in biological processes having a defined sequence of nucleotides (i.e., rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. A polynucleotide that encodes a protein includes any polynucleotides that have different nucleotide sequences but encode the same amino acid sequence of the protein due to the degeneracy of the genetic code. Polynucleotides and nucleotide sequences that encode proteins may include introns and may be genomic DNA.

As used herein, the term "vector" refers to a polynucleotide compound used for introducing exogenous or endogenous polynucleotide into host cells. A vector comprises a nucleotide sequence which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

As used herein, the term "transformation" or the term "transfection" refers to a variety of art-recognized techniques for introducing exogenous polynucleotide (e.g., DNA) into a cell. A cell is "transformed" or "transfected" when exogenous DNA has been introduced inside the cell membrane. The terms "transformation" and "transfection" and terms derived from each are used interchangeably.

As used herein, an "expression vector" refers to a recombinant expression cassette which has a polynucleotide which encodes a polypeptide (i.e., a protein) that can be transcribed and translated by a cell. The expression vector can be a plasmid, virus, or polynucleotide fragment.

The term "expression" refers to the production of a protein or nucleotide sequence in a cell or in a cell-free system, and includes transcription into an RNA product, post-transcriptional modification and/or translation into a protein product or polypeptide from a DNA encoding that product, as well as possible post-translational modifications.

As used herein, the term "comparing the expression level" refers to comparing the deferential expression of a polynucleotide or a polypeptide in two or more samples.

As used herein, the term "differential expression" refers to both quantitative, as well as qualitative, differences in a polynucleotide or a polypeptide expression patterns among two or more samples. A polynucleotide or a polypeptide is said to be "differentially expressed" if its expression is detectable in one sample, but not in another sample, by known methods for polynucleotide or polypeptide detection (e.g., electrophoresis). A polynucleotide or a polypeptide is also said to be "differentially expressed" if the quantitative difference of its expression (i.e., increase or decrease, measured in µg, µmol or copy number) between two samples is about 20%, about 30%, about 50%, about 70%, about 90% to about 100% (about two-fold) or more, up to and including about 1.2 fold, 2.5 fold, 5-fold, 10-fold, 20-fold, 50-fold or more. A "differentially expressed" gene transcript means a mRNA transcript that is found in different numbers of copies between two or more samples.

As used herein, an "increased amount of a SPARC family polypeptide or polynucleotide" refers to a greater level of expression of at least 20%, e.g., 30%, 40%, 50%, 60%, 70%, 80%, or 90%, or 2-fold, 3-fold, 4-fold, 5-fold or more in a cell, compared to a control cell. A cell expressing a SPARC family polypeptide or polynucleotide is said to have an increase amount of such polypeptide or polynucleotide if the expression is as defined herein above when compared with a chemotherapy resistant cell.

The term "secreted protein" refers to a protein having at least a portion which is extracellular and includes proteins which are completely extracellular (i.e., not attached to a cell). "Level of secretion" refers to the level (i.e., amount) of a secreted protein in the extracellular compartment.

As used herein, the term "proliferation" refers to the rate of cell division and the ability of a cell to continue to divide. One complete cell division process is referred to as a "cycle". By an "increase in cell proliferation" is meant to increase the cell division rate so that the cell has a higher rate of cell division compared to normal cells of that cell type, or to allow the cell division to continue for more cycles without changing the rate of each cell division, e.g., increase by 10% or higher (e.g., 20%, 30%, 40% 50%, up to 2 fold, 5 fold, 10 fold or higher. By an "decrease in cell proliferation" is meant to decrease the cell division rate so that the cell has a lower rate of cell division compared to normal cells of that cell type, or to reduce the number of cycles of the cell division without changing the rate of each cell division, e.g., decrease by 10% or higher (e.g., 20%, 30%, 40% 50%, up to 2 fold, 5 fold, 10 fold or higher).

The present invention provides compositions and methods for sensitizing cancer therapeutic treatments. Such sensitizing compositions and methods are particularly useful in enhancing the response of patients who are resistant to a treatment. They are also useful in reducing the side-effects of cancer therapy, for example, by enhancing the response of a patient to a smaller strength (i.e., dosage) of the treatment. The composition of the present invention may reduce the dosage of a therapeutic treatment agent by at least 20%, for example, 30%, 40%, 50%, and up to 60%.

The SPARC Family Polypeptides and Polynucleotides

In one embodiment, the present invention provides (a) a SPARC family polypeptide selected from the group consisting of SEQ ID Nos. 1-17; (b) a polypeptide having an amino acid sequence of at least 60% homology to said SPARC family polypeptide in (a); (c) a polypeptide fragment of (a)-(b) wherein said fragment is at least 50 amino acids in length, and (d) a fusion polypeptide comprising the polypeptide of (a)-(c).

A SPARC family polypeptide provided by the present invention may be a wild-type polypeptide or a variant thereof, it may be the full length polypeptide or a fragment thereof. A SPARC family polypeptide is within the scope of the present invention so long as it retains the function of sensitizing a cancer sample or a patient to a therapeutic treatment, albeit that a lower activity may exist for a variant or a fragment polypeptide when compared to the wile-type or full length polypeptide.

Based on sequence homology, several members of the SPARC family have been identified, such as SMOC-1 (Vannahme et al., 2002, J. Biol. Chem. 277(41):37977-37986), hevin (Bendik I, Schraml P, Ludwig C U, Cancer Res. 1998; 58(4):626-9), SC1 (Johnston I G, Paladino T, Gurd J W, Brown I R, Neuron. 1990 4(1):165-76), QR-1, follistatin-like proteins (TSC-36) (Shibanuma, M., Mashimo, J., Mita, A., Kuroki, T. and Nose, K, 1993, Eur. J. Biochem. 217 (1) 13-19) and testican (Alliel, P. M., Perin, J. P., Jolles, P. and Bonnet, F. J, 1993, Eur. J. Biochem. 214 (1), 347-350). A SPARC family polypeptide of the present invention includes, but is not limited to, SPARC and any of its identified family members known in the art or as described herein.

The alignment of the various polynucleotide sequences permit one skilled in the art to select conserved portions of the proteins (i.e. those portions in common between two or more sequences) as well as unconserved portions (i.e. those portions unique to two or more sequences). In one embodiment, the present invention contemplates conserved fragments 10 amino acids in length or greater, and more typically greater than 50 amino acids in length. Preferably, the SPARC family polypeptide of the present invention contains one or two or three domains (i.e. the Acidic N-terminal domain, the follistatin-like domain, and/or the EC domain), conserved among the SPARC family members.

The therapy-sensitizing fragment or a variant of a wild-type SPARC family protein may be delineated by routine sequence manipulations known to those skilled in the art, including, but not limited to, deletion mutations, point mutations, fusions as described herein below and as described in J. Sambrook, E. F. Fritsch, and T. Maniatis, Molecular Cloning: A. Laboratory Manual, 2 Ed., Cold Spring Harbor Laboratory Press, Cold Spring Harbor, N.Y., 1989, and Ausubel et al., Current Protocols in Molecular Biology, 1994, incorporated by reference herein.

A mutation in the DNA encoding the variant polypeptide must not alter the reading frame and preferably will not create complementary regions that could produce secondary mRNA structures. At the genetic level these variants are prepared by site directed mutagenesis of nucleotides in the DNA encoding the peptide molecule thereby producing DNA encoding the variant, and thereafter expressing the DNA in recombinant cell culture.

In vitro Production and Purification of a SPARC Family Polypeptide

A SPARC family polypeptide provided by the present invention may be produced in a prokaryotic or eukaryotic cell using any known method, for example, recombinant DNA techniques. Recombination techniques may be conducted as described herein below, or for example, by the methods disclosed in T. Maniatis et al., "Molecular Cloning", 2nd Ed., Cold Spring Harbor Laboratory, Cold Spring Harbor, N. T. (1989); Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", Tokyo Kagaku Dojin, Japan (1992); R. Wu (ed.), "Methods in Enzymology", Vol. 68, Academic Press, New York (1980); R. Wu et al. (ed.), "Methods in Enzymology", Vols. 100 & 101, Academic Press, New York (1983); R. Wu et al. (ed.), "Methods in Enzymology", Vols. 153, 154 & 155, Academic Press, New York (1987), etc. as well as by techniques disclosed in the references cited therein, the disclosures of which are hereby incorporated by reference. Such techniques and means may also be those which are individually modified/improved from conventional techniques depending upon the object of the present invention.

A SPARC family polypeptide may be expressed and purified from a recombinant host cell. Recombinant host cells may be prokaryotic or eukaryotic, including but not limited to bacteria such as *E. coli*, fungal cells such as yeast, insect cells including but not limited to *drosophila* and silkworm derived cell lines, and mammalian cells and cell lines.

In certain embodiments, when expressing and purifying a SPARC family polypeptide of the present invention, techniques for improving protein solubility are employed to prevent the formation of inclusion body (which are insoluble fractions), and therefore obtaining large quantities of the polypeptide. SPARC accumulated in inclusion bodies is an inactive-type SPARC not retaining its physiological activities.

Solubility of a purified SPARC family polypeptide may be improved by methods known in the art, and as described herein below.

For example, solubility may also be improved by expressing a functional fragment, but not the full length SPARC family polypeptide. The fragment expressed should retain the sensitizing activity as described herein, albeit the activity may be lower than that of a full length polypeptide.

In one embodiment, a fragment containing one or two or three domains of the three conserved domains of the SPARC family members is expressed.

In addition, to increase the solubility of an expressed protein (e.g., in *E. coli*), one can reduce the rate of protein synthesis by lowering the growth temperature, using a weaker promoter, using a lower copy number plasmid, lowering the inducer concentration, changing the growth medium as described in Georgiou, G. & Valax, P. (1996, Current Opinion Biotechnol. 7, 190-197). This decreases the rate of protein synthesis and usually more soluble protein is obtained. One can also add prostethic groups or co-factors which are essential for proper folding or for protein stability, or add buffer to control pH fluctuation in the medium during growth, or add 1% glucose to repress induction of the lac promoter by lactose, which is present in most rich media (such as LB, 2xYT). Polyols (e.g. sorbitol) and sucrose may also be added to the media because the increase in osmotic pressure caused by these additions leads to the accumulation of osmoprotectants in the cell, which stabilize the native protein structure. Ethanol, low molecular weight thiols and disulfides, and NaCl may be added. In addition, chaperones and/or foldases may be co-expressed with the desired polypeptide. Molecular chaperones promote the proper isomerization and cellular targeting by transiently interacting with folding intermediates. The best characterized *E. coli* chaperone systems are: GroES-GroEL, DnaK-DnaJ-GrpE, ClpB. Foldases accelerate rate-limiting steps along the folding pathway. Three types of foldases play an important role: peptidyl prolyl cis/trans isomerases (PPI's), disulfide oxidoreductase (DsbA) and disulfide isomerase (DsbC), protein disulfide isomerase (PDI) which is an eukaryotic protein that catalyzes both protein cysteine oxidation and disulfide bond isomerization. Co-expression of one or more of these proteins with the target protein could lead to higher levels of soluble protein.

A SPARC family polypeptide of the present invention may be produced as a fusion protein in order to improve its solubility and production. The fusion protein comprises a SPARC family polypeptide and a second polypeptide fused together in frame. The second polypeptide may be a fusion partner known in the art to improve the solubility of the polypeptide to which it is fused, for example, NusA, bacterioferritin (BFR), GrpE, thioredoxin (TRX) and glutathione-S-transferase (GST). Madison, Wis.-based Novagen Inc. provides the pET 43.1 vector series which permit the formation of a NusA-target fusion. DsbA and DsbC have also shown positive effects on expression levels when used as a fusion partner, therefore can be used to fuse with a SPARC polypeptide for achieving higher solubility.

In one embodiment, a SPARC family polypeptide is produced as a fusion polypeptide comprising the SPARC family polypeptide and a fusion partner thioredoxin, as described in U.S. Pat. No. 6,387,664, hereby incorporated by reference in its entirety. The thioredoxin-SPARC fusion can be produced in *E. coli* as an easy-to-formulate, soluble protein in a large quantity without losing the physiological activities of SPARC. Although U.S. Pat. No. 6,387,664 provides a fusion SPARC protein with SPARC fused to the C-terminus of thioredoxin, it is understood, for the purpose of the present invention, a SPARC family polypeptide may be fused either to the N-terminus or the C-terminus of a second polypeptide, so long as its sensitizing function is retained.

In addition to increase solubility, a fusion protein comprising a SPARC family polypeptide may be constructed for the easy detection of the expression of the SPARC family polypeptide in a cell. In one embodiment, the second polypeptide which fused to the SPARC family polypeptide is a reporter polypeptide. The reporter polypeptide, when served for such detection purpose, does not have to be fused with the SPARC family polypeptide. It may be encoded by the same polynucleotide (e.g., a vector) which also encodes the SPARC family polypeptide and be co-introduced and co-expressed in a target cell.

Preferably, the reporter polypeptide used in the invention is an autofluorescent protein (e.g., GFP, EGFP). Autofluorescent proteins provide a ready assay for identification of expression of a polynucleotide (and the polypeptide product) of interest. Because the activity of the reporter polypeptide (and by inference its expression level) can be monitored quantitatively using a flow sorter, it is simple to assay many independent transfectants either sequentially or in bulk population. Cells with the best expression can then be screened for or selected from the population. This is useful when selecting a recombinant cell comprising a SPARC family polypeptide or polynucleotide for sensitizing treatment according to the present invention. Quantitative parameters such as mean fluorescence intensity and variance can be determined from the fluorescence intensity profile of the cell population (Shapiro, H., 1995, Practical Flow Cytometry, 217-228). Non-limiting examples of reporter molecules useful in the invention include luciferase (from firefly or other species), chloramphenicol acetyltransferase, β-galactosidase, green fluorescent protein (GFP), enhanced green fluorescent protein (EGFP), and dsRed.

Expression of the SPARC polypeptide (either by itself, or as a fusion protein) can also be directly determined by an immunoassay such as an ELISA (enzyme-linked immunoabsorbent assay) (see e.g., U.S. Pat. No. 5,962,320; U.S. Pat. No. 6,187,307; U.S. Pat. No. 6,194,205), western blot, or by other methods routine in the art. The expression of a SPARC family polypeptide can be indirectly detected by detecting the transcript of the protein (e.g., by hybridization analysis such as Northern blot or DNA Microarray, or by PCR).

In one embodiment, a polynucleotide encoding a second polypeptide is fused to a polynucleotide encoding a SPARC family polypeptide through an intervening linker sequence which encodes for a linker polypeptide.

In another embodiment, the linker polypeptide comprises a protease cleavage site comprising a peptide bond which is hydrolyzable by a protease. As a result, the SPARC family polypeptide can be separated from the second polypeptide after expression by proteolysis. The linker can comprise one or more additional amino acids on either side of the bond to which the catalytic site of the protease also binds (see, e.g., Schecter and Berger, 1967, Biochem. Biophys. Res. Commun. 27, 157-62). Alternatively, the cleavage site of the linker can be separate from the recognition site of the protease and the two cleavage site and recognition site can be separated by one or more (e.g., two to four) amino acids. In one aspect, the linker comprises at least 2, 3, 4, 5, 6, 7, 8, 9, 10, 20, 30, 40, 50 or more amino acids. More preferably the linker is between 5 and 25 amino acids in length, and most preferably, the linker is between 8 and 15 amino acids in length.

Some proteases useful according to the invention are discussed in the following references: V. Y. H. Hook, *Proteolytic and cellular mechanisms in prohormone and proprotein processing*, RG Landes Company, Austin, Tex., USA (1998); N. M. Hooper et al., 1997, Biochem. J. 321:265-279; Werb, 1997, Cell 91: 439-442; Wolfsberg et al., 1995, J. Cell Biol. 131: 275-278; Murakami and Etlinger, 1987, Biochem. Biophys. Res. Comm. 146: 1249-1259; Berg et al., 1995, Biochem. J. 307: 313-326; Smyth and Trapani, 1995, Immunology Today 16: 202-206; Talanian et al., 1997, J. Biol. Chem. 272: 9677-9682; and Thornberry et al., 1997, J. Biol. Chem. 272: 17907-17911. Suitable proteases include, but are not limited to, those listed in Table 1 below.

TABLE 1

Proteases and Their Cleavage Signals

| Protease | Cleavage Signal (Exemplary Linker Polynucleotide Sequence) |
|---|---|
| subtilisin/kexin family | RXKR (SEQ ID NO. 49) |
| (furin, PC1, PC2, PC4, PACE4, PC5, PC) | (CGC NNN AAG CGC) (SEQ ID NO. 50) |
| MMP-2 | PLGLWA (SEQ ID NO. 51) |
| | (CCC CTG GGC CTG TGG GCC) (SEQ ID NO. 52) |
| MT1-MMP | PLGLWA (SEQ ID NO. 51) |
| | (CCC CTG GGC CTG TGG GCC) (SEQ ID NO. 52) |
| | Cleavage Signal-Amino Acid Sequence (Exemplary Linker Polynucleotide Sequence) |
| caspase-1 | YEVDGW (SEQ ID NO. 53) |

TABLE 1-continued

Proteases and Their Cleavage Signals

| Protease | |
|---|---|
| | (TAC GAG GTG GAC GGC TGG) (SEQ ID NO. 54) |
| caspase-2 | VDVADGW (SEQ ID NO. 55) |
| | (GTG GAC GTG GCC GAC GGC TGG) (SEQ ID NO. 56) |
| caspase-3 | VDQMDGW (SEQ ID NO. 57) |
| | (GTG GAC CAG ATG GAC GGC TGG) (SEQ ID NO. 58) |
| caspase-4 | LEVDGW (SEQ ID NO. 59) |
| | (CTG GAG GTG GAC GGC TGG) (SEQ ID NO. 60) |
| caspase-6 | VQVDGW (SEQ ID NO. 61) |
| | (GTG CAG GTG GAC GGC TGG) (SEQ ID NO. 62) |
| caspase-7 | VDQVDGW (SEQ ID NO. 63) |
| | (GTG GAC CAG GTG GAC GGC TGG) (SEQ ID NO. 64) |
| caspase-8 | DXXD (SEQ ID NO. 65) |
| | (GAC NNN NNN GAC) (SEQ ID NO. 66) |
| caspase-9 | DXXD (SEQ ID NO. 65) |
| | (GAC NNN NNN GAC) |
| alpha-secretase | amyloid precursor protein (APP) |
| proprotein convertase (subtilisin/kexin isozyme SKI-1) | RGLT (SEQ ID NO. 67) |
| | (CGC GGC CTG ACC) (SEQ ID NO. 68) |
| proprotein convertases | cleavage at hydrophobic residues (e.g., Leu, Phe, Val, or Met) or at small amino acid residues such as Ala or Thr |
| foot and mouth disease virus, protease 2A | NFDLLKLAGDVESNPGP (SEQ ID NO. 69) |
| | (AAC TTC GAC CTG CTG AAG CTG GCC GGC GAC GTG GAG AGC AAC CCC GGC CCC) (SEQ ID NO. 70) |
| signal peptidase | A-X-A-X (SEQ ID NO. 71) |

TABLE 1-continued

Proteases and Their Cleavage Signals

| Protease | |
|---|---|
| | (GCC NNN GCC NNN) (SEQ ID NO. 72) |
| aminopeptidases (e.g., arginine aminopeptidase, lysine aminopeptidase, aminopeptidase B, trypsin) | LTK (SEQ ID NO. 73) |
| | (CTG ACC AAG) (SEQ ID NO. 74) |
| insulin degrading enzyme | GGFLRKVGQ (SEQ ID NO. 75) |
| | (GGC GGC TTC CTG CGC AAG GTG GGC CAG) (SEQ ID NO. 76) |

Additional linker polypeptides can be obtained from the substrates for proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); prolyl endopeptidase; and high molecular weight protease.

Cell surface proteases also can be used with cleavable linkers according to the invention and include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; Urokinase plasminogen activator; Tissue plasminogen activator; Plasmin; Thrombin; BMP-1 (procollagen C-peptidase); ADAM 1, 2, 3, 4, 5, 6, 7, 8, 9, 10, and 11; and, Granzymes A, B, C, D, E, F, G, and H.

An alternative to relying on cell-associated proteases is to use a self-cleaving linker. For example, the foot and mouth disease virus (FMDV) 2A protease may be used as a linker. This is a short polypeptide of 17 amino acids that cleaves the polyprotein of FMDV at the 2A/2B junction. The sequence of the FMDV 2A propeptide is NFDLLKLAGDVESNPGP (SEQ ID NO. 77). Cleavage occurs at the C-terminus of the peptide at the final glycine-proline amino acid pair and is independent of the presence of other FMDV sequences and cleaves even in the presence of heterologous sequences.

Insertion of this sequence between two protein coding regions (i.e., between the SPARC family polypeptide and the second polypeptide of a fusion protein according to the invention) results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (see, e.g., P. deFelipe et al., Gene Therapy 6: 198-208 (1999)). Self-cleaving linkers and additional protease-linker combinations are described further in WO 0120989, the entirety of which is incorporated by reference herein.

Polynucleotides encoding linker sequences described above can be cloned from sequences encoding the natural substrates of an appropriate protease or can be chemically synthesized using methods routine in the art.

When expressing a SPARC family polypeptide in a human cell, e.g., in vitro or in vivo, the codons selected for such the polynucleotide encoding the SPARC family polypeptide are preferably those which are most frequently used in humans, such as those listed in Table 2 below. The exemplary polynucleotide sequences shown in Table 4 rely on codons which are most frequently used in humans.

TABLE 2

Preferred DNA Codons For Human Use

| Amino Acids | 3 Letter Code | 1 Letter Code | Codons Preferred in Human Genes |
|---|---|---|---|
| Alanine | Ala | A | GCC |
| | | | GCT |
| | | | GCA |
| | | | GCG |
| Cysteine | Cys | C | TGT |
| | | | TGT |
| Aspartic Acid | Asp | D | GAC |
| | | | GAT |
| Glutamic Acid | Glu | E | GAG |
| | | | GAA |
| Phenylalanine | Phe | F | TTC |
| | | | TTT |
| Glycine | Gly | G | GGC |
| | | | GGG |
| | | | GGA |
| | | | GGT |
| Histidine | His | H | CAC |
| | | | CAT |
| Isoleucine | Ile | I | ATC |
| | | | ATT |
| | | | ATA |
| Lysine | Lys | K | AAG |
| | | | AAA |
| Leucine | Leu | L | CTG |
| | | | TTG |
| | | | CTT |
| | | | CTA |
| | | | TTA |
| Methionine | Met | M | ATG |

TABLE 2-continued

Preferred DNA Codons For Human Use

| Amino Acids | 3 Letter Code | 1 Letter Code | Codons Preferred in Human Genes |
|---|---|---|---|
| Asparagine | Asn | N | AAC |
| | | | AAT |
| Proline | Pro | P | CCC |
| | | | CCT |
| | | | CCA |
| | | | CCG |
| Glutamine | Gln | Q | CAG |
| | | | CAA |
| Arginine | Arg | R | CGC |
| | | | AGG |
| | | | CGG |
| | | | AGA |
| | | | CGA |
| | | | CGT |
| Serine | Ser | S | AGC |
| | | | TCC |
| | | | TCT |
| | | | AGT |
| | | | TCA |
| | | | TCG |
| Threonine | Thr | T | ACC |
| | | | ACA |
| | | | ACT |
| | | | ACG |
| Valine | Val | V | GTG |
| | | | GTC |
| | | | GTT |
| | | | GTA |
| Tryprophan | Trp | W | TGG |
| Tyrosine | Tyr | Y | TAC |
| | | | TAT |

The uppermost codons represent those most preferred for use in human genes. Underlined codons are almost never used in human genes and are therefore not preferred.

In another embodiment, the present invention provides (a) a polynucleotide encoding the polypeptide of a SPARC family polypeptide or a fusion polypeptide comprising a SPARC family polypeptide; and (b) a polynucleotide hybridizing to the polynucleotide of (a) under a stringent hybridization condition.

Techniques for polynucleotide manipulation to perform the above embodiments of the invention are well known in the art. (See, e.g., Sambrook et al., 1989; Ausubel et al. 1987 and in Annual Reviews of Biochemistry, 1992, 61:131-156). Reagents useful in applying such techniques, such as restriction enzymes and the like, are widely known in the art and commercially available from a number of vendors.

Polynucleotide sequences for use in the present invention may also be produced in part or in total by chemical synthesis, e.g. by the phosphoramidite method described by Beaucage, et al., 1981, Tetra. Letts., 22:1859-1862, or the triester method (Matteucci et al., 1981, J. Am. Chem. Soc., 103:3185), which may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

In one embodiment, the SPARC family polynucleotide provided by the present invention exists as a vector, preferably, an expression vector.

Expression Vectors

A polynucleotide coding for a SPARC family polypeptide sequence may be incorporated into vectors capable of introduction into and replication in a prokaryotic or eukaryotic cell to produce a SPARC family polypeptide of the present invention for sensitizing treatment, or it can be used to transfect or infect a cell or tissue and achieve the sensitizing function directly by expressing the SPARC family polypeptide. The vectors may or may not integrate within the genome of the transfected or infected cell.

Useful polynucleotide molecules encoding a SPARC family polypeptide of the present invention may be cloned into an expression vector before they are introduced into an appropriate cell and may be passage in cells to generate useable quantities of these polynucleotides.

Suitable vectors for the invention may be plasmid or viral vectors. Plasmid expression vectors include, but are not limited to, plasmids including pBR322, pUC, pcDNA3.1 or Bluescript™. Viral vectors include, but are not limited to baculoviruses, adenoviruses, poxviruses, adenoassociated viruses (AAV), and retrovirus vectors (Price et al, 1987, Proc. Natl. Acad. Sci. USA, 84:156-160) such as the MMLV based replication incompetent vector pMV-7 (Kirschmeier et al., 1988, DNA, 7:219-225), as well as human and yeast modified chromosomes (HACs and YACs).

The expression vectors may comprise one or more regulatory elements to drive and/or enhance expression of upstream or downstream polynucleotides. These regulatory sequences are selected on the basis of the cells to be used for introduction and/or expression, and are operatively linked to a polynucleotide sequence to be expressed. The term "regulatory elements" is intended to include promoters, enhancers and other expression control elements (e.g., polyadenylation signals). Such regulatory elements are described, for example, in Goeddel; 1990, *Gene Expression Technology: Methods in Enzymology* 185, Academic Press, San Diego, Calif.

Regulatory elements include those which direct expression of a nucleotide sequence in many types of subject cells as well as those which direct expression of the nucleotide sequence only in certain subject cells (e.g., tissue-specific regulatory sequences).

Regulatory elements also include those which direct constitutive expression of an operatively linked polynucleotide sequence and those which direct inducible expression of the polynucleotide sequence.

Preferably, suitable promoters may be used. For example, such promoters may include tryptophan (trp) promoter, lactose (lac) promoter, tryptophan-lactose (tac) promoter, lipoprotein (lpp) promoter, λ phage $P_L$ promoter, etc. in the case of plasmids where *Escherichia coli* is used as a host; and GAL1, GAL10 promoters, etc. in the case of plasmids where yeast is used as a host.

Some eukaryotic promoters and enhancers have a broad range of cells in which they can activate and/or modulate transcription while others are functional only in a limited subset of cell types (See e.g., Voss et al., 1986, Trends Biochem. Sci., 11:287; and Maniatis et al., supra, for reviews). For example, the SV40 early gene enhancer is very active in a wide variety of cell types from many mammalian species and has been widely used for the expression of proteins in mammalian cells (Dijkema et al., 1985, EMBO J. 4:761). Two other examples of promoter/enhancer elements active in a broad range of mammalian cell types are those from the human elongation factor 1α gene (Uetsuki et al., 1989, J. Biol. Chem., 264:5791; Kim et al., 1990, Gene, 91:217; and Mizushima, et al., 1990, Nagata, Nuc. Acids. Res., 18:5322) and the long terminal repeats of the Rous sarcoma virus (Gorman et al., 1982, Proc. Natl. Acad. Sci. USA, 79:6777) and the human cytomegalovirus (Boshart et al., 1985, Cell, 41:521).

Suitable promoters for eukaryotic cell expression include, but are not limited to, TRAP promoters, adenoviral promoters, such as the adenoviral major late promoter; the cytomegalovirus (CMV) promoter; the respiratory syncytial virus (RSV) promoter; inducible promoters, such as the MMT promoter, the metallothionein promoter, heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the polynucleotide encoding the polypeptide and the sequences of native promoters may be found in the art (see Agrawal et al., 2000, J. Hematother. Stem Cell Res., 795-812; Cournoyer et al., 1993, Annu. Rev. Immunol., 11:297-329; van de Stolpe et al., 1996, J. Mol. Med., 74:13-33; Herrmann, 1995, J. Mol. Med., 73:157-63)

A variety of enhancer sequences can be used in the instant invention including but not limited to: Immunoglobulin Heavy Chain enhancer; Immunoglobulin Light Chain enhancer; T-Cell Receptor enhancer; HLA DQ α and DQ β enhancers; β-Interferon enhancer; interleukin-2 enhancer; Interleukin-2 Receptor enhancer; MHC Class II $5_a^k$ enhancer; MHC Class II HLA-DRα enhancer; β-Actin enhancer; Muscle Creatine Kinase enhancer; Prealbumin (Transthyretin) enhancer; Elastase I enhancer; Metallothionein enhancer; Collagenase enhancer; Albumin Gene enhancer; α-Fetoprotein enhancer; β-Globin enhancer; c-fos enhancer; c-HA-ras enhancer; Insulin enhancer; Neural Cell Adhesion Molecule (NCAM) enhancer; $α_1$-Antitrypsin enhancer; $H_2B$ (TH2B) Histone enhancer; Mouse or Type I Collagen enhancer; Glucose-Regulated Proteins (GRP94 and GRP78) enhancer; Rat Growth Hormone enhancer; Human Serum Amyloid A (SAA) enhancer; Troponin I (TN I) enhancer; Platelet-Derived Growth Factor enhancer; Duchenne Muscular Dystrophy enhancer; SV40 Polyoma enhancer; Retrovirusal enhancer; Papilloma Virus enhancer; Hepatitis B Virus enhancer; Human Immunodeficiency enhancer; Cytomegalovirus enhancer; and Gibbon Ape Leukemia Virus enhancer.

Exemplary inducible promoter/enhancer sequences and their inducers are listed below.

TABLE 3

Useful Inducible Promoters/Enhancers

| Element | Inducer |
| --- | --- |
| MTII | PhorbolEster(TFA) |
|  | Heavymetals |
| MMTV (mouse mammary tumor virus) | Glucocorticoids |
| β-Interferon | poly(rI) X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC ClassI Gene H-2kB | Interferon |
| HSP70 | Ela, SV40 Large T Antigen |
| Proliferin | Phorbol Ester (TPA) |
| Tumor Necrosis Factor | FMA |
| Thyroid Stimulating Hormone α Gene | Thyroid Hormone |

Additional Eukaryotic regulatory sequences may be obtained from the Eukaryotic Promoter Data Base EPDB) also can be used to drive expression of a polynucleotide.

In certain embodiments of the invention, the delivery of a vector in a cell may be identified in vitro or in vivo by including a selection marker in the expression construct, such as described herein above. The marker would result in an identifiable change to the modified cell permitting easy identification of expression. Usually the inclusion of a drug selection marker aids in cloning and in the selection of transformants. Genes which can be used as selectable markers in Eukaryotic cells are known in the art and include, examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., 1989, Molecular Cloning: A Laboratory Manual, 2nd ed., Cold Spring Harbor Laboratory Press, New York pp. 16.9-16.15.

Alternatively, genes encoding enzymes, such as herpes simplex virus thymidine kinase (tk) (eukaryotic) or chloramphenicol acetyltransferase (CAT) (prokaryotic) may be employed to provide selectable markers. Immunologic markers also can be employed. The exact type selectable marker employed is not believed to be important, so long as it is capable of being expressed simultaneously with the polynucleotide encoding a polypeptide of interest. Further examples of selectable markers are well known to one of skill in the art.

Where a cDNA insert is employed to express a SPARC family polypeptide of the invention, one typically will desire to include a polyadenylation signal to effect proper polyadenylation of the polynucleotide transcript. The nature of the polyadenylation signal is not believed to be crucial to the successful practice of the invention, and any such sequence may be employed. These elements can serve to enhance message levels and to minimize read through from the expression cassette into other sequences.

Recombinant Cell Production:—Introducing a SPARC Family Polynucleotide into a Cell for Expression and/or Sensitization As described above, a SPARC family polynucleotide of the invention may be introduced into a cell in order to express the SPARC family polypeptide for purification or to express and achieve the sensitizing effect of the invention according to methods well known in the art, for example, in Current Protocols in Molecular Biology, Ausubel, F. M. et al. (eds.), 1989, Greene Publishing Associates, Section 9.1 and in Molecular Cloning: A Laboratory Manual, 2nd Edition, Sambrook et al., 1989, Cold Spring Harbor Laboratory Press.

Several non-viral methods for the transfer of vectors into cultured mammalian cells are contemplated by the present invention. These include calcium phosphate precipitation (Graham, et al., 1973; Chen, et al., 1987; Rippe, et al., 1990) DEAE-dextran (Gopal, 1985), electroporation (Tur-Kaspa et al., 1986; Potter et al., 1984), direct microinjection (Harland, et al., 1985), DNA-loaded liposomes (Nicolau, et al., 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu, et al., 1987; Wu, et al., 1988). Some of these techniques may be successfully adapted for in vivo or ex vivo use.

Once the vector has been delivered into the cell, the polynucleotide encoding a SPARC family polypeptide may be positioned and expressed at different sites. In certain embodiments, the polynucleotide encoding a SPARC family polypeptide may be stably integrated into the genome of the cell. This integration may be via homologous recombination (gene replacement) or it may be integrated in a random, non-specific location (gene augmentation), see Holmes-Son et al., 2001, Adv. Genet. 43: 33-69. In yet further embodiments, the polynucleotide encoding a SPARC family polypeptide may be stably maintained in the cell as a separate, episomal segment of DNA. Such polynucleotide segments or "episomes" encode sequences sufficient to permit maintenance and replication independent of or in synchronization with the subject cell cycle. How the expression construct is delivered to a cell and where in the cell the polynucleotide remains is well known in the art and is dependent on the type of expression construct employed.

Cell lines derived from mammalian species which may be suitable for transfection and infection of a SPARC family polynucleotide and for expression and purification of a recombinant polypeptide, may be commercially available. These cell lines include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, HEK-293 (ATCC CRL1573), NS0 (ECACC85110503) and HT1080.

Cell cultures may be prepared in various ways for gene transfer in vitro. In order for the cells to be kept viable while in vitro and in contact with the expression construct, it is necessary to ensure that the cells maintain contact with the correct ratio of oxygen and carbon dioxide and nutrients but are protected from microbial contamination.

Transfer of the construct may be performed by any of the methods known in the art and as described herein below. Some methods may be particularly applicable for transfer in vitro but it may be applied to in vivo use as well.

Transfection Mediated by CaPO$_4$

A polynucleotide encoding a SPARC family polypeptide can be introduced into cells by forming a precipitate containing the polynucleotide and calcium phosphate. For example, a HEPES-buffered saline solution can be mixed with a solution containing calcium chloride and polynucleotide to form a precipitate and the precipitate is then incubated with cells. A glycerol or dimethyl sulfoxide shock step can be added to increase the amount of polynucleotide taken up by certain cells. CaPO$_4$-mediated transfection can be used to stably (or transiently) transfect cells and is only applicable to in vitro modification of cells. Protocols for CaPO$_4$-mediated transfection can be found in *Current Protocols in Molecular Biology*, Ausubel, F. M. et al. (eds.), 1989, Greene Publishing Associates, Section 9.1 and in *Molecular Cloning: A Laboratory Manual, 2nd Edition*, Sambrook et al., 1989, Cold Spring Harbor Laboratory Press, Sections 16.32-16.40 or other standard laboratory manuals.

Dubensky et al. (1984) successfully injected polyomavirus DNA in the form of CaPO$_4$ precipitates into liver and spleen of adult and newborn mice demonstrating active viral replication and acute infection. Benvenisty and Neshif (1986) also demonstrated that direct intraperitoneal injection of CaPO$_4$ precipitated plasmids results in expression of the transfected genes. Thus the polynucleotide encoding a SPARC family polypeptide may also be transferred in a similar manner in vivo to express a desired SPARC family polypeptide as described above.

Transfection Mediated by DEAE-Dextran

A polynucleotide encoding a SPARC family polypeptide can be introduced into cells by forming a mixture of the polynucleotide and DEAE-dextran and incubating the mixture with the cells. A dimethylsulfoxide or chloroquine shock step can be added to increase the amount of polynucleotide uptake. Protocols for DEAE-dextran-mediated transfection can be found in *Current Protocols in Molecular Biology*, Ausubel, F. M. et al. (eds.), 1989, Greene Publishing Associates, Section 9.2 and in *Molecular Cloning: A Laboratory Manual, 2nd Edition*, Sambrook et al., 1989, Cold Spring Harbor Laboratory Press, Sections 16.41-16.46 or other standard laboratory manuals.

Electroporation

A polynucleotide encoding a SPARC family polypeptide can also be introduced into cells by incubating the cells and the polynucleotide together in an appropriate buffer and subjecting the cells to a high-voltage electric pulse. The efficiency with which polynucleotide is introduced into cells by electroporation is influenced by the strength of the applied field, the length of the electric pulse, the temperature, the conformation and concentration of the polynucleotide and the ionic composition of the media. Electroporation can be used to stably (or transiently) transfect a wide variety of cell types. Protocols for electroporating cells can be found in Ausubel, F. M. et al. (eds.), supra, Section 9.3 and in Sambrook et al., supra, Sections 16.54-16.55 or other standard laboratory manuals.

Liposome-Mediated Transfection ("Lipofection")

A polynucleotide encoding a SPARC family polypeptide also can be introduced into cells by mixing the polynucleotide with a liposome suspension containing cationic lipids. The polynucleotide/liposome complex is then incubated with cells. Liposome mediated transfection can be used to stably (or transiently) transfect cells in culture in vitro. Protocols can be found in Ausubel, F. M. et al. (eds.), supra, Section 9.4 and other standard laboratory manuals. Additionally, gene delivery in vivo has been accomplished using liposomes. See for example Nicolau et al., 1987, *Meth. Enz.*, 149:157-176; Wang, et al., 1987, *Proc. Natl. Acad. Sci. USA*, 84:7851-7855; Brigham et al., 1989, *Am. J. Med. Sci.*, 298:278; and Gould-Fogerite et al., 1989, *Gene*, 84:429-438.

Direct Injection

A polynucleotide encoding a SPARC family polypeptide can be introduced into cells by directly injecting the polynucleotide into the cells. For an in vitro culture of cells, polynucleotide can be introduced by microinjection. Since each cell is microinjected individually, this approach is very labor intensive when modifying large numbers of cells. However, a situation where microinjection is a method of choice is in the production of transgenic animals (discussed in greater detail below). In this situation, the polynucleotide is stably introduced into a fertilized oocyte which is then allowed to develop into an animal. The resultant animal contains cells carrying the polynucleotide introduced into the oocyte. Direct injection may be used to introduce the polynucleotide encoding a SPARC family polypeptide into cells in vivo (see e.g., Acsadi et al., 1991, *Nature*, 332: 815-818; Wolff et al., 1990, *Science*, 247:1465-1468). A delivery apparatus (e.g., a "gene gun") for injecting DNA into cells in vivo can be used. Such an apparatus is commercially available (e.g., from BioRad).

Receptor-Mediated DNA Uptake

A polynucleotide encoding a SPARC family polypeptide also can be introduced into cells by complexing the polynucleotide to a cation, such as polylysine, which is coupled to a ligand for a cell-surface receptor (see for example Wu, et al., 1988, *J. Biol. Chem.*, 263:14621; Wilson et al., 1992, *J. Biol. Chem.*, 267:963-967; and U.S. Pat. No. 5,166,320). Binding of the polynucleotide-ligand complex to the receptor facilitates uptake of the polynucleotide by receptor-mediated endocytosis. Receptors to which a polynucleotide-ligand complex have targeted include the transferrin receptor and the asialoglycoprotein receptor. A polynucleotide-ligand complex linked to adenovirus capsids which naturally disrupt endosomes, thereby releasing material into the cytoplasm can be used to avoid degradation of the complex by intracellular lysosomes (see for example Curiel et al., 1991, *Proc. Natl. Acad. Sci. USA*, 88:8850; Cristiano et al., 1993, *Proc. Natl. Acad. Sci. USA*, 90:2122-2126). Receptor-mediated polynucleotide uptake can be used to introduce the polynucleotide encoding a SPARC family polypeptide into cells either in vitro or in vivo and, additionally, has the added feature that polynucleotide can be selectively targeted to a particular cell type by use of a ligand which binds to a receptor selectively expressed on a target cell of interest.

Viral-Mediated Gene Transfer

Another approach for introducing a polynucleotide encoding a SPARC family polypeptide into a cell is by use of a viral vector containing the polynucleotide encoding a SPARC family polypeptide. Infection of cells with a viral vector has the advantage that a large proportion of cells receive the polynucleotide, which can obviate the need for selection of cells which have received the polynucleotide. Additionally, molecules encoded within the viral vector, e.g., by a cDNA contained in the viral vector, are expressed efficiently in cells which have taken up viral vector polynucleotide and viral vector systems can be used either in vitro or in vivo.

Nonreplicating viral vectors can be produced in packaging cell lines which produce virus particles which are infectious but replication-defective, rendering them useful vectors for introduction of polynucleotide into a cell lacking complementary genetic information enabling encapsidation (Mann et al., 1983, cell, 33:153; Miller and Buttimore, Mol. Cell. Biol., 1986, 6:2895 (PA317, ATCC CRL9078). Packaging cell lines which contain amphotrophic packaging genes able to transform cells of human and other species origin are preferred.

Retroviruses

The retroviruses are a group of single-stranded RNA viruses characterized by an ability to convert their RNA to double-stranded DNA in infected cells by a process of reverse-transcription (Coffin, 1990, in Fields et al., Ceds, *Virology*, Raven Press, New York, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, functions as a signal for packaging of the genome into virions. Two long terminal repeat (LTR) sequences are present at the 5' and 3' ends of the viral genome. These contain strong promoter and enhancer sequences and are also required for integration in the subject cell genome (Coffin, supra).

Defective retroviruses are well characterized for use in gene transfer for gene therapy purposes (for a review see Miller, 1990, Blood 76:271).

Protocols for producing recombinant retroviruses and for infecting cells in vitro or in vivo with such viruses can be found in *Current Protocols in Molecular Biology*, Ausubel, F. M. et al. (eds.), 1989, Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al., 1985, Science, 230:1395-1398; Danos, et al., 1988, Proc. Natl. Acad. Sci. USA, 85:6460-6464; Wilson et al., 1988, Proc. Natl. Acad. Sci. USA, 85:3014-3018; Armentano et al., 1990, Proc. Natl. Acad. Sci. USA, 87:6141-6145; Huber et al., 1991, Proc. Natl. Acad. Sci. USA, 88:8039-8043; Ferry et al., 1991, Proc. Natl. Acad. Sci. USA, 88:8377-8381; Chowdhury et al., 1991, Science, 254:1802-1805; van Beusechem et al., 1992, Proc. Natl. Acad. Sci. USA, 89:7640-7644; Kay et al., 1992, Human Gene Therapy, 3:641-647; Dai et al., 1992, Proc. Natl. Acad. Sci. USA, 89:10892-10895; Hwu et al., 1993, J. Immunol., 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign polynucleotide inserted into it) to be integrated into the subject genome to stably introduce polynucleotide into the cell. Thus, it may be necessary to stimulate replication of the target cell.

Adenovirus

Knowledge of the genetic organization of adenovirus, a 36 kB, linear and double-stranded DNA virus, allows substitution of a large piece of adenoviral DNA with foreign sequences up to 7 kB (Grunhaus, et al., 1992, Seminar in Virology, 3:237-252). In contrast to retrovirus, the infection of adenoviral DNA into subject cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target-cell range, and high infectivity. Both ends of the viral genome contain 100-200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5' tripartite leader (TL) sequence which makes them preferred mRNAs for translation.

The genome of an adenovirus can be manipulated such that it encodes and expresses a gene product of interest but is inactivated in terms of its ability to replicate in a normal lytic viral life cycle. See for example Berkner, et al., 1988, BioTechniques, 6:616; Rosenfeld, et al., 1991, Science, 252:431-434; and Rosenfeld, et al., 1992, Cell, 68:143-155. Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types, including airway epithelium (Rosenfeld, et al., 1992, cited supra), endothelial cells (Lemarchand, et al., 1992, Proc. Natl. Acad. Sci. USA, 89:6482-6486), hepatocytes (Herz, et al., 1993, Proc. Natl. Acad. Sci. USA, 90:2812-2816) and muscle cells (Quantin, et al., 1992, Proc. Natl. Acad. Sci. USA, 89:2581-2584). Additionally, introduced adenoviral polynucleotide (and foreign DNA contained therein) is not integrated into the genome of a subject cell but remains episomal, thereby avoiding potential problems that can occur as a result of insertional mutagenesis in situations where introduced polynucleotide becomes integrated into the subject genome (e.g., retroviral DNA). Moreover, the carrying capacity of the adenoviral genome for foreign DNA is large (up to 8 kilobases) relative to other gene delivery vectors (Berkner, et al. cited supra; Haj-Ahmand, et al., 1986, J. Virol., 57:267). Most replication-defective adenoviral vectors currently in use are deleted for all or parts of the viral E1 and E3 genes but retain as much as 80% of the adenoviral genetic material.

Recombinant adenovirus may be generated by methods known in the art, e.g., as described in U.S. Pat. No. 6,194,191, incorporated herein by reference.

Generation and propagation of the adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones, et al., 1978), the current adenovirus vectors, with the help of 293 cells, carry foreign DNA in either the E1, the E3 or both regions (Graham, et al., 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication-defective and will not have an adenovirus E1 region. Thus, it will be most convenient to introduce the polynucleotide encoding a polypeptide of interest at the position from which the E1 coding sequences have been removed. However, the position of insertion of the coding region of a selected polynucleotide within the adenovirus sequences is not critical to the present invention.

Adenovirus is easy to grow and manipulate and exhibits broad subject range in vitro and in vivo. This group of viruses can be obtained in high titers, e.g., $10^9$-$10^{11}$ plaque-forming unit (PFU)/ml, and they are highly infective. The life cycle of adenovirus does not require integration into the subject cell genome.

Adenovirus vectors have been used in eukaryotic gene expression (Levrero, et al., 1991, Gene, 101:195-202; Gomez-Foix, et al., 1992, J. Biol. Chem., 267:25129-25134) and vaccine development (Grunhaus, et al., 1992, Seminar in Virology, 3:237-252; Graham, et al., 1992, Biotechnology, 20:363-390). Animal studies suggested that recombinant adenovirus could be used for gene therapy (Stratford-Perricaudet, et al., 1991, in: Human Gene Transfer, O. Cohen-Haguenauer, Ceds), John Libbey Eurotext, France; Stratford-Perricaudet, et al., 1990, Hum. Gene Ther., 1:241-256; Rich, et al., 1993, Nature, 361:647-650). Experiments in administering recombinant adenovirus to different tissues include trachea instillation (Rosenfeld, et al., 1991, Science, 252:431-434; Rosenfeld, et al., 1992, Cell, 68:143-155), muscle injection (Ragot, et al., 1993, Nature, 361:647-650), peripheral intravenous injection (Herz, et al., 1993, Proc. Nat'l. Acad. Sci. USA 90:2812-2816), and stereotactic inoculation into the brain (Le Gal La Salle et al., 1993, Science, 259:988-990).

Other Viral Vectors as Expression Vectors

Other viral vectors may be employed as expression constructs in the present invention. Vectors derived from viruses such as vaccinia virus (Ridgeway, 1988, in: Rodriguez R L, Denhardt D T, ed. *Vectors: A Survey of Molecular Cloning Vectors and Their Uses*. Stoneham: Butterworth, pp. 467-492; Baichwal, et al., 1986 In: Kucherlapati R, ed. Gene Transfer. New York: Plenum Press, pp. 117-148; Coupar, et al., 1988, Gene, 68:1-10), adeno-associated virus (AAV) (Baichwal, et al., 1986, supra; Hermonat, et al., 1984, Proc. Natl. Acad. Sci. USA, 81:6466-6470) and herpesviruses may be employed. They offer several attractive features for various mammalian cells (Friedmann, 1989, Science, 244:1275-1281; Baichwal, et al., 1986, supra; Coupar, et al., 1988, supra; Horwich, et al., 1990, J. Virol., 64:642-650).

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol., 158:97-129). It is also one of the few viruses that may integrate its DNA into non-dividing cells, and exhibits a high frequency of stable integration (see, for example, Flotte et al., 1992, Am. J. Respir. Cell. Mol. Biol., 7:349-356; Samulski et al., 1989, J. Virol., 63:3822-3828; and McLaughlin et al., 1989, J. Virol., 62:1963-1973). Vectors containing as little as 300 base pairs of AAV can be packaged and can integrate. Space for exogenous polynucleotide is limited to about 4.5 kb. An AAV vector such as that described in Tratschin et al., 1985, Mol. Cell. Biol., 5:3251-3260 can be used to introduce polynucleotide into cells. A variety of polynucleotides have been introduced into different cell types using AAV vectors (see for example Hermonat, et al., 1984, Proc. Natl. Acad. Sci. USA, 81:6466-6470; Tratschin, et al., 1985, Mol. Cell. Biol., 4:2072-2081; Wondisford, et al., 1988, Mol. Endocrinol., 2:32-39; Tratschin, et al., 1984, J. Virol., 51:611-619; and Flotte, et al., 1993, J. Biol. Chem., 268:3781-3790).

After the transfer of a polynucleotide encoding a SPARC family polypeptide into cells, the cells may be selected and used for sensitizing treatment according to the present invention. The efficacy of a particular expression vector system and method of introducing polynucleotide into a cell can be assessed by standard approaches routinely used in the art. For example, polynucleotide introduced into a cell can be detected by a filter hybridization technique (e.g., Southern blotting) and RNA produced by transcription of introduced polynucleotide can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. Alternatively, an expression system can first be optimized using a reporter gene linked to the regulatory elements and vector to be used as described herein above. The reporter gene encodes a separate gene product which is easily detectable and, thus, can be used to evaluate the efficacy of the system.

Since a SPARC family polypeptide is a secreted protein, its extracellular level may also be detected to determine its expression using methods known in the art, such as Immuno-blotting or Elisa.

Another way of increase the expression of a SPARC polynucleotide or polypeptide in a cell is by endogenous gene activation, i.e., inserting a strong promoter before the natural SPARC family gene sequence in the genome of the cell. Endogenous gene activation is a method of introducing, by homologous recombination with genomic DNA, DNA sequences (e.g., strong promoters) which are not normally functionally linked to the endogenous gene and (1) which, when inserted into the host genome at or near the endogenous gene, serve to alter (e.g., activate) the expression of the endogenous gene, and further (2) allow for selection of cells in which the activated endogenous gene is amplified. Expression of proteins by endogenous gene activation is well known in the art and is disclosed, for example in U.S. Pat. Nos. 5,733,761, 5,641,670, and 5,733,746, and international patent publication Nos. WO 93/09222, WO 94/12650, WO 95/31560, WO 90/11354, WO 91/06667 and WO 91/09955, the contents of each of which are incorporated herein by reference in its entirety.

In one embodiment, a endogenous SPARC family gene expression is activated (e.g., increased) by inserting a tetracycline-inducible tetracycline promoter/operator to control its expression.

The methods described above to transfer polynucleotide into cells and to make recombinant cells of the invention are merely for purposes of illustration and are typical of those that might be used. However, other procedures may also be employed to obtain expression of a SPARC family polypeptide in cells, as is understood in the art.

Cancer Therapy

Cancer is typically treated by surgery, chemotherapy or radiation therapy. Biological therapies such as immunotherapy and gene therapy are also being developed. Other therapies include hyperthermic therapy, photodynamic therapy, etc. (see National Cancer Institute home page at world wide web nci.nih.gov).

Chemotherapy

Chemotherapy is the use of anti-cancer (cytotoxic) drugs to destroy cancer cells. There are over 50 different chemotherapy drugs and some are given on their own, but often several drugs may be combined (this is known as combination chemotherapy). An example list of chemotherapy agents, as described at World wide web cancerbacup.org.uk/info/actinomycin.htm, include: Actinomycin D, Adriamycin, Altretamine, Asparaginase, Bleomycin, Busulphan, Capecitabine, Carboplatin, Carmustine, Chlorambucil, Cisplatin, CPT-11, Cyclophosphamide, Cytarabine, Dacarbazine, Daunorubicin, Doxorubicin, Epirubicin, Etoposide, Fludarabine, Fluorouracil, Gemcitabine, Hydroxyurea, Idarubicin, fosfamide, Irinotecan, Liposomal Doxorubicin, Lomustine, Melphalan, Mercaptopurine, Methotrexate, Mitomycin, Mitozantrone, Oxaliplatin, Procarbazine, Steroids, Streptozocin, Taxol, Taxotere, Taxotere—the TACT trial, Tamozolomide, Thioguanine, Thiotepa, Tomudex, Topotecan, Treosulfan, UFT (Uracil-tegufur), Vinblastine, Vincristine, Vindesine, Vinorelbine.

Because cancer cells may grow and divide more rapidly than normal cells, many anticancer drugs are made to kill growing cells. But certain normal, healthy cells also multiply quickly, and chemotherapy can affect these cells, too. This damage to normal cells causes side effects. The fast-growing, normal cells most likely to be affected are blood cells forming in the bone marrow and cells in the digestive tract (mouth, stomach, intestines, esophagus), reproductive system (sexual organs), and hair follicles. Some anticancer drugs may affect cells of vital organs, such as the heart, kidney, bladder, lungs, and nervous system.

The kinds of side effects one has and how severe they are depend on the type and dose of chemotherapy one gets and how its body reacts. Side effects of chemotherapy include fatigue, nausea and vomiting, pain, hair loss, anemia, central nervous system problems, infection, blood clotting problems, mouth, gum, and throat problems, diarrhea, constipation, nerve and muscle effects, effects on skin and nails, radiation recall, kidney and bladder effects, flu-like symptoms, and fluid retention.

Radiation Therapy

One type of radiation therapy commonly used involves photons, "packets" of energy. X-rays were the first form of photon radiation to be used to treat cancer. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy.

Gamma rays are another form of photons used in radiotherapy. Gamma rays are produced spontaneously as certain elements (such as radium, uranium, and cobalt 60) release radiation as they decompose, or decay. Each element decays at a specific rate and gives off energy in the form of gamma rays and other particles. X-rays and gamma rays have the same effect on cancer cells.

Another technique for delivering radiation to cancer cells is to place radioactive implants directly in a tumor or body cavity. This is called internal radiotherapy. (Brachytherapy, interstitial irradiation, and intracavitary irradiation are types of internal radiotherapy.) In this treatment, the radiation dose is concentrated in a small area, and the patient stays in the hospital for a few days. Internal radiotherapy is frequently used for cancers of the tongue, uterus, and cervix.

Several new approaches to radiation therapy are being evaluated to determine their effectiveness in treating cancer. One such technique is intraoperative irradiation, in which a large dose of external radiation is directed at the tumor and surrounding tissue during surgery.

Another investigational approach is particle beam radiation therapy. This type of therapy differs from photon radiotherapy in that it involves the use of fast-moving subatomic particles to treat localized cancers. A sophisticated machine is needed to produce and accelerate the particles required for this procedure. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation.

Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

Radioactive seed implants can be used as the sole treatment modality for adenocarcinoma of the prostate for appropriate patients with early stage disease. The two most common sources are Iodine-125 and Palladium-103 with no compelling clinical data that one is superior to the other. The radioactive seed implant can be individually customized to a patient's prostate to maximize the dose to the gland while minimizing the dose to the surrounding normal structures. Prostate brachytherapy offers the highest level of conformal radiation therapy for adenocarcinoma of the prostate. The prostate brachytherapy team at Thomas Jefferson University has extensive experience in prostate brachytherapy and has presented work at national and international forums.

Prostate brachytherapy or radioactive seed implant is a highly technical, operator dependent method delivers the radiation energy by placing many small radioactive seeds directly inside the prostate, effectively delivering the treatment "from the inside-out". This is done in the operating room under general anesthesia, as a one-time procedure. These seeds can deliver high doses of radiation directly to the tumor, with little harm to the normal, healthy tissue around the prostate. This may be combined with 3-dimensional conformal radiation therapy in some settings.

Other recent radiotherapy research has focused on the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells. The success of this technique will depend upon both the identification of appropriate radioactive substances and determination of the safe and effective dose of radiation that can be delivered in this way.

Radiation therapy may be used alone or in combination with chemotherapy or surgery. Like all forms of cancer treatment, radiation therapy can have side effects. Possible side effects of treatment with radiation include temporary or permanent loss of hair in the area being treated, skin irritation, temporary change in skin color in the treated area, and tiredness. Other side effects are largely dependent on the area of the body that is treated.

Hyperthermia Therapy

Hyperthermia, a procedure in which body tissue is exposed to high temperatures (up to 106° F.), is under investigation to assess its effectiveness in the treatment of cancer. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (radiation therapy, chemotherapy, and biological therapy) to try to increase their effectiveness.

Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes.

In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally.

Whole-body heating is used to treat metastatic cancer that has spread throughout the body. It can be accomplished using warm-water blankets, hot wax, inductive coils (like those in electric blankets), or thermal chambers (similar to large incubators).

Hyperthermia does not cause any marked increase in radiation side effects or complications. Heat applied directly to the skin, however, can cause discomfort or even significant local pain in about half the patients treated. It can also cause blisters, which generally heal rapidly. Less commonly, it can cause burns.

Photodynamic Therapy

Photodynamic therapy (also called PDT, photoradiation therapy, phototherapy, or photochemotherapy) is a treatment for some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent.

In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells.

The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer.

An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs.

Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath.

In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

Laser Therapy

Laser therapy involves the use of high-intensity light to destroy cancer cells. This technique is often used to relieve symptoms of cancer such as bleeding or obstruction, especially when the cancer cannot be cured by other treatments. It may also be used to treat cancer by shrinking or destroying tumors.

The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel).

Although there are several different kinds of lasers, only three kinds have gained wide use in medicine:

- Carbon dioxide (CO2) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the CO2 laser is also able to cut the skin. The laser is used in this way to remove skin cancers.
- Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers.
- Argon laser—This laser can pass through only superficial layers of tissue and is therefore useful in dermatology and in eye surgery. It also is used with light-sensitive dyes to treat tumors in a procedure known as photodynamic therapy (PDT).

Lasers have several advantages over standard surgical tools, including:

- Lasers are more precise than scalpels. Tissue near an incision is protected, since there is little contact with surrounding skin or other tissue.
- The heat produced by lasers sterilizes the surgery site, thus reducing the risk of infection.
- Less operating time may be needed because the precision of the laser allows for a smaller incision.
- Healing time is often shortened; since laser heat seals blood vessels, there is less bleeding, swelling, or scarring.
- Laser surgery may be less complicated. For example, with fiber optics, laser light can be directed to parts of the body without making a large incision.
- More procedures may be done on an outpatient basis.

There are also disadvantages with laser surgery:

- Relatively few surgeons are trained in laser use.
- Laser equipment is expensive and bulky compared with the usual surgical tools, such as scalpels.
- Strict safety precautions must be observed in the operating room. (For example, the surgical team and the patient must use eye protection.)

Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells.

CO2 and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread.

Lasers are used to treat many types of cancer. Laser surgery is a standard treatment for certain stages of glottis (vocal cord), cervical, skin, lung, vaginal, vulvar, and penile cancers.

In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer.

Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

Gene Therapy

Gene therapy is an experimental medical intervention that involves modifying the genetic material of living cells to fight disease. Gene therapy is being studied in clinical trials (research studies with humans) for many different types of cancer and for other diseases.

One of the goals of gene therapy is to supply cells with healthy copies of missing or altered genes. Instead of giving a patient a drug, doctors attempt to correct the problem by altering the genetic makeup of some of the patient's cells. Examples of diseases that could be treated this way include cystic fibrosis and hemophilia.

Gene therapy is also being studied as a way to change how a cell functions; for example, by stimulating immune system cells to attack cancer cells.

In general, a gene is delivered to the cell using a "vector." The most common types of vectors used in gene therapy are viruses. Viruses used as vectors in gene therapy are genetically disabled; they are unable to reproduce themselves. Most gene therapy clinical trials rely on mouse retroviruses to deliver the desired gene. Other viruses used as vectors include adenoviruses, adeno-associated viruses, poxviruses, and the herpes virus.

A gene therapy can be done both ex vivo and in vivo. In most ex vivo gene therapy clinical trials, cells from the patient's blood or bone marrow are removed and grown in the laboratory. The cells are exposed to the virus that is carrying the desired gene. The virus enters the cells, and the desired gene becomes part of the cells' DNA. The cells grow in the laboratory and are then returned to the patient by injection into a vein. In in vivo gene therapy, vectors or liposomes are used to deliver the desired gene to cells inside the patient's body.

Immunotherapy

Cancer may develop when the immune system breaks down or is not functioning adequately. Immunotherapy uses the body's immune system, either directly or indirectly, to fight cancer or to lessen the side effects that may be caused by some cancer treatments. Immunotherapy is designed to repair, stimulate, or enhance the immune system's responses.

Immune system cells include the following: Lymphocytes are a type of white blood cell found in the blood and many other parts of the body. Types of lymphocytes include B cells, T cells, and Natural Killer cells. B cells (B lymphocytes) mature into plasma cells that secrete antibodies (immunoglobulins), the proteins that recognize and attach to foreign substances known as antigens. Each type of B cell makes one specific antibody, which recognizes one specific antigen. T cells (T lymphocytes) directly attack infected, foreign, or cancerous cells. T cells also regulate the immune response by signaling other immune system defenders. T cells work primarily by producing proteins called lymphokines. Natural Killer cells (NK cells) produce powerful chemical substances that bind to and kill any foreign invader. They attack without first having to recognize a specific antigen. Monocytes are white blood cells that can swallow and digest microscopic organisms and particles in a process known as phagocytosis. Monocytes can also travel into tissue and become macrophages.

Cells in the immune system secrete two types of proteins: antibodies and cytokines. Antibodies respond to antigens by latching on to, or binding with, the antigens. Specific antibodies match specific antigens, fitting together much the way a key fits a lock. Cytokines are substances produced by some immune system cells to communicate with other cells. Types of cytokines include lymphokines, interferons, interleukins, and colony-stimulating factors. Cytotoxic cytokines are released by a type of T cell called a cytotoxic T cell. These cytokines attack cancer cells directly.

Nonspecific immunomodulating agents are substances that stimulate or indirectly augment the immune system. Often, these agents target key immune system cells and cause secondary responses such as increased production of cytokines and immunoglobulins. Two nonspecific immunomodulating agents used in cancer treatment are *bacillus* Calmette-Guerin (BCG) and levamisole. BCG, which has been widely used as a tuberculosis vaccine, is used in the treatment of superficial bladder cancer following surgery. BCG may work by stimulating an inflammatory, and possibly an immune, response. A solution of BCG is instilled in the bladder and stays there for about 2 hours before the patient is allowed to empty the bladder by urinating. This treatment is usually performed once a week for 6 weeks. Levamisole is used along with fluorouracil (5-FU) chemotherapy in the treatment of stage III (Dukes' C) colon cancer following surgery. Levamisole may act to restore depressed immune function.

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, and vaccines. Immunotherapy may be used to stop, control, or suppress processes that permit cancer growth; make cancer cells more recognizable, and therefore more susceptible, to destruction by the immune system; boost the killing power of immune system cells, such as T cells, NK cells, and macrophages; alter cancer cells' growth patterns to promote behavior like that of healthy cells; block or reverse the process that changes a normal cell or a precancerous cell into a cancerous cell; enhance the body's ability to repair or replace normal cells damaged or destroyed by other forms of cancer treatment, such as chemotherapy or radiation; and prevent cancer cells from spreading to other parts of the body.

Some BRMs are a standard part of treatment for certain types of cancer, while others are being studied in clinical trials. BRMs are being used alone or in combination with each other. They are also being used with other treatments, such as radiation therapy and chemotherapy.

Interferons (IFNs) are types of cytokines that occur naturally in the body. They were the first cytokines produced in the laboratory for use as BRMs. There are three major types of interferons—interferon alpha, interferon beta, and interferon gamma; interferon alpha is the type most widely used in cancer treatment. Interferons can improve the way a cancer patient's immune system acts against cancer cells. In addition, interferons may act directly on cancer cells by slowing their growth or promoting their development into cells with more normal behavior. Some interferons may also stimulate NK cells, T cells, and macrophages, boosting the immune system's anticancer function. The U.S. Food and Drug Administration (FDA) has approved the use of interferon alpha for the treatment of certain types of cancer, including hairy cell leukemia, melanoma, chronic myeloid leukemia, and AIDS-related Kaposi's sarcoma. Studies have shown that interferon alpha may also be effective in treating other cancers such as metastatic kidney cancer and non-Hodgkin's lymphoma.

Like interferons, interleukins (IL) are cytokines that occur naturally in the body and can be made in the laboratory. Many interleukins have been identified; interleukin-2 (IL-2 or aldesleukin) has been the most widely studied in cancer treatment. IL-2 stimulates the growth and activity of many immune cells, such as lymphocytes, that can destroy cancer cells. The FDA has approved IL-2 for the treatment of metastatic kidney cancer and metastatic melanoma.

Colony-stimulating factors (CSFs) (sometimes called hematopoietic growth factors) usually do not directly affect tumor cells; rather, they encourage bone marrow stem cells to divide and develop into white blood cells, platelets, and red blood cells. Bone marrow is critical to the body's immune system because it is the source of all blood cells. The CSFs' stimulation of the immune system may benefit patients undergoing cancer treatment. Because anticancer drugs can damage the body's ability to make white blood cells, red blood cells, and platelets, patients receiving anticancer drugs have an increased risk of developing infections, becoming anemic, and bleeding more easily. By using CSFs to stimulate blood cell production, doctors can increase the doses of anticancer drugs without increasing the risk of infection or the need for transfusion with blood products. CSFs are particularly useful when combined with high-dose chemotherapy. Some examples of CSFs and their use in cancer therapy are as follows: G-CSF (filgrastim) and GM-CSF (sargramostim) can increase the number of white blood cells, thereby reducing the risk of infection in patients receiving chemotherapy. G-CSF and GM-CSF can also stimulate the production of stem cells in preparation for stem cell or bone marrow transplants; Erythropoietin can increase the number of red blood cells and reduce the need for red blood cell transfusions in patients receiving chemotherapy; and Oprelvekin can reduce the need for platelet transfusions in patients receiving chemotherapy.

CSFs are used in clinical trials to treat some types of leukemia, metastatic colorectal cancer, melanoma, lung cancer, and other types of cancer.

Monoclonal Antibodies (MOABs) are also being evaluated in cancer therapy. These antibodies are produced by a single type of cell and are specific for a particular antigen. MOABs specific to the antigens found on the surface of the cancer cell being treated are being created.

MOABs are made by injecting human cancer cells into mice so that their immune systems will make antibodies against these cancer cells. The mouse cells producing the antibodies are then removed and fused with laboratory-grown cells to create "hybrid" cells called hybridomas. Hybridomas can indefinitely produce large quantities of these pure antibodies, or MOABs. MOABs may be used in cancer treatment in a number of ways: MOABs that react with specific types of cancer may enhance a patient's immune response to the cancer. MOABs can be programmed to act against cell growth factors, thus interfering with the growth of cancer cells. MOABs may be linked to anticancer drugs, radioisotopes (radioactive substances), other BRMs, or other toxins. When the antibodies latch onto cancer cells, they deliver these poisons directly to the tumor, helping to destroy it. MOABs may help destroy cancer cells in bone marrow that has been removed from a patient in preparation for a bone marrow transplant. MOABs carrying radioisotopes may also prove useful in diagnosing certain cancers, such as colorectal, ovarian, and prostate.

Rituxan® (rituximab) and Herceptin® (trastuzumab) are examples of monoclonal antibodies that have been approved by the FDA. Rituxan is used for the treatment of B-cell non-Hodgkin's lymphoma that has returned after a period of improvement or has not responded to chemotherapy. Herceptin is used to treat metastatic breast cancer in patients with tumors that produce excess amounts of a protein called HER-2. (Approximately 25 percent of breast cancer tumors produce excess amounts of HER-2.) MOABs are begun tested in clinical trials to treat lymphomas, leukemias, colorectal cancer, lung cancer, brain tumors, prostate cancer, and other types of cancer.

Cancer vaccines are another form of immunotherapy currently under study. Vaccines for infectious diseases, such as measles, mumps, and tetanus, are effective because they expose the body's immune cells to weakened forms of antigens that are present on the surface of the infectious agent. This exposure causes the immune cells to produce more plasma cells, which make antibodies. T cells that recognize the infectious agent also multiply. These activated T cells later remember the exposure. The next time the agent enters the body, cells in the immune system are already prepared to respond and stop the infection.

For cancer treatment, researchers are developing vaccines that may encourage the patient's immune system to recognize cancer cells. These vaccines may help the body reject tumors and prevent cancer from recurring. In contrast to vaccines against infectious diseases, cancer vaccines are designed to be injected after the disease is diagnosed, rather than before it develops. Cancer vaccines given when the tumor is small may be able to eradicate the cancer. Early cancer vaccine clinical trials (research studies with people) involved mainly patients with melanoma. Currently, cancer vaccines are also being studied in the treatment of many other types of cancer, including lymphomas and cancers of the kidney, breast, ovary, prostate, colon, and rectum. Researchers are also investigating ways that cancer vaccines can be used in combination with other BRMs.

Like other forms of cancer treatment, biological therapies can cause a number of side effects, which can vary widely from patient to patient. Rashes or swelling may develop at the site where the BRMs are injected. Several BRMs, including interferons and interleukins, may cause flu-like symptoms including fever, chills, nausea, vomiting, and appetite loss. Fatigue is another common side effect of BRMs. Blood pressure may also be affected. The side effects of IL-2 can often be severe, depending on the dosage given. Patients need to be closely monitored during treatment. Side effects of CSFs may include bone pain, fatigue, fever, and appetite loss. The side effects of MOABs vary, and serious allergic reactions may occur. Cancer vaccines can cause muscle aches and fever.

Sensitizing Compositions and Methods—Dosage, Mode of Administration, and Pharmaceutical Formulations The present invention provides for a composition comprising a SPARC family polypeptide or a polynucleotide encoding such polypeptide and a therapeutic agent. The SPARC polypeptide or polynucleotide is provided as a therapeutically effective amount so as to sensitize a cancer cell or patient to the treatment by said therapeutic agent.

The therapeutic agent may be any suitable agent for a specific therapy as described herein and as known in the art. It may be a chemotherapy agent, i.e., a drug, for example, 5-fluorouracil; it may be a radiation agent, such as a radiolabeled antibody, a radiosensitizer, or a radioactive seed implant. The therapeutic agent may also be a photosensitizing agent, such as porfimer sodium; or a gene therapy agent (e.g., a vector), or it may be an immunotherapy agent, such as a immune cell, an antibody, or cytokine.

The present invention provides a composition comprising a SPARC family polypeptide and a chemotherapy-resistant cell.

The present invention also provides a recombinant cell comprising a heterologous transcription control region operatively associated with a SPARC family polynucleotide.

In addition to sensitizing a sample or a mammal to cancer therapy, the use of the subject compositions of the present invention can reduce the dosage of a therapy, therefore reducing the side effects caused by cancer therapy.

The above compositions may be a pharmaceutical composition which includes a pharmaceutically acceptable carrier or excipient.

As used herein, a "carrier" refers to any substance suitable as a vehicle for delivering an APC to a suitable in vitro or in vivo site of action. As such, carriers can act as an excipient for formulation of a therapeutic or experimental reagent containing an APC. Preferred carriers are capable of maintaining an APC in a form that is capable of interacting with a T cell. Examples of such carriers include, but are not limited to water, phosphate buffered saline, saline, Ringer's solution, dextrose solution, serum-containing solutions, Hank's solution and other aqueous physiologically balanced solutions or cell culture medium. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer.

A composition comprising a SPARC family polypeptide and a therapeutic agent may be used to sensitize a cancer in vitro by directly contacting the cancer sample with an effective amount of the purified SPARC family polypeptide. A mammal (e.g., a cancer patient) can be administered a composition comprising a SPARC family polypeptide to achieve the sensitizing effect in vivo. In addition, a cancer sample, either cells or tissue, may be obtained from the mammal and sensitized using the SPARC family polypeptide ex vivo before being returned back to the mammal.

A SPARC family polynucleotide of the present invention may be introduced into a cancer cell in vitro to sensitizing the response of the cancer cell, or it may be delivered to a mammal in vivo through an appropriate vector as known in the art and as described herein above. In addition, the polynucleotide may be introduced ex vivo into cancer cells or tissue obtained from a mammal in need, and the cells or tissue then returned to the mammal in need. Being a secreted protein, a SPARC family polypeptide made by such ex vivo introduced cells may function in the local environment to sensitize not only the modified cells, but also the neighboring non-modified cancer cells.

A composition comprising a recombinant cell may be introduced into a mammal for sensitizing treatment.

Subject dose size, number of doses, frequency of dose administration, and mode of administration can be determined and optimized using methods known in the art (see, e.g., Hardman et al., Ceds 1995, Goodman & Gilman's *The Pharmacological Basis of Therapeutics*, Ninth Edition, McGraw-Hill).

Dosages of each therapy in treating various cancer patients are known in the art and can be determined by a skilled physician. For example, a suitable SPARC polypeptide dose may be in the range of 0.01 to 100 mg SPARC polypeptide per kilogram body weight of the recipient per day, preferably in the range of 0.2 to 10 mg per kilogram body weight per day. A SPARC polynucleotide of the present invention may be administered at a suitable dose in the range of 0.01 to 100 mg polynucleotide per kilogram body weight of the recipient per day, preferably in the range of 0.2 to 10 mg per kilogram body weight per day. The cells comprising a recombinant SPARC polynucleotide may be administered at a dosage in the range of 104-1010 per kilogram body weight of the recipient, preferably in the range of 106-108 per kilogram body weight of the recipient. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of the SPARC family polypeptide per unit dosage form. Dosages of the SPARC family polypeptide or the SPARC family polynucleotide, or the cells comprising a recombinant SPARC family polynucleotide useful according to the invention will vary depending upon the condition to be treated or prevented and on the identity of the SPARC family polypeptide or polynucleotide being used. Estimates of effective dosages and in vivo half-lives for the individual composition encompassed by the invention can be made on the basis of in vivo testing using an animal model, such as the mouse model described herein or an adaptation of such method to larger mammals.

In vitro/Ex vivo Applications

Compositions provided by the present invention may be used to sensitize a cancer cell in vitro using methods known in the art, and as described herein before. Thus the present invention provides a method for sensitizing a cancer cell to a therapeutic treatment, the method comprising contacting the cancer sample with an effective amount of a composition comprising a SPARC family polypeptide or a polynucleotide encoding a SPARC family polypeptide. The present invention also provides a method for ex vivo sensitizing a mammal diagnosed with cancer to a therapeutic treatment, the method comprising: (1) Obtaining a cancer sample from the mammal; (2) contacting the cancer sample with an effective amount of a composition comprising a SPARC family polypeptide or a polynucleotide encoding a SPARC family polypeptide; and (3) returning the cancer sample after the contacting of (2) to the mammal.

Ex vivo gene therapy refers to the isolation of cells from an animal, the delivery of a polynucleotide into the cells, in vitro, and then the return of the modified cells back into the animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. This method is applicable because a SPARC family polypeptide is a secreted polypeptide. The return of the modified cells back to a mammal may increase the extracellular concentration of a SPARC family polypeptide locally and therefore sensitizing the unmodified cancer cells which are in proximity with the modified cells.

When tissue sample needs to be taken from a mammal for ex vivo application, cellular extracts may be prepared from tissue biopsies of patients including, but not limited to brain, heart, lung, lymph nodes, eyes, joints, skin and neoplasms associated with these organs. "Tissue biopsy" also encompasses the collection of biological fluids including but not limited to blood, plasma, sputum, urine, cerebrospinal fluid, lavages, and leukophoresis samples. In a preferred embodiment, "tissue biopsies" according to the invention are taken from tumors of the breast, ovary or prostate. "Tissue biopsies" are obtained using techniques well known in the art including needle aspiration and punch biopsy of the skin.

Generally, when a polynucleotide is introduced into cells in culture (e.g., by one of the transfection techniques described above) only a small fraction of cells (about 1 out of $10^5$) typically integrate the transfected polynucleotide into their genomes (i.e., the polynucleotide is maintained in the cell episomally). Thus, in order to identify cells which have taken up exogenous polynucleotide, it is advantageous to transfect polynucleotide encoding a selectable marker into the cell along with the polynucleotide(s) of interest, i.e., a SPARC family polynucleotide, as described herein before.

In vivo Applications

The composition provided by the present invention can be administered to a mammal, e.g., in a method of sensitizing a therapeutic treatment. Thus the present invention provides a method for in vivo sensitizing a mammal diagnosed with cancer to a therapeutic treatment, the method comprising administrating to the mammal an effective amount of a composition comprising a SPARC family polypeptide or a polynucleotide encoding a SPARC family polypeptide.

The manner of administration of a composition of the present invention can depend upon the particular purpose for the delivery, the overall health and condition of the patient and the judgment of the physician or technician administering the target vehicle. A composition of the present invention can be administered to an animal using a variety of methods. Such delivery methods can include parenteral, topical, oral or local administration, such as intradermally. A composition can be administered in a variety of unit dosage forms depending upon the method of administration. Preferred delivery methods for a composition of the present invention include intravenous administration, local administration (e.g., intra-tumoral) by, for example, injection, intradermal injection, intramuscular injection, intraperitoneal injection and inhalation. For particular modes of delivery, a composition of the present invention can be formulated in an excipient of the present invention. A composition of the present invention can be administered to any animal, preferably to mammals, and more preferably to humans.

Injection: The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration: Pharmaceutical compositions for oral administration are formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use are obtained through a combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which are used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Nasal administration: For nasal administration, penetrants appropriate to the particular barrier to be permeated are used in the formulation. Such penetrants are generally known in the art.

Subcutaneous and intravenous use: For subcutaneous and intravenous use, the composition of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The composition useful according to the invention may also be presented as liposome formulations.

Gene therapy using the compositions provided by the present invention may be carried out according to generally accepted methods, for example, as described by Friedman in "Therapy for Genetic Disease," T. Friedman, ed., Oxford University Press (1991), pp. 105-121, hereby incorporated by reference.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

After pharmaceutical compositions comprising a therapeutic agent of the invention formulated in a acceptable carrier have been prepared, they are placed in an appropriate container and labeled for treatment of an indicated condition with information including amount, frequency and method of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., location of the disease, age, weight, and gender of the patient, diet, time and frequency of administration, drug combination(s), reaction sensitivities, and tolerance/response to therapy). Long acting pharmaceutical compositions might be administered every 3 to 4 days, every week, or once every two weeks depending on half-life and clearance rate of the particular formulation. General guidance as to particular dosages and methods of delivery for other applications is provided in the literature (see U.S. Pat. Nos. 4,657,760; 5,206,344; and 5,225,212, herein incorporated by reference). Those skilled in the art will typically employ different formulations for oligonucleotides and gene therapy vectors than for proteins or their inhibitors. Similarly, delivery of polynucleotides or polypeptides will be specific to particular cells, conditions, locations, and the like.

The composition provided by the present invention may be formulated as described in U.S. Pat. No. 6,187,330 (hereby incorporated by reference in its entirety) which provides a composition for the controlled release of a peptide or protein comprising a biocompatible, bioerodable polymer having dispersed therein a glassy matrix phase comprising the peptide or protein and a thermoprotectant, said glassy matrix phase having a glass transition temperature above the melting point of the polymer. Since the peptide or protein drug is stable within the composition, it can conveniently be formed, in its melt stage, into suitably shaped devices to be used as drug delivery implants, e.g. in the form of rods, films, beads or other desired shapes.

Determining Resistance or Sensitivity to a Therapeutic Treatment

The determination of a cancer sample (e.g., cells or tissue) responding to a therapeutic treatment can be carried out by any methods known in the art. For example, by a cell culture drug resistance testing (CCDRT). CCDRT refers to testing a cancer sample (e.g., taken from a mammal patient) in the laboratory to drugs that may be used to treat the patient's cancer. The testing can identify the cancer sample is sensitive to which drugs and resistant to which drugs, which indicates which drugs are more likely to work and which drugs are less likely to work in the patient. The sensitivity of the cancer sample (therefore, the patient) can be sensitized by treatment with the composition provided by the present invention. CCDRT can be performed again with the sensitizing treatment and determine if a sensitizing composition provided by the present invention can sensitize the response of the cancer sample to a specific treatment or not. A composition can be said to sensitize a therapeutic treatment if the response as measured by CCDRT is increased by at least 20%, e.g., 30%, 40%, 50% 80%, 100% (2-fold), or 3-fold, 4-fold, 5-fold, or more when compared to the response in the absence of the sensitizing composition.

CCDRT typically include the cell proliferation assays and cell death assays.

The cell proliferation assay measures the proliferation of cells. It can be done by the radioactive thymidine incorporation assay originally described by Tanigawa and Kern (supra). In this assay, applied only to solid tumors and not to hematologic neoplasms, tumor cells suspended in soft agarose are cultured for 4-6 days in the continuous presence of antineoplastic drugs. At the end of the culture period, radioactive thymidine is introduced and differences in putative thymidine incorporation into DNA are compared between control and drug-treated cultures. Kern and Weisenthal analyzed the clinical correlation data and defined the concept of "extreme drug resistance," or EDR [Kern D H, Weisenthal L M. J Natl Cancer Inst 1990; 82: 582-588]. This was defined as an assay result which was one standard deviation more resistant than the median result for comparison, database assays. Patients treated with single agents showing EDR in the assay virtually never enjoyed a partial or complete response. Kern and Weisenthal also defined "low drug resistance" (LDR) as a result less resistant than the median and "intermediate drug resistance" (IDR) as a result more resistant than the median but less resistant than EDR (in other words, between the median and one standard deviation more resistant than the median).

The principles and clinical correlation data with the thymidine "EDR" assay were reviewed in 1992 (Weisenthal L M, Kern D H. Oncology (USA) 1992; 5: 93-103]. There have been only a few follow-up studies published since this time. One such study showed that EDR to one or more of the single agents used in a two drug combination is not apparently associated with a lower probability of response to the two drug combination in the setting of intraperitoneal chemotherapy of appendiceal and colon cancers (Fernandez-Trigo V, Shamsa F, Vidal-Jove J, Kern D H, Sugarbaker P H. Am J Clin Oncol 1995; 18: 454-460). It is, however, possible that response to the high drug concentrations achievable with intraperitoneal chemotherapy may be more closely associated with drug penetration to the tumor than to intrinsic drug resistance of the tumor cells. It was also shown that EDR to paclitaxel does not appear to be a prognostic factor in ovarian cancer patients or in patients with primary peritoneal carcinoma treated with paclitaxel plus platinum (Eltabbakh G H, Piver M S, Hempling R E, et al. Gynecol Oncol 1998; 70: 392-397; Eltabbakh G H. J Surg Oncol 2000; 73: 148-152). However, it was recently reported that EDR to platinum in ovarian cancer may have prognostic implications (Fruehauf, J., et al. Proc ASCO, v.20, Abs 2529, 2001). It was also reported that previously-untreated breast cancer patients with tumors showing LDR (defined above) had superior times to progression and overall survivals than patients with tumors showing either IDR or EDR (Mehta, R. S., et al, Breast Cancer Res Treat 66:225-37, 2001).

The thymidine "EDR" assay has a very high specificity (>98%) for the identification of inactive single agents, but a low sensitivity (<40%). In other words, a drug with assay-defined "EDR" is predicted to be almost certain to be inactive as a single agent (high specificity for identifying inactive drugs), but many drugs without "EDR" will also be inactive (low sensitivity for identifying inactive drugs).

A second form of cell proliferation assay is the adhesive tumor cell culture system, based on comparing monolayer growth of cells over a proprietary "cell adhesive matrix" (Ajani J A, Baker F L, Spitzer G, et al. J Clin Oncol 1987). Positive clinical correlations were also described in this publication.

In some embodiments, colony formation assays are used to measure cell proliferation. In this test cells are grown in vitro in soft agar (tissue culture medium containing agar as a gelling agent; also referred to as semi-solid agar) or other highly viscous media, containing, for example, methylcellulose, plasma gel or fibrin clots. These semi-solid media reduce cell movement and allow individual cells to develop into cell clones that are identified as single colonies. These assays are also generally referred to as Clonogenic assays. The colony formation assays are well known in the art, for example, see Rizzino, A Soft agar growth assays for transforming growth factors and mitogenic peptides. Methods in Enzymology 146: 341-53 (1987) and In some embodiments, apoptosis is mearued by a terminal deoxynucleotide transferase-mediated dUTP nick end labeling (TUNEL) assay which is well known in the art and Materials and Methods available as supporting online material on Science Online.

As opposed to measuring cell proliferation, there is a closely-related family of assays based on the concept of total cell kill, or, in other words, cell death occurring in the population of tumor cells (Weisenthal L M, Shoemaker R H, Marsden J A, Dill P L, Baker J A, Moran E M. Recent Results Cancer Res 1984; 94: 161-173; Weisenthal L M, Lippman M E. Cancer Treat Rep 1985; 69: 615-632; Weisenthal L M. *Cell culture assays for hematologic neoplasms based on the concept of total tumor cell kill*. In: Kaspers G J L, Pieters R, Twentyman P R, Weisenthal L M, Veerman A J P, eds. *Drug Resistance in Leukemia and Lymphoma*. Langhorne, P A: Harwood Academic Publishers, 1993: 415-432; Weisenthal L M. Contrib Gynecol Obstet 1994; 19: 82-90). The concepts underlying cell death assays are relatively simple, even though the technical features and data interpretation can be very complex.

The basic technology concepts are straightforward. For example, a fresh specimen is obtained from a viable neoplasm. The specimen is most often a surgical specimen from a viable solid tumor. Less often, it is a malignant effusion, bone marrow, or peripheral blood specimen containing "tumor" cells (a word used to describe cells from either a solid or hematologic neoplasm). These cells are isolated and then cultured in the continuous presence or absence of drugs, most often for 3 to 7 days. At the end of the culture period, a measurement is made of cell injury, which correlates directly with cell death. There is evidence that the majority of available anticancer drugs may work through a mechanism of causing sufficient damage to trigger so-called programmed cell death, or apoptosis (Hickman J A. Cancer Metastasis Rev 1992; 11: 121-139; Zunino F, Perego P, Pilotti S, Pratesi G, Supino R, Arcamone F. Pharmacol Ther 1997; 76: 177-185).

Although there are methods for specifically measuring apoptosis which can be applied to cultured cells, there are practical difficulties in applying these methods to mixed (and clumpy) populations of tumor cells and normal cells. Thus, more general measurements of cell death have been applied. These include: (1) delayed loss of cell membrane integrity (which has been found to be a useful surrogate for apoptosis), as measured by differential staining in the DISC assay method, which allows selective drug effects against tumor cells to be recognized in a mixed population of tumor and normal cells (Weisenthal L M, Kern D H. Oncology (USA) 1992; 5: 93-103; Weisenthal L M, Marsden J A, Dill P L, Macaluso C K. Cancer Res 1983; 43: 749-757), (2) loss of mitochondrial Krebs cycle activity, as measured in the MTT assay (Carmichael J, DeGraff W G, Gazdar A F, Minna J D, Mitchell J B. Cancer Res 1987; 47: 936-942), (3) loss of cellular ATP, as measured in the ATP assay (Kangas L, Gronroos M, Nieminen A L. Med Biol 1984; 62: 338-343; Garewal H S, Ahmann F R, Schifman R B, Celniker A. J Natl Cancer Inst 1986; 77: 1039-1045; Sevin B-U, Peng Z L, Perras J P, Ganjei P, Penalver M, Averette H E. Gynecol Oncol 1988; 31: 191-204), and (4) loss of cell membrane esterase activity and cell membrane integrity, as measured by thefluorescein diacetate assay (Rotman B, Teplitz C, Dickinson K, Cozzolino J P. In vitro Cell Dev Biol 1988; 24: 1137-1138; Larsson R, Nygren P, Ekberg M, Slater L. Leukemia 1990; 4: 567-571; Nygren P, Kristensen J, Jonsson B, et al. Leukemia 1992; 6: 1121-1128).

In some embodiments, apoptosis is measured by a terminal deoxynucleotide transferase-mediated dUTP nick end labeling (TUNEL) assay which is well known in the art and for example as described in Materials and Methods available as supporting online material on Science Online.

In addition, the sensitivity or resistance of an animal to a treatment may be directly determined by measuring tumor size before and after treatment and/or over a period of time of treatment. If tumor size is decreased by 50%, preferably 75%, more preferably 85%, most preferably 100% with a treatment, than the animal is said to be sensitive (not resistant) to the treatment. Otherwise, the animal is considered to be resistant to the treatment. If the tumor size is reduced by at least 25%, preferably 50%, more preferably 75%, most preferably 100% after the administering of a treatment sensitizing composition of the present invention compared to the tumor after treatment but in the absence of the a composition of the present invention, then the composition is said to be effective in sensitizing the treatment in the animal. In human, the tumor size may be compared over a window of 6 month period of treatment, in other animals, this window varies for example a 4-6 week window may be used for mouse. It is understood that the actual time window for comparing tumor size may be determined according to knowledge in the art and the particular tumor to be treated.

Furthermore, whether a cell is resistant to a treatment may be also determined by measuring the expression of a SPARC family polypeptide or polynucleotide as described herein before. Thus the present invention provides a method for evaluating a first cancer sample for its resistance to a therapeutic treatment, comprising: (a) measuring expression level of a SPARC family mRNA or polypeptide, or extracellular level of a SPARC family polypeptide in the first cancer sample; (b) measuring expression level of the SPARC family mRNA or polypeptide, or extracellular level of the SPARC family polypeptide in a second cancer sample which does not exhibit resistance to the therapeutic treatment; (c) comparing the expression levels or the extracellular levels obtained in (a) and (b), wherein a lower level of expression or extracellular level in (a) is indicative of the first cancer sample being resistant to the therapeutic treatment.

The present invention further provides a method for identifying an agent which modulates a SPARC family mRNA or polypeptide expression, or a SPARC family polypeptide secretion, comprising: (a) measuring expression level of the SPARC family mRNA or polypeptide, or extracellular level of the SPARC family polypeptide in a sample; (b) contacting a candidate agent with the sample; (c) after the contacting of (b), measuring expression or extracellular level of the SPARC family mRNA or polypeptide, or extracellular level of the SPARC family polypeptide in the sample of (b); (d) comparing the expression levels or the extracellular levels in (a) and (c), wherein a differential level of expression or extracellular level in (a) and (c) indicates the candidate agent being an agent which modulates the SPARC family mRNA or polypeptide expression, or the SPARC family polypeptide secretion.

Expression levels of a SPARC polypeptide or a polynucleotide and the secretion levels of a SPARC polypeptide can be measured as described herein before and by any method known in the art.

An agent, which enhances the expression or secretion of a SPARC family member, may itself be used as a therapy sensitizing agent as described in the present invention. The agent may be a chemical, or a biological molecule (e.g., a protein, or a polynucleotide, etc.)

Animal Models

The therapeutic effects of the compositions provided by the present invention may be tested in various animal models. This may be done in vitro, ex vivo, or in vivo as described herein before.

Mouse models for proliferative disorders are known in the art and can be found, for example, on Jackson laboratory mouse database at world wide web wwwjax.org and The Jackson Laboratory catalog—Jax-Mice—June 2001-May 2003, or Jackson-Grusby L. 2002, Oncogene. 12;21(35):5504-14; Ghebranious N, Donehower L A., 1998, Oncogene. 24;17(25):3385-400; Palapattu G S, Bao S, Kumar T R, Matzuk M M. 1998, Cancer Detect Prev. 22(1): 75-86). For example, tumor mouse models include those used for the study of Chronic Myelogenous Leukemia (CML), defects in cell cdhesion molecules, genes regulating growth and proliferation, growth factors/receptors/cytokines, increased tumor incidence, oncogenes, toxicology and tumor suppressor genes.

EXAMPLES

The invention is based on the observation that SPARC was found to be significantly underexpressed in chemotherapy resistant cells, that SPARC polypeptide sensitizes cancer therapy resistant cells to cancer treatment, that SPARC encoding DNA sensitizes cells to cancer therapy, and that animals engrafted with SPARC transfectant cells show a dramatic reduction in tumor growth compared to animals engrafted with a control.

Example 1

Materials and Methods

Cell Culture—The colorectal cell line MIP-101 was maintained in Dulbecco's modified Eagle's medium (DMEM) (Invitrogen) supplemented with 10% fetal bovine serum (FBS) (Invitrogen), 1% penicillin/streptomycin (Invitrogen) at 37° C. and 5% CO2. Resistant MIP101 cells were developed following long-term incubation with incremental concentrations of 5-fluorouracil (5-FU), irinotecan (CPT-11), cisplatin (CIS), and etoposide (ETO). Stable MIP101 cells transduced with SPARC (MIP/SP) were maintained in DMEM supplemented with 10% FBS, 1% penicillin/streptomycin, and 0.1% Zeocin at 37° C. and 5% $CO_2$.

Analytical Reverse Transcription-Polymerase Chain Reaction—Total RNA was extracted from cultured cells ($2\times10^6$ cells, 75% confluence) using TRIZOL reagent (Invitrogen) according to the manufacturer's protocol. RT-PCR was performed using a commercially available kit (BD Biosciences) following the manufacturer's protocol using 1 ug of total RNA. The specific primers used to amplify SPARC: 5'CGA AGA GGA GGT GGT GGC CGA AA-3' (sense) (SEQ ID NO. 78) and 5'GGT TGT TGT CCT CAT CCC TCT CAT AC-3' (antisense) (SEQ ID NO. 79). GAPDH: 5'-CTC TCT GCT CCT CCT GTT CGA CAG-3' (sense) (SEQ ID NO. 80) and 5'-AGG GGT CTT ACT CCT TGG AGG CCA-3' (antisense) (SEQ ID NO. 81) was used as internal control and to normalize the gene expression levels. The following settings were used for the reaction: 50° C.×1 hr, followed by 37 cycles of 94° C.×1 min, 65° C.×1 min, 72° C.×2 min, followed by 72° C.×10 min and incubation at 4° C. The PCR products were separated on 1% agarose gel in TAE buffer (stained with ethidium bromide 0.5 ug/ml) by electrophoresis for 1 hr at 100 V and subsequently photographed.

Quantitation of Apoptosis—For the TUNEL assay, cells were plated onto glass coverslips in 6-well plates at 250,000 cells/plate overnight prior to any induction study 24 hours later. For the assessment of apoptosis following exogenous SPARC (Haematologic Technologies Inc), cells were incubated with SPARC 5 µg/ml for 24 hrs followed by a 12-hr exposure to 5-FU 1000 µM. Cells were then processed for labeling by Apoptosis Detection Kit (Promega) according to the manufacturer's instructions. For quantitation of apoptosis, cells were plated at 250,000 cells/plate in 6-well plates overnight, followed by 12-hr incubation with the following chemotherapy agents: 5-FU 1000 µM, CPT-11 200 µM, cisplatin 100 µM, and etoposide 10 µM. Cells were collected by using a nonenzymatic cell dissociation medium (Sigma), washed with phosphate-buffered saline and subsequently stained for Annexin V and propidium iodide using an Apoptosis detection kit (R & D Research) according to the manufacturer's protocol. The proportion of cells labeled with Annexin V and propidium iodide was analyzed by XL Flow Cytometry Analyzer. Data was collected from 100,000 events.

Transfection and Selection of Clone—The SPARC cDNA was cloned into pcDNA3.1 expression vector. Transfections were performed with 2.0 µg of the gene/expression vector construct using the polyethylenimine method of Boussiff et al. (1995) with minor modifications (Tai et al., 2002). After transfection, cells were washed with phosphate-buffered saline (PBS, pH 7.4) and maintained in culture medium for 24 hours, followed by a change to an appropriate selection medium containing 1% Zeocin. Cells were selected based on Zeocin resistance and individual colonies and clones from these colonies were then propagated for further verification. Stably transduced clones (MIP/SP) were screened for SPARC mRNA expression by reverse-transcription polymerase chain reaction (RT-PCR) analysis. MIP/SP clones with the highest expression of SPARC mRNA (by RT-PCR) and protein (by Western blot) were selected for subsequent in-vitro and in-vivo studies. Control cell lines used for this study included MIP101 cells stably transduced with pcDNA3.1 empty vector only (MIP/Zeo) and selected based on Zeocin resistance.

Western Blot Analysis—Total protein was extracted from cell lines cultured on 10-cm plates using CHAPS lysis buffer. 10-30 ug of total protein were electrophoresed using SDS-PAGE and transferred to PVDF membrane. After blocking with 5% nonfat milk solution, the membranes were incubated with anti-SPARC antibody (1:1000, Haematologic Technologies Inc) overnight at 4° C. The membrane was subsequently incubated with rabbit anti-mouse HRP-conjugated secondary antibody (1:2000) for 1-hr at room temperature and detected by Extendi-Dura chemiluminescence kit (Pierce). The same membrane was stripped using Western Blot Restore Stripping Buffer (Pierce) and subsequently re-probed for tubulin with a primary anti-tubulin mouse antibody (Sigma) and rabbit anti-mouse HRP-conjugated secondary antibody (1:2000) as an internal control.

Immunohistochemistry—Paraffin sections of human colorectal cancers or normal colonic epithelium were kindly provided by Dr. Maximo Loda (Dana Farber Cancer Institute, Boston). Prior to staining, the sections were washed with 0.1% Tris-buffered saline (TBS) containing 0.1% Triton X-100 (Sigma), treated with 1% $H_2O_2$ for 30 min, washed in TBS/0.1% Triton for 30 min (×3) at room temperature, blocked with 3% BSA in TBS/0.1% Triton for 1 hr. Sections were then incubated with mouse anti-SPARC antibody (1:50) overnight at 4° C. (Haematologic Technologies Inc.), washed several times with TBS/Triton and counterstained with avidin-biotin-peroxidase (ABC) complex solution (Vecstain ABC kits, Vector Laboratories Inc, Burlingame, Calif.) for 1 hr, followed by incubation in DAB solution. Sections were mounted using Permount.

Colony forming Assay—For clonogenic cell survival studies, MIP101 parental cells and MIP/SP cells were plated at 1,000 cells/plate in 48-well plates and incubated with increasing concentrations of 5-FU (0, 10 µM, 100 µM, 1000 µM), CPT-11 (0, 1 µM, 10 µM, 100 µM), or etoposide (0, 10 µM, 100 µM, 1000 µM) for 4 days. Cells were then washed with PBS and incubated in fresh medium containing the appropriate concentrations of chemotherapy for an additional 7 days. Each well was stained with crystal violet and the colonies with more than 50 cells were counted. The number of colonies formed in the treated group was calculated based on the colonies formed from the control, untreated cells.

Concentrated SPARC-containing supernatant [SPARC(s)]—MIP/SP cells were plated at $1\times10^6$ cells in 100 cm flasks in DMEM (10% FBS, 1% penicillin/streptomycin, 0.1% Zeocin) for 24 hrs. Cells were subsequently washed with PBS twice and incubated in serum-free VP-SFM medium supplemented with glutamine 4 mM (Invitrogen) for 72 hrs. This medium was concentrated from 500 ml to 2 ml using Centricon Filter units (Millipore) at 4° C. All media collected and processed by this method were used for subsequent animal studies.

Animal Studies—Tumor xenograft animal models were used to assess the effect of SPARC on tumor progression in-vivo. NIH nude mice (6 weeks old, Taconic Laboratories) were engrafted following subcutaneous injection of $2\times10^6$ cells into the left flank. Treatment regimens were initiated once the average tumor size was 50-75 $mm^3$ in size. Tumor measurements were performed using a hand-held caliper (Fisher) twice weekly and weight measurements were made concurrently until the completion of the study. Chemotherapy was provided using a 3-week cycle regimen for a total of 6 cycles: 5-FU 25 mg/kg or CPT-11 25 mg/kg intraperitoneal injections three times on week 1 of each cycle, followed by 2 weeks of treatment-free periods. Dosing schedule for SPARC(s) was 100 µL of SPARC(s) three times per week until the completion of the chemotherapy cycle.

Example 2

SPARC Expression in Chemotherapy Resistant Cells

Figure 3:
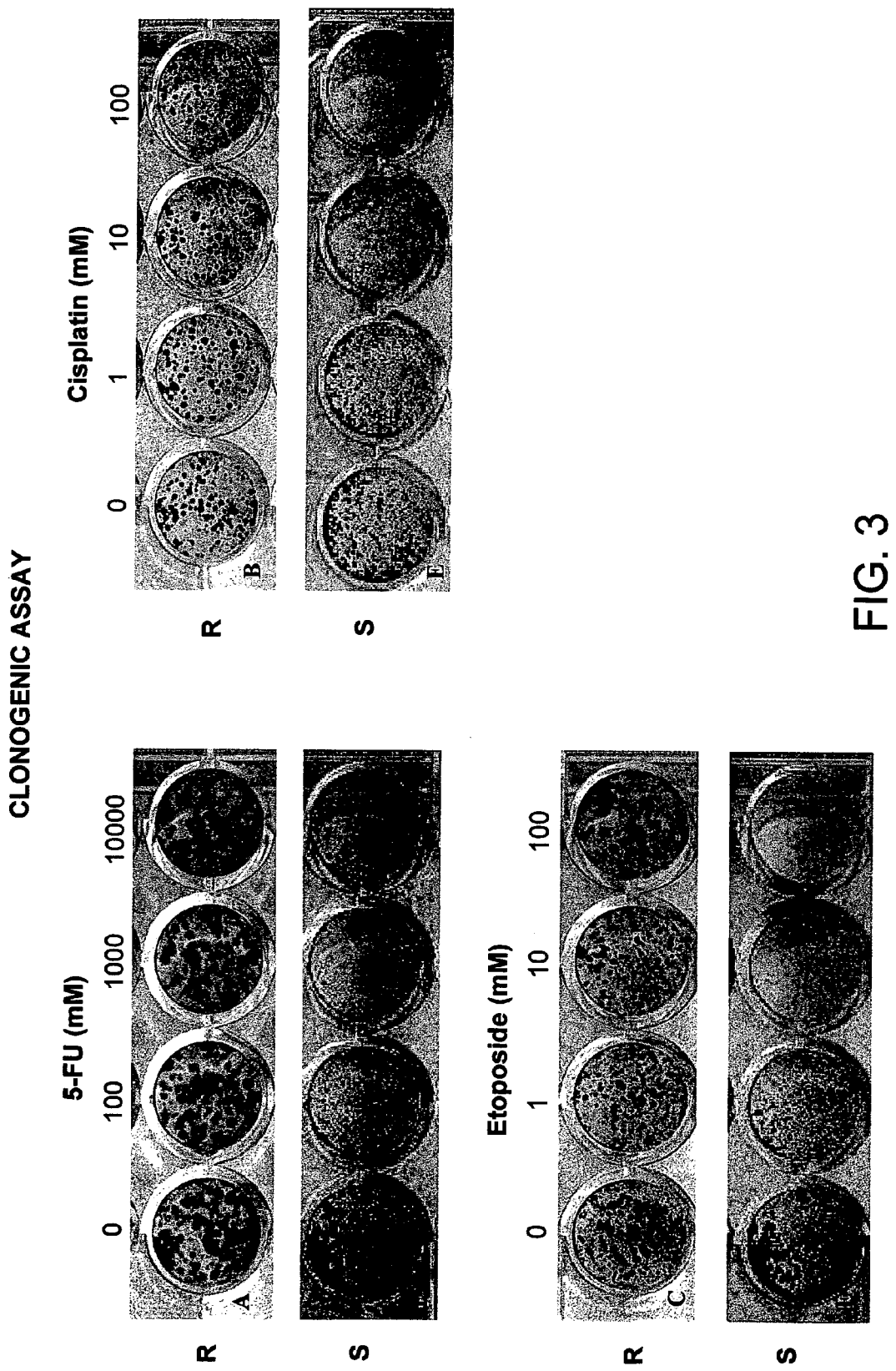
FIG. 3 is a picture showing colony formation assays of chemotherapy sensitive and resistant cells according to one embodiment of the invention.
Figure 4:
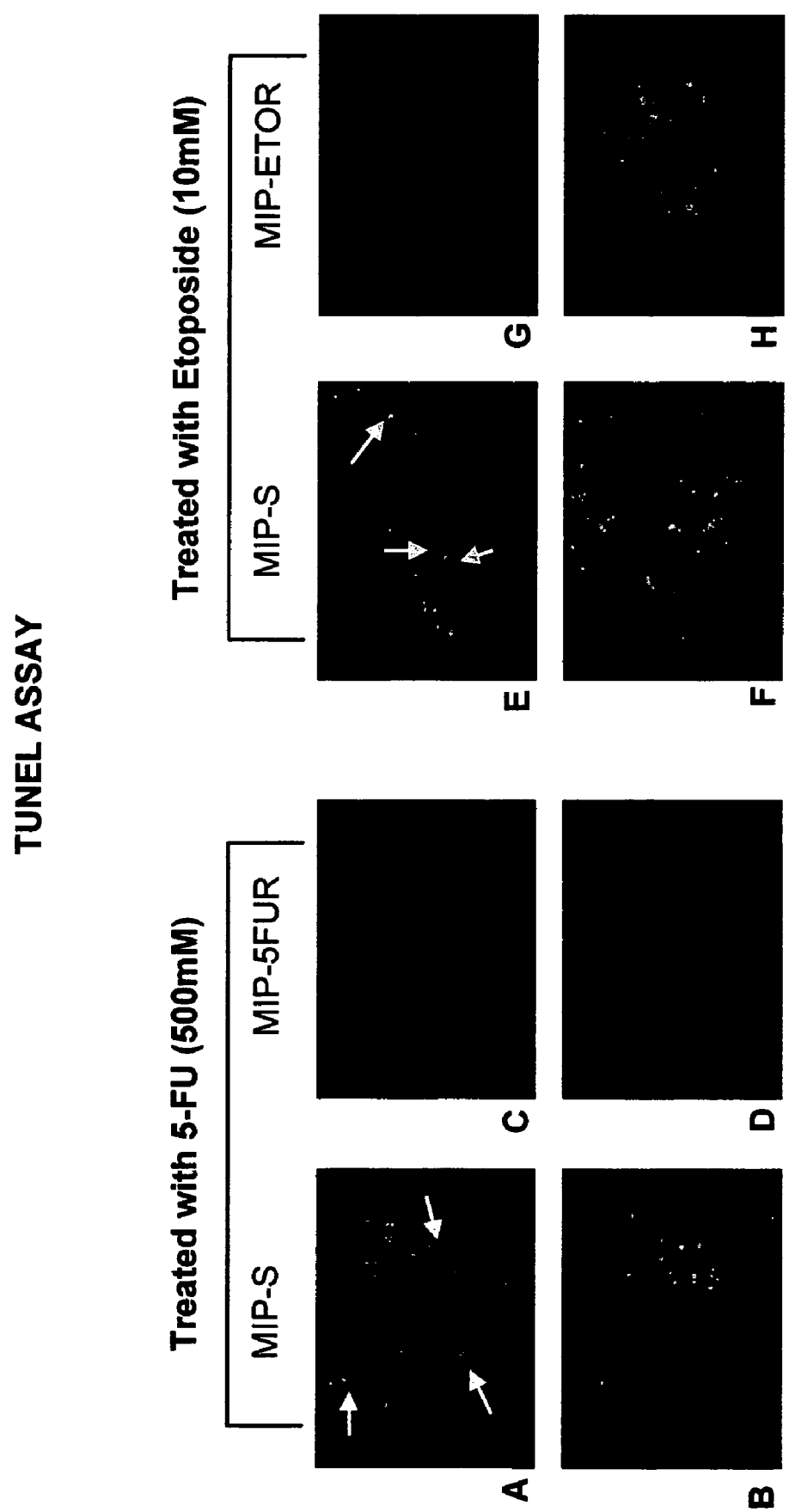
FIG. 4 is a picture showing TUNEL assays of chemotherapy sensitive and resistant cells according to one embodiment of the invention.

Two chemotherapy resistant clones (MIP-5FUR and MIP-ETOR), as supported by colony formation assays (FIG. 3) and TUNEL assay (FIG. 4), were used for the detection of SPARC in chemotherapy resistant cells. Microarray analysis identified a number of genes underexpressed in the resistant cells, including SPARC.

Figure 5A:
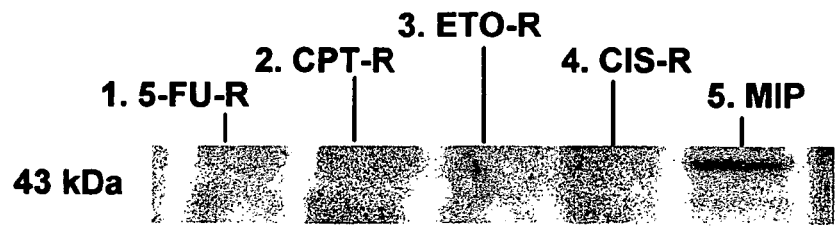
FIG. 5 (A and B) is a picture showing the decreased level of SPARC polypeptide in chemotherapy resistant cell lines according to one embodiment of the invention.
Figure 5B:
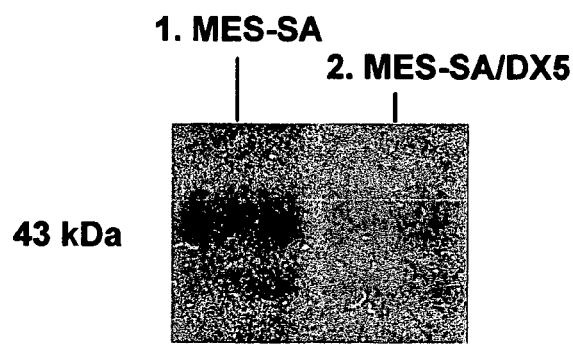

Underexpression at the gene expression level also translated into lower levels of SPARC protein levels in the chemotherapy resistant cell lines (FIG. 5A). This feature was not unique to the resistant cell lines developed solely for the purposes of the current study, since another well established uterine sarcoma cell line, MES-SA, also showed decreased expression of SPARC when it is resistant to a different chemotherapeutic agent, doxorubicin. (FIG. 5B). Furthermore, in normal human pathological samples, SPARC protein expression appears to be highest in the villi, with a decreasing gradient towards colonic crypts. This variable expression is lost in malignancy, with a general decrease in expression of SPARC in colorectal adenocarcinoma of various stages.

Figure 12:
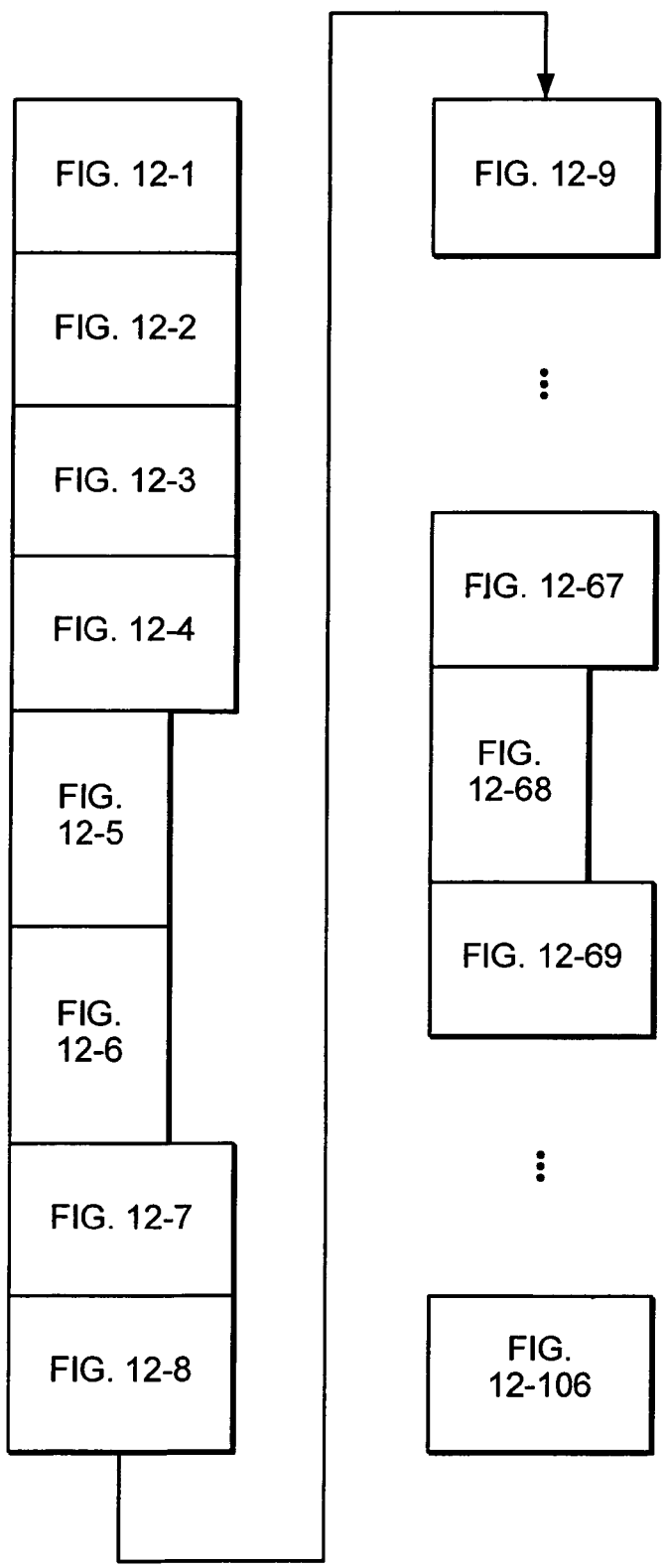
FIG. 12 is a figure containing the polynucleotide and polypeptide sequences of the SPARC family members according to one embodiment of the invention.
Figures 12, 13, 14, 15, 16, 17, 18, 19, 20, 21, 22, 23, 24, 25, 26, 27, 28, 29, 30, 31, 32, 33:
FIG. 13 is a figure showing the sequence alignment among different SPARC family polypeptides and polynucleotides according to one embodiment of the invention.
FIG. 14 shows effect of chemotherapy on tumor xenografts of SPARC-overexpressing cells according to one embodiment of the invention.
FIG. 15 shows effect of radiation therapy on tumor xenografts of SPARC-overexpressing cells according to one embodiment of the invention.
FIG. 16 shows treatment of MIP 101 tumor xenografts with combination therapy with SPARC(s) intraperitoneally according to one embodiment of the invention.
FIG. 17 shows treatment of MIP 101 tumor xenografts with combination therapy with SPARC(s) subcutaneously according to one embodiment of the invention.
FIG. 18 shows treatment of MIP/5FU tumor xenografts with combination therapy with SPARC(s) according to one embodiment of the invention.
FIG. 19 shows human SPARC mRNA and protein levels in colorectal cancer cell lines sensitive and resistant to chemotherapy according to one embodiment of the invention.
FIG. 20 shows SPARC protein expression in human colonic epithelium according to one embodiment of the invention.
FIG. 21 shows assessment of the effect of SPARC in influencing the sensitivity of cells to chemotherapy according to one embodiment of the invention.
Figures 12, 91:
Figures 1, 13:
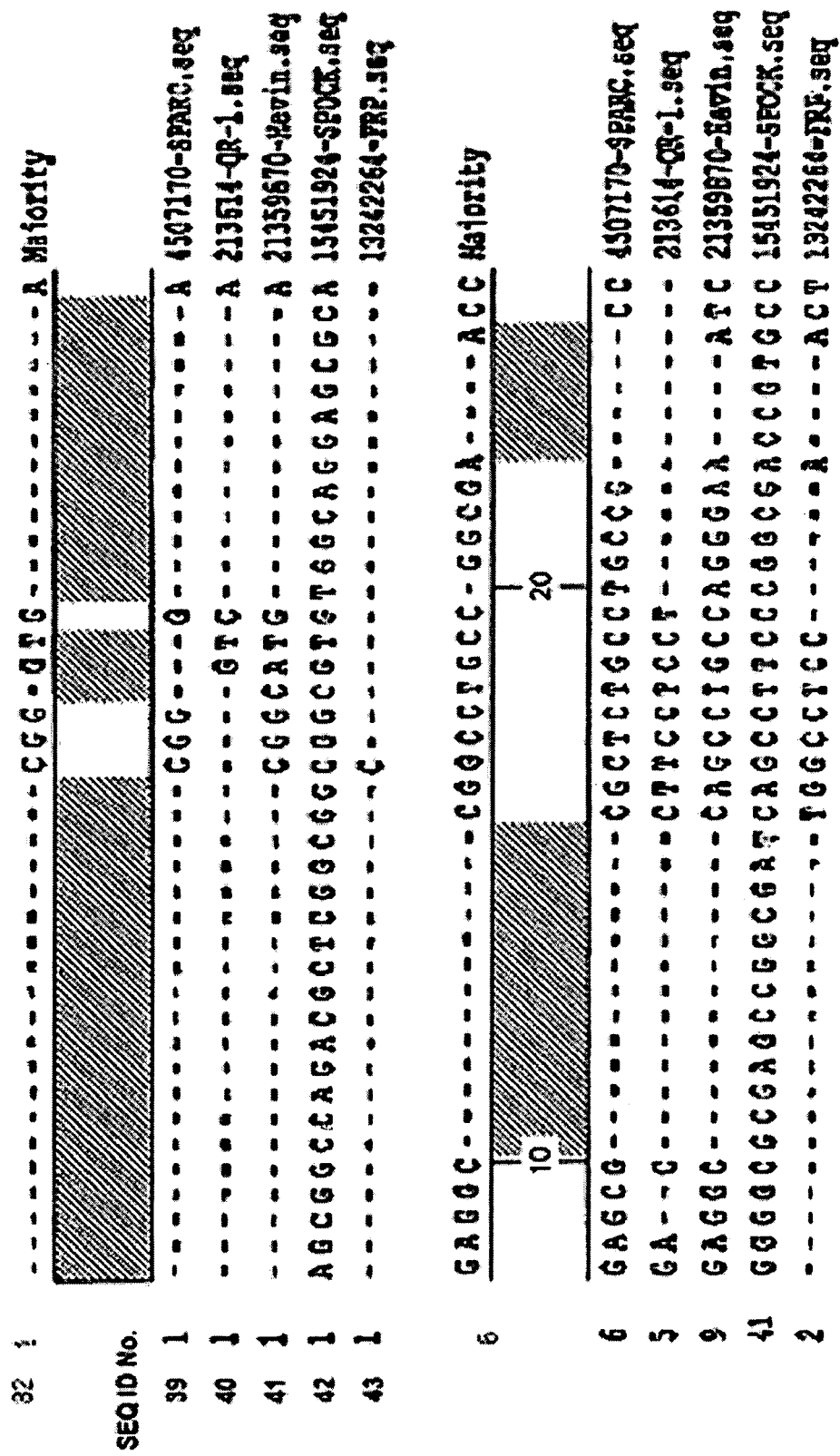
Figures 3, 13:
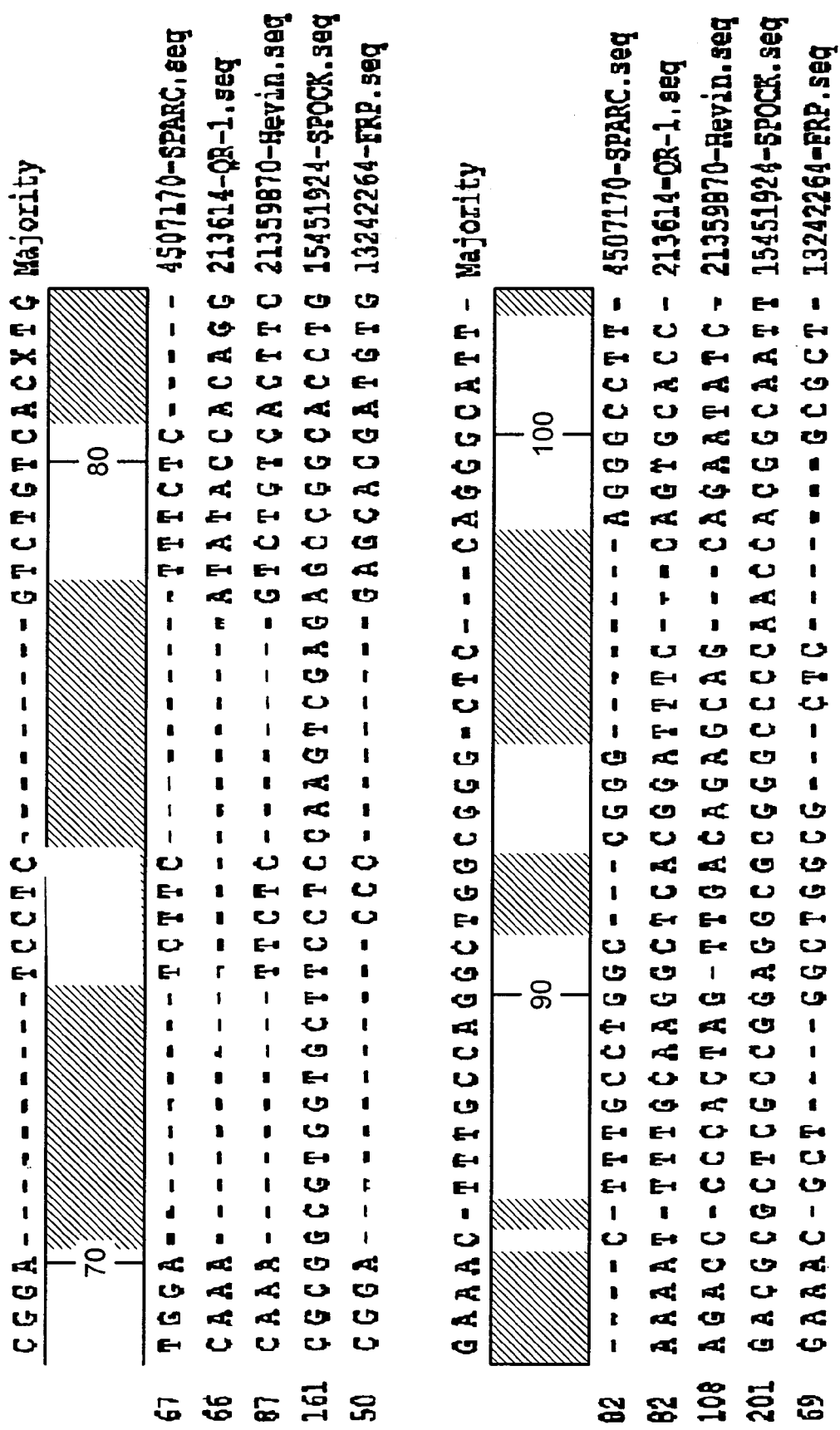
Figures 4, 13:
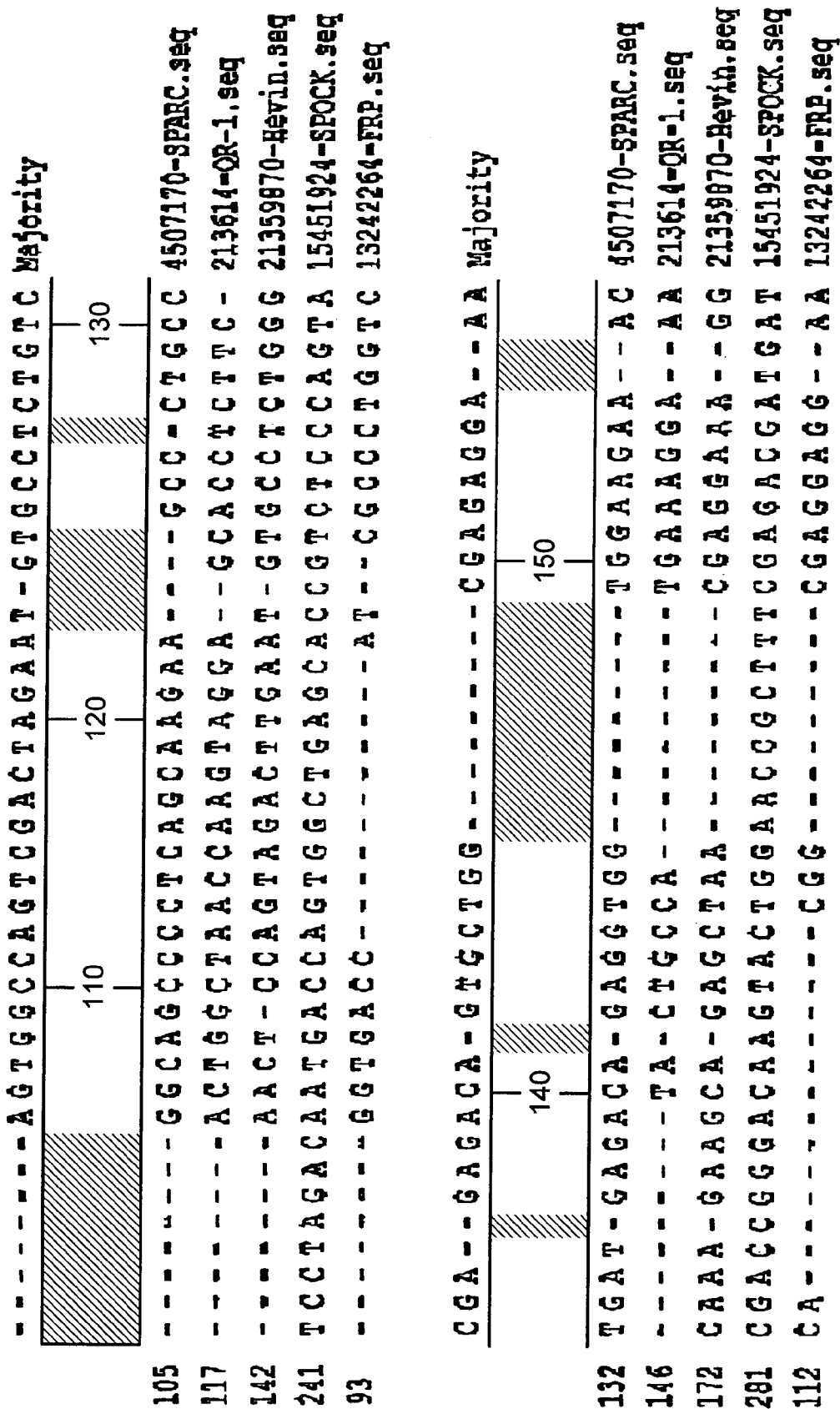
Figures 5, 13:
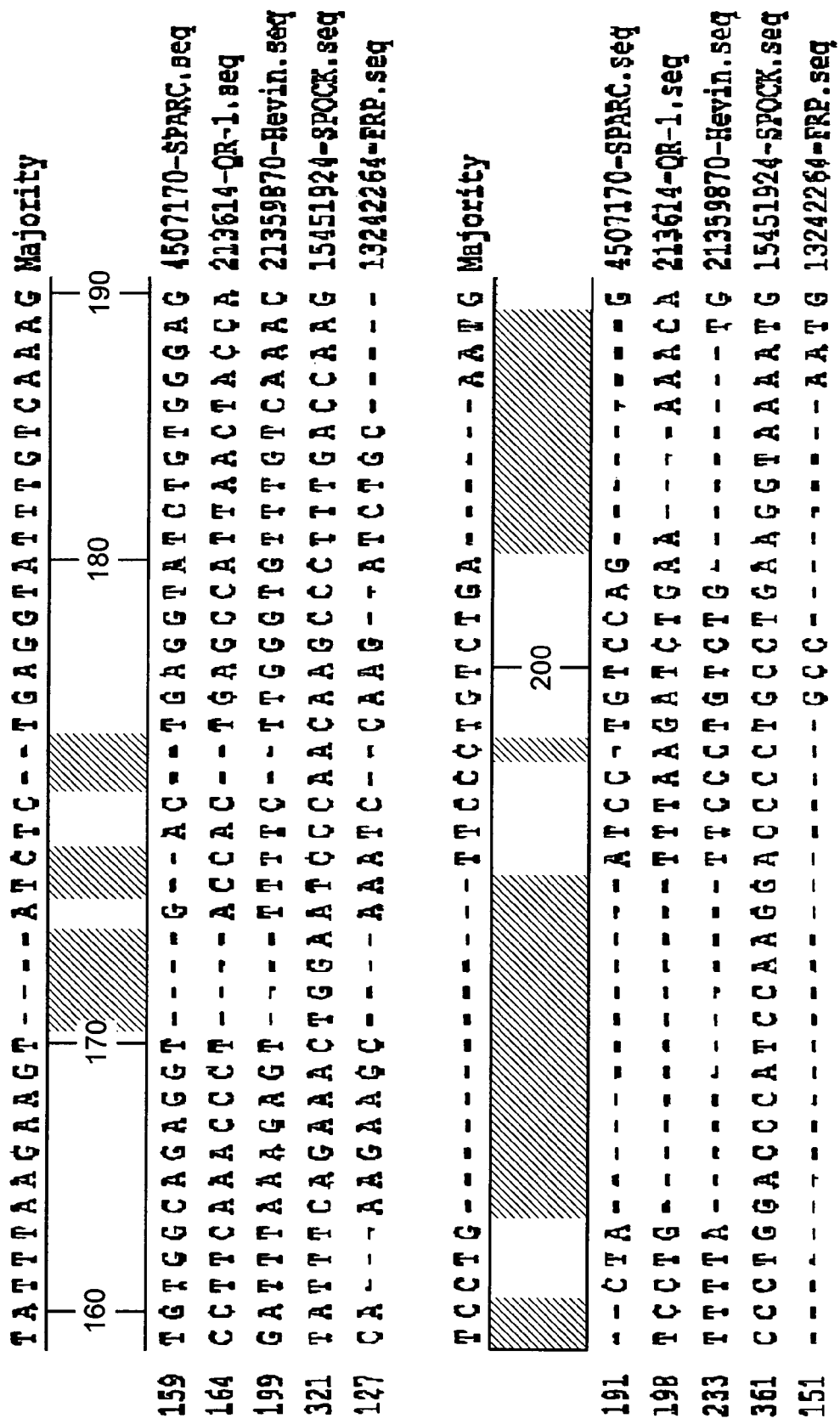
Figures 11, 13:
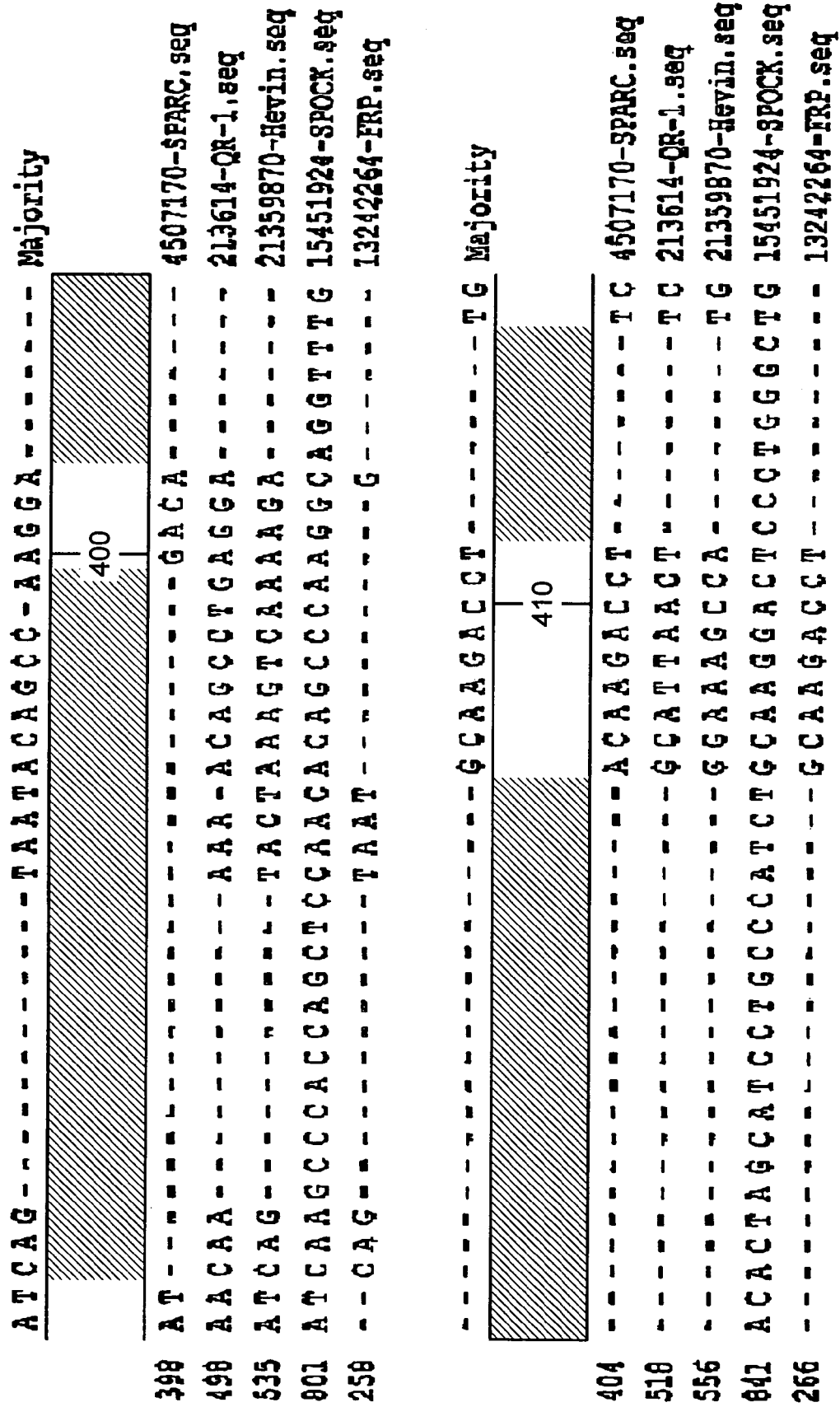
Figures 13, 14:
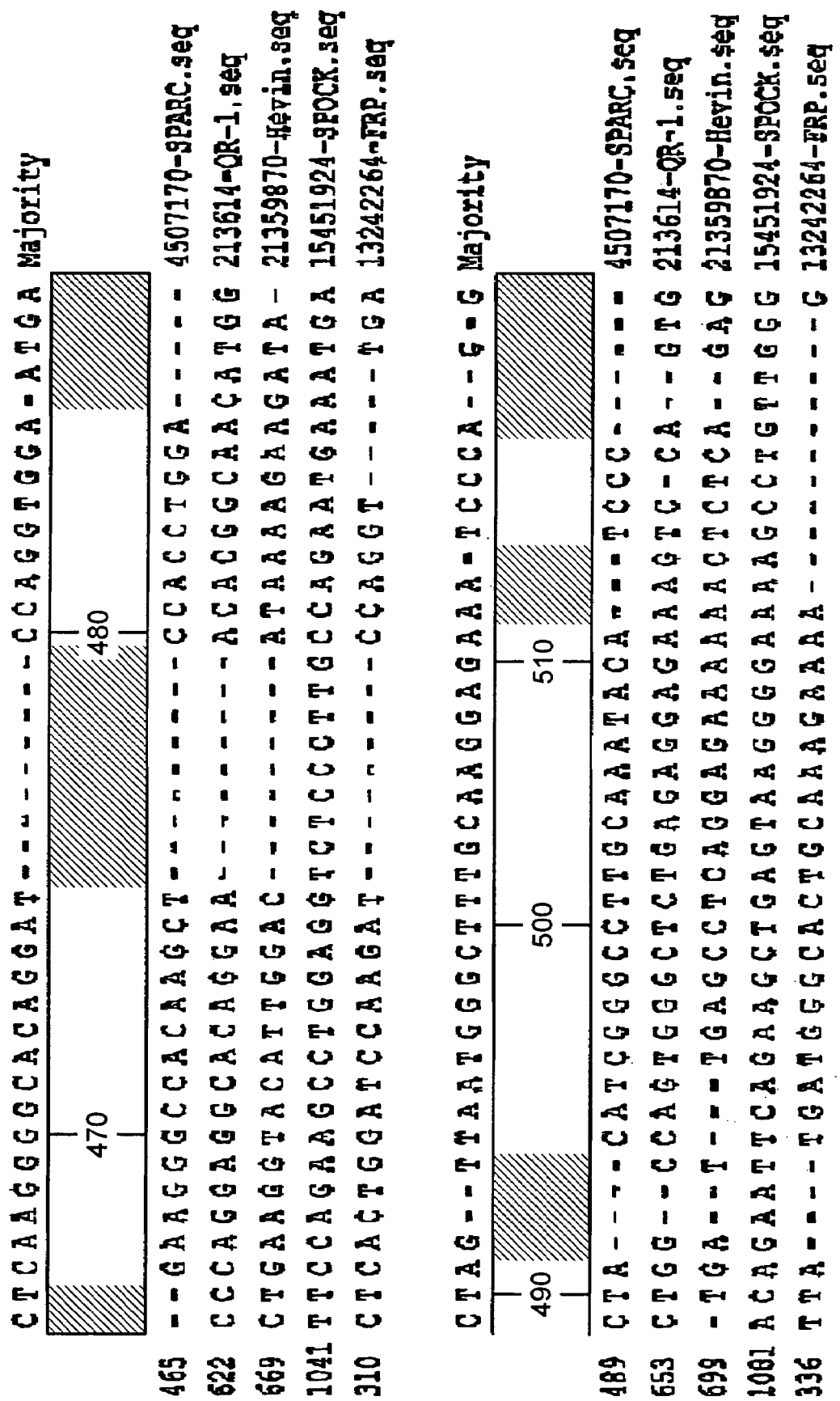
Figures 13, 14, 15:
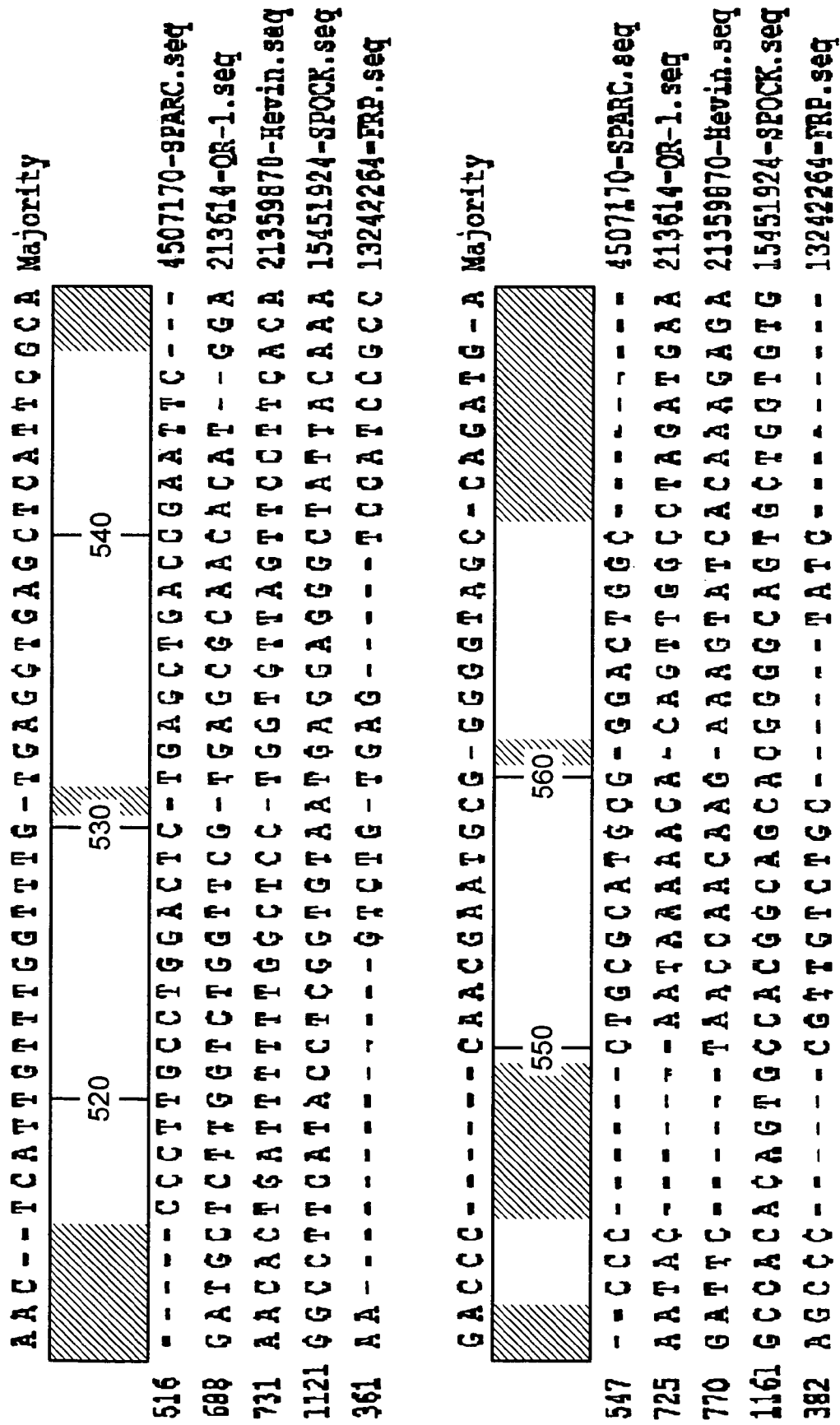
Figures 13, 14, 15, 16:
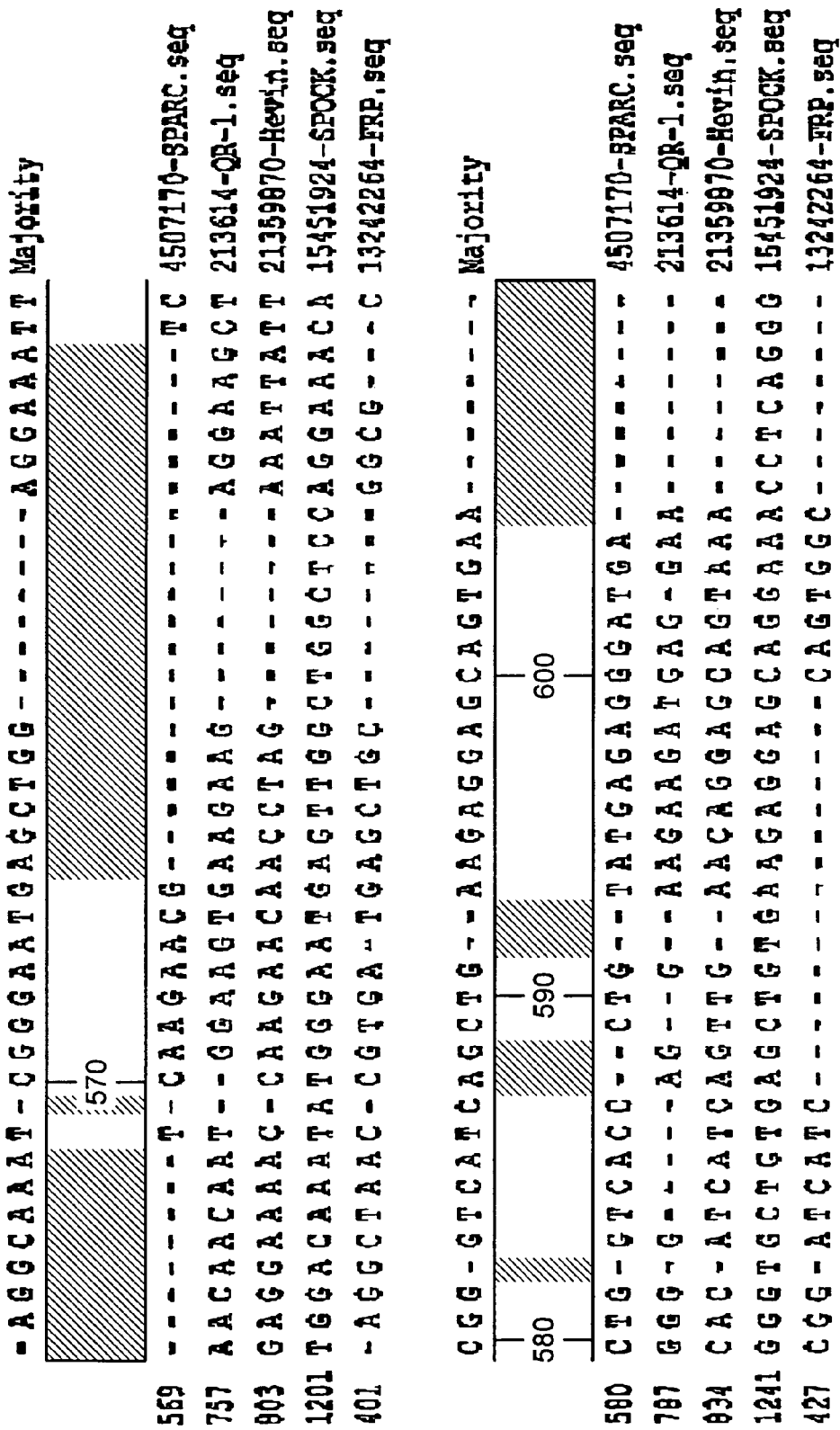
Figures 13, 14, 15, 16, 17, 18, 19, 20, 21:
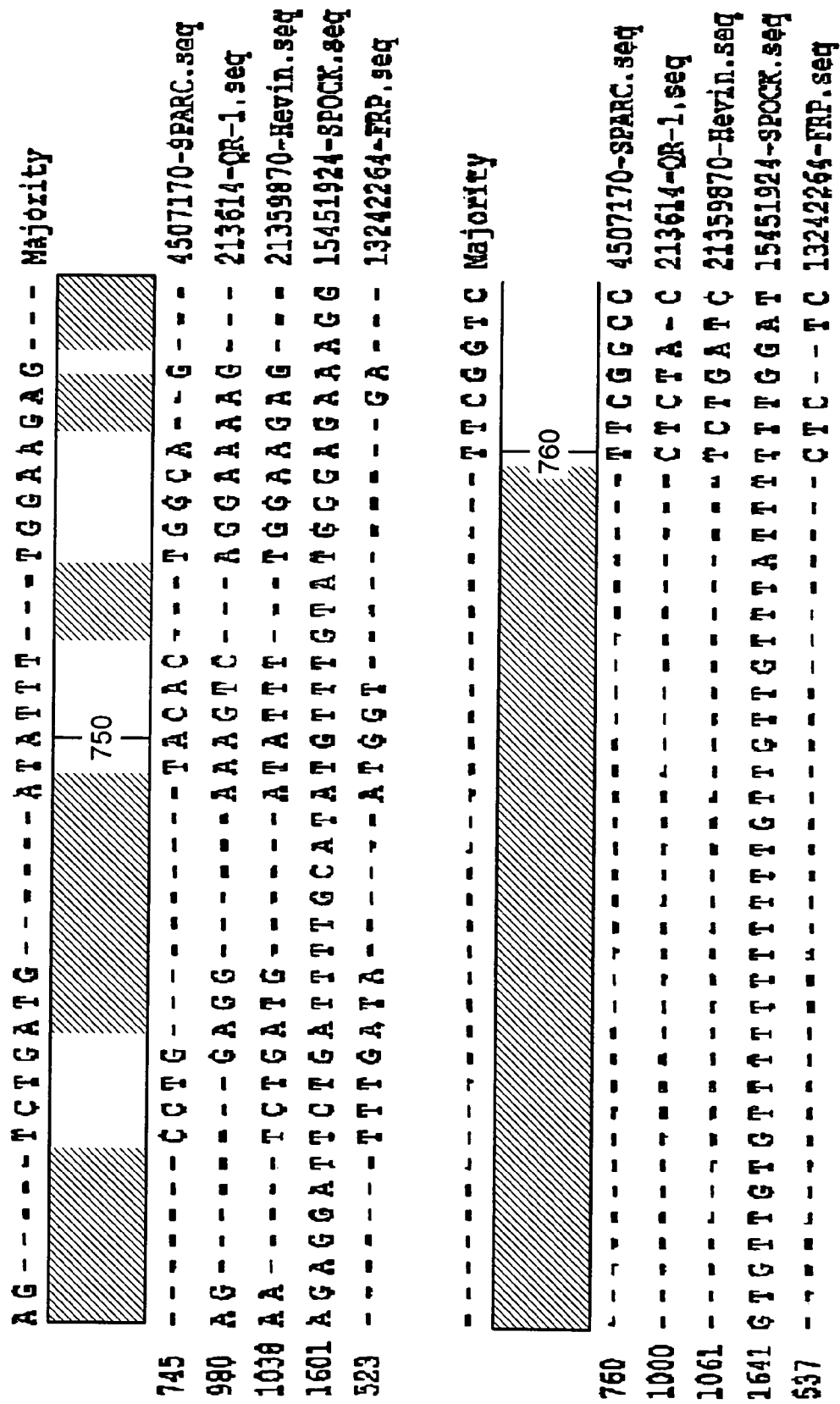
Figures 13, 14, 15, 16, 17, 18, 19, 20, 21, 22, 23, 24:
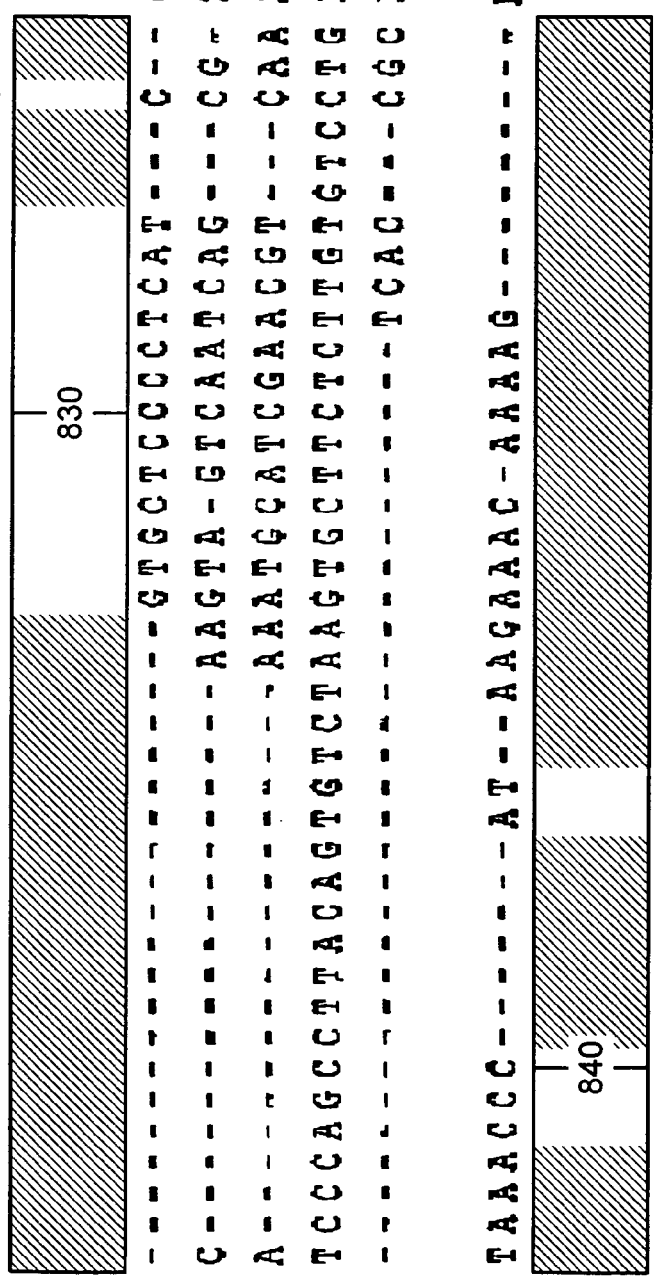
Figures 13, 14, 15, 16, 17, 18, 19, 20, 21, 22, 23, 24, 25, 26, 27, 28, 29, 30:
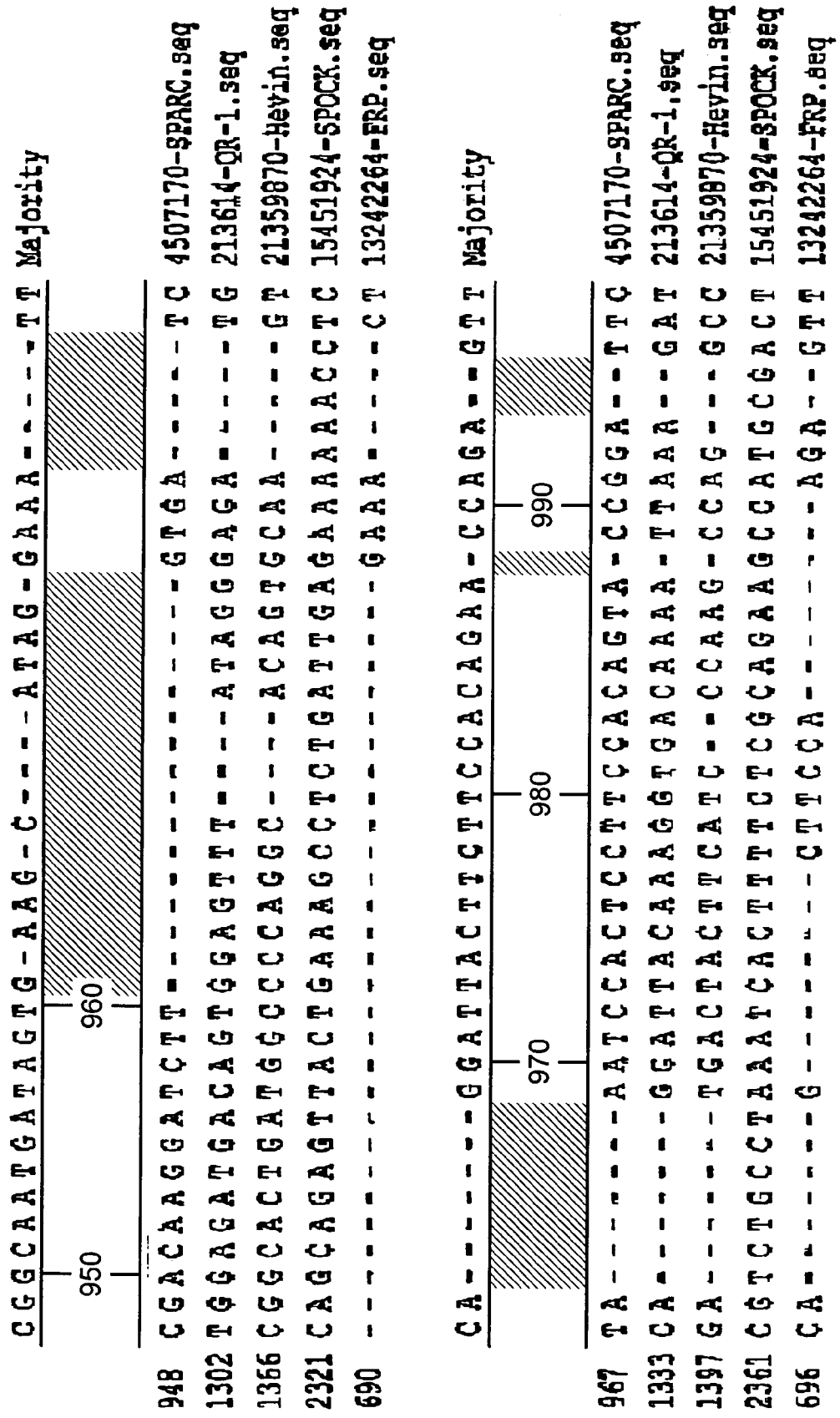
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
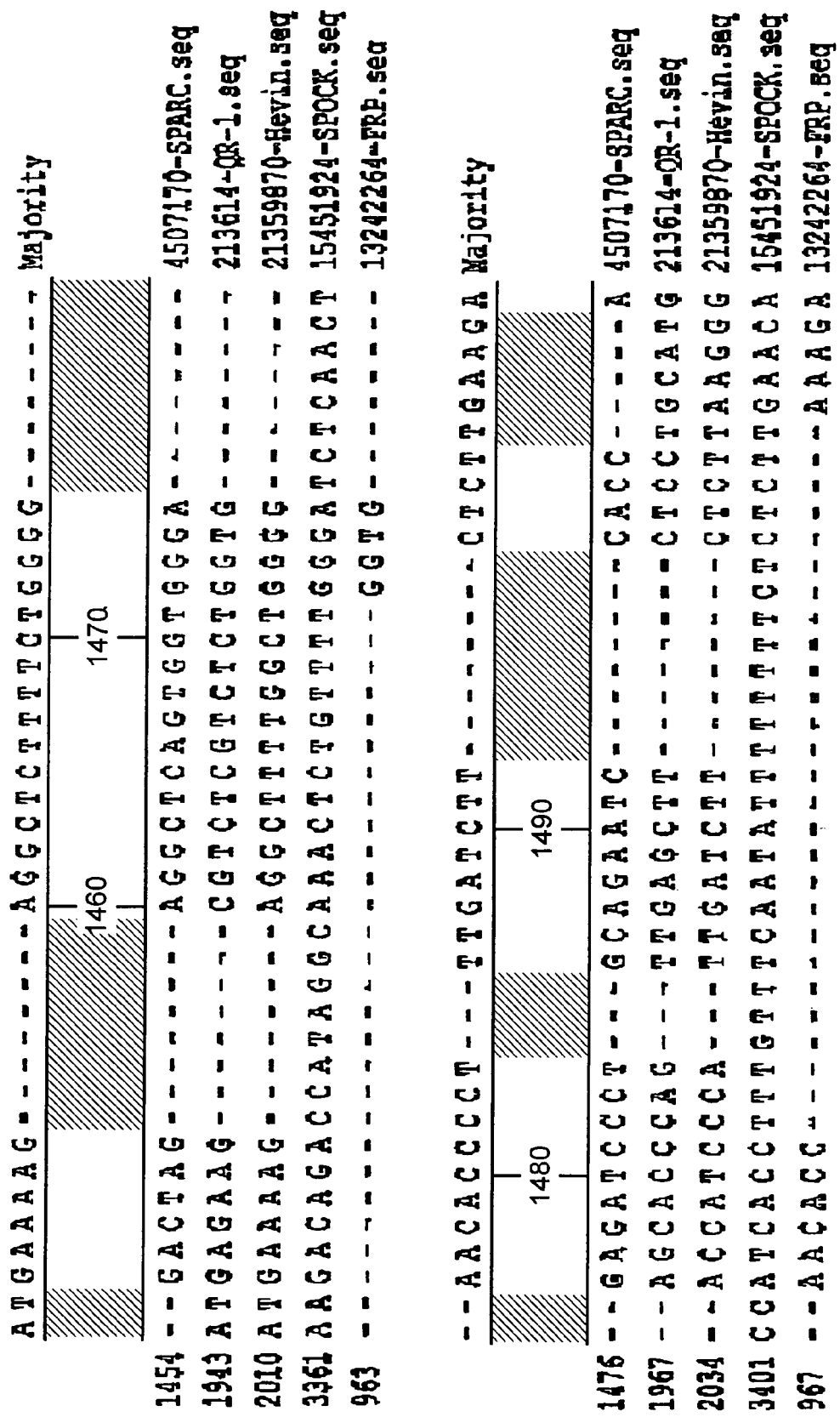
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
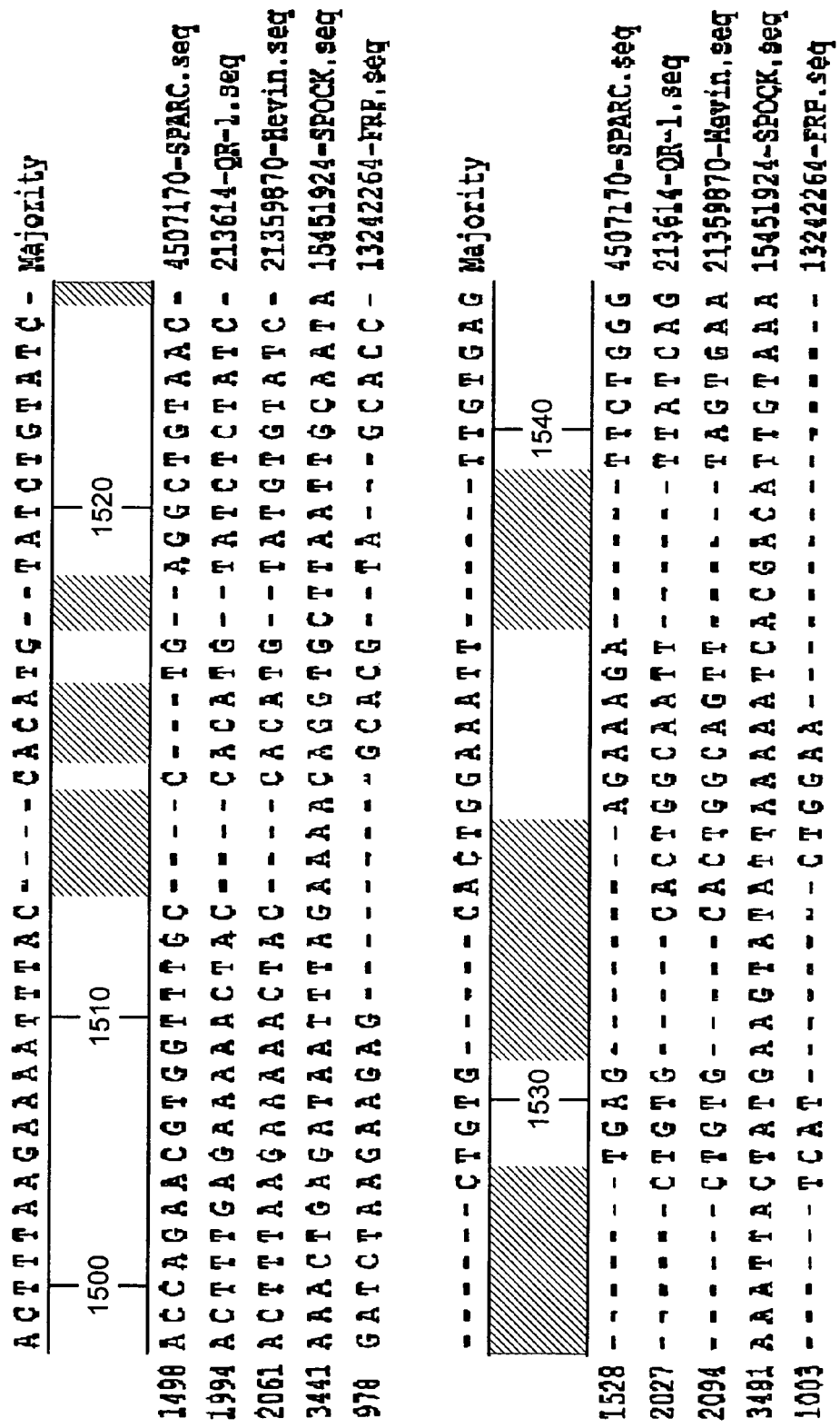
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
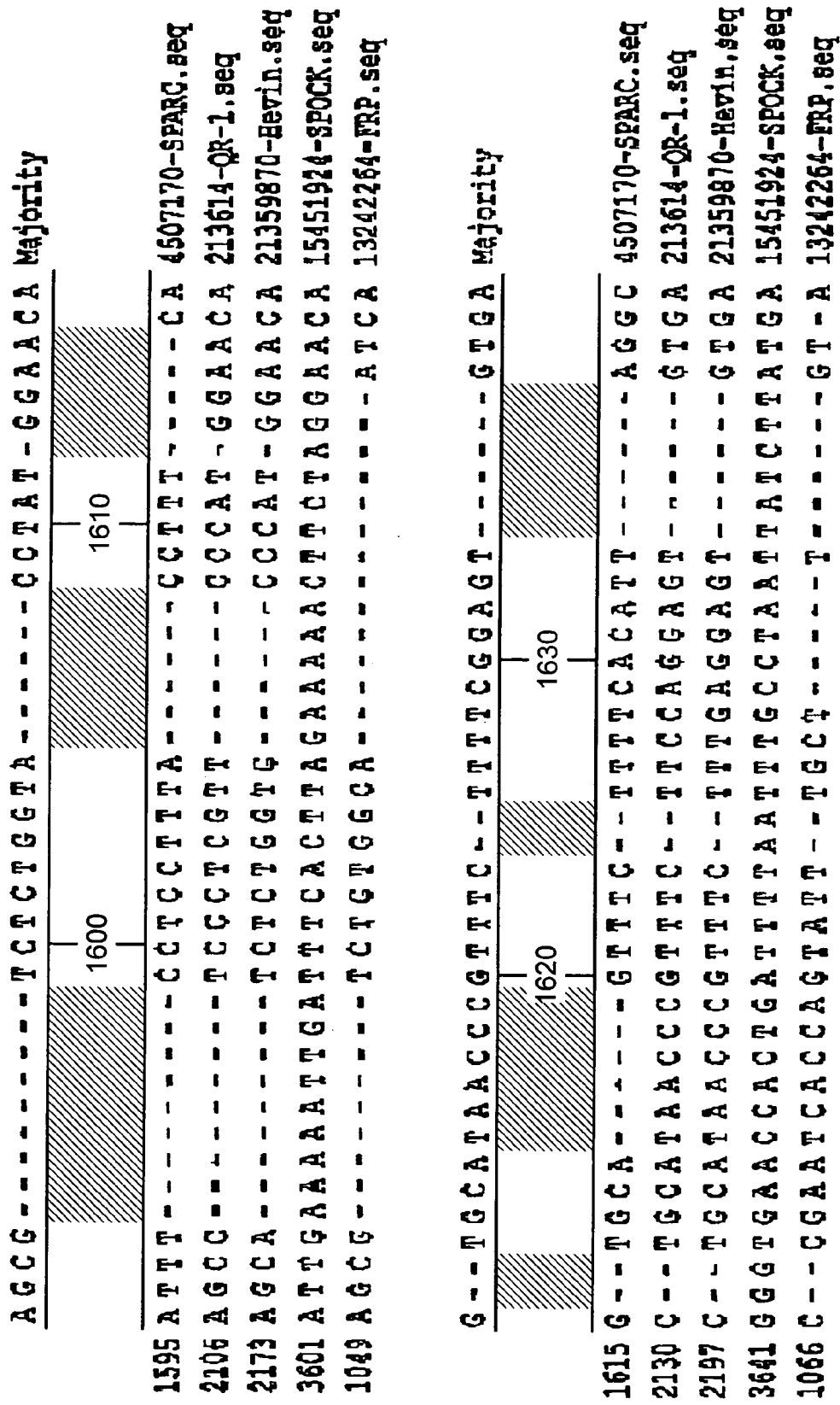
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
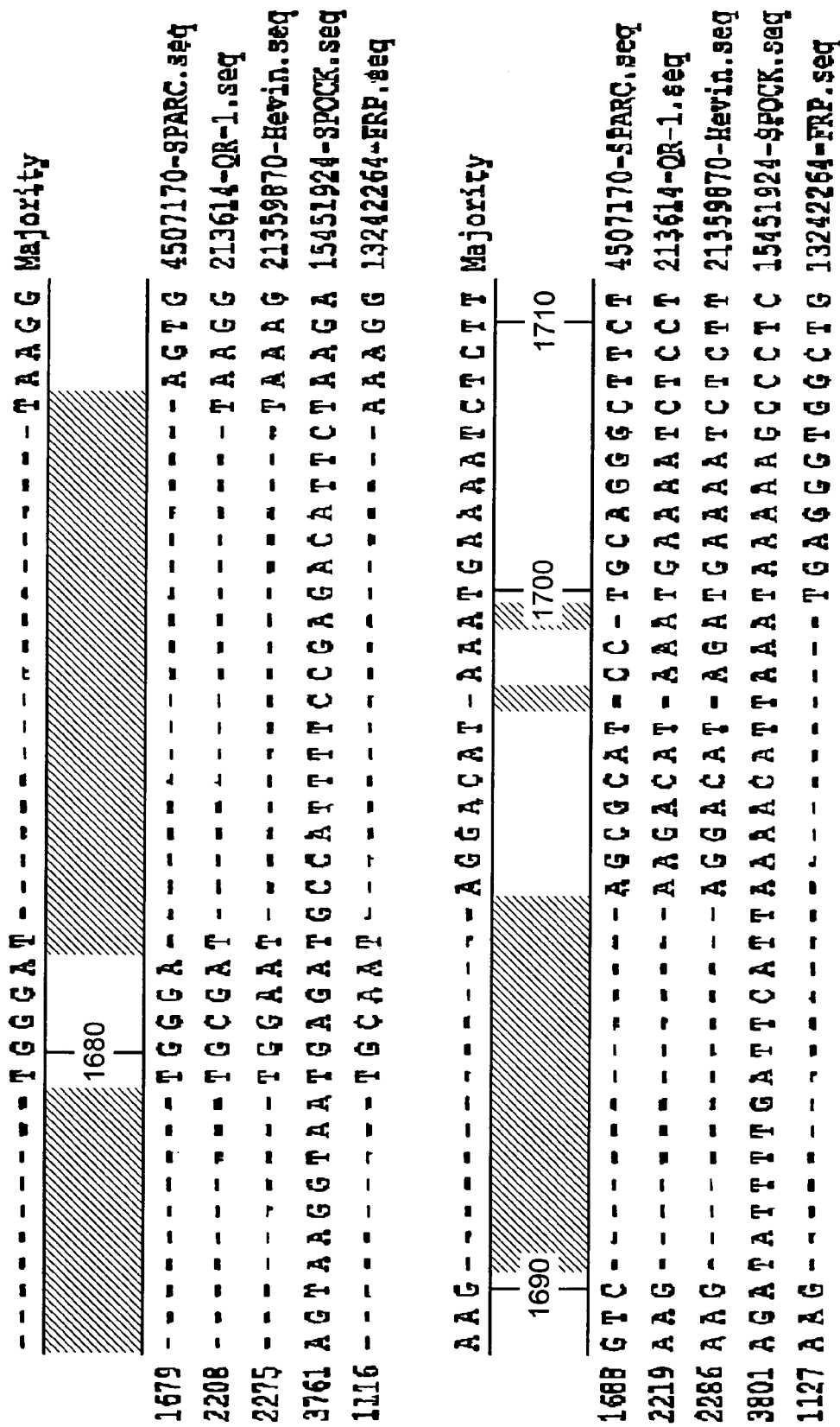
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
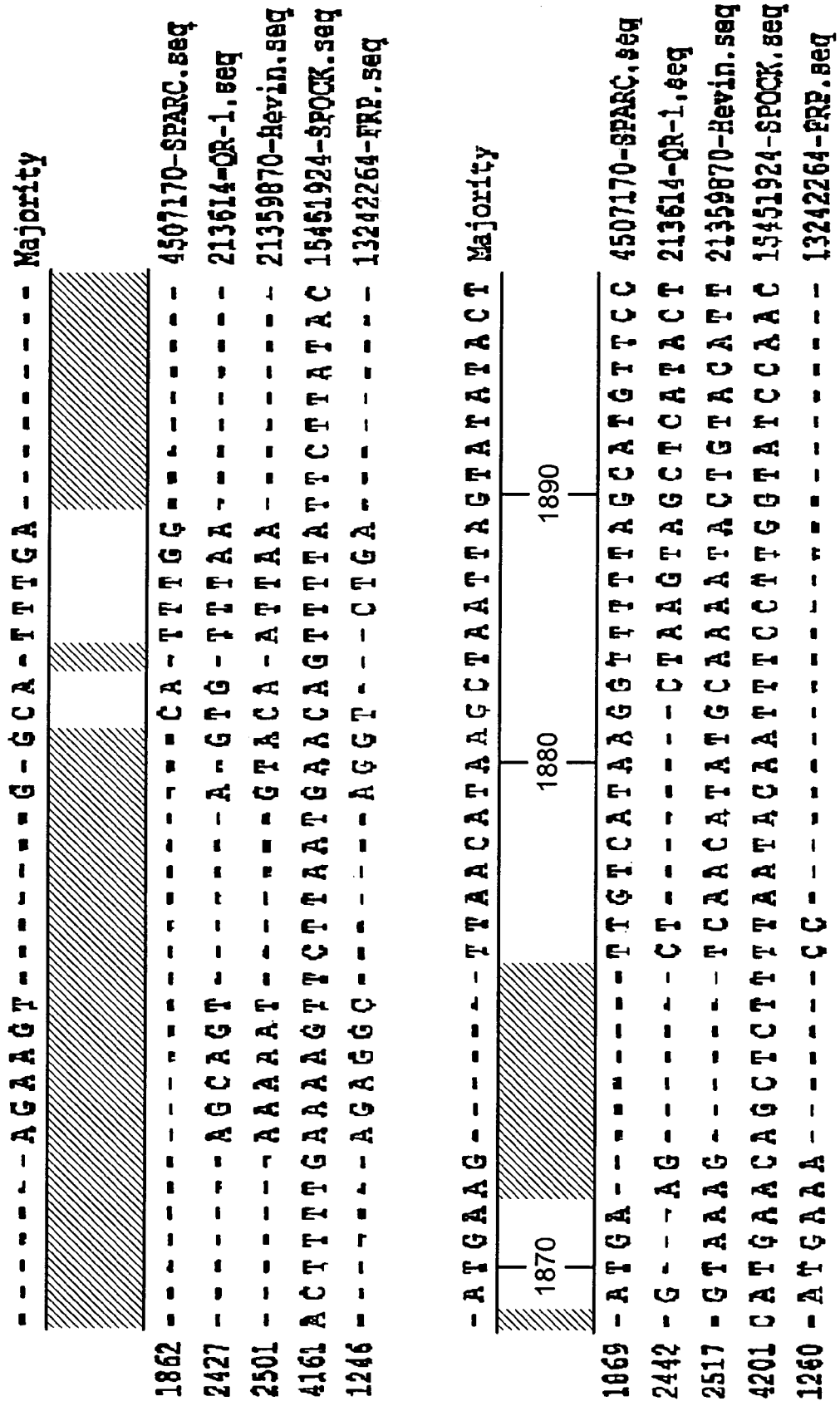
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
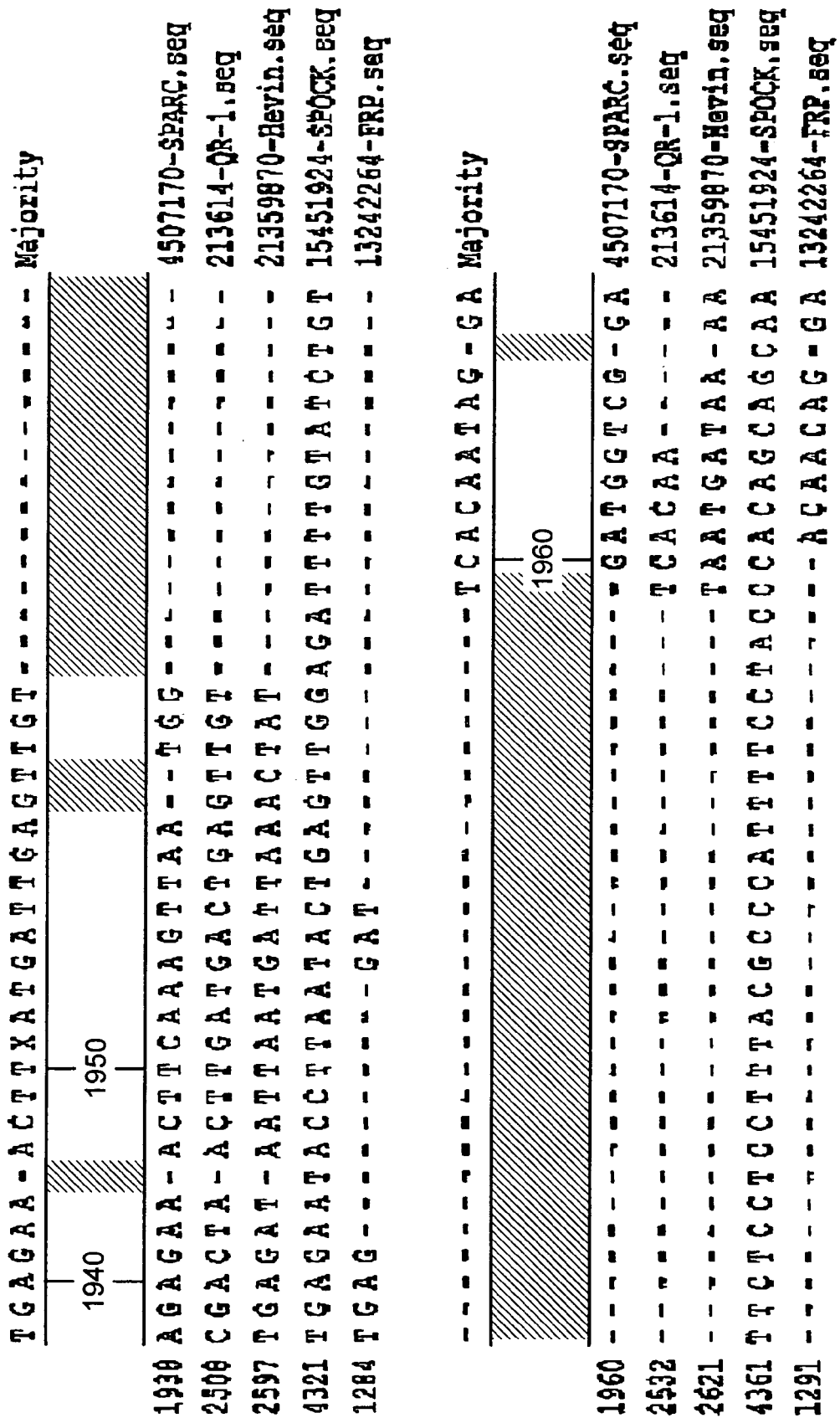
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57:
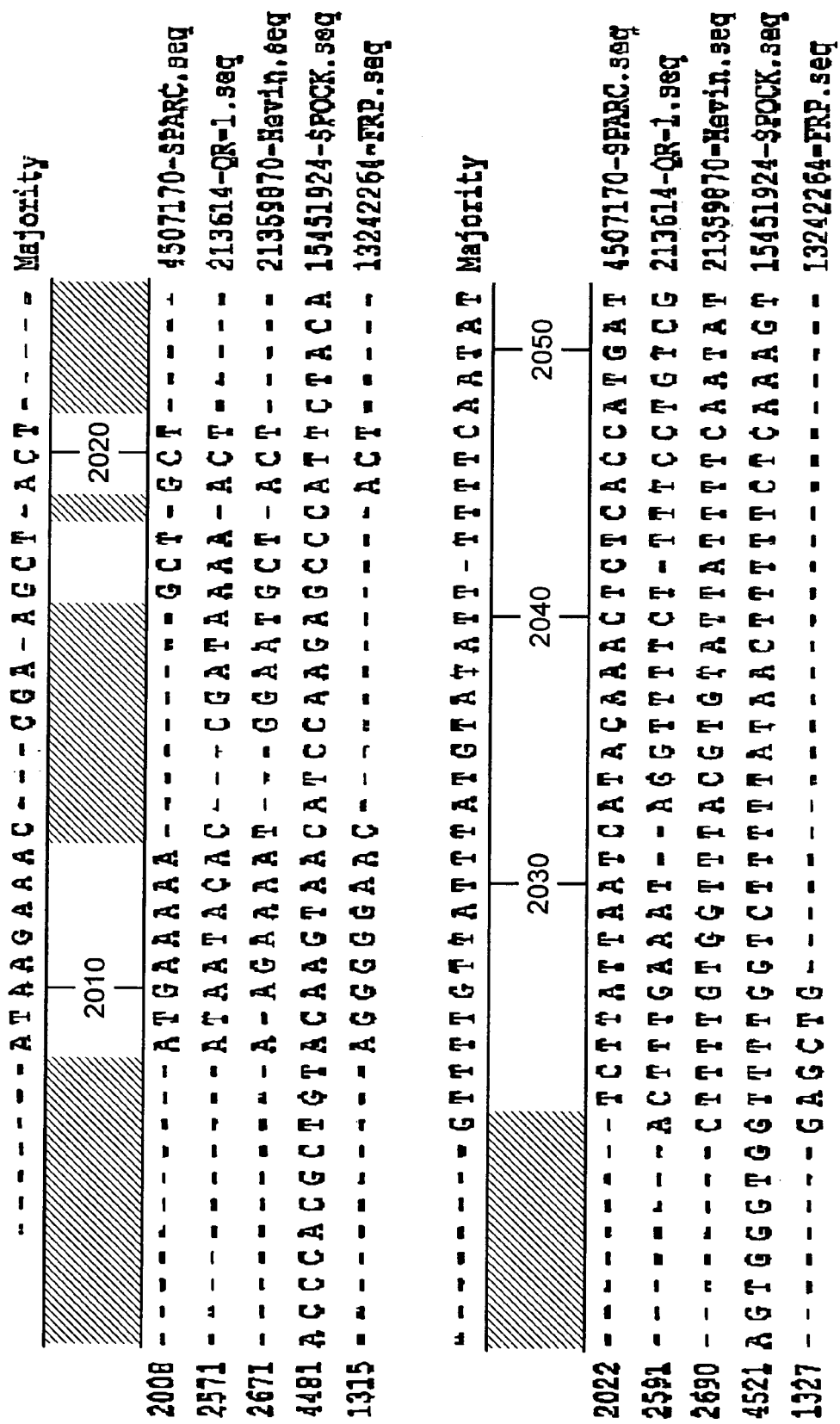
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58:
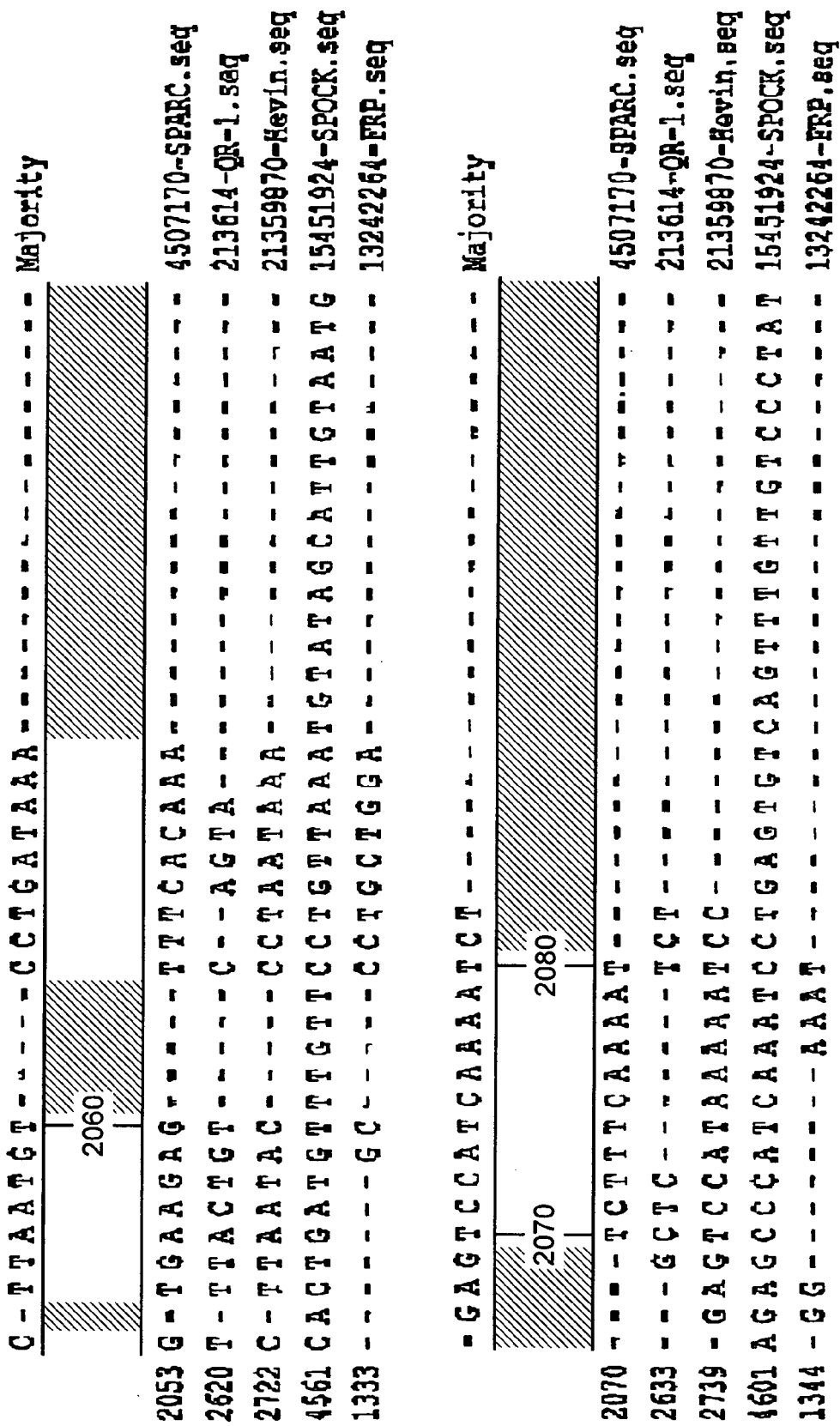
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60:
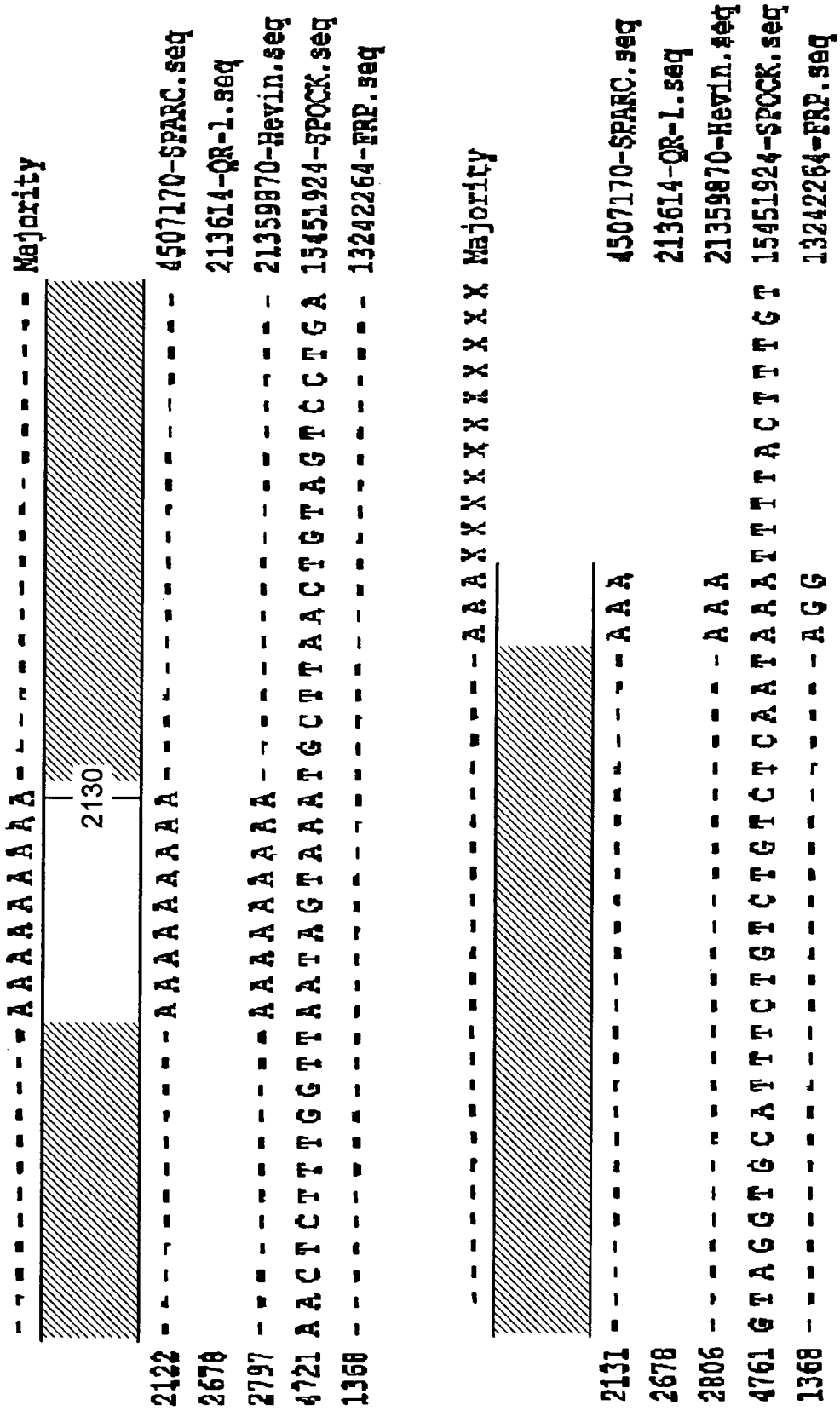
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61:
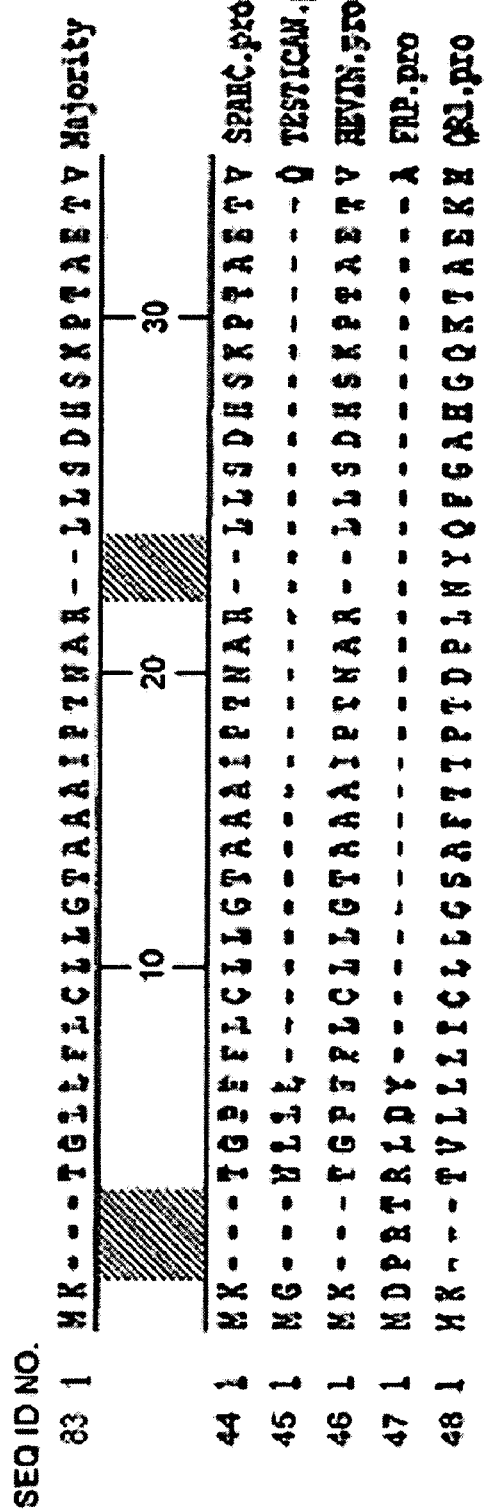
Figures 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62:
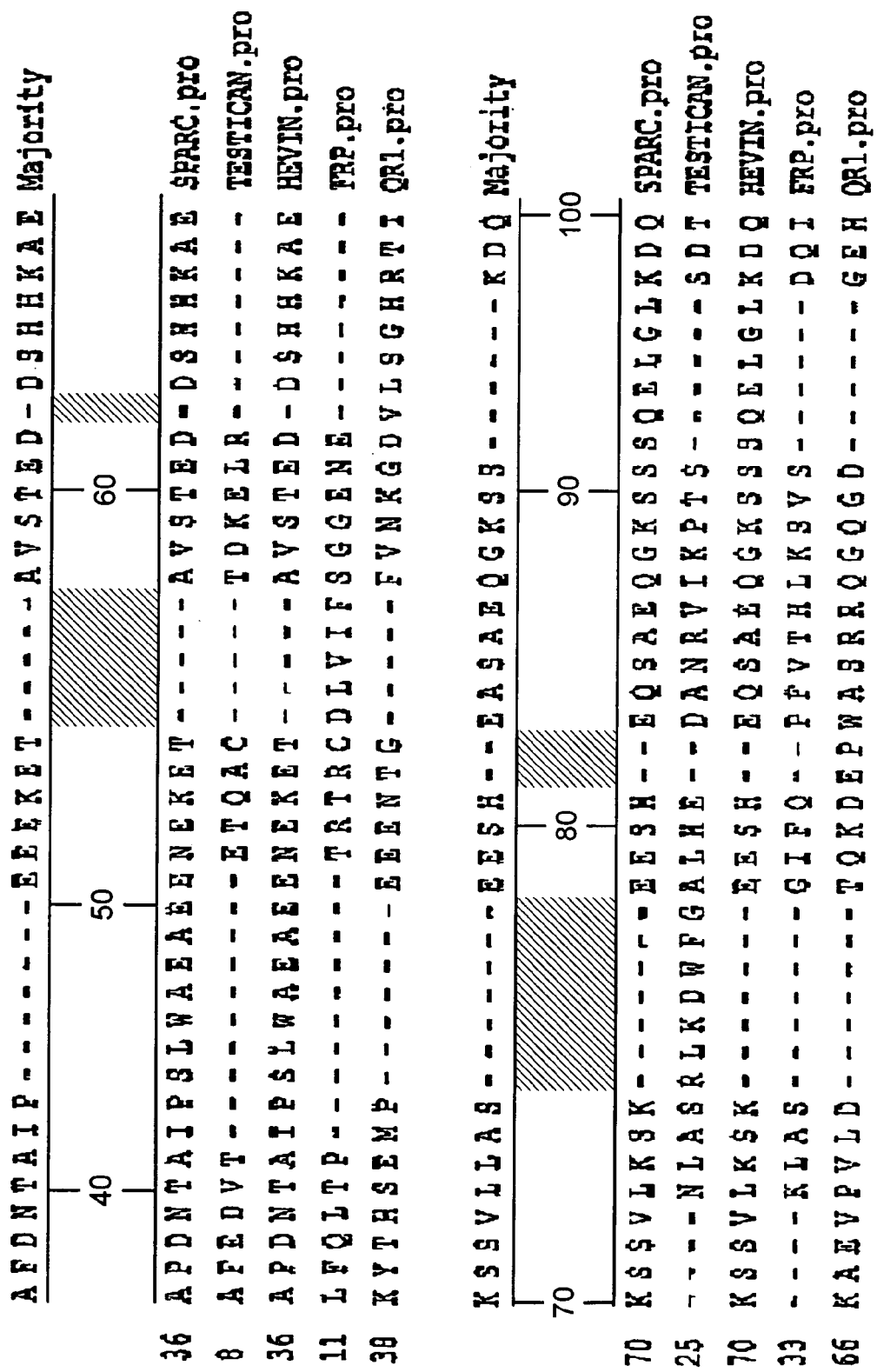
Figures 13, 66:
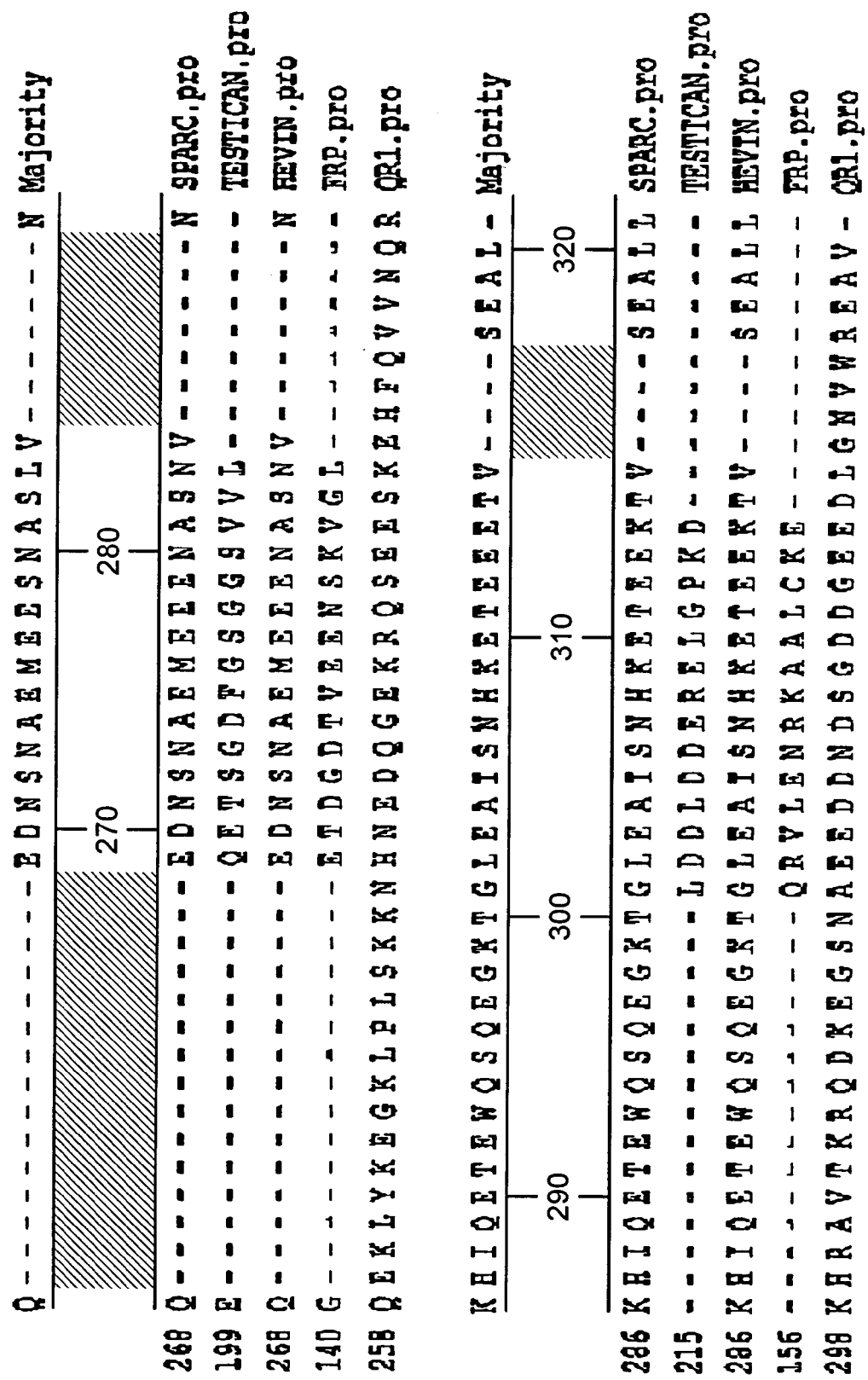
Figures 13, 71:
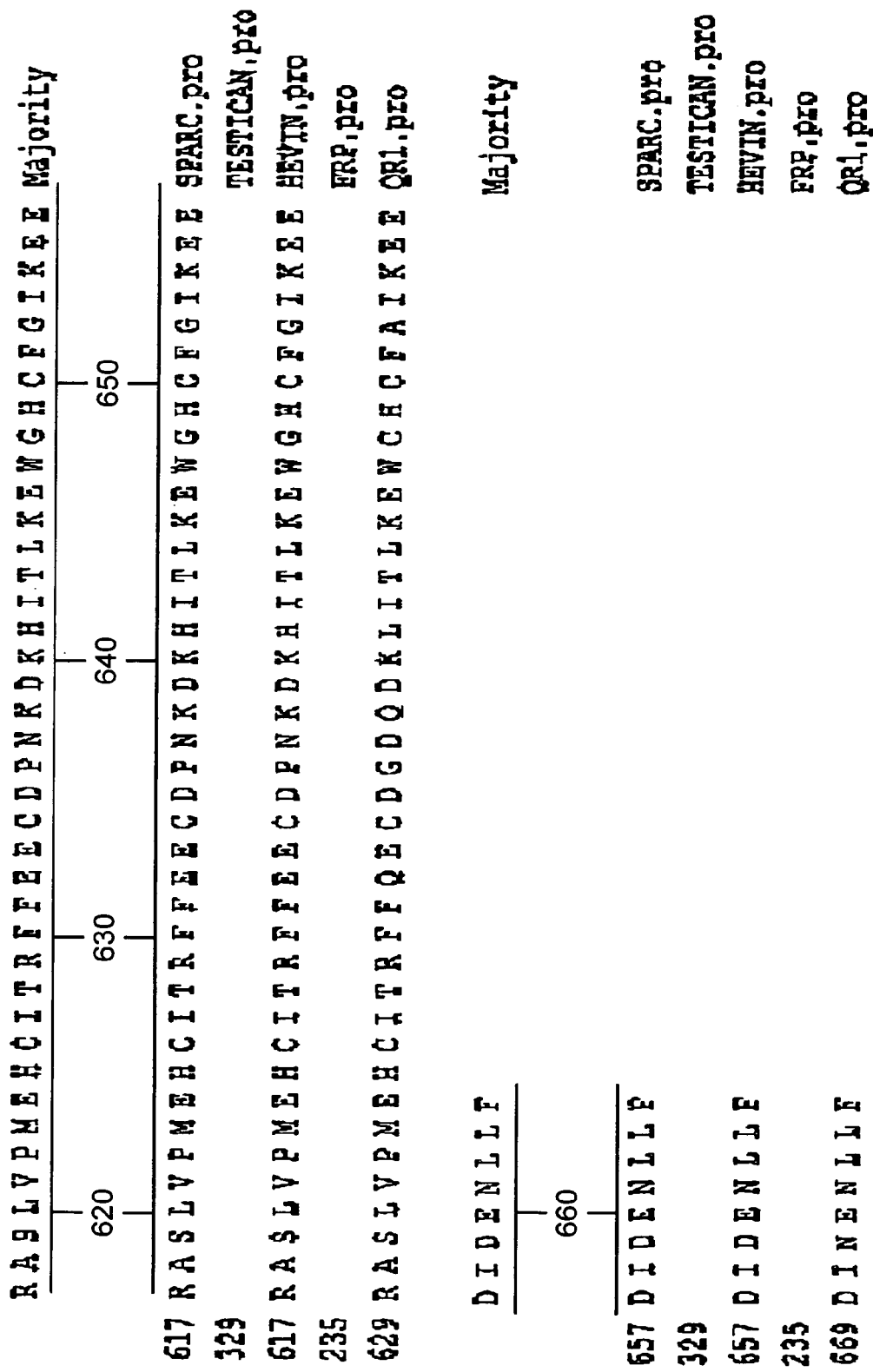
Figure 14:
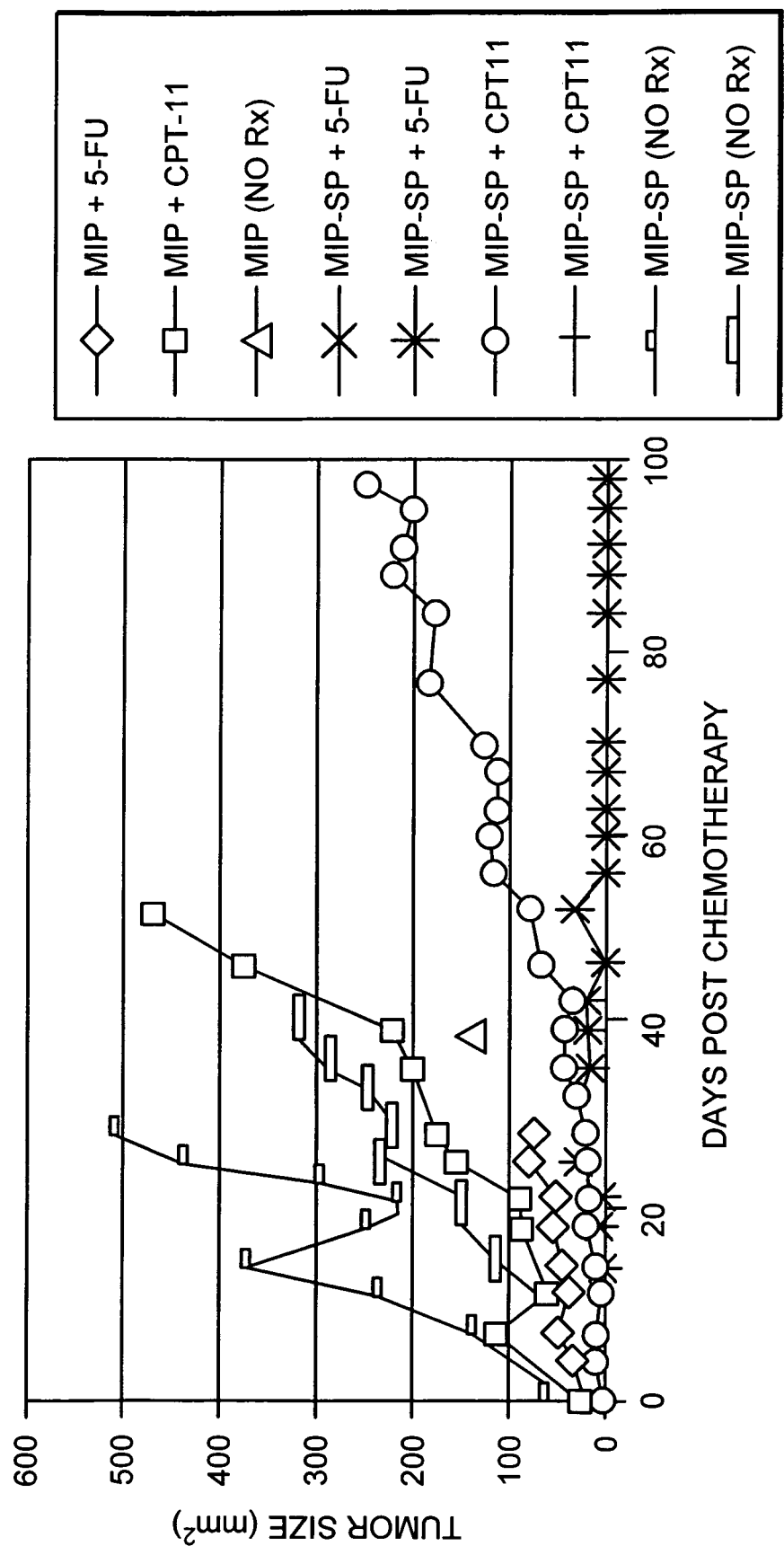
Figure 15:
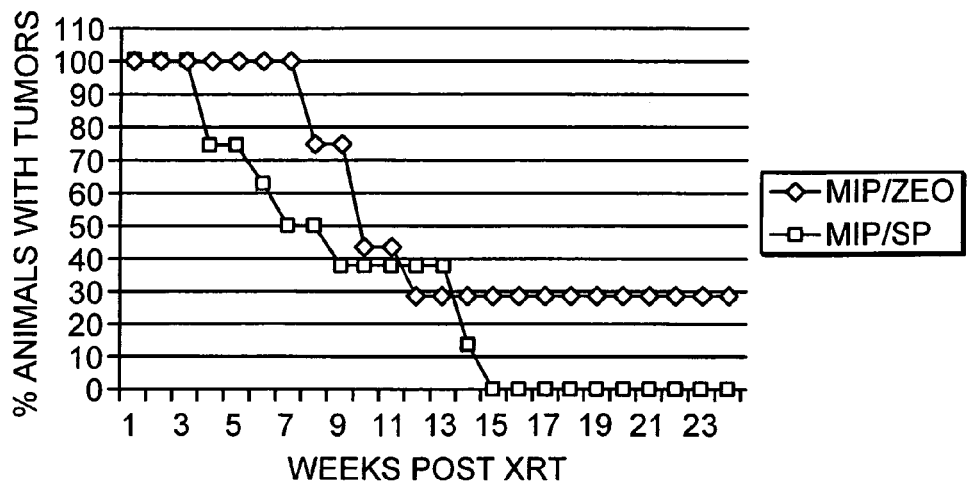
Figure 16:
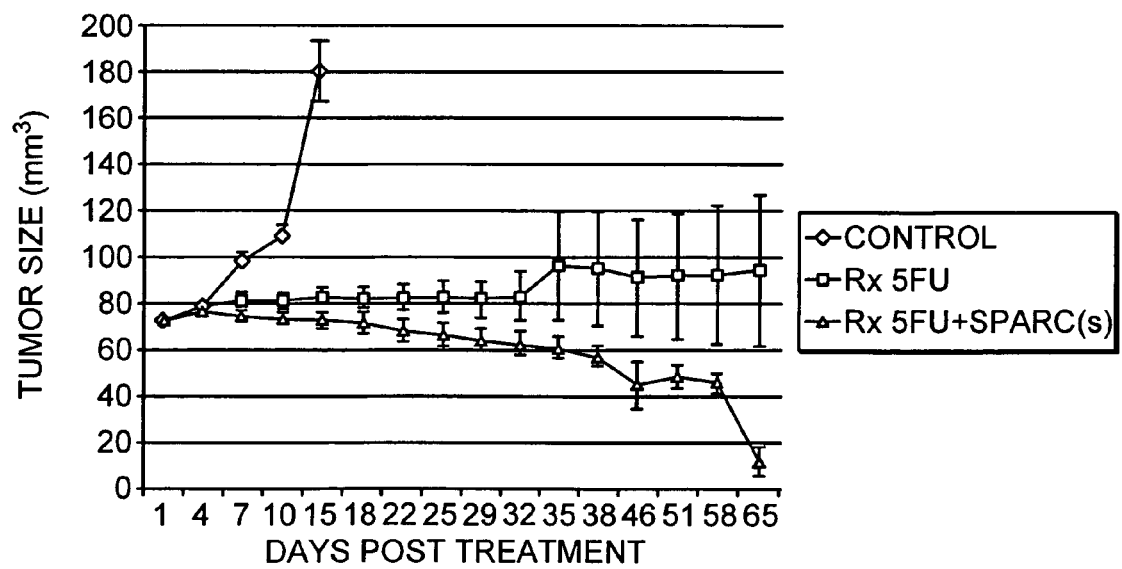
Figure 17:
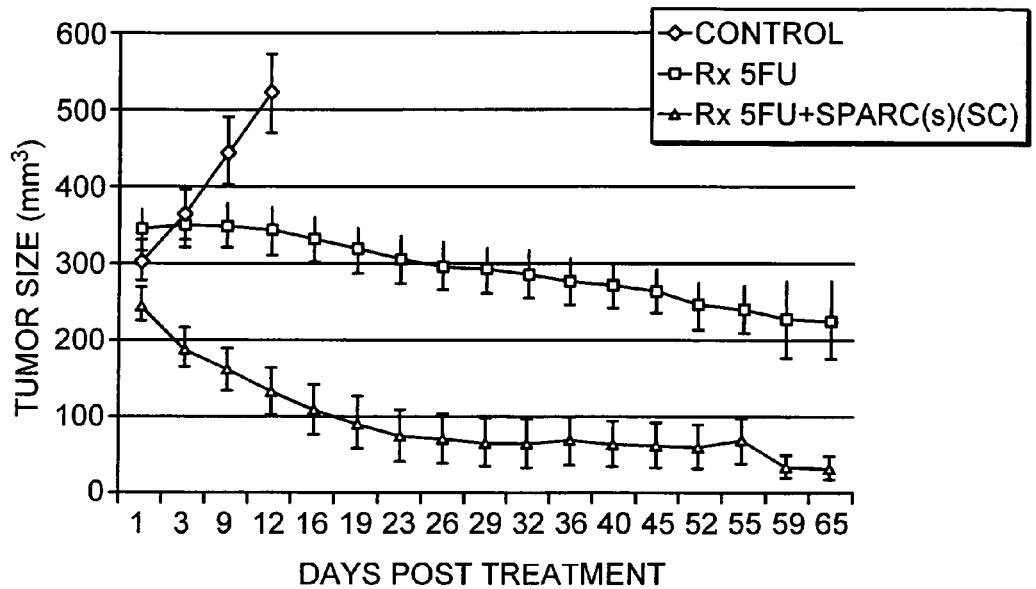
Figure 18:
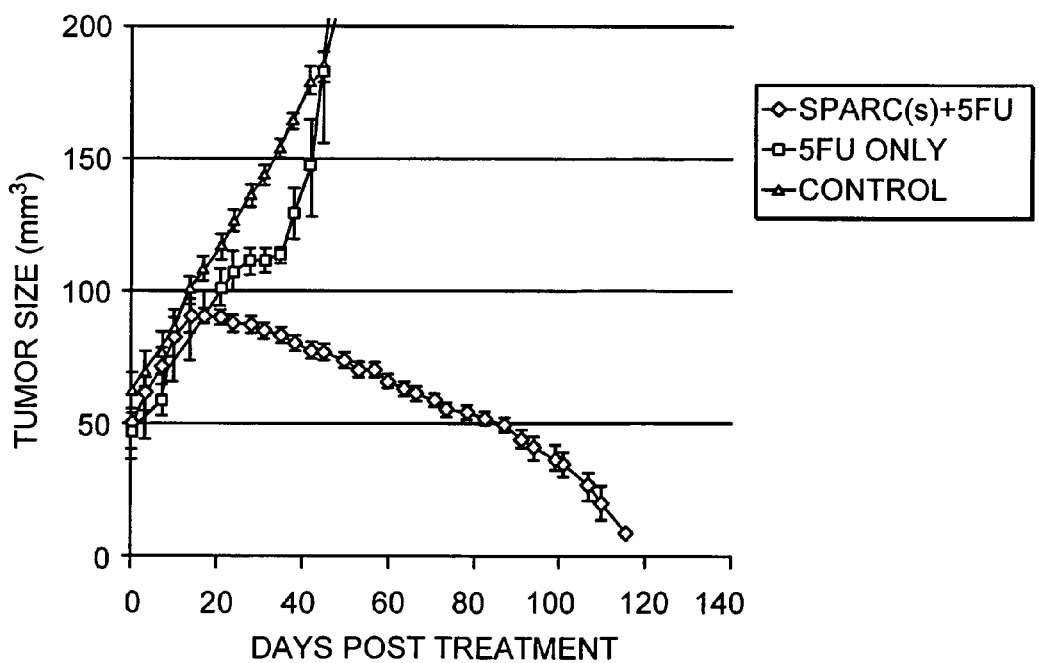
Figure 19A:
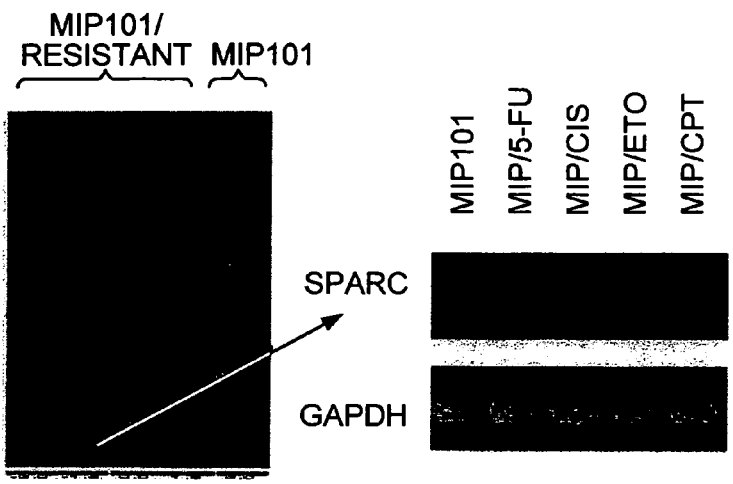
Figure 19B:
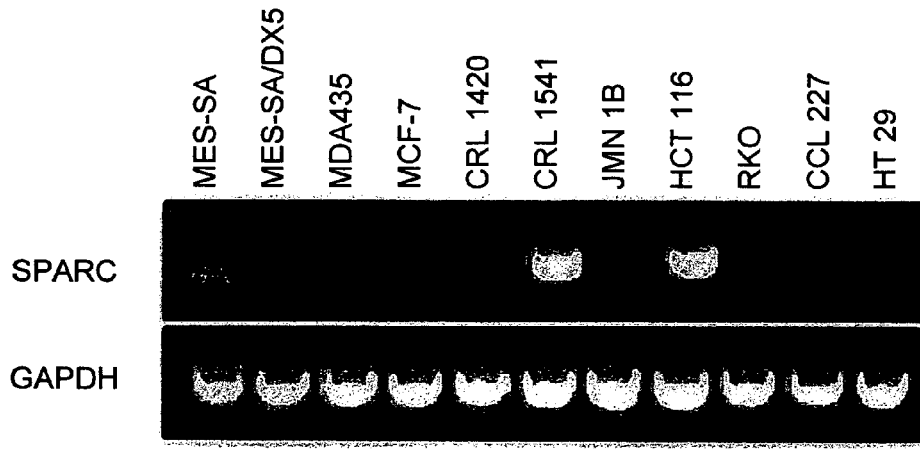
Figure 19C:
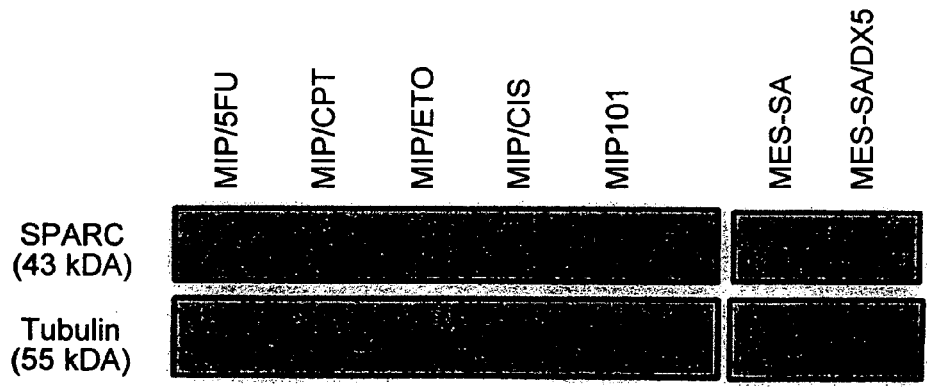
Figure 20A:
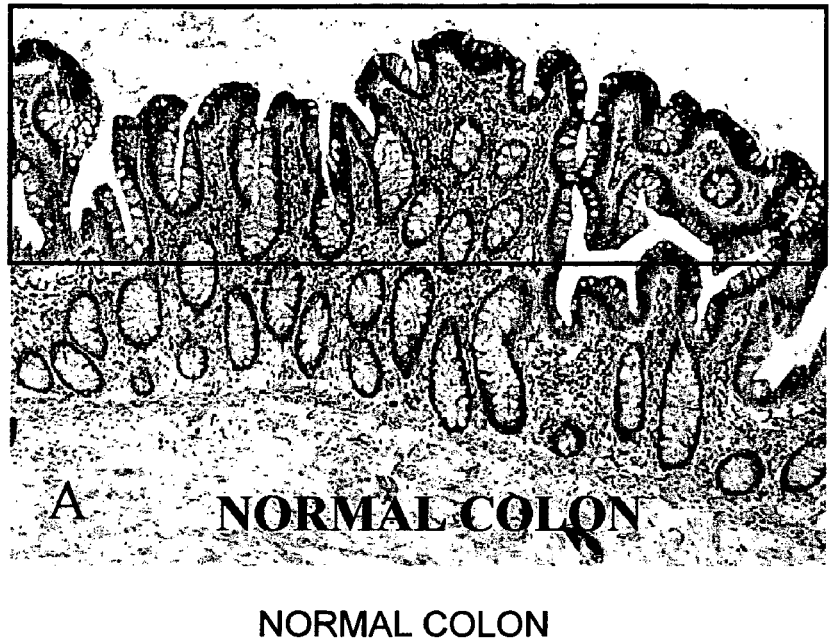
Figure 20B:
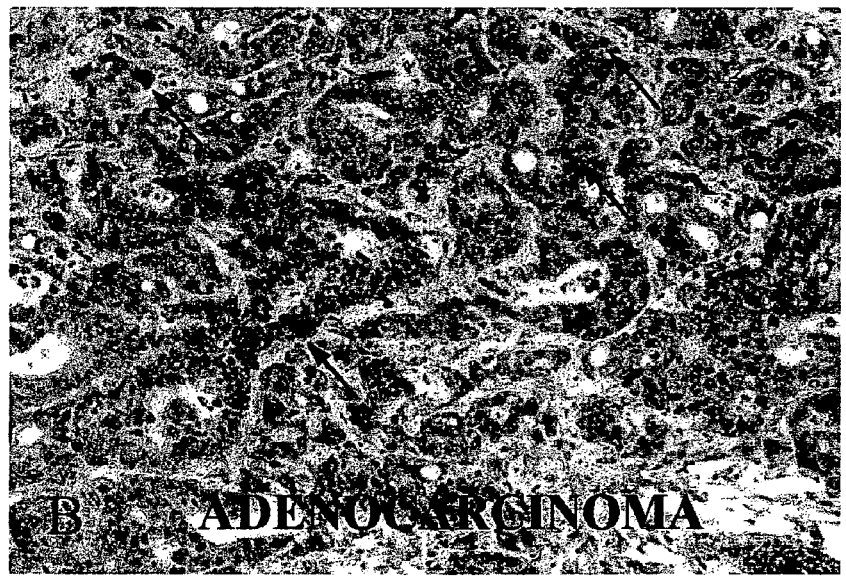
Figure 20C:
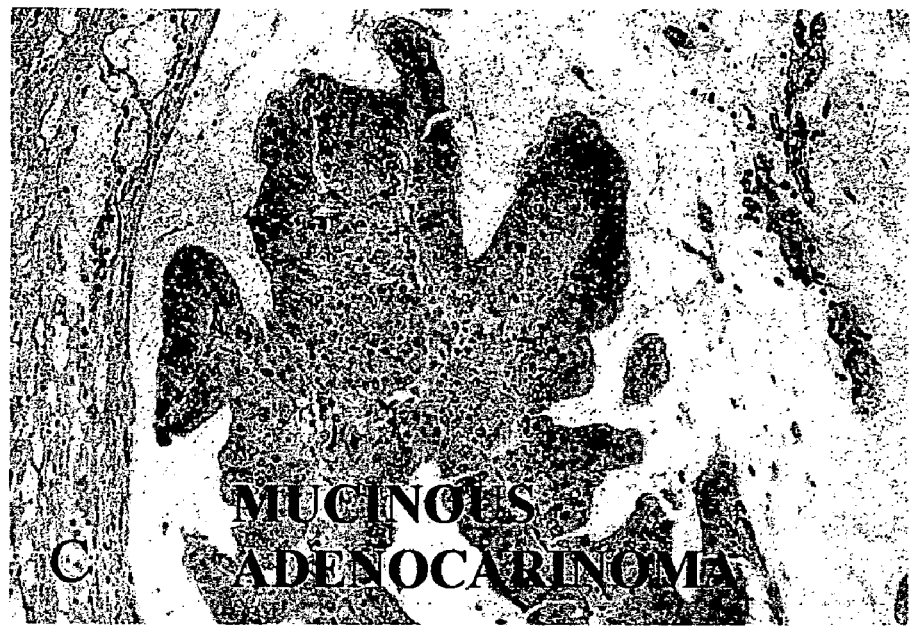
Figure 20D:
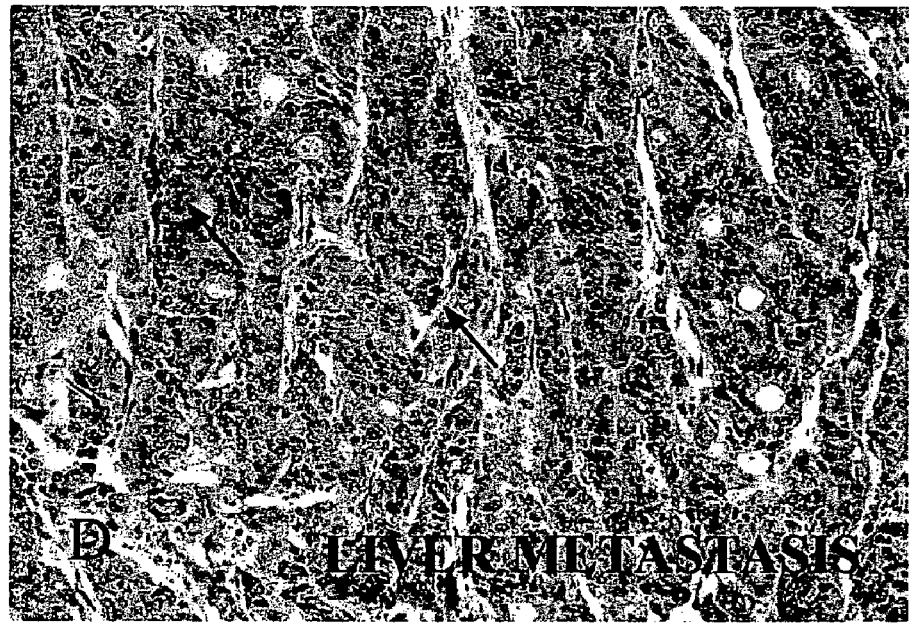
Figure 21A:
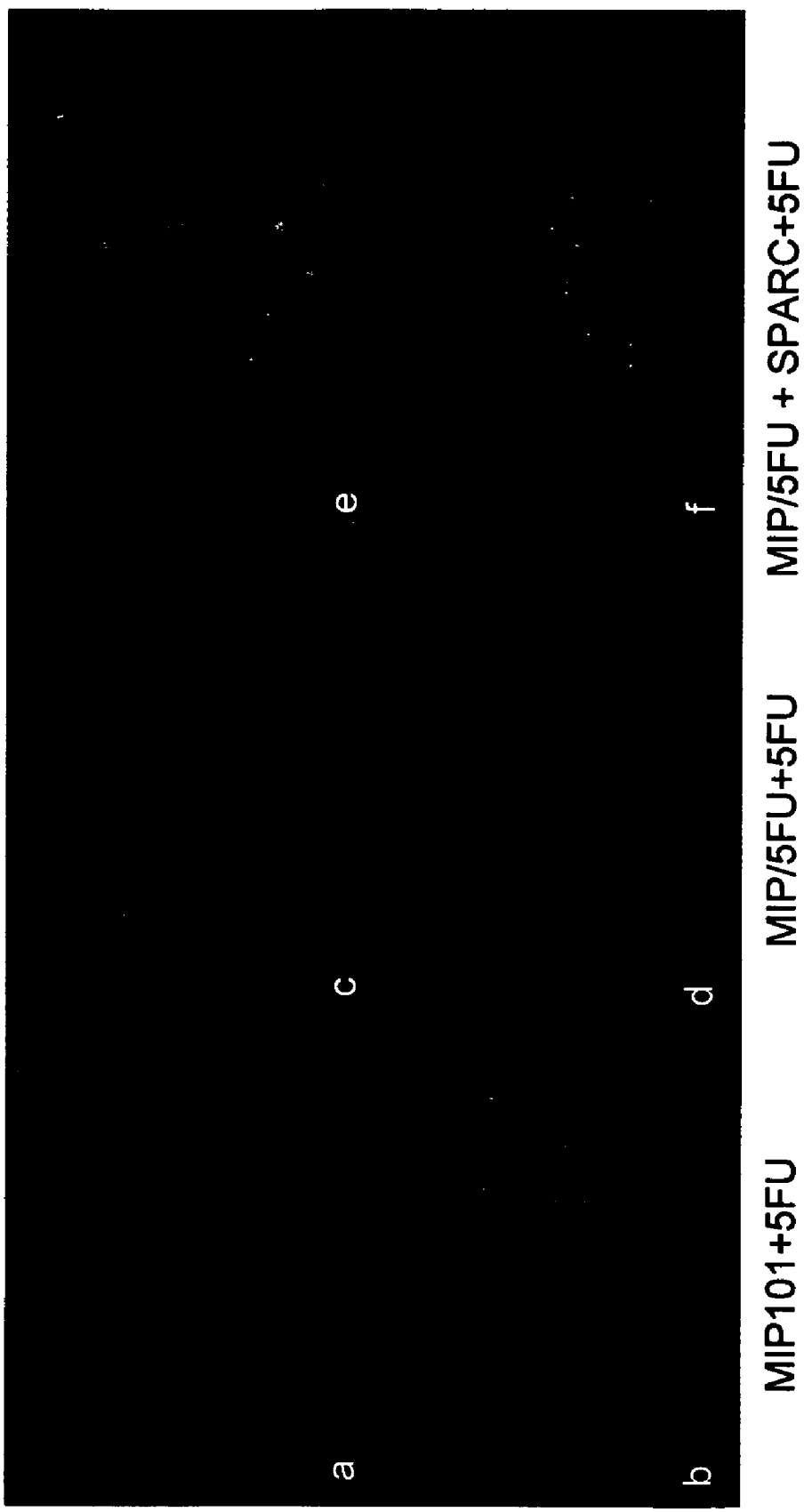
Figure 21B:
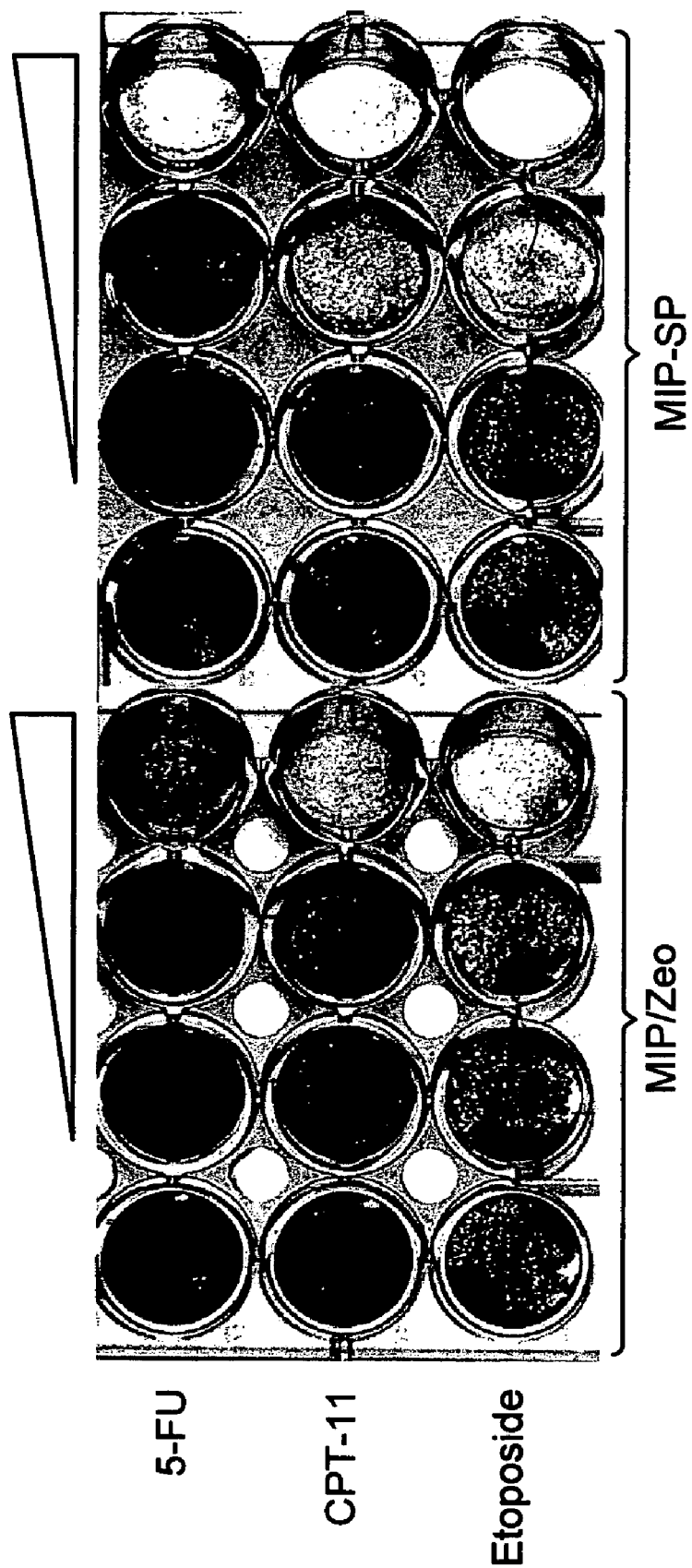
Figure 21C:
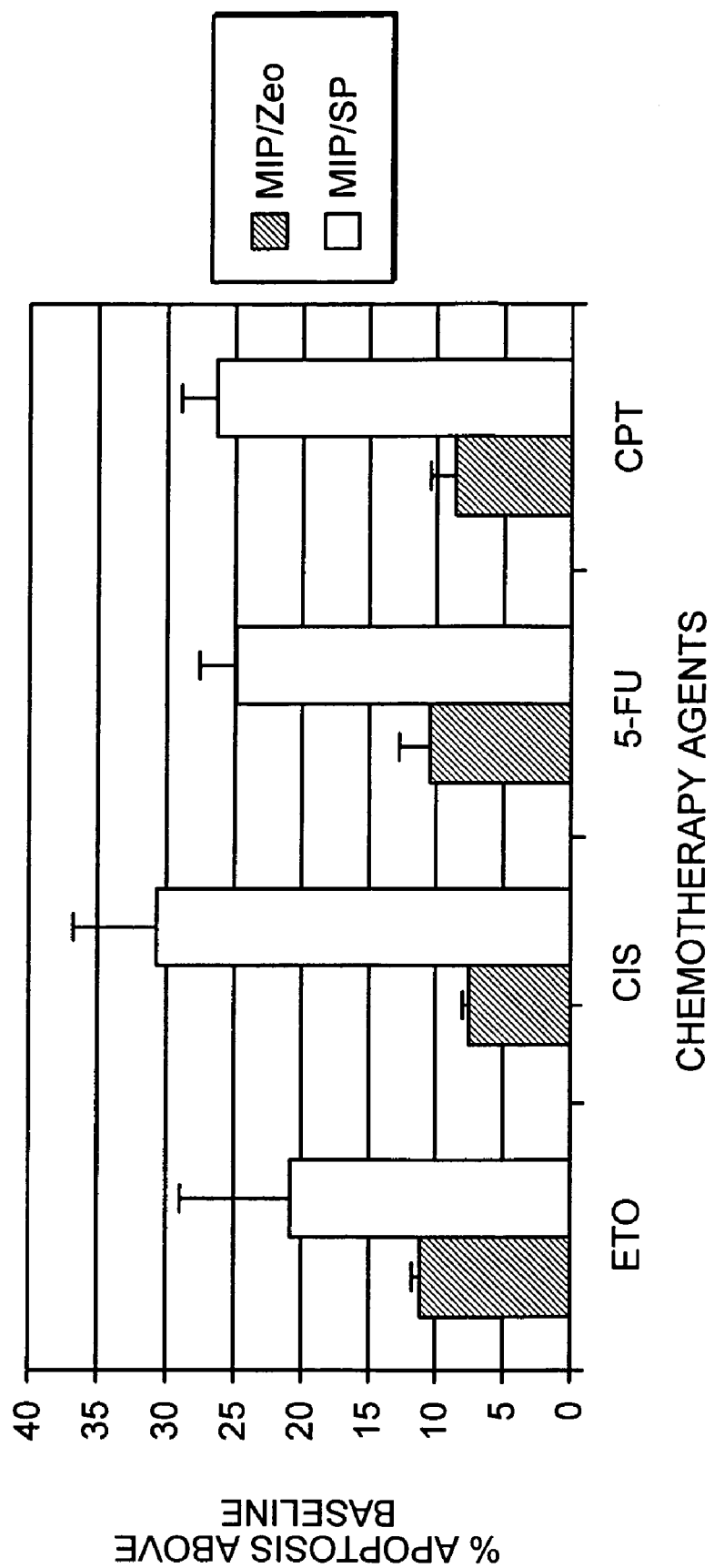

FIG. 19 shows human SPARC mRNA and protein levels in colorectal cancer cell lines sensitive and resistant to chemotherapy. (A) Oligonucleotide microarray cluster analysis diagram (left panel) reveals that SPARC gene expression is significantly lower in cell lines resistant to chemotherapy, which was confirmed by semi-quantitative RT-PCR (right panel). (B) Detection of SPARC expression levels in a paired uterine sarcoma cell line sensitive to chemotherapy (MES-SA) and resistant to doxorubicin (MES-SA/DX5) shows a similar decrease in expression in the resistant cell line. In breast cancer cell lines, MDA435 had slightly higher levels of SPARC expression than MCF-7. Low levels of expression were detected in pancreatic cancer cell line (CRL 1420), lung cancer cell line (JMN 1B), colorectal cancer lines (RKO, CCL 227, HT 29). High levels of SPARC expression was detected in normal colon cell line (CRL 1541) and a colon cancer cell line (HCT 116). (C)SPARC protein expression verifies that there is a significant decrease in this protein in the MIP101 resistant clones (resistant cell lines: MIP/5FU, MIP/CPT, MIP/ETO, MIPT/CIS) in comparison to the normal parental cell line (lane 5, MIP101). Similarly, another set of resistant cell line of uterine sarcoma origin (MES-SA/DX5, uterine sarcoma resistant to doxorubicin) shows decreased expression of SPARC in comparison to the parental sensitive cell lines (MES-SA, parental uterine sarcoma).

FIG. 20 shows SPARC protein expression in human colonic epithelium. (A) Normal colon shows a differential pattern of SPARC protein expression with higher levels of the protein within the superficial cells proximal of the lumen and a gradient of decreasing expression towards the crypts. SPARC protein levels in (B) Adenocarcinoma of the colon, (C) mucinous adenocarcinoma and (D) adenocarcinoma of the colon metastatic to liver show low level of SPARC protein diffusely within the malignant epithelium. Sections 6 μm cross sections, ×20 magnification.

Example 3

SPARC Polypeptide Sensitizes Resistant Cells to 5-FU Treatment

Figure 6:
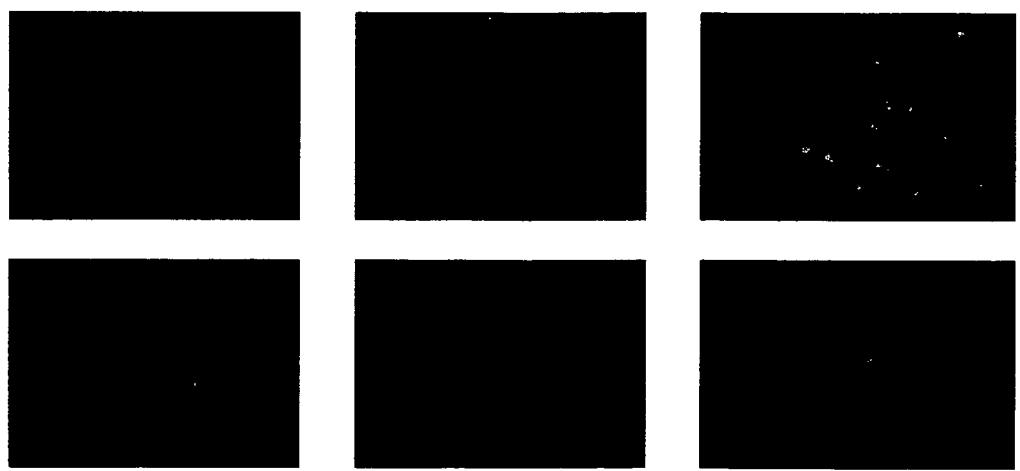
FIG. 6 is a Tunel assay showing the response of the resistant MIP101 cells to exogenous SPARC in reversing the resistant phenotype according to one embodiment of the invention.

In order to further delineate this potential role, we assessed the response of the resistant MIP101 cells (FIG. 6) to exogenous SPARC in reversing the resistant phenotype. As indicated by initial experiments, MIP101 cells resistant to 5-FU (MIP-5FUR) could not be triggered to undergo apoptosis with 5-FU at a concentration of 500 uM, while a significant number of cells from the parental, sensitive cell line underwent apoptosis following exposure to a similar concentration of 5-FU. A significant finding was observed with exogenous exposure of resistant cells with SPARC: incubation of the resistant clones with SPARC for a 24-hr period followed by a 12-hr exposure to a chemotherapeutic agent was sufficient in reversing the resistant phenotype, as apoptotic cells were once again detected by TUNEL assay in cells exposed to concentrations of chemotherapy that previously did not stimulate cell death. Incubation with exogenous SPARC alone without subsequent exposure to chemotherapy did not induce apoptosis in either the parental MIP 101 or the resistant cells.

FIG. 21 shows assessment of the effect of SPARC in influencing the sensitivity of cells to chemotherapy. (A) Effect of exposure of MIP/5FU cells to exogenous SPARC in combination with 5-FU in-vitro. Assessment of apoptosis by TUNEL assay shows positively stained cells in sensitive MIP101 cells exposed to 5-FU 1000 uM (a, TUNEL stain; b, DAPI stain) but lack of apoptosis in the resistant phenotype (c, TUNEL stain; d, DAPI stain) following exposure to a similar concentration of 5-FU. However, following a 24 hr exposure to SPARC (5 ug/ml), 5-FU resistant cells once again became sensitive to 5-FU 1000 uM as shown by TUNEL-positive stained cells (e; f, DAPI stain), indicating the presence of apoptotic cells. This is the first indication that exogenous exposure to SPARC reverses the resistant phenotype of the 5-FU resistant cells and thereby suggesting that SPARC may function as a chemotherapy sensitizer. (B) Stably transduced MIP101 cell lines overexpressing SPARC (MIP/SP) and control (MIP/Zeo) exposed to increasing concentrations of chemotherapy (5-FU, CPT-11 and etoposide) showed fewer cell colonies of MIP/SP cells when exposed to lower drug concentrations than MIP/Zeo cells, thereby indicating increased sensitivity of the SPARC overexpressing clones to chemotherapy as fewer cells survived at relatively lower concentrations of chemotherapy. (B) Greater number of MIP101 overepressing SPARC (MIP/SP) undergo apoptosis following a 12-hr exposure to various chemotherapeutic agents (ETO=etoposide, CIS=cisplatin, 5-FU=5-fluorouracil, CPT=CPT-11) in comparison to control cells (MIP/Zeo) ($p<0.05$). Analysis of apoptosis following Annexin V labeling by flow cytometry represent results of three independent studies performed in triplicate. Results of the clonogenic assay (B) is a representative experiment that was repeated three times with similar results.

Example 4

Figure 7:
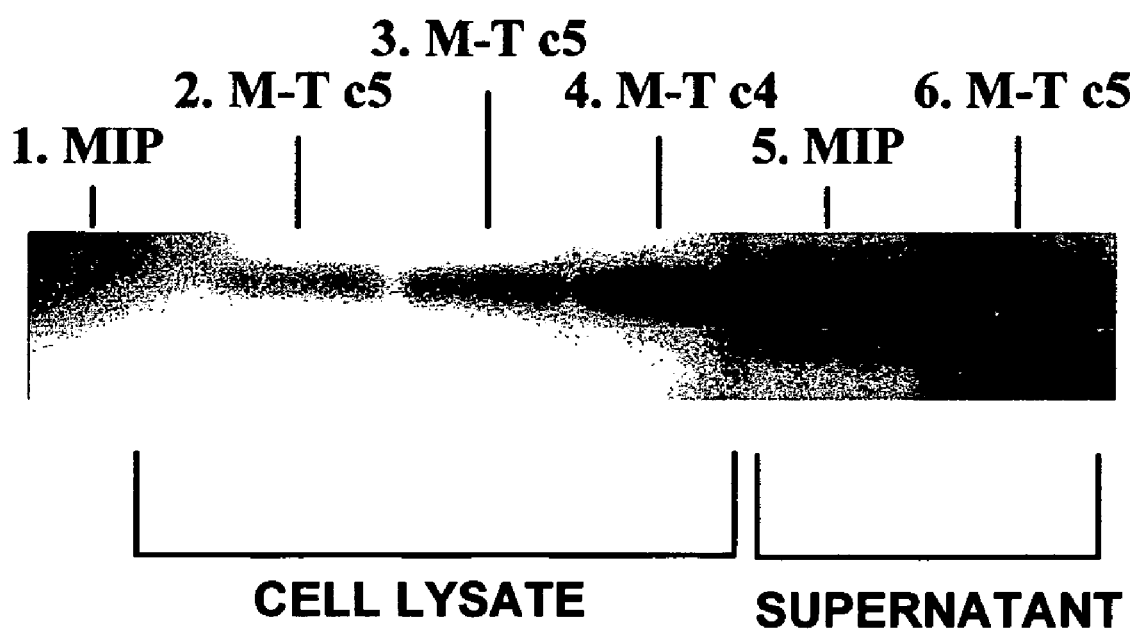
FIG. 7 is a immuno blot assay showing recombinant cells expressing SPARC polypeptide according to one embodiment of the invention.

SPARC Polynucleotide Sensitizes Recombinant Cells to Various Chemotherapy Treatment In order to test this hypothesis, MIP101 cells were transfected with SPARC for the purposes of generating overexpression systems for additional in vitro studies. Two clones overexpressing SPARC (clones 4, 5; FIG. 7) were used for subsequent studies.

Figure 9:
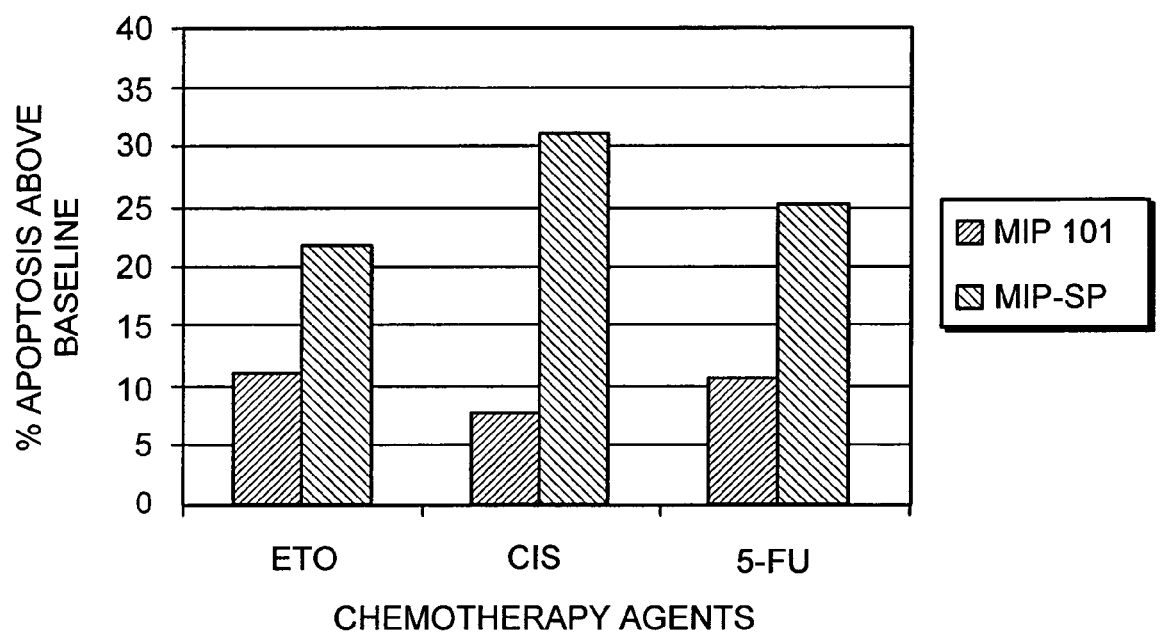
FIG. 9 is a graph showing the percentage of apoptosis of cells following exposure to chemotherapeutic agents according to one embodiment of the invention.
Figure 10:
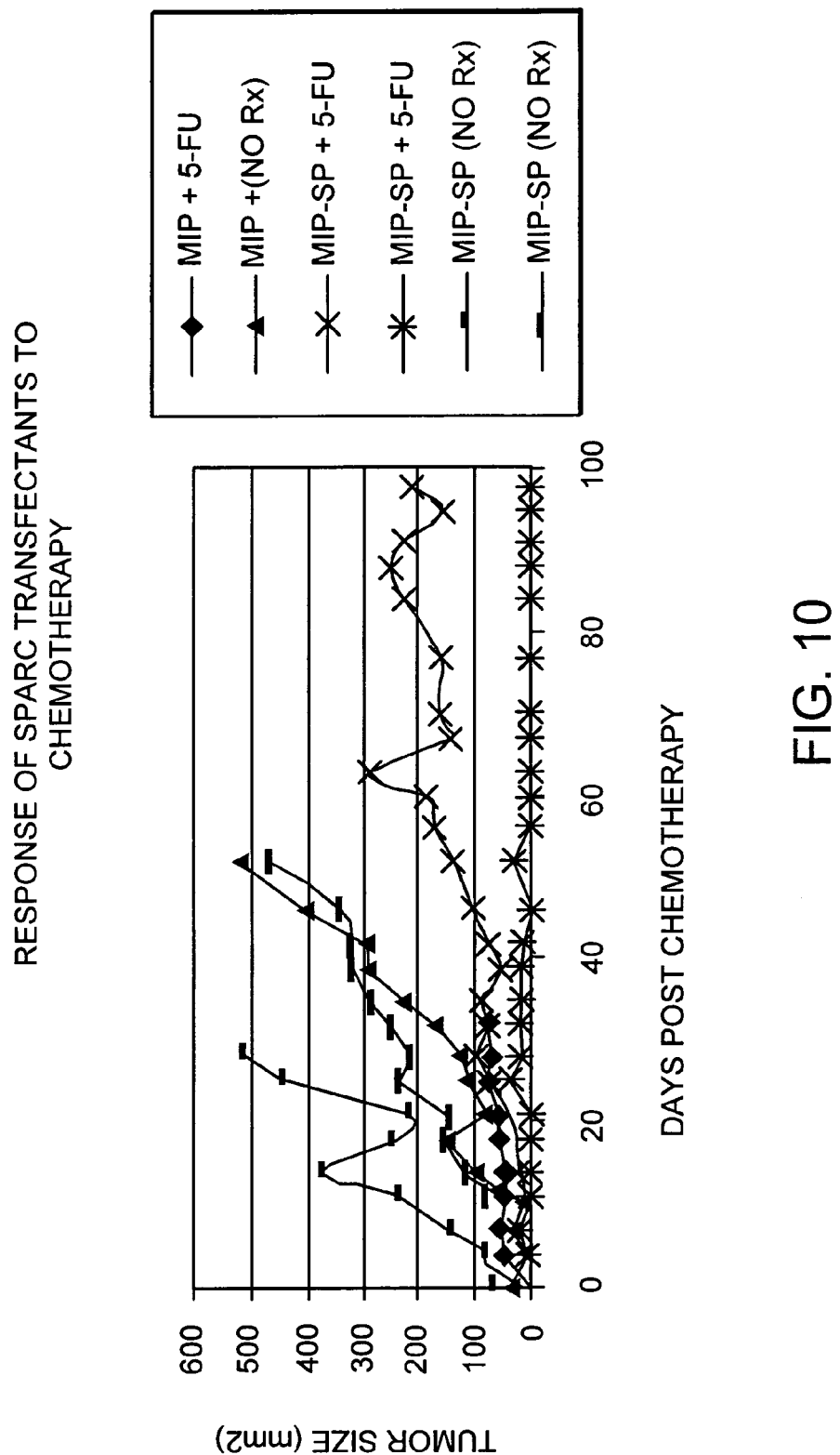
FIG. 10 is a graph showing the response of SPARC transfectants to chemotherapy agents according to one embodiment of the invention.

The sensitivity of the SPARC-transfectants to various chemotherapeutic agents was assessed by colony formation assay, which showed that clones overexpressing SPARC were unable to form tumorigenic colonies at higher concentrations of chemotherapy when compared to the parental cell lines. Similarly, FACS analysis of cell populations induced to undergo apoptosis following exposure to chemotherapeutic agents showed a dramatic shift toward early apoptosis in SPARC-transfectants (FIG. 8D) following a 12-hr exposure to chemotherapy. A smaller population of cells from the parental cell line underwent apoptosis following induction with chemotherapy only (FIG. 8C). Overall, there appeared to be at least a 2-fold increase in the population of SPARC-overexpressing cells undergoing apoptosis in comparison to the parental MIP101 cell line following exposure to various chemotherapeutic agents (FIG. 9). FIG. 10 shows the response of SPARC transfectants to chemotherapy agents.

Example 5

SPARC Sensitizing is Observed In vivo

Figure 11:
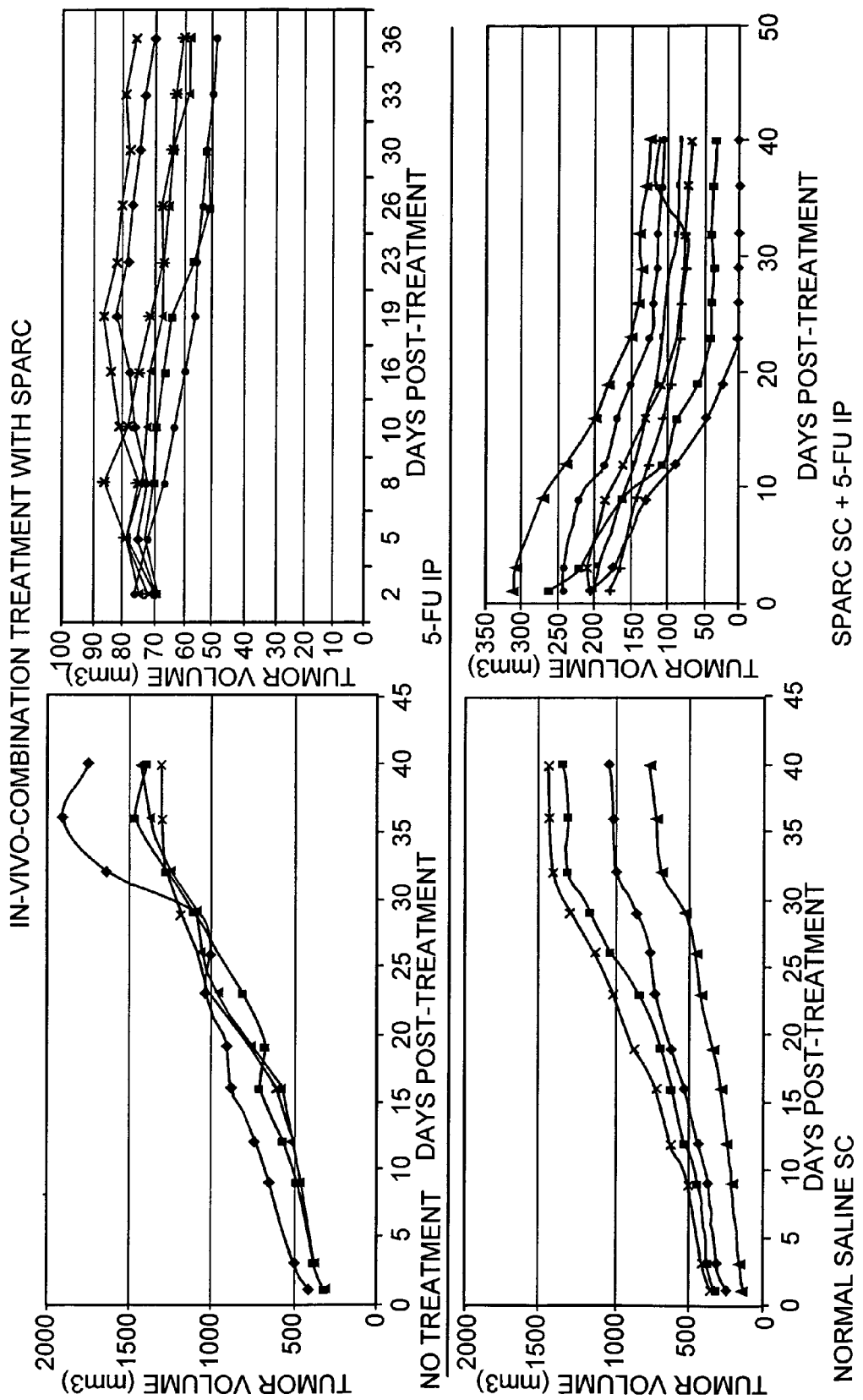
FIG. 11 is a graph presentation showing complete tumor regression in animals transplanted with SPARC-transfectants following 6 cycles of chemotherapy in two animals according to one embodiment of the invention.

The increased sensitivity to chemotherapy in vitro translated to the in-vivo model system, two of four animals showing complete tumor regression in animals transplanted with SPARC-transfectants following 6 cycles of chemotherapy (FIG. 11). The remaining animals engrafted with SPARC-transfectants had a dramatic reduction in tumor growth rate in comparison to animals engrafted with the parental MIP101. All control animals (xenografts of MIP101 treated with chemotherapy) had tumors >400 mm$^2$ by 50 days post initiation of chemotherapeutic treatment, while animals engrafted with SPARC-transfectant that did not undergo complete tumor regression, had tumors that remained <300 mm$^2$ 140 days post-initiation of chemotherapy (result not shown).

Example 6

Method of Screening for an Agent which Modulates a SPARC Polypeptide Expression

The screening of a modulator of SPARC polypeptide expression can be performed as a simple mammalian cell-based screen. A mammalian tissue culture cell line, e.g., Hela cells are first preincubated with random candidate small molecules. Cell clones are then screened using anti-SPARC western blots or ELISA. Alternatively, a RT-PCR reaction is carried out to examining the modulation on SPARC mRNA expression.

Example 7

Additional Animal Model Therapy

Various animal model therapy was carried out and the results are shown in FIG. 14.

In FIG. 14, xenograft animals with tumors engrafted with either MIP101 or MIP/SP treated with different chemotherapeutic agent (5-FU or CPT-11) show a more rapid rate of tumor regression of tumor xenografts of MIP/SP in comparison to tumor xenografts of the parental MIP101 cell line (MIP). Two of four animals carrying MIP/SP xenografts had complete tumor regression, while the remaining two had a much slower rate of tumor growth in comparison to the control animals carrying MIP 101 exposed to a similar treatment regimen. Representative animals with a tumor xenografts of MIP-SPARC treated with 2 cycles of 5-FU had complete remission by 23 days post-transplant or significantly smaller tumors following only 2 cycles of CPT-11 in comparison to an animal transplanted with a xenograft of the parental MIP101.

In FIG. 15, more animals with xenografts of MIP/SP cells showed evidence of complete tumor regression earlier in the post-radiation treatment period than animals with xenografts of control MIP/Zeo cells. By 15 weeks after radiation therapy, none of the MIP/SP xenograft animals had evidence of tumor, while 30% of MIP/Zeo xenografts continued to harbor tumors (n=10 animals/group; total dose of radiation: 100 Gy).

In FIG. 16, combination treatment with SPARC(s) (IP, intraperitoneal) and 5-FU resulted in tumor regression that was significantly greater than treatment with 5-FU alone by 51 days after initiation of treatment. (B) This combination treatment of SPARC(s) (IP) and 5-FU resulted in complete tumor regression in several animals by 84 days post-treatment, while this was not observed in animals treated with 5-FU alone. (mean±SE, n=6 animals/group).

In FIG. 17, combination treatment with SPARC(s) (SC, subcutaneous) and 5-FU resulted in tumor regression that was significantly greater than treatment with 5-FU alone throughout the treatment period. This combination treatment of SPARC(s) (SC) and 5-FU resulted in complete tumor regression in several animals by 42 days post-treatment, while this was not observed in animals treated with 5-FU alone. (mean+SE, n=6 animals/group).

In FIG. 18, animals engrafted with MIP/5FU resistant cells were treated with either 5FU alone or combination SPARC(s) and 5-FU showed that rapid tumor growth continued in animals treated with 5-FU alone, while dramatic tumor regression was observed in animals treated with the combination therapy beginning at 28 days post-treatment. Several animals receiving combination SPARC(s) and 5FU therapy showed complete tumor regression by 117 days post-treatment. (mean+SE, n=6 animals/group).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

SEQUENCE LISTING

<160> NUMBER OF SEQ ID NOS: 81

<210> SEQ ID NO 1
<211> LENGTH: 303
<212> TYPE: PRT
<213> ORGANISM: Homo sapiens

<400> SEQUENCE: 1

Met Arg Ala Trp Ile Phe Phe Leu Leu Cys Leu Ala Gly Arg Ala Leu

```
                1               5               10              15
Ala Ala Pro Gln Gln Glu Ala Leu Pro Asp Glu Thr Glu Val Val Glu
                20              25              30

Glu Thr Val Ala Glu Val Thr Glu Val Ser Val Gly Ala Asn Pro Val
                35              40              45

Gln Val Glu Val Gly Glu Phe Asp Asp Gly Ala Glu Glu Thr Glu Glu
                50              55              60

Glu Val Val Ala Glu Asn Pro Cys Gln Asn His Cys Lys His Gly
65              70              75              80

Lys Val Cys Glu Leu Asp Glu Asn Asn Thr Pro Met Cys Val Cys Gln
                85              90              95

Asp Pro Thr Ser Cys Pro Ala Pro Ile Gly Glu Phe Glu Lys Val Cys
                100             105             110

Ser Asn Asp Asn Lys Thr Phe Asp Ser Ser Cys His Phe Ala Thr
                115             120             125

Lys Cys Thr Leu Glu Gly Thr Lys Lys Gly His Lys Leu His Leu Asp
                130             135             140

Tyr Ile Gly Pro Cys Lys Tyr Ile Pro Pro Cys Leu Asp Ser Glu Leu
145             150             155             160

Thr Glu Phe Pro Leu Arg Met Arg Asp Trp Leu Lys Asn Val Leu Val
                165             170             175

Thr Leu Tyr Glu Arg Asp Glu Asp Asn Asn Leu Leu Thr Glu Lys Gln
                180             185             190

Lys Leu Arg Val Lys Lys Ile His Glu Asn Glu Lys Arg Leu Glu Ala
                195             200             205

Gly Asp His Pro Val Glu Leu Leu Ala Arg Asp Phe Glu Lys Asn Tyr
                210             215             220

Asn Met Tyr Ile Phe Pro Val His Trp Gln Phe Gly Gln Leu Asp Gln
225             230             235             240

His Pro Ile Asp Gly Tyr Leu Ser His Thr Glu Leu Ala Pro Leu Arg
                245             250             255

Ala Pro Leu Ile Pro Met Glu His Cys Thr Thr Arg Phe Phe Glu Thr
                260             265             270

Cys Asp Leu Asp Asn Asp Lys Tyr Ile Ala Leu Asp Glu Trp Ala Gly
                275             280             285

Cys Phe Gly Ile Lys Gln Lys Asp Ile Asp Lys Asp Leu Val Ile
                290             295             300
```

<210> SEQ ID NO 2
<211> LENGTH: 2133
<212> TYPE: DNA
<213> ORGANISM: Homo sapiens

<400> SEQUENCE: 2

```
cgggagagcg cgctctgcct gccgcctgcc tgcctgccac tgagggttcc cagcaccatg      60
agggcctgga tcttctttct cctttgcctg gccgggaggg ccttggcagc ccctcagcaa     120
gaagccctgc ctgatgagac agaggtggtg aagaaactg tggcagaggt gactgaggta     180
tctgtgggag ctaatcctgt ccaggtggaa gtaggagaat tgatgatgg tgcagaggaa     240 accgaagagg aggtggtggc ggaaaatccc tgccagaacc accactgcaa acacggcaag     300
gtgtgcgagc tggatgagaa caacaccccc atgtgcgtgt gccaggaccc caccagctgc     360
ccagccccca ttggcgagtt tgagaaggtg tgcagcaatg acaacaagac cttcgactct     420
tcctgccact tctttgccac aaagtgcacc ctggagggca ccaagaaggg ccacaagctc     480
```

```
cacctggact acatcgggcc ttgcaaatac atccccccdt gcctggactc tgagctgacc    540
gaattccccc tgcgcatgcg ggactggctc aagaacgtcc tggtcaccct gtatgagagg    600
gatgaggaca caaccttct gactgagaag cagaagctgc gggtgaagaa gatccatgag     660
aatgagaagc gcctggaggc aggagaccac cccgtggagc tgctggcccg ggacttcgag    720
aagaactata acatgtacat cttccctgta cactggcagt tcggccagct ggaccagcac    780
cccattgacg ggtacctctc ccacaccgag ctggctccac tgcgtgctcc cctcatcccc    840
atggagcatt gcaccacccg cttttttcgag acctgtgacc tggacaatga caagtacatc    900
gccctggatg agtgggccgg ctgcttcggc atcaagcaga aggatatcga caaggatctt    960
gtgatctaaa tccactcctt ccacagtacc ggattctctc tttaaccctc cccttcgtgt   1020
ttcccccaat gtttaaaatg tttggatggt tgttgttct gcctggagac aaggtgctaa    1080
catagattta agtgaataca ttaacggtgc taaaaatgaa aattctaacc caagacatga   1140
cattcttagc tgtaacttaa ctattaaggc cttttccaca cgcattaata gtcccatttt   1200
tctcttgcca tttgtagctt tgcccattgt cttattggca catggtgga cacggatctg    1260 ctgggctctg ccttaaacac acattgcagc ttcaactttt ctctttagtg ttctgtttga   1320
aactaatact taccgagtca gactttgtgt tcatttcatt tcagggtctt ggctgcctgt   1380
gggcttcccc aggtggcctg gaggtgggca aagggaagta acagacacac gatgttgtca   1440
aggatggttt tgggactaga ggctcagtgg tgggagagat ccctgcagaa tccaccaacc   1500
agaacgtggt ttgcctgagg ctgtaactga gagaaagatt ctgggggctgt cttatgaaaa   1560 tatagacatt ctcacataag cccagttcat caccatttcc tcctttacct ttcagtgcag   1620
tttcttttca cattaggctg ttggttcaaa cttttgggag cacggactgt cagttctctg    1680
ggaagtggtc agcgcatcct gcagggcttc tcctcctctg tcttttggag aaccagggct    1740
cttctcaggg gctctaggga ctgccaggct gtttcagcca ggaaggccaa aatcaagagt    1800
gagatgtaga aagttgtaaa atagaaaaag tggagttggt gaatcggttg ttctttcctc    1860
acatttggat gattgtcata aggtttttag catgttcctc ctttcttca ccctccccctt    1920 tgttcttcta ttaatcaaga gaaacttcaa agttaatggg atggtcggat ctcacaggct    1980
gagaactcgt tcacctccaa gcatttcatg aaaaagctgc ttcttattaa tcatacaaac    2040
tctcaccatg atgtgaagag tttcacaaat cttcaaaat aaaagtaat gacttagaaa      2100 ctgaaaaaaa aaaaaaaaaa aaaaaaaaaa aaa                                 2133
```

<210> SEQ ID NO 3
<211> LENGTH: 302
<212> TYPE: PRT
<213> ORGANISM: Mus musculus

<400> SEQUENCE: 3

```
Met Arg Ala Trp Ile Phe Phe Leu Leu Cys Leu Ala Gly Arg Ala Leu
1               5                   10                  15

Ala Ala Pro Gln Gln Thr Glu Val Ala Glu Glu Ile Val Glu Glu
            20                  25                  30

Thr Val Val Glu Glu Thr Gly Val Pro Val Gly Ala Asn Pro Val Gln
        35                  40                  45

Val Glu Met Gly Glu Phe Glu Asp Gly Ala Glu Thr Val Glu Glu
    50                  55                  60

Val Val Ala Asp Asn Pro Cys Gln Asn His His Cys Lys His Gly Lys
65                  70                  75                  80
```

Val Cys Glu Leu Asp Glu Ser Asn Thr Pro Met Cys Val Cys Gln Asp
                    85                  90                  95

Pro Thr Ser Cys Pro Ala Pro Ile Gly Glu Phe Glu Lys Val Cys Ser
                100                 105                 110

Asn Asp Asn Lys Thr Phe Asp Ser Ser Cys His Phe Phe Ala Thr Lys
            115                 120                 125

Cys Thr Leu Glu Gly Thr Lys Lys Gly His Lys Leu His Leu Asp Tyr
        130                 135                 140

Ile Gly Pro Cys Lys Tyr Ile Ala Pro Cys Leu Asp Ser Glu Leu Thr
145                 150                 155                 160

Glu Phe Pro Leu Arg Met Arg Asp Trp Leu Lys Asn Val Leu Val Thr
                165                 170                 175

Leu Tyr Glu Arg Asp Glu Gly Asn Asn Leu Leu Thr Glu Lys Gln Lys
                180                 185                 190

Leu Arg Val Lys Lys Ile His Glu Asn Glu Lys Arg Leu Glu Ala Gly
            195                 200                 205

Asp His Pro Val Glu Leu Leu Ala Arg Asp Phe Glu Lys Asn Tyr Asn
        210                 215                 220

Met Tyr Ile Phe Pro Val His Trp Gln Phe Gly Gln Leu Asp Gln His
225                 230                 235                 240

Pro Ile Asp Gly Tyr Leu Ser His Thr Glu Leu Ala Pro Leu Arg Ala
                245                 250                 255

Pro Leu Ile Pro Met Glu His Cys Thr Thr Arg Phe Phe Glu Thr Cys
                260                 265                 270

Asp Leu Asp Asn Asp Lys Tyr Ile Ala Leu Glu Glu Trp Ala Gly Cys
            275                 280                 285

Phe Gly Ile Lys Glu Gln Asp Ile Asn Lys Asp Leu Val Ile
        290                 295                 300

<210> SEQ ID NO 4
<211> LENGTH: 2079
<212> TYPE: DNA
<213> ORGANISM: Mus musculus

<400> SEQUENCE: 4
gcattcctgc agcccttcag accgccagaa ctcttctgcc gcctgcctgc ctgcctgcct     60
gcctgcctgt gccgagagtt cccagcatca tgagggcctg gatcttcttt ctcctttgcc    120
tggccgggag ggccctggca gcccctcagc agactgaagt tgctgaggag atagtggagg    180
aggaaaccgt ggtggaggag acaggggtac ctgtgggtgc aacccagtc caggtggaaa     240 tgggagaatt tgaggacggt gcagaggaaa cggtcgagga ggtggtggct gacaacccct    300
gccagaacca tcattgcaaa catggcaagg tgtgtgagct ggacgagagc aacacccca     360 tgtgtgtgtg ccaggacccc accagctgcc ctgctcccat ggcgagttt gagaaggtat     420 gcagcaatga caacaagacc ttcgactctt cctgccactt ctttgccacc aagtgcaccc    480
tggagggcac caagaagggc cacaagctcc acctggacta catcggacca tgcaaataca    540 tcgcccctg cctggattcc gagctgaccg aattccctct gcgcatgcgt gactggctca    600
aaaatgtcct ggtcaccttg tacgagagag atgagggcaa caacctcctc actgagaagc    660
agaagctgcg tgtgaagaag atccatgaga atgagaagcg cctggaggct ggagaccacc    720
ccgtggagct gttggcccga gactttgaga agaactacaa tatgtacatc ttccctgtcc    780
actggcagtt tggccagctg atcagcacc ctattgatgg gtacctgtcc cacactgagc    840

```
tggcccact  gcgtgctccc  ctcatcccca  tggaacattg  caccacacgt  ttctttgaga     900
cctgtgacct  agacaacgac  aagtacattg  ccctggagga  atgggccggc  tgctttggca     960
tcaaggagca  ggacatcaac  aaggatctgg  tgatctaagt  tcacgcctcc  tgctgcagtc    1020
ctgaactctc  tccctctgat  gtgtcacccc  tcccattacc  ccttgttta   aaatgtttgg    1080
atggttggct  gttccgcctg  gggataaggt  gctaacatag  atttaactga  atacattaac    1140
ggtgctaaaa  aaaaaaaaa   aacaaagtaa  gaaagaaact  agaacccaag  tcacagcatt    1200
ttcccacata  actctgaggc  catggcccat  ccacagcctc  ctggtcccct  gcactaccca    1260
gtgtctcact  ggctgtgttg  gaaacggagt  tgcataagct  caccgtccac  aagcacgaga    1320
tatctctagc  tttcatttca  attttgcatt  tgactcttaa  cactcaccca  gactctgtgc    1380
ttatttcatt  ttgggggatg  tgggcttttt  ccctggtgg   tttggagtta  ggcagaggga    1440
agttacagac  acaggtacaa  aatttgggta  aagatactgt  gagacctgag  acccaccag     1500
tcagaaccca  catggcaagt  cttagtagcc  taggtcaagg  aaagacagaa  taatccagag    1560
ctgtggcaca  catgacagac  tcccagcagc  ccgggacctt  gctgtcttct  cgactcttcg    1620
ggcgtttctt  tccatgtttg  gctgttggtt  ttagttttgg  tgagccatgg  gtgggccaga    1680
acatcactca  actgcaattg  ggctttcagg  ttcttgccgg  gagctctagg  cactgggagg    1740
ctgtttcagg  aaagtgagac  tcaagaggaa  gacagaaaag  gttgtaacgt  agaggaagtg    1800
agactggtga  attggtttga  ttttttttcac  atctagatgg  ctgtcataaa  gtttctagca    1860
tgttccccct  cacctctccc  cacccctgc   cacttgaaac  cttctactaa  tcaagagaaa    1920
cttccaagcc  aacggaatgg  tcagatctca  caggctgaga  aattgttccc  ctccaagcat    1980
ttcatgaaaa  agctgcttct  cattaaccat  gcaaactctc  acagcgatgt  gaagagcttg    2040
acaagtcttt  caaataaaa   agtaacaact  tagaaacgg                             2079
```

<210> SEQ ID NO 5
<211> LENGTH: 345
<212> TYPE: PRT
<213> ORGANISM: Homo sapiens

<400> SEQUENCE: 5

```
Met Leu Pro Cys Phe Gln Leu Leu Arg Ile Gly Gly Arg Gly Gly
1               5                   10                  15

Asp Leu Tyr Thr Phe His Pro Pro Ala Gly Ala Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
    50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160
```

-continued

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255

Val Asp Lys Ala Pro Leu Thr Pro Thr Gly Asn Arg Arg Gly Arg Pro
                260                 265                 270

Arg Lys Tyr Pro Val Ser Ala Pro Met Ala Pro Pro Ala Val Gly Gly
            275                 280                 285

Gly Glu Pro Cys Ala Ala Pro Cys Cys Cys Leu Pro Gln Glu Glu Thr
    290                 295                 300

Val Ala Trp Val Gln Cys Asp Gly Cys Asp Val Trp Phe His Val Ala
305                 310                 315                 320

Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 6
<211> LENGTH: 265
<212> TYPE: PRT
<213> ORGANISM: Homo sapiens

<400> SEQUENCE: 6

Met His Phe Tyr Arg Leu Phe Leu Gly Ala Thr Arg Arg Phe Leu Asn
1               5                   10                  15

Pro Glu Trp Lys Gly Glu Ile Asp Asn Trp Cys Val Tyr Val Leu Thr
            20                  25                  30

Ser Leu Leu Pro Phe Lys Ile Gln Ser Gln Asp Ile Lys Ala Leu Gln
        35                  40                  45

Lys Glu Leu Glu Gln Phe Ala Lys Leu Leu Gln Lys Arg Ile Thr
    50                  55                  60

Leu Gly Tyr Thr Gln Ala Asp Val Gly Leu Thr Leu Gly Val Leu Phe
65              70                  75                  80

Gly Lys Val Phe Ser Gln Thr Thr Ile Cys Arg Phe Glu Ala Leu Gln
                85                  90                  95

Leu Ser Phe Lys Asn Met Cys Lys Leu Arg Pro Leu Leu Gln Lys Trp
            100                 105                 110

Val Glu Glu Ala Asp Asn Asn Glu Asn Leu Gln Glu Ile Cys Lys Ala
        115                 120                 125

Glu Thr Leu Val Gln Ala Arg Lys Arg Lys Arg Thr Ser Ile Glu Asn
    130                 135                 140

Arg Val Arg Gly Asn Leu Glu Asn Leu Phe Leu Gln Cys Pro Lys Pro
145                 150                 155                 160

Thr Leu Gln Gln Ile Ser His Ile Ala Gln Gln Leu Gly Leu Glu Lys
                165                 170                 175

Asp Val Val Arg Val Trp Phe Cys Asn Arg Arg Gln Lys Gly Lys Arg

```
                180              185              190
Ser Ser Ser Asp Tyr Ala Gln Arg Glu Asp Phe Glu Ala Ala Gly Ser
        195                      200                      205

Pro Phe Ser Gly Gly Pro Val Ser Phe Pro Leu Ala Pro Gly Pro His
    210                      215                      220

Phe Gly Thr Pro Gly Tyr Gly Ser Pro His Phe Thr Ala Leu Tyr Ser
225                      230                      235                      240

Ser Val Pro Phe Pro Glu Gly Glu Ala Phe Pro Pro Val Ser Val Thr
                    245                      250                      255

Thr Leu Gly Ser Pro Met His Ser Asn
            260                      265

<210> SEQ ID NO 7
<211> LENGTH: 14468
<212> TYPE: DNA
<213> ORGANISM: Homo sapiens

<400> SEQUENCE: 7
tctaaggctg ttctgatctc ttcatctgtc ccttcacctg gcccctgtac ccccttcccc      60
tttggacccc ttgaaccctc ccaggacccc cgctcagccc cttcccgccc ccaaccgact     120
cttcccgaac gtcccttacc aaccgcgaga gcccccctact gcgctttggc cacaccccct    180
acgcctcgct cccggccccg cctctgcccc tgaccgcgcc tgcgcaaggc gggcgcccta    240
aagtcctatt tcactctgtt gggaggaggg ggaaaggtgt acgcaggcgc agtggcgtct    300
aaatttgggc ccactaaatg cgtcggagca tctccgcgcc caggcggctc ctcctcactg    360
cggcaacccg ggaaaacttg tgaactaatc agaaaaagtg aaggcgggga gatcttgggg    420
cgctgtccaa tggcgcggaa gagaacaaat gagctggcca atcgggaacg gcacgggggc    480
gggctcgctc ggcgcgaagt cgggcccgg gaattccgaa ggaggggtag gcgctgcccg     540
cgcgcagagg ccgcgcccct cctggcccccg gcttcttggc tgtcaaacag atgcagcaac    600
gtcggctcct gccgaggagc ccaaggggtc ccgggatccg ccgcacaggc tggcactgct    660
tgaagaggag gctactcgga gactgcgccg gcgggtaga tccgaaacgg ggctggggcg    720
gagtgggaaa aggccgggta tgccttgcat gatcgcgggg agctccttcc tgtttttatc    780
ccacctagag aagccgggaa gtaggggttt aggtccaatt tgttggagta cttaaggact    840
cgtttgcact ttcttttggg ggatgacagt ggattcattg ccctcggagg ttcaaccagt    900
tatgagtgag ggattggcca aagatcgggg gcgcaggcaa gcaggagtgc tctattagga    960
taagcaagtt tgacaggaag aagctgctct tctccgaatt acacagaggt gatgtgttcg   1020
tattgcacgt agacgtgtgt ataacaggac ctccttcccc gcgccccgcc accccgacac   1080
acacaggagc tgcctaaagt atccttgcct tgcagattgg aggctcccca aatattttgt   1140
gatctgagga tccagctcaa gtgaggtgcc ataggacgtg ttcctgagtt tgcattgcac   1200
ggagaccttc ctggaatttt tcatttgcaa gtcggcttaa ccaattttgc attgagtcct   1260
aggctgcttg cactctgaat ttgggctatt caggtagtgt gctcaaagtt gaaaccgcat   1320
acagcacaac tcaagtttgc atcagactgg gaagcgaact taagccagcg gtgcgtggcc   1380
caggagtggg aaaggaaatg gatgcctgaa gtggaagagg tggtgcagag ggggcaccgc   1440
ccatgctgcc ctgcttccaa ctgctgcgca taggggcgg caggggcggt gatctctaca   1500
ccttccaccc cccgccgggg gctggctgca cctatcgctt gggccacagg gccgacctgt   1560
gtgatgtggc cctgcggccc cagcaggagc ctggcctcat ctctgggatc cacgccgaac   1620
```

```
tgcatgccga gccccggggt gatgactgga gggtcagcct ggaagaccac agcagccaag    1680
gtgagcatta agcagggcag ctttgccoct gggtggttga agcgccaggc tggaatgagt    1740
aaggtctcca caagaccctg ctgcctgcct cccatactcc catcagattg gatggatagt    1800
cgtggtccag accttcatct tcccaccaga agtgtgcaca gtcagaagct ctctgccaga    1860
ctgacccttt ttggtccgt ttagctcata caggacctgg gatatcatca gaaagatatc     1920
acagtgggga tgttctgagg ccactagagg ccaagtttag acttgattca gtttccagct    1980
ttgctgaggc actctgttcc tgggttaggg cagttctatg ttgaataatg ttttaataa     2040 tctgggcatg tctttctccg tgacttgagg cagttagcct cagaaagcct agattcacat    2100
ttgagttttg ccactgcctc ttggtaaagt cagctgtagg agtgttatgg ttattagact    2160
atagtagcca acattcatct agtgcttact gttatgagcc aggccctatt ttaagtgtat    2220
tgaatgtagg tggtactaat attatcctca tttacagtaa aggaaaatga ggcacaaaga    2280
ggttaaggaa cttgtccagg gctgggcatg gtggtttaca cctataatcc agcactttgg    2340
gaggctaagg cagggtggat cacttgagct caggagttcg agaccagcct gggcaacatg    2400
gtgaaaacct gtctctacca aaaaattaat taattttta aaaaagcct gggcgcggtg      2460 gctcacgcct gtaatcccag cactttggga ggccgagatg ggcagatcac gaggtcagga    2520
gttcgagacc atcctgacca acatgttgaa accccatctg tgctgaaaaa aaaatacaaa    2580
aattagccag gtgtggtggc gtgcacctgt aaccccagct actcaggagg ctgaagcagc    2640
agaatcactt gaacccggga ggcggaggtt gcagtgagct gagatcgcac cactgcactc    2700
cagcttgggc gacagagcga gactccatct caaacaaaca aacaaccaa aagcttgccc     2760 agggtcacat aactggtaag tggtagagct aggatctgaa cgagctggag ctgggggaga    2820
gtgagcatgt ttgaaaactg gaccttaggg cggggcacgg tggctcacgc ctgtaatccc    2880
agcactttgg gaggctgagg cgggcagatc aggaggtcag gagtatgaga ccagcctggc    2940
caacatggta aaaccctgtc tctgctaaaa ataaaaaaat tagccagacg tggtggcaca    3000
tgcctgtaat cccagctact caggaggctg aggcaggaga attgcttgaa cctgggaggc    3060
ggttcaagct tgggcaatag agcaaaactc catctcaaaa aaaaaaaag aaagaaaaaa     3120 aaagaagaaa gaaagaaaat tggaccttag gacagtgagg gcagggatcc tttgtaggaa    3180
agcacaagaa acacagactt gttcctagct gacaaggagt gtactgcctg gtacctgtca    3240
cctgctgagg ggcttaggat gtgagggaga atctgactac agtttcatat tcttccccag    3300
aaatcataca gatttctcca ctcctgactc tggtcatttc tgttttttgtc ctccatattt    3360 gcctggtgcc ccaccatcaa caggtacttt ggtcaataat gtccgactcc caagaggtca    3420
caggctggaa ttgagtgatg gagacctcct gacctttggc cctgaaggc ccccaggaac     3480 cagcccctcg gagttctact tcatgttcca acaagtacga gtcaagcctc aggactttgc    3540
tgccattacc atcccacggt ctaggggaga agcccgggtt ggggctggtt tccggcctat    3600
gctgccctcc caggggctc cacagcggcc tctcagcacc ttctcccctg cccccaaggc     3660
cacactgatc ctaaactcca taggcagcct cagcaagctc cggccccagc ccctcacctt    3720
ctcccctagt tggggtggac caaagagcct gcctgttccc gccccacctg ggaagtggg     3780 gaccacgcct tctgctccac cccaacgcaa tcggaggaaa tctgttcacc gagtgttggc    3840
ggaactggat gatgagagtg agcctcctga gaacccgcca ccggtcctta tggagcccag    3900
gaagaaactc cgtgtagaca aagcccccact gactcccact gggtaagtgg agtcctcact    3960
tggccctctc agtgttttac tgcttttcga ttccttgtat ccctaggctg tgaggaggtc    4020
```

```
cccctgcctg gggggatggg cacgggaggt ggaatagatg gaatggcaag acctgggtta      4080
gctctgatag gaaaagaaaa atatgtgcag gagaacatga gaggtgggt gggcagtgc        4140 ttataaaaca accggagtga gcatgtcctg cttttacat tcatatggct ttaaccccat       4200
tcttctagtg cctaaggatg gggaactttc aggctcacac tagaggtttt taggcccacc     4260
ctatgtgttt ttaaggacag agtccaggct caccttagtt ctcagaccac tgtgcctctg     4320
tggcctcacc ctatgaccag ccatagggtg gcaaggtcta ggccttctcc tacaggtttc     4380
cggtgaccct tgtgtctgtg tcacttcctt cagaaatcga cgtggccgtc ctcggaagta     4440
cccagtgagc gctcccatgg ctcccctgc agttgggggc gggagccct gtgcagctcc       4500 ttgttgctgc ctgccccagg aagagacagt ggcctgggtt cagtgtgatg gctgtgacgt     4560
ctggttccat gtggcctgtg ttggctgcag catccaggct gccagggagg ccgacttccg     4620
atgcccaggg tgccgggctg gcattcagac ctaaggtcca ccgccaaggc accatcggac     4680
acacctgccc atgagtagac acagcagcga gcaaataggt ctgataaata cccccccttcc   4740 cttccctccc caagagggaa tgactacagg gaagaaggat ggattgatgt ggactcattc     4800
agggcctgga gcagaccctg gtggccaaga cagaagagat ggtttcctgc caaagatatt     4860
gccacctcca ggaaattgcc agtgagctgg aagttcccac tattacaagc cataaggcca     4920
tgttgccatg gacaccagaa tatctgtagt cagagcacct atcagttgca aaagccatgc     4980
ctgcaaccga tggaaaatgt aagagggagt tcttaaggtt cttggtggca tcacccaagg    5040
cattctggga aaacctaggg cctggcccca aaacttccct actctgtggc tagtcctgct     5100
gccaacaaaa tcgtagcgac ctggcttttc acagctttgc ttttatttcc aagtcaagga    5160
caagccgctt cattcactcc tgggcattta ctcttcttgt gggtctgtga tattccttgc    5220
tttccaggga gaatgtgctt ggcaaggtct ggagaactaa ttcagaatct taggggaagg   5280
ggagagatgg aaatacaaac ctgcttactg gaaaggtgca aatatatggg ttgagctgga   5340
ggtaggaata caggtaatta aggttttctag tttaagggaa aacagatcta ttgccattta   5400
aataaggtaa ctgggatttg gttaagttca caaagatagc agaagattta tttacaggct    5460
tcacctgtac tgtcagggca agagaaagcc tggtaaacca gctacagcag tttaccagtg   5520
tgatggctgt gacacagctc cactccacgg gtggacacag cagagggcaa ctgggctggc    5580
ctggttcagt gtgaatcaaa ccgcttaacc cacacatggt acatgtgatt ttcttttgtg   5640
agccttacac caagccaaac tattgtcaaa gcatcatttc tatagaaata aagccttatc   5700
ttgacctgtt ctattaaaac ctgccacatc cgcccttttcc tacctagatt taatgagccc  5760
aagttttttt acatggaaga aatgactctg ggcaaagac ccctaatgaa ctagtggcag     5820
agccaggaat aaaacttgag taactaatga gtcacttatg ggcagagtat gcaaaaacct   5880
taagtggaaa ccaaatagac cctggtatca agaaagcaca aagtattaat agaagtttct   5940
ggttggggtg atctaggttc aacagaaata agatgatttc taagtataaa gccatttaag  6000
aattccagag tagggtggga aagcaaaaag ccagctctga acaggtaaca gctacatggt  6060
gactgagtct atgggcaaaa gttcttgcat cacaggcttt tgggaactag cctatcacag   6120
ggccctgtac aaataaactt ggctgcaatc ccagctctcc ctctgatgtt gtgtgacctt    6180
aaggagtgta aatggcacct tagtttcagg gtcacttggg tatgagcatt ggatattccc   6240
atccccacct cagtaactga aggacaaacc aagataagtg tgtctatcta ctgtgtccca   6300
agcttcttta tttaagaaaa aagtgataca tgatgtggga ttaaaatcaa gagcatcatt  6360
```

```
gaacttcacc ttccctccaa ccagttgccc caaactcccc tgcccccacc ctttgtgttc    6420
ccaattcctt ccttagtgaa tgaagaactt aatcccaaaa accctggcac aaactccagg    6480
ttttctttcc ctagctcctc ccctccccct gtcccccatt cctagaaggg caggcacctc    6540
agtttgaatg catgggagag cccagagtgg tgacagagac aggggaaag gcttccccct     6600 cagggaaagg gaccgaggag tacagtgcag tgaagtgagg gctcccatag cctgggtac    6660 caaaatgggg ccctggggcc agaggaaagg acactggtcc ccctgagaaa ggagacccag    6720
cagcctcaaa atcctctcgt tgtgcatagt cgctgcttga tcgcttgccc ttctggcgcc    6780
ggttacagaa ccacactcgg accacctgcc agtgaatgac agaaaggaga atgacattag    6840
acaatgagct gagagacggg cctgactctg cttggacatt ctatccaaag ccaacagccc    6900
tagagcagtt agaggaggac attagagaat gagctgagac aggcctgact gcttggacat    6960
tctgtccaaa gccaacagcc ctagagcagt tggaggagcc agagctaggg aaagcgaggt    7020
ggtgacaggg gaaagagatg gagcccgcag agagacatgg cactcacatc cttctcgagc    7080
ccaagctgct gggcgatgtg gctgatctgc tgcagtgtgg gtttcgggca ctgcaggaac    7140
aaattctcca ggttgcctct cactcggttc tcgatactgg ttcgctttct ctttcgggcc    7200
tgcacgaggg tttctgcttt gcatatctgt gcaggtggga aggggtgac aagggcaagc     7260 tttggacttg ctgagtaaca gcatcacagg ggtctgtgac tagatgtgtc agcagagcca    7320
ggtggtggtg tgaaaaggca ggatcctgga agggttggct ctggaccttaa tcccagcaga   7380 actgaggaat ttcactccat cccactgaga accactgcac caaagacgga gagctacgag    7440
ccagtgatgg aagcaatgga aattaggcca agaaagggaa ggtccccggg tatccccctc    7500
ccacccttac ctcctgaaga ttttcattgt tgtcagcttc ctccacccac ttctgcagca    7560
agggccgcag cttacacatg ttcttgaagc taagctgcag agcctcaaag cggcagatgg    7620
tcgtttggct gaataccttc cctgggggag gccagtcaaa agagaagcaa aatgagggag    7680
cacgcagggc ccttgtgacc ctgagatcca agcttaccac ctcttcccag agggagctca    7740
aagcccaagc atcttctccc tctccctact cctcttcatg ggtgagggta gagtctgccc    7800
ctgcccctcc ccactaggtt cagggatact ccttagaggg gagatgcggt cagaatctgc    7860
agaggggaac ccaccaaata gaaccccag ggtgagcccc acatcggcct gtgtatatcc      7920
cagggtgatc ctcttctgct tcaggagctt ggcaaattgc tcgagttctt tctgcagagc    7980
tttgatgtcc tgggactgga ttttaaaagg cagaagactt gtaagaacat aaacacacca    8040
gttatcaatc tccccttcc attcgggatt caagaaccta cgtgtggccc caaggaatag     8100
tctgtagaag tgcatctgcc ttccaagctg cccacctaac ttctagaaat aacctaccca    8160
caaatgtcat tcacccattc cctgttcact gactcatgca tgtaacaaag gactactctt    8220
cccccagaaa ctggcacatc caagggatgc agagcatggt gaaaggacag aaagagagac    8280
cctggcctcg aggagaacac ctgtcaggtt atgaaggtta gaagttcttt gctgggcgcg    8340
gtggctcatg cctataattc cagcactttg ggaggccgag gtgggcagat cacgaggtca    8400
ggagttcaag accagcatgg ccaacatggt gaaaccccgt ctctactaaa aacacaaaaa    8460
ttagctgggc acggtggcac gcacctgtaa tcccagctac tcaggaggct gaggcaggag    8520
aatcacttga acccgggagg cggaggttgc agtgagctga gatcacgcca ctgcactcca    8580
gcctgggtga cagagcaaga ctctgtctca agaaaaaaa aaagaagat agttcattta     8640 atacctgcaa aattctctca ctcaagtatc acccccagtt taaggatgtt ttgagattag    8700
agaaatagat aagctgctaa gttctgggtt aattaaaaag gaagagcatc atgtctcaga    8760
```

```
agctaaattc agtatatact ctccccagct tgctttgagg gtcccacaaa ctataacatg   8820
gcatgcatac acacaaacac agcaaaaaag taacaggtgt cataagaatg gataaagtgc   8880
tttgtgtgta cttactcctc attttttaaa ttgattatcc ctcatcttta ctgtatcttt   8940
ttcactatag aggcatccta attgatttt aaattcaaga gatttatcga gccttcta     9000 taagccagcg gctatacaaa gtggacaaag agccctgaca tccagcatga cagaagtgct   9060
attcggcact tgttcttcaa gttgcccact tggatctctt ccaagtgcac tttccttttt   9120
tccctgccct ataactttt aataataaac ttccactcct gctctgaaaa ataaaaaagt    9180
aaataaaata aaaaatggcc aggcacagtg gctcatgtct gtaaatccta gcactttggg   9240
aggccaaggt gggcagactg cttgagccca agagttagaa agcagcctgg gtaacatagt   9300
gagacccgtg ccgccccttc tcccacccct gctgcctcta tttaaaaaat atatatatat   9360
tatgaaaaaa agcaaagcag tccgggcgca gtggtcatgc ctgtaatccc ttcactttgg   9420
gaggccaagg tgggtagatc acttgaggtc aggagttcaa gactagcctg gtcaacatag   9480
tgagactctg tctctactaa aaatacaaaa attagctggg catcatggcg ctcccctata   9540
atcccagcta ctcaggaggc tggggcagga gaattgcttg aacctaggag gtggagtttg   9600
cagtgagcca agatcgcacc actgcactcc agcctgaggg acagagtgag actccatctc   9660
aaaaattaaa aaaaaataa agcagtctat aggagtaggg taaaggaggg aaggagatta   9720
tggaggaggg tgacacttt aaagacagag aaggtgattg tttgagcaaa ggacaagagt    9780
ctaatgtggc aaggccctga agtgggcctt ccagagccca aagctggtct ggtggctagg   9840
tagatcctgt tgcagacata gtgactttgt tttagtccaa gtgaaatgat ctctcaccct   9900
ttttctcccc ccccaagacg gaatctcgtt ctatcgccca ggctggagtg ctgtggcgtg   9960
atcttggctc actgcaatct ccgccttctg ggttcaagct attctgcctc agccgcctga   10020
gtagctggga ctacaggcac ccaccaccat gcccggctaa ttttttgtatt tttagtagat   10080 atggggtttc accatgttgg ccaggctggt caggagacct caagtgatct gtccaccttg   10140
gcttcccaaa gtgctgggat tacaggtgtg aaccaccgca cctagcctca cctttttttt    10200
tttttttttg agagtttcgc ttttgttgcc taggctggag tgcactggcg cgatctcggc   10260
tcaccgcaac ctacatctcc caggttcaag cgattctcct gcctcagctt cctgagtagc   10320
tgagattaca ggcatgcgtc accacgccca gctaattttg tattttagt agagatgggg    10380 tttcgccatg ttggtcaggc tggactcgaa ctcccaacct caggtgattc gcctgcctcg   10440
gcctcccaaa gtgcctggcc acccttttta aaacactgac tctagttgac gtgttggcca   10500
cagacagtag ggaggaagca gtataatttg agaagctact gcggtaatcc cagcagagat   10560
gatggtggct gaggccaggg ttaggttgtg attgattcag gatgtttctt aaggatagga   10620
tgtaggacgt gaaagaaact gaggatgact gggtttggcc ttgagcaact gggtgatcag   10680
ggtggagcag ttcagggagc catcacaaga gacagaaaac gcggtagtca tctggtgtct   10740
aaatggcatt taagccttga gggtgggtga gaggaaggaa gggtagatag agcagaggtt   10800
gaaggactga gccctggggc atgccatatg aggctgccgg cggacagagg tgcacagcta   10860
gtgagaaaaa aacaaggcct ttttgtagtc ctgaagcctc aaggaagtgt tcaatggtg    10920 cttgatcata tcaatttcaa ataggctgtt ttcatcccca acttctgctc agccaataac   10980
tcaaactgat aaatgccctc tgctatcctg gattttccaa attctgtttt ggggttttgg   11040
aataaacact ggtccaaatc ctcgcttcat catttagcag ttaaaacccg ttaaatagga   11100
```

```
taataatacc tccccctagg agattttgtg ctggttaatg agataatgat gtataaacgg    11160
agcacacagc caggcactta ggaagtggac cacaattgcc agccattatc attcaaggct    11220
cagcagtgac ctcctgcgaa gaggttgggg cttctcggtc actccagaaa ccagtcacac    11280
ctttctgtga ggtctcaagg cttagtattt aatctctaat tgcttacact tgtcgccttg    11340
gaggactgga agatacatct ttaatagtcc tcagcagggc tggatgcctt caatcccgca    11400
gcagctctat atttgcaaat ggcctggaga aatctctcac cattttcttt gtttacaact    11460
ttggaactga ggctgaagtc aatcaaaatc cagctttcta caaggggtgc cagggtgtgc    11520
accttaacac agtggccagt cattggcctg aggcagagat ccggggaaga caagccctat    11580
acttgactgg aggtaaaccc agctcacaac gcgcacacac acagcccaaa caggagatcc    11640
tatcagaaac gagtcacacc ctagactttc aggaacaata atcctggaat gagcactgtt    11700
tttaccctca ggctatgctt aaccctaagg ccaaaatctt gggtctgata agggtcaaat    11760
tttcaagcag gactaagggt gggaaaaggg gctcaaacca accccaagct gggtctggtg    11820
ctgggccagt aatgagtgac cagaccctgg gcaggcctag gagatgtgag agaccctgac    11880
aagggctggg ccagacagag caaaggccag cctgggccag cttccgactc tcccaggccg    11940
ctctgccctc acctgcagtt gtctcttcga aatccagctt ccagttccca cctggcccct    12000
gcctgccagg gctgcctgca gttgatacac accccctccct ggccagggca gctgaccctg    12060
cctgctcctc tcctgggtgc caggtctggg cagctgcagg tgaccacttc cccatcaggc    12120
tgccctgtca tgaccacctc cccacacccc aaccccgtcg aagctcactt gcctcctccg    12180
ggttttgctc cagcttctcc ttctccagct tcacggcacc aggggtgacg gtgcagggct    12240
ccggggaggc cccatcggag ttgctctcca ccccgactcc tgcttcgccc tcaggctgag    12300
aggtctccaa gccgccttgg ggcactagcc ccactccaac ctggggccca cagtacgcca    12360 tcccccaca gaactcatac ggcgggggc atggggaat cccccacacc tcagagcctg       12420
gcccaacccc cggcccgatt cctggccctc caggagggcc ttggaagctt agccaggtcc    12480
gaggatcaac ccagcccggc tccggccccc ctggcccatc acctccacca cctggagggg    12540
gcgagaaggc aaaatctgaa gccaggtgtc ccgccatggg gaaggaaggc gccccaagcc    12600
gggggcctgg tgaaatgagg gcttgcgaag ggactactca accctctct ccctccccag     12660 tcccacccac tagccttgac ctctggcccc gcccctgga tgggtggagg agagggaggt     12720 gggggagaa actgaggcga aggatgtttg cctaatggtg gtggcaatgg tgtctgtgga     12780
aggggaaaac cgggagacac aactggcgcc cctccaggac ctcagtgcag gtcccccaca    12840
gaaacttttt ttattttat tttttaagac agggtctcac tttgttgccc agactggagt     12900
gcagtggagt acaatgatgg ctcaatgtag cctcgatcta ctgggccaaa gcaatccttc    12960
tgctccagcc tcctaagtgg ctgggactac aggcttggac cactgtgccc tgttagtttt    13020
tttattttta gtagagatgg ggccttgcta tgttacccag gctggtcttg aattcctgtc    13080
ctcaagaaat cctcccgcct ctgccgccca gtgtcatgat taaaggcgtg agccaccaca    13140
cccaactttc aactcccaac ccgctccctg gcactctctc aggctctgca catcccagct    13200
gtctggaatc actcccacac ctccatgttc ttcaggaacc caggtgcttg acccccctctc   13260 cacagacctc tggcactgtg ccttcagggg ccagtcaccc tctcagctcc tcaaatttat    13320
tgaatgtgtg tgtggcgcta tccctcaatg catcaacagc cataagcaca atggccagct    13380
gctcccttat gccttccccc gatccatcca gaatcctagg cattcccatc ccgatactgg    13440
ccaaatccag ccaccccgca gcctgggtgc ctggcaccat ctgcccagcc tgccaaattt    13500
```

```
cacccccatct tcaagagtag actgccagac aaggcctccg tgctatatcc ccccaccccc   13560
catcccccca ccctccgtc ttccagaatc agactccaga ctctcctcat ctaacagact    13620
aaggggttgg ccctacttc ccttcaagg gaccagactt tggactgatt gggcctcagt     13680
ttcccaacct ttgctgaaac agagtgataa acacccgct ttgggcccc tccactatgg     13740 aacctgcaca tcaggttcct tgctcccctc tcaaccaaaa ctcagacatc taataccacg   13800
gtaggccccg ttctccctcc cccacctccc tggcccaggc ctccagccct aggccctggg   13860
tggggaaaac caggggtgg ggggtgtgga gaaaaatat ctgacttcag gttcaaagaa     13920
gcctgggagg gactggggga aggggcagg acaatggcct tggctggaca atcccggtcc    13980
ccagaggggg cagctctaac cctaaacaag tgctcaaccc ttgaatgggc ctggatggct   14040
cccctgggga ctgcttcctg ctccccaacc ccccagtccc aatcccctca cacagaatcc   14100
ccttcagaga cgctaaaagg agctccagca acccccctct gcaatcccct caaagactga   14160
gcctcagacg ggcaccaagg gccccctaca gggacctagg tatctagttc ctccttcctc   14220
tgggggactc aggcgtccag cttcatcgtg catccctccc cgagcccgga agattgaggg   14280
atgtgctttg tttagtgggg ctggctggca gaaagacgca gaggaggtgg cgagtgattt   14340
gtggagcggt gcaggaaggc tgccctaagc tcccccttcag ggtctgtttt tctgggcctg  14400
gcctgagtat cctgaggctc atgctgctgg tctagtgctt gattctgttt gcaagagaat   14460
agccaacg                                                              14468

<210> SEQ ID NO 8
<211> LENGTH: 345
<212> TYPE: PRT
<213> ORGANISM: Homo sapiens

<400> SEQUENCE: 8

Met Leu Pro Cys Phe Gln Leu Leu Arg Ile Gly Gly Arg Gly Gly
1               5                   10                  15

Asp Leu Tyr Thr Phe His Pro Ala Gly Ala Gly Cys Thr Tyr Arg
                20                  25                  30

Leu Gly His Arg Ala Asp Leu Cys Asp Val Ala Leu Arg Pro Gln Gln
            35                  40                  45

Glu Pro Gly Leu Ile Ser Gly Ile His Ala Glu Leu His Ala Glu Pro
        50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190
```

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Leu Glu Asn Pro Pro Pro Val Leu Met Glu Pro Arg Lys Lys Leu Arg
                245                 250                 255

Val Asp Lys Ala Pro Leu Thr Pro Thr Gly Asn Arg Arg Gly Arg Pro
            260                 265                 270

Arg Lys Tyr Pro Val Ser Ala Pro Met Ala Pro Pro Ala Val Gly Gly
        275                 280                 285

Gly Glu Pro Cys Ala Ala Pro Cys Cys Cys Leu Pro Gln Glu Glu Thr
    290                 295                 300

Val Ala Trp Val Gln Cys Asp Gly Cys Asp Val Trp Phe His Val Ala
305                 310                 315                 320

Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 9
<211> LENGTH: 3021
<212> TYPE: DNA
<213> ORGANISM: Homo sapiens

<400> SEQUENCE: 9
tcgtctcctg ccgaggagcc caagggggtcc cgggatccgc cgcacaggct ggcactgctt    60
gaagaggagg ctactcggag actgcgccgc gcggattgga ggctccccaa atattttgcg   120
atctgaggat ccagctcaag tgaggtgcca taggacgtgt tcctgagttt gcattgcacg   180
gagaccttcc tggaattttt catttgcaag tcggcttaac caattttgca ttgagtccta   240
ggctgcttgc actctgaatt tgggctattc aggtagtgtg ctcaaagttg aaaccgcata   300
cagcacaact caagtttgca tcagactggg aagcgaactt aagccagcgg tgcgtggccc   360
aggagtggga aaggaaatgg atgcctgaag tggaagaggt ggtgcagagg gggcaccgcc   420
catgctgccc tgcttccaac tgctgcgcat aggggcggc aggggcggtg atctctacac   480
cttccacccc cccgccgggg ctggctgcac ctatcgcttg gccacaggg ccgacctgtg   540 tgatgtggcc ctgcggcccc agcaggagcc tggcctcatc tctgggatcc acgccgaact   600
gcatgccgag ccccgggggtg atgactggag ggtcagcctg aagaccaca gcagccaagg   660 tactttggtc aataatgtcc gactcccaag aggtcacagg ctggaattga gtgatggaga   720
cctcctgacc tttggccctg aagggccccc aggaaccagc ccctcggagt tctacttcat   780
gttccaacaa gtacgagtca agcctcagga ctttgctgcc attaccatcc acggtctag   840 gggagaagcc cgggttgggg ctggtttccg gcctatgctg ccctcccagg gggctccaca   900
gcggcctctc agcaccttct cccctgcccc caaggccaca ctgatcctaa actccatagg   960
cagcctcagc aagctccggc cccagcccct caccttctcc cctagttggg gtggaccaaa  1020
gagcctgcct gttccgccc cacctgggga agtggggacc acgccttctg ctccacccca  1080
acgcaatcgg aggaaatctg ttcaccgagt gttggcggaa ctggatgatg agagtgagcc  1140
tcttgagaac ccgccaccgg tcctatgga gcccaggaag aaactccgtg tagacaaagc  1200
cccactgact cccactggaa atcgacgtgg ccgtcctcgg aagtacccag tgagcgctcc  1260

-continued

```
catggctccc cctgcagttg ggggcgggga gccctgtgca gctccttgtt gctgcctgcc    1320
ccaggaagag acagtggcct gggttcagtg tgatggctgt gacgtctggt ccatgtggc    1380 ctgtgttggc tgcagcatcc aggctgccag ggaggccgac ttccgatgcc agggtgccg    1440 ggctggcatt cagacctaag gtccaccgcc aaggcaccat cggacacacc tgcccatgag    1500
tagacacagc agcgagcaaa taggtctgat aaataccccc cttcccttcc ctccccagga    1560
gggaatgact acagggaaga aggatggatt gatgtggact cattcagggc tggagcaga    1620 ccctggtggc caagacagaa gagatggttt cctgccaaag atattgccac ctccaggaaa    1680
ttgccagtga gctggaagtt cccactatta caagccataa ggccatgttg ccatggacac    1740
cagaatatct gtagtcagag cacctatcag ttgcaaaagc catgcctgca accgatggaa    1800
aatgtaagag ggagttctta aggttcttga tggcatcacc caaggcattc tgggaaaacc    1860
tagggcctgg ccccaaaact tccctactct gtggctagtc ctgctgccaa caaaatcgta    1920
gcgacctggc ttttcacagc tttgctttta tttccaagtc aaggacaagc cgcttcattc    1980
actcctgggc atttactctt cttgtgggtc tgtgatattc cttgctttcc agggagaatg    2040
tgcttggcaa ggtctggaga actaattcag aatcttaggg gaaggggaga gatggaaata    2100
caaacctgct tactgaaaag gtgcaaatat atgggttgag ctggaggtag gaatacaggt    2160
aattaaggtt tctggtttaa gggaaaacag atctattgcc atttaaataa ggtaactggg    2220
atttggttaa gttcacaaag ttagcagaag atttatttac aggcttcacc tgtactgtca    2280
gggcaagaga aagcctggta aaccagctac agcagtttac cagtgtgatg gctgtgacac    2340
agctccactc cacgggtgga cacagcagag ggcaactggg ctggcctggt tcagtgtgaa    2400
tcaaaccgct taacccacac atggtacatg tgattttctt ttgtgagcct tacaccaagc    2460
caaactattg tcaaagcatc atttctatag aaataaagcc ttatcttgac ctgttctatt    2520
aaaacctgcc acatccgccc tttcctacct agatttaatg agcccaagtt tttttacatg    2580
gaagaaatga ctctggggca agaccccta atgaactagt ggcagagcca ggaataaaac    2640
ttgagtaact aatgagtcac ttatgggcag agtatgcaaa aaccttaagt ggaaaccaaa    2700
tagaccctgg tatcaagaaa gcacaaagta ttaatagaag tttctggttg gggtgatcta    2760
ggttcaacag aaataagatg atttctaagt ataaagccat tttagaattc cagagtaggg    2820
tgggaaagca aaaagccagc tctgaacagg taacagctac atggtgactg agtctatggg    2880
caaaagttct tgcatcacag gcttttggga actagcctat cacagggccc tgtacaaata    2940
aacttggctg caatcccaaa aaaaaaaaaa aaaaaaaaaa aaaaaaaaaa aaaaaaaaaa    3000
aaaaaaaaaa aaaaaaaaaa a                                              3021
```

<210> SEQ ID NO 10
<211> LENGTH: 359
<212> TYPE: PRT
<213> ORGANISM: Homo sapiens

<400> SEQUENCE: 10

```
Met Leu Pro Cys Phe Gln Leu Leu Arg Ile Gly Gly Arg Gly Gly
1               5                   10                  15

Asp Leu Tyr Thr Phe His Pro Pro Ala Gly Val Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
```

```
        50                  55                  60
Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255

Val Asp Lys Ala Pro Leu Thr Pro Thr Gly Asn Ala Arg Gly Arg Pro
            260                 265                 270

Arg Lys Tyr Pro Val Ser Ala Pro Met Ala Pro Pro Ala Val Gly Ala
        275                 280                 285

Gly Ser Pro Val Gln Leu Leu Val Ala Ala Cys Pro Arg Lys Arg Gln
    290                 295                 300

Trp Pro Gly Phe Ser Val Met Ala Val Thr Ser Gly Ser Met Trp Pro
305                 310                 315                 320

Val Leu Ala Ala Ala Ser Arg Leu Pro Gly Arg Pro Thr Ser Asp Ala
                325                 330                 335

Gln Gly Ala Gly Leu Ala Phe Ser Leu Arg Ser Thr Ala Lys Ala Pro
            340                 345                 350

Ser Asp Thr Pro Ala His Glu
            355

<210> SEQ ID NO 11
<211> LENGTH: 1080
<212> TYPE: DNA
<213> ORGANISM: Homo sapiens

<400> SEQUENCE: 11
atgctgccct gcttccaact gctgcgcata gggggcggca ggggcggtga tctctacacc      60
ttccaccccc ccgccggggt tggctgcacc tatcgcttgg gccacagggc cgacctgtgt     120
gatgtggccc tgcggcccca gcaggagcct ggcctcatct ctgggatcca cgccgaactg     180
catgccgagc cccggggtga tgactggagg gtcagcctgg aagaccacag cagccaaggt     240
actttggtca ataatgtccg actcccaaga ggtcacaggc tggaattgag tgatggagac     300
ctcctgacct ttggccctga agggccccca ggaaccagcc cctcggagtt ctacttcatg     360
```

```
ttccaacaag tacgagtcaa gcctcaggac tttgctgcca ttaccatccc acggtctagg      420
ggagaagccc gggttggggc tggtttccgg cctatgctgc cctcccaggg ggctccacag      480
cggcctctca gcaccttctc ccctgccccc aaggccacac tgatcctaaa ctccataggc      540
agcctcagca agctccggcc ccagcccctc accttctccc ctagttgggg tggaccaaag      600
agcctgcctg ttcccgcccc acctggggaa gtggggacca cgccttctgc tccaccccaa      660
cgcaatcgga ggaaatctgt tcaccgagtg ttggcggaac tggatgatga gagtgagcct      720
cctgagaacc cgccaccggt ccttatggag cccaggaaga aactccgtgt agacaaagcc      780
ccactgactc ccactggaaa tgcacgtggc cgtcctcgga gtacccagt gagcgctccc       840
atggctcccc ctgcagttgg ggcggggagc cctgtgcagc tccttgttgc tgcctgcccc      900
aggaagagac agtggcctgg gttcagtgtg atggctgtga cgtctggttc catgtggcct      960
gtgttggctg cagcatccag gctgccaggg aggccgactt ccgatgccca gggtgccggg     1020
ctggcattca gcctaaggtc caccgccaag gcaccatcgg acacacctgc ccatgagtag     1080
```

<210> SEQ ID NO 12
<211> LENGTH: 345
<212> TYPE: PRT
<213> ORGANISM: Homo sapiens

<400> SEQUENCE: 12

```
Met Leu Pro Cys Phe Gln Leu Leu Arg Ile Gly Gly Gly Arg Gly Gly
  1               5                  10                  15

Asp Leu Tyr Thr Phe His Pro Ala Gly Ala Gly Cys Thr Tyr Arg
             20                  25                  30

Leu Gly His Arg Ala Asp Leu Cys Asp Val Ala Leu Arg Pro Gln Gln
         35                  40                  45

Glu Pro Gly Leu Ile Ser Gly Ile His Ala Glu Leu His Ala Glu Pro
     50                  55                  60

Arg Gly Asp Asp Trp Arg Val Ser Leu Glu Asp His Ser Ser Gln Gly
 65                  70                  75                  80

Thr Leu Val Asn Asn Val Arg Leu Pro Arg Gly His Arg Leu Glu Leu
                 85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Val Pro Ala Pro Pro
        195                 200                 205

Gly Glu Val Gly Thr Thr Pro Ser Ala Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Val Leu Met Glu Pro Arg Lys Lys Leu Arg
                245                 250                 255
```

```
Val Asp Lys Ala Pro Leu Thr Pro Thr Gly Asn Arg Arg Gly Arg Pro
            260                 265                 270

Arg Lys Tyr Pro Val Ser Ala Pro Met Ala Pro Pro Ala Val Gly Gly
        275                 280                 285

Gly Glu Pro Cys Ala Ala Pro Cys Cys Cys Leu Pro Gln Glu Glu Thr
    290                 295                 300

Val Ala Trp Val Gln Cys Asp Gly Cys Asp Val Trp Phe His Val Ala
305                 310                 315                 320

Cys Val Gly Cys Ser Ile Gln Ala Ala Arg Glu Ala Asp Phe Arg Cys
                325                 330                 335

Pro Gly Cys Arg Ala Gly Ile Gln Thr
            340                 345

<210> SEQ ID NO 13
<211> LENGTH: 4651
<212> TYPE: DNA
<213> ORGANISM: Homo sapiens

<400> SEQUENCE: 13
ccgccacccc gacacacaca ggagctgcct aaagtatcct tgccttgcag attggaggct      60
ccccaaatat tttgtgatct gaggatccag ctcaagtgag gtgccatagg acgtgttcct     120
gagtttgcat tgcacggaga ccttcctgga attttcatt tgcaagtcgg cttaaccaat      180
tttgcattga gtcctaggct gcttgcactc tgaatttggg ctattcaggt agtgtgctca     240
aagttgaaac cgcatacagc acaactcaag tttgcatcag actgggaagc gaacttaagc     300
cagcggtgcg tgggcaggg gtggggaagg aaatggatgc ctgaagtgga agaggtggtg      360 cagaggggc accgcccatg ctgccctgct tccaactgct cgcatagggg gcggcaggg       420 gcggtgatct ctacaccttc accccccccg ccggggctgg ctgcacctat cgcttgggcc     480
acagggccga cctgtgtgat gtggccctgc ggccccagca ggagcctggc ctcatctctg     540
ggatccacgc cgaactgcat gccgagcccc ggggtgatga ctggagggtc agcctggaag     600
accacagcag ccaaggtgag cattaagcag ggcagctttg ccctgggtg gttgaagcgc      660 caggctggaa tgagtaaggt ctccacaaga ccctgctgcc tgcctcccat actcccatca     720
gattggatgg atagtcgtgg tccagacctt catcttccca ccagaagtgt gcacagtcag     780
aagctctctg ccagactgac cctttttggt cccgtttagc tcatacagga cctgggatat     840
catcagaaag atatcacagt ggggatgttc tgaggccact agaggccaag tttagacttg     900
attcagtttc cagctttgct gaggcactct gttcctgggt tagggcagtt ctatgttgaa     960
taatgttttt aataatctgg gcatgtcttt ctccgtgact tgaggcagtt agcctcagaa    1020
agcctagatt cacatttgag ttttgccact gcctcttggt aaagtcagct gtaggagtgt    1080
tatggttatt agactatagt agccaacatt catctagtgc ttactgttat gagccaggcc    1140
ctattttaag tgtattgaat gtaggtggta ctaatattat cctcatttac agtaaaggaa    1200
aatgaggcac aaagaggtta aggaacttgt ccagggctgg gcatggtggt ttacacctat    1260
aatccagcac tttgggaggc taaggcaggg tggatcactt gagctcagga gttcgagacc    1320
agcctgggca acatggtgaa acctgtctc taccaaaaaa ttaattaatt ttttaaaaaa     1380
agcctgggcg cggtggctca cgcctgtaat cccagcactt gggaggccg agatgggcag    1440 atcacgaggt caggagttcg agaccatcct gaccaacatg ttgaaacccc atctgtgctg    1500 aaaaaaaat acaaaaatta gccaggtgtg gtggcgtgca cctgtaaccc cagctactca    1560
```

```
ggaggctgaa gcagcagaat cacttgaacc cgggaggcgg aggttgcagt gagctgagat    1620
cgcaccactg cactccagct tgggcgacag agcgagactc catctcaaac aaacaaacaa    1680
accaaaagct tgcccagggt cacataactg gtaagtggta gagctaggat ctgaacgagc    1740
tggagctggg ggagagtgag catgtttgaa aactggacct tagggcgggg cacggtggct    1800
cacgcctgta atcccagcac tttgggaggc tgaggcgggc agatcaggag gtcaggagta    1860
tgagaccagc ctggccaaca tggtaaaacc ctgtctctgc taaaaataaa aaaattagcc    1920
agacgtggtg gcacatgcct gtaatcccag ctactcagga ggctgaggca ggagaattgc    1980
ttgaacctgg gaggcggttc aagcttgggc aatagagcaa aactccatct caaaaaaaaa    2040
aaaaagaaag aaaaaaaaag aagaaagaaa gaaaattgga ccttaggaca gtgagggcag    2100
ggatcctttg taggaaagca caagaaacac agacttgttc ctagctgaca aggagtgtac    2160
tgcctggtac ctgtcacctg ctgagggct taggatgtga gggagaatct gactacagtt     2220
tcatattctt ccccagaaat catacagatt tctccactcc tgactctggt catttctgtt    2280
tttgtcctcc atatttgcct ggtgccccac catcaacagg tactttggtc aataatgtcc    2340
gactcccaag aggtcacagg ctggaattga gtgatgagaa cctcctgacc tttggccctg    2400
aagggccccc aggaaccagc ccctcggagt tctacttcat gttccaacaa gtacgagtca    2460
agcctcagga ctttgctgcc attaccatcc acggtctagg ggagaagcc cggttgggg      2520 ctggtttccg gcctatgctg ccctcccagg gggctccaca gcggcctctc agcaccttct    2580
cccctgcccc caaggccaca ctgatcctaa actccatagg cagcctcagc aagctccggc    2640
cccagcccct caccttctcc cctagttggg gtggaccaaa gagcctgcct gttcccgccc    2700
cacctgggga agtggggacc acgccttctg ctccacccca acgcaatcgg aggaaatctg    2760
ttcaccgagt gttggcggaa ctggatgatg agagtgagcc tcctgagaac ccgccaccgg    2820
tccttatgga gcccaggaag aaactccgtg tagacaaagc cccactgact cccactgggt    2880
aagtggagtc ctcacttggc cctctcagtg ttttactgct tttcgattcc ttgtatccct    2940
aggctgtgag gaggtccccc tgcctggggg gatgggcacg ggaggtggaa tagatggaat    3000
ggcaagacct gggttagctc tgataggaaa agaaaaatat gtgcaggaga acatgagagg    3060
tggggtgggg cagtgcttat aaaacaaccg gagtgagcat gtcctgcttt ttacattcat    3120
atggctttaa ccccattctt ctagtgccta aggatgggga actttcaggc tcacactaga    3180 ggttttagg cccaccctat gtgtttttaa ggacagagtc caggctcacc ttagttctca     3240
gaccactgtg cctctgtggc ctcacccat gaccagccat agggtggcaa ggtctaggcc      3300
ttctcctaca ggtttccggt gacccttgtg tctgtgtcac ttcagaaatc gacgtggccg    3360
tcctcggaag tacccagtga gcgctcccat ggctccccct gcagttgggg gcggggagcc    3420
ctgtgcagct ccttgttgct gcctgcccca ggaagagaca gtggcctggg ttcagtgtga    3480
tggctgtgac gtcggttcc atgtggcctg tgttggctgc agcatccagg ctgccaggga     3540
ggccgacttc cgatgcccag ggtgccgggc tggcattcag acctaaggtc caccgccaag    3600
gcaccatcgg acacacctgc ccatgagtag acacagcagc gagcaaatag gtctgataaa    3660
tacccccctt cccttccctc cccaagaggg aatgactaca gggaagaagg atggattgat    3720
gtggactcat tcagggcctg gagcagaccc tggtggccaa gacagaagag atggtttcct    3780
gccaaagata ttgccacctc caggaaattg ccagtgagct ggaagttccc actattacaa    3840
gccataaggc catgttgcca tggacaccag aatatctgta gtcagagcac ctatcagttg    3900
caaaagccat gcctgcaacc gatggaaaat gtaagaggga gttcttaagg ttcttggtgg    3960
```

```
catcacccaa ggcattctgg gaaaacctag ggcctggccc caaaacttcc ctactctgtg   4020
gctagtcctg ctgccaacaa atcgtagcg acctggcttt tcacagcttt gcttttattt   4080
ccaagtcaag gacaagccgc ttcattcact cctgggcatt tactcttctt gtgggtctgt   4140
gatattcctt gctttccagg gagaatgtgc ttggcaaggt ctggagaact aattcagaat   4200
cttaggggaa ggggagagat ggaaatacaa acctgcttac tggaaaggtg caaatatatg   4260
ggttgagctg gaggtaggaa tacaggtaat taaggtttct agtttaaggg aaaacagatc   4320
tattgccatt taaataaggt aactgggatt tggttaagtt cacaaagata gcagaagatt   4380
tatttacagg cttcacctgt actgtcaggg caagagaaag cctggtaaac cagctacagc   4440
agtttaccag tgtgatggct gtgacacagc tccactccac gggtggacac agcagagggc   4500
aactgggctg gcctggttca gtgtgaatca aaccgcttaa cccacacatg gtacatgtga   4560
ttttcttttg tgagccttac accaagccaa actattgtca aagcatcatt tctatagaaa   4620
taaagcctta tcttgacctg ttctattaaa a                                 4651
```

<210> SEQ ID NO 14
<211> LENGTH: 359
<212> TYPE: PRT
<213> ORGANISM: Homo sapiens

<400> SEQUENCE: 14

```
Met Leu Pro Cys Phe Gln Leu Leu Arg Ile Gly Gly Arg Gly Gly
1               5                   10                  15

Asp Leu Tyr Thr Phe His Pro Pro Ala Gly Val Gly Cys Thr Tyr Arg
            20                  25                  30

Leu Gly His Arg Ala Asp Leu Cys Asp Val Ala Leu Arg Pro Gln Gln
        35                  40                  45

Glu Pro Gly Leu Ile Ser Gly Ile His Ala Glu Leu His Ala Glu Pro
    50                  55                  60

Arg Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Glu Gly Pro Pro Gly Thr
            100                 105                 110

Ser Pro Ser Glu Phe Tyr Phe Met Phe Gln Gln Val Arg Val Lys Pro
        115                 120                 125

Gln Asp Phe Ala Ala Ile Thr Ile Pro Arg Ser Arg Gly Glu Ala Arg
    130                 135                 140

Val Gly Ala Gly Phe Arg Pro Met Leu Pro Ser Gln Gly Ala Pro Gln
145                 150                 155                 160

Arg Pro Leu Ser Thr Phe Ser Pro Ala Pro Lys Ala Thr Leu Ile Leu
                165                 170                 175

Asn Ser Ile Gly Ser Leu Ser Lys Leu Arg Pro Gln Pro Leu Thr Phe
            180                 185                 190

Ser Pro Ser Trp Gly Gly Pro Lys Ser Leu Pro Val Pro Ala Pro Pro
        195                 200                 205

Gly Glu Val Gly Thr Thr Pro Ser Ala Pro Gln Arg Asn Arg Arg
    210                 215                 220

Lys Ser Val His Arg Val Leu Ala Glu Leu Asp Asp Glu Ser Glu Pro
225                 230                 235                 240

Pro Glu Asn Pro Pro Pro Val Leu Met Glu Pro Arg Lys Lys Leu Arg
```

```
                    245                 250                 255
Val Asp Lys Ala Pro Leu Thr Pro Thr Gly Asn Ala Arg Gly Arg Pro
            260                 265                 270

Arg Lys Tyr Pro Val Ser Ala Pro Met Ala Pro Ala Val Gly Ala
        275                 280                 285

Gly Ser Pro Val Gln Leu Leu Val Ala Ala Cys Pro Arg Lys Arg Gln
            290                 295                 300

Trp Pro Gly Phe Ser Val Met Ala Val Thr Ser Gly Ser Met Trp Pro
305                 310                 315                 320

Val Leu Ala Ala Ala Ser Arg Leu Pro Gly Arg Pro Thr Ser Asp Ala
                325                 330                 335

Gln Gly Ala Gly Leu Ala Phe Ser Leu Arg Ser Thr Ala Lys Ala Pro
            340                 345                 350

Ser Asp Thr Pro Ala His Glu
        355

<210> SEQ ID NO 15
<211> LENGTH: 5522
<212> TYPE: DNA
<213> ORGANISM: Homo sapiens

<400> SEQUENCE: 15
gaattccgaa ggaggggtag gcgctgcccg cgcgcagagg ccgcgcccct cctggccccg      60
gcttcttggc tgtcaaacag tagcagcaac gtcggctcct gccgaggagc ccaagggggtc    120 ccgggatccg ccgcacaggc tggcactgct tgaagaggag gctactcgga gactgcgccg    180
cgcgggtaga tccgaaacgg ggctggggcg gagtgggaaa aggccgggta tgccttgcat    240
gatcgcgggg agctccttcc tgtttttatc ccacctagag aagccgggaa gtaggggttt    300
aggtccaatt tgttggagta cttaaggact cgtttgcact ttcttttggg ggatgacagt    360
ggattcattg ccctcggagg ttcaaccagt tatgagtgag ggattggcca aagatcggg    420 gcgcaggcaa gcaggagtgc tctattagga taagcaagtt tgacaggaag aagctgctct    480
tctccgaatt acacagaggt gatgtgttcg tattgcacgt agacgtgtgt ataacaggac    540
ctccttcccc gcgccccgcc acccgacac acacaggagc tgcctaaagt atccttgcct     600
tgaagattgg aggctcccca aatatttggt gatctgagga tccagctcaa gtgaggtgcc    660
ataggacgtg ttcctgagtt tgcattgcac ggagaccttc ctggaatttt tcatttgcaa    720
gtcggcttaa ccaatttggc attgagtcct aggctgcttg cactctgaat ttgggctatt    780
caggtagtgt gctcaaagtt gagaccgcat acagaacaac tcaagtttgc atcagactgg    840
gaagcgaact taagccagcg gtgcgtggcc caggagtggg aaaggaaatg gatgcctgaa    900
gtggaagagg tggtgcagag ggggcaccgc ccatgctgcc ctgcttccaa ctgctgcgca    960
tagggggcgg caggggcggt gatctctaca ccttccaccc cccgccgggg ttggctgca   1020 cctatcgctt gggccacagg gccgacctgt gtgatgtggc cctgcggccc cagcaggagc   1080
ctggcctcat ctctgggatc cacgccgaac tgcatgccga gccccggggt gatgactgga   1140
gggtcagcct ggaagaccac agcagccaag gtgagcatta agcagggcag ctttgcccct   1200
gggtggttga agcgccaggc tggaatgagt aaggtctcca caagaccttg ctgtctgcct   1260
cccatactcc catcagattg gatggatagt cgtggtccag accttcatct tcccaccaga   1320
agtgtgcaca gtcagaagct ctctgccaga ctgacccttt ttggtcccgt ttagctcata   1380
caggacctgg gatatcatca gaaagatatc acagtgggga tgttctgagg ccactagagg   1440
```

```
ccaagtttag acttgattca gtttccagct ttgctgaggc actctgttcc tgggttaggg    1500
cagttctatg ttgaataatg tttttaataa tctgggcatg tctttctccg tgacttgagg    1560
cagttagcct cagaaagcct agattcacat ttgagtttgg ccactgcctc ttggtaaagt    1620
cagctgtagg agtgttatgg ttattagact atagtagcca acattcatct agtgcttact    1680
gttatgagcc aggccctatt taagtgtat tgaatgtagg tggtactaat attatcctca     1740
tttacagaaa aggaaaatga ggcacaaaga ggttaaggaa cttgtccagg gctgggcatg    1800
gtggtttaca cctataatcc agcactttgg gaggctaagg cagggtggat cacttgagct    1860
caggagttcg agaccagcct gggcaacatg gtgaaaacct gtctctacca aaaaattaat    1920
tagttttta aaaaaagcct gggcgcggtg ggtcacgcct gtaatcccag cactttggga     1980
ggccgagatg ggcagatcac gaggtcagga gttcgagacc atcctgacca acatgttgaa    2040
accccatctg tgctgaaaaa aaaaaaccca aattaaccag gtgtggtggc gtgcacctgt    2100
aaccccagct actcaggagg ctgaagcagc agaatcactt gaacccggga ggcggaggtt    2160
ggagtgagct gagatcgcac cactgcactc cagcttgggc gacagagcga gactccatct    2220
caaacaaaca aacaaaccaa aagcttgccc agggtcacat aactggtaag tggtagagct    2280
aggtactgaa cgagctggag ctgggggaga gtgagcatgt ttgaaaactg gaccttaggg    2340
cggggcacgg tccgtcacgc ctgtaatccc agcactttgg gaggctgagg cgggcagatc    2400
aggaggtcag gagtatgaga ccagcctggc caacatggta aaaccctgtc tctcgtaaaa    2460
ataaaaaaat tagccagacg tggtggcaca tgcctgtaat cccagctact caggaggctg    2520
aggcaggaga attgcttgaa cctgggaggc ggagtgcagt gagctgagat tgcactactg    2580
cactccagct tgggcaatag agcaaatctc catctcaaaa aaaaaaaaa gaaagaaaaa     2640
aaaagaagaa agaaagaatt ttggcccctta ggacagtgag ggcagggttc ctttgtggga   2700
aagcacaaga aacacagatt tgttcctagc tgacaaggag tgtactgcct ggtacctgtc    2760
acctgctgag gggcttagga tgtgagggag aatctgacca cagtttcata ttcttcccca    2820
gaaatcatac agatttctcc actcctgact ctggtcaatt ctgttttgt cctccatatt     2880
tgcctggtgc cccaccatca acaggtactt tggtcaataa tgtccgactc ccaagaggtc    2940
acaggctgga attgagtgat ggagacctcc tgacctttgg ccctgaaggg cccccaggaa    3000
ccagcccctc ggagttctac ttcatgttcc aacaagtacg agtcaagcct caggactttg    3060
ctgccattac catcccacgg tctagggag aagcccgggt tggggctggt ttccggccta     3120
tgctgccctc ccagggggct ccacagcggc ctctcagcac cttctcccct gccccaagg     3180
ccacactgat cctaaactcc ataggcagcc tcagcaagct ccggcccag ccctcacct      3240
tctcccctag ttggggtgga ccaaagagcc tgcctgttcc cgcccacct ggggaagtgg     3300
ggaccacgcc ttctgctcca ccccaacgca atcggaggaa atctgttcac cgagtgttgg    3360
cggaactgga tgatgagagt gagcctcctg agaacccgcc accggtcctt atggagccca    3420
ggaagaaact ccgtgtagac aaagccccac tgactcccac tgggtaagtg agtcctcac    3480
ttggccctct cagtgtttta ctgcttttcg attccttgta tccctaggct gtgaggaggt    3540
cccctgcct ggggggatgg gcacgggagg tggaatagat ggaatggcaa gacctgggtt     3600
agctctgata gggaaagaaa aatatgtgca ggagaacatg agaggtgggg tgggcagtg     3660
ctataaaaca accggagtga gcatgtcctg ctttttacat tcatatggct ttaaccccac    3720
tttctagtgc ctaaggatgg ggaactttca ggctcacact agaggttttt aggcccaccc    3780
catgtgtttt taaggacaga gtccaggctc accttagttc tcagaccact gtgcctctgt    3840
```

```
ggcctcaccc tatgaccagc catagggtgg caaggtctag gccttctcag atttccggtg    3900
acccttgtgt ctctctcact tccttcagaa atgcacgtgg ccgtcctcgg aagtacccag    3960
tgagcgctcc catggctccc cctgcagttg gggcggggag ccctgtgcag ctccttgttg    4020
ctgcctgccc caggaagaga cagtggcctg ggttcagtgt gatggctgtg acgtctggtt    4080
ccatgtggcc tgtgttggct gcagcatcca ggctgccagg gaggccgact tccgatgccc    4140
agggtgccgg gctggcattc agcctaaggt ccaccgccaa ggcaccatcg acacacctg     4200 cccatgagta gacacagcag cgagcaaata ggtctgataa ataccccct tcccttccct     4260 ccccaagagg gaatgactac agggaagaag gatggattga tgtggactca ttcagggcct    4320
ggagcagacc ctggtggcca agacagaaga gatggtttcc ttccaaagat attgccacct    4380
ccaggaaatt gccagtgagc tggaagttcc cactattaca agccataagg ccatgtcgcc    4440
atggacacca gaatatctgt agtcagagca cctatcagtt gcaaaagcca tgcctgcaac    4500
cgatggaaaa tgtaagaggg agttcttaag gttcttggtg gaatcaccca aggtattctg    4560
ggaaaaccta gggcctggcc ccaaaacttc cctactctgt ggctagtcct gctgccaaca    4620
aaatcgtagc gacctggctt ttcacagctt tgcttttatt tccaagtcaa ggacaagccg    4680
cttcattcac tcctgggcat ttactcttct tgtgggtctg tgatattcct tgcttcccag    4740
ggagaatgtg cttggcaagg tctggagaac taattcagaa tcttagggga aggggagaga    4800
tggaaataca aacctgctta ctggaaaggt gcaaatatg ggttgagctg gaggtaggaa    4860
tacaggtaat taaggtttct agtttaaggg aaaacagatc tatttgccat ttaaatatgg    4920
taactgggat ttggttaagt tcacccagat agcagaagat ttatttacag gcttcacctg    4980
tactgtcagg gacaagagaa aagcctggta aaccaagcta cagcagttta ccagtgtgat    5040
ggctctcaca cagctccacc ccccgggtgg acacagcaga gggcacctgg gctggcctgg    5100
ttcagtgtga atcaaaccgc ttaacccaca catggtacat gtgattttct tttgtgagcc    5160
ttacaccaag ccaaactatt gtcaaagcat catttctata gaaataaagc cttatcttga    5220
cctgttctat taaaacctgc cacatccgcc ctttcctacc tagatttaat gagcccaagt    5280
ttttttacat ggaagaaatg actctggggc aaagacccct aatgaactag tggcagagcc    5340
aggaataaaa cttgagtaac taatgagtca cttatgggca gagtatgcaa aaaccttaag    5400
tggaaaccaa atagaccctg gtatcaagaa agcacaaagt attaatagaa gtttctggtt    5460
ggggtgatct aggttcaaca gaaataagat gatttctaag tataaagctc aaaattgaat    5520
tc                                                                  5522
```

<210> SEQ ID NO 16
<211> LENGTH: 650
<212> TYPE: PRT
<213> ORGANISM: Mus musculus

<400> SEQUENCE: 16

Met Lys Ala Val Leu Leu Leu Cys Ala Leu Gly Thr Ala Val Ala
1               5                   10                  15

Ile Pro Thr Ser Thr Arg Phe Leu Phe Asp His Ser Asn Pro Thr Thr
            20                  25                  30

Ala Thr Leu Val Thr Pro Glu Asp Ala Thr Val Pro Ile Ala Gly Val
        35                  40                  45

Glu Ala Thr Ala Asp Ile Glu Asn His Pro Asn Asp Lys Ala Glu Lys
    50                  55                  60

-continued

```
Pro Ser Ala Leu Asn Ser Glu Glu Thr His Glu Gln Ser Thr Glu
 65                  70                  75                  80

Gln Asp Lys Thr Tyr Ser Phe Glu Val Asp Leu Lys Asp Glu Asp
                     85                  90                  95

Gly Asp Gly Asp Leu Ser Val Asp Pro Thr Glu Gly Thr Leu Thr Leu
                100                 105                 110

Asp Leu Gln Glu Gly Thr Ser Glu Pro Gln Gln Lys Ser Leu Pro Glu
                115                 120                 125

Asn Gly Asp Phe Pro Ala Thr Val Ser Thr Ser Tyr Val Asp Pro Asn
130                 135                 140

Gln Arg Ala Asn Ile Thr Lys Gly Lys Glu Ser Gln Glu Gln Pro Val
145                 150                 155                 160

Ser Asp Ser His Gln Gln Pro Asn Glu Ser Ser Lys Gln Thr Gln Asp
                165                 170                 175

Leu Lys Ala Glu Glu Ser Gln Thr Gln Asp Pro Asp Ile Pro Asn Glu
                180                 185                 190

Glu Glu Glu Glu Glu Glu Asp Glu Glu Glu Glu Glu Glu Glu Pro
                195                 200                 205

Glu Asp Ile Gly Ala Pro Ser Asp Asn Gln Glu Gly Lys Glu Pro
210                 215                 220

Leu Glu Glu Gln Pro Thr Ser Lys Trp Glu Gly Asn Arg Glu Gln Ser
225                 230                 235                 240

Asp Asp Thr Leu Glu Glu Ser Ser Gln Pro Thr Gln Ile Ser Lys Thr
                245                 250                 255

Glu Lys His Gln Ser Glu Gln Gly Asn Gln Gly Gln Glu Ser Asp Ser
                260                 265                 270

Glu Ala Glu Gly Glu Asp Lys Ala Ala Gly Ser Lys Glu His Ile Pro
                275                 280                 285

His Thr Glu Gln Gln Asp Gln Glu Gly Lys Ala Gly Leu Glu Ala Ile
                290                 295                 300

Gly Asn Gln Lys Asp Thr Asp Glu Lys Ala Val Ser Thr Glu Pro Thr
305                 310                 315                 320

Asp Ala Ala Val Val Pro Arg Ser His Gly Gly Ala Gly Asp Asn Gly
                325                 330                 335

Gly Gly Asp Asp Ser Lys His Gly Ala Gly Asp Asp Tyr Phe Ile Pro
                340                 345                 350

Ser Gln Glu Phe Leu Glu Ala Glu Arg Met His Ser Leu Ser Tyr Tyr
                355                 360                 365

Leu Lys Tyr Gly Gly Gly Glu Glu Thr Thr Thr Gly Glu Ser Glu Asn
                370                 375                 380

Arg Arg Glu Ala Ala Asp Asn Gln Glu Ala Lys Lys Ala Glu Ser Ser
385                 390                 395                 400

Pro Asn Ala Glu Pro Ser Asp Glu Gly Asn Ser Arg Glu His Ser Ala
                405                 410                 415

Gly Ser Cys Thr Asn Phe Gln Cys Lys Arg Gly His Ile Cys Lys Thr
                420                 425                 430

Asp Pro Gln Gly Lys Pro His Cys Val Cys Gln Asp Pro Glu Thr Cys
                435                 440                 445

Pro Pro Ala Lys Ile Leu Asp Gln Ala Cys Gly Thr Asp Asn Gln Thr
                450                 455                 460

Tyr Ala Ser Ser Cys His Leu Phe Ala Thr Lys Cys Arg Leu Glu Gly
465                 470                 475                 480

Thr Lys Lys Gly His Gln Leu Gln Leu Asp Tyr Phe Gly Ala Cys Lys
```

```
                485                 490                 495
Ser Ile Pro Ala Cys Thr Asp Phe Glu Val Ala Gln Phe Pro Leu Arg
            500                 505                 510

Met Arg Asp Trp Leu Lys Asn Ile Leu Met Gln Leu Tyr Glu Pro Asn
        515                 520                 525

Pro Lys His Gly Gly Tyr Leu Asn Glu Lys Gln Arg Ser Lys Val Lys
    530                 535                 540

Lys Ile Tyr Leu Asp Glu Lys Arg Leu Leu Ala Gly Asp His Pro Ile
545                 550                 555                 560

Glu Leu Leu Leu Arg Asp Phe Lys Lys Asn Tyr His Met Tyr Val Tyr
                565                 570                 575

Pro Val His Trp Gln Phe Asn Glu Leu Asp Gln His Pro Ala Asp Arg
            580                 585                 590

Ile Leu Thr His Ser Glu Leu Ala Pro Leu Arg Ala Ser Leu Val Pro
        595                 600                 605

Met Glu His Cys Ile Thr Arg Phe Phe Glu Glu Cys Asp Pro Asn Lys
    610                 615                 620

Asp Lys His Ile Thr Leu Lys Glu Trp Gly His Cys Phe Gly Ile Lys
625                 630                 635                 640

Glu Glu Asp Ile Asp Glu Asn Leu Leu Phe
                645                 650

<210> SEQ ID NO 17
<211> LENGTH: 2797
<212> TYPE: DNA
<213> ORGANISM: Mus musculus

<400> SEQUENCE: 17
ccatcctaat acgactcact atagggctcg agcggccgcc cgggcaggtc tttgctgcaa      60
agctcagcag cacagaggga gcgagatcca ggaatgtgca acagaaacca tgacagcctg     120
aaacaccctg tggtgccaac ctccaaattc tcatctgtca cttcagaccc tgactggctg     180
acagagcagc agaatttcaa ctccaataaa cgtgaatgtg cttttaggca aagcaaccaa     240
gctgacgagg gaggggggtg gaagagctag ctcctcttgg gcatttgtca aacttttacc     300
tcctggctgt gtgcaaggag gggactcaac ttcggcttca agctaccaag gctctggatc     360
cagccacctc tccgcagatc tagccagcat gaaggctgtg cttctcctcc tgtgcgcctt     420
gggaaccgct gtggcaatcc cgacaagtac aaggtttctc tttgaccact ccaacccaac     480
tactgcaaca ctggtgacac cggaagacgc tacagtcccc attgccgggg ttgaagctac     540
agcagacata gaaaaccatc ccaatgacaa ggctgaaaaa ccttcagcac ttaattcaga     600
agaggaaact catgaacagt caacagagca ggacaaaacc tacagcttcg aggtggacct     660
gaaggatgag gaggatggag atggggattt aagtgtagat ccaacggaag gaacactaac     720 actgatcta caagaaggca caagtgagcc tcaacgaaa gtctcccgg agaacggcga       780 tttccccgcg accgtgtcca cttcctatgt ggatcctaac caacgcgcaa acatcacaaa     840
gggaaaggag agtcaggagc aacctgtaag tgactcacac cagcaaccga atgaaagcag     900
caagcaaacc caagacttaa aggctgaaga agccagaca caagatccag acattcccaa     960
tgaagaagag gaagaagaag aggacgaaga gaggaagaa gaggaagagc cggaagacat     1020
tggtgccccc agtgataacc aagaggaggg aaaagaacct ctggaggagc agcctaccag     1080
caagtgggaa ggaaacagag agcaatctga tgacacctta gaagagtcca gtcagcccac     1140
tcagataagc aagacagaga agcatcaatc tgagcaagga aaccaaggc aggagagtga     1200
```

```
ctctgaggca gaaggagagg acaaggctgc aggcagcaag gaacacattc cacatacaga    1260
gcagcaggac caagaaggga agctggcct tgaagctatt ggcaaccaga aggacactga     1320
tgagaaggcc gtttccacag aacctaccga tgctgccgtg gtgcctagga gtcacggagg    1380
agctggtgat aacgggggcg gggatgactc taagcatggt gcaggcgatg actacttcat    1440
ccccagccag gaattcctag aggccgaaag gatgcattcc ctctcctatt acctcaaata    1500
tggcggcggc gaggagacaa cgactggcga gagtgagaac cggagggagg ctgcagacaa    1560
ccaagaggcc aagaaagctg agagctcacc aaatgctgaa ccttcagatg agggcaactc    1620
aagggagcac agtgctggtt cttgcacgaa cttccaatgt aaaagggac acatttgcaa     1680
aaccgatcca caagggaaac ctcactgtgt ttgccaagat ccagagactt gtccccctgc    1740
aaaaatccta gatcaggctt gtggcactga caaccaaacc tacgccagct cctgtcacct    1800
gtttgctacc aagtgcaggc tggagggac caaaaaggga caccaactgc agctggatta    1860
cttcggagct tgcaaatcta ttcctgcttg tacggacttt gaagtggctc agtttcccct    1920
gcggatgaga gactggctca aaaacatcct catgcagctt tatgaaccaa atcccaaaca    1980
tggcggctat ctcaatgaaa agcaaagaag caaagtcaaa aaaatttacc tggatgagaa    2040
gagactcttg gctggagacc atcccattga acttctcttg agggacttta agaaaaacta    2100
ccacatgtat gtgtatcctg tgcactggca gtttaatgaa ctggaccagc atcctgcaga    2160
caggatcttg acacactctg aacttgctcc tctgcgagct tccctggtgc ccatggaaca    2220
ctgcataact cgcttctttg aggagtgtga ccccaacaag gataagcaca tcaccttgaa    2280
ggaatggggc cactgctttg gaattaaaga ggaggatata gatgaaaacc tcctcttttg    2340
aattaagatt tgagagaatc ggaactttcc atccacctca cctgctttac ccgcttcaga    2400
aatacgagca gccatgacac tatacattca tatgtagcaa acatgtgtg tgcatgtgag     2460
agaagacaat ggtagtaatt acttctgggt gatatatata tgagccaggc acttaatatt    2520
aacttaggaa atgaaacttt aaaattaagt agagtcaatg tctataaaag actgtcctgt    2580
ctggggacag ttagccacca tggcaatgtc actctgtgca tctgcgttta taattgataa    2640
ttataaacta ttaaaaaaac aatgttcata ttgtccataa taccttatgc atgctgagga    2700
agtgagatac tgctcttttg agataaatat gcctcctttt cagtgtcttg atgtcctaat    2760
aaaaaatcta taaacctcc ccaaaaaaaa aaaaaaa                              2797
```

<210> SEQ ID NO 18
<211> LENGTH: 650
<212> TYPE: PRT
<213> ORGANISM: Mus musculus

<400> SEQUENCE: 18

```
Met Lys Ala Val Leu Leu Leu Cys Ala Leu Gly Thr Ala Val Ala
1               5                   10                  15

Ile Pro Thr Ser Thr Arg Phe Leu Ser Asp His Ser Asn Pro Thr Thr
                20                  25                  30

Ala Thr Leu Val Thr Pro Glu Asp Ala Thr Val Pro Ile Ala Gly Val
            35                  40                  45

Glu Ala Thr Ala Asp Ile Glu Asn His Pro Asn Asp Lys Ala Glu Lys
        50                  55                  60

Pro Ser Ala Leu Asn Ser Glu Glu Thr His Glu Gln Ser Thr Glu
65                  70                  75                  80

Gln Asp Lys Thr Tyr Ser Phe Glu Val Asp Leu Lys Asp Glu Glu Asp
```

-continued

```
                85                  90                  95
Gly Asp Gly Asp Leu Ser Val Asp Pro Thr Glu Gly Thr Leu Thr Leu
            100                 105                 110
Asp Leu Gln Glu Gly Thr Ser Glu Pro Gln Gln Lys Ser Leu Pro Glu
            115                 120                 125
Asn Gly Asp Phe Pro Ala Thr Val Ser Thr Ser Tyr Val Asp Pro Asn
            130                 135                 140
Gln Arg Ala Asn Ile Thr Lys Gly Lys Glu Ser Gln Glu Gln Pro Val
145                 150                 155                 160
Ser Asp Ser His Gln Gln Pro Asn Glu Ser Ser Lys Gln Thr Gln Asp
                165                 170                 175
Leu Lys Ala Glu Glu Ser Gln Thr Gln Asp Pro Asp Ile Pro Asn Glu
            180                 185                 190
Glu Glu Glu Glu Glu Glu Glu Glu Glu Glu Glu Glu Glu Glu Glu Pro
            195                 200                 205
Glu Asp Ile Gly Ala Pro Ser Asp Asn Gln Glu Gly Lys Glu Pro
    210                 215                 220
Leu Glu Glu Gln Pro Thr Ser Lys Trp Glu Gly Asn Arg Glu Gln Ser
225                 230                 235                 240
Asp Asp Thr Leu Glu Glu Ser Ser Gln Pro Thr Gln Ile Ser Lys Thr
                245                 250                 255
Glu Lys His Gln Ser Glu Gly Asn Gln Gly Gln Glu Ser Asp Ser
            260                 265                 270
Glu Ala Glu Gly Glu Asp Lys Ala Ser Gly Ser Lys Glu His Ile Pro
            275                 280                 285
His Thr Glu Gln Gln Asp Gln Glu Gly Lys Ala Gly Leu Glu Ala Ile
            290                 295                 300
Gly Asn Gln Lys Asp Thr Asp Glu Lys Ala Val Ser Thr Glu Pro Thr
305                 310                 315                 320
Asp Ala Ala Val Val Pro Arg Ser His Gly Gly Ala Gly Asp Asn Gly
                325                 330                 335
Gly Gly Asp Asp Ser Lys His Gly Ala Gly Asp Asp Tyr Phe Ile Pro
            340                 345                 350
Ser Gln Glu Phe Leu Glu Ala Glu Arg Met His Ser Leu Ser Tyr Tyr
            355                 360                 365
Leu Lys Tyr Gly Gly Gly Glu Glu Thr Thr Thr Gly Glu Ser Glu Asn
            370                 375                 380
Gln Arg Glu Ala Ala Asp Asn Gln Glu Ala Lys Lys Ala Glu Ser Ser
385                 390                 395                 400
Pro Asn Ala Glu Pro Ser Asp Glu Gly Asn Ser Arg Glu His Ser Ala
                405                 410                 415
Gly Ser Cys Thr Asn Phe Gln Cys Lys Arg Gly His Ile Cys Lys Thr
            420                 425                 430
Asp Pro Gln Gly Lys Pro His Cys Val Cys Gln Asp Pro Glu Thr Cys
            435                 440                 445
Pro Pro Ala Lys Ile Leu Asp Gln Ala Cys Gly Thr Asp Asn Gln Thr
            450                 455                 460
Tyr Ala Ser Ser Cys His Leu Phe Ala Thr Lys Cys Arg Leu Glu Gly
465                 470                 475                 480
Thr Lys Lys Gly His Gln Leu Gln Leu Asp Tyr Phe Gly Ala Cys Lys
                485                 490                 495
Ser Ile Pro Ala Cys Thr Asp Phe Glu Val Ala Gln Phe Pro Leu Arg
            500                 505                 510
```

```
Met Arg Asp Trp Leu Lys Asn Ile Leu Met Gln Leu Tyr Glu Pro Asn
            515                 520                 525

Pro Lys His Gly Gly Tyr Leu Asn Glu Lys Gln Arg Ser Lys Val Lys
        530                 535                 540

Lys Ile Tyr Leu Asp Glu Lys Arg Leu Leu Ala Gly Asp His Pro Ile
545                 550                 555                 560

Glu Leu Leu Leu Arg Asp Phe Lys Lys Asn Tyr His Met Tyr Val Tyr
                565                 570                 575

Pro Val His Trp Gln Phe Asn Glu Leu Asp Gln His Pro Ala Asp Arg
            580                 585                 590

Ile Leu Thr His Ser Glu Leu Ala Pro Leu Arg Ala Ser Leu Val Pro
        595                 600                 605

Met Glu His Cys Ile Thr Arg Phe Phe Glu Glu Cys Asp Pro Asn Lys
        610                 615                 620

Asp Lys His Ile Thr Leu Lys Glu Trp Gly His Cys Phe Gly Ile Lys
625                 630                 635                 640

Glu Glu Asp Ile Asp Glu Asn Leu Leu Phe
                645                 650

<210> SEQ ID NO 19
<211> LENGTH: 2734
<212> TYPE: DNA
<213> ORGANISM: Mus musculus

<400> SEQUENCE: 19
cagcacggag ggagcgagat ccaggaatct gcaacagaaa ccatgacagc ctgaaacacc      60
ctgtggtgcc aacctccaaa ttctcatctg tcacttcaga ccctgactgg ctgcagagc     120
agcagaattt caactccaat aaacgtgaat gtgcttctag gcaaagcagc caagctgacg     180
agggaggggg gtggaagagc tagctcctct tgggcatttg tcaaactttt acctcctggc     240
tgtgtgcaag gagggactc aacttcggct tcaagctacc aaggctctgg atccagccac     300
ctctccgcag atctagccag catgaaggct gtgcttctcc tcctgtgcgc cttgggaacc     360
gctgtggcaa tcccgacaag tacaaggttt ctctctgacc actccaaccc aactactgca     420
acactggtga caccggaaga cgctacagtc cccattgccg gggttgaagc tacagcagac     480
atagaaaacc atcccaatga caaggctgaa aaaccttcag cacttaattc agaagaggaa     540
actcatgaac agtcaacaga gcaggacaaa acctacagct tcgaggtgga cctgaaggat     600
gaggaggatg gagatgggga tttaagtgta gatccaacgg aaggaacact aacactggat     660
ctacaagaag gtacaagtga gcctcaacag aaaagtctcc cggaaaacgg ggatttcccc     720
gcgaccgtgt ccacttccta tgtggatcct aaccaacgcg caaacatcac aaagggaaag     780
gagagtcagg agcaacctgt aagtgactca caccagcaac cgaatgaaag cagcaagcaa     840
acccaagact taaggctgaa agaaagccag acacaagatc cagacattcc caatgaagaa     900
gaggaagaag aagaggaaga agaagaggaa gaagaggaag agccggaaga cattggtgcc     960
cccagtgata accaagagga gggaaaagaa cctctggagg agcagcctac cagcaagtgg    1020
gaaggaaaca gagagcaatc tgatgacacc ttagaagagt ccagtcagcc cactcagata    1080
agcaagacag agaagcatca atctgagcaa ggaaaccaag gcaggagag tgactctgag    1140
gcagaaggag aggacaaggc ttcaggcagc aaggaacaca ttccacatac agagcagcag    1200
gaccaagaag ggaaagctgg ccttgaagct attggcaacc agaaggacac tgatgagaag    1260
gccgtttcca cagaacctac cgatgctgcc gtggtgccta ggagtcacgg aggagctggt    1320
```

```
gataacgggg gcggggatga ctctaagcat ggtgcaggcg atgactactt catccccagc    1380
caggaattcc tagaggccga aggatgcat tccctctcct attacctcaa atatggcggg    1440
ggcgaggaga caacgactgg cgagagtgag aaccagaggg aggctgcaga caaccaagag    1500
gccaagaaag ctgagagctc accaaatgct gaaccttcag atgagggcaa ctcaagggag    1560
cacagtgctg gttcttgcac gaacttccaa tgtaaaaggg gacacatttg caaaaccgat    1620
ccacaaggga aacctcactg tgtttgccaa gatccagaga cttgtccccc tgcaaaaatc    1680
ctagatcagg cttgtggcac tgacaaccaa acctacgcca gctcctgtca cctgtttgct    1740
accaagtgca ggctggaggg gaccaaaaag ggacaccaac tgcagctgga ttacttcgga    1800
gcttgcaaat ctattcctgc ttgtacggac tttgaagtgg ctcagtttcc cctgcggatg    1860
agagactggc tcaaaaacat cctcatgcag ctttatgaac caaatcccaa acatggcggc    1920
tatctcaatg aaaagcaaag aagcaaagtc aaaaaaattt acctggatga aagagactc    1980 ttggctggag accatcccat tgaacttctc ttgagggact taagaaaaa ctaccacatg    2040 tatgtgtatc ctgtgcactg gcagtttaat gaactggacc agcatcctgc agacaggatc    2100
ttgacacact ctgaacttgc tcctctgcga gcttccctgg tgcccatgga acactgcata    2160
actcgcttct ttgaggagtg tgaccccaac aaggataagc acatcacctt gaaggaatgg    2220
ggccactgct ttgaattaa agaggaggat atagatgaaa acctcctctt ttgaattaag    2280
atttgagaga atcggaactt ccatccacc tcacctgctt taaccgcttc agaaatacga    2340
gcagccatga cactatacat tcatatgtag caaaacattt gtttggcatg tgagagaaga    2400
caatggtagt aattacttct tggtgatata tatatgagcc aggcacttaa tattaactta    2460
ggaaatgaaa ctttaaaatt aagtagagtc aatgtctata aaagactgtc ctgtctgggg    2520
acagttagcc accatggcaa tgtcactctg tgcatctgcg tttataattg ataattataa    2580
actattaaaa aaacaatgtt catattgtcc ataatacctt atgcatgctg aggaagtgag    2640
atactgctct tttgagataa atatgcctcc ttttcagtgt cttggatgtc ctaataaaaa    2700
atctataaaa ccccccaaaaa aaaaaaaaaa aaaa                              2734
```

<210> SEQ ID NO 20
<211> LENGTH: 355
<212> TYPE: PRT
<213> ORGANISM: Homo sapiens

<400> SEQUENCE: 20

```
Met Ala Ala Pro Ala Phe Glu Pro Gly Arg Gln Ser Asp Leu Leu Val
1               5                  10                  15

Lys Leu Asn Arg Leu Met Glu Arg Cys Leu Arg Asn Ser Lys Cys Ile
            20                  25                  30

Asp Thr Glu Ser Leu Cys Val Val Ala Gly Glu Lys Val Trp Gln Ile
        35                  40                  45

Arg Val Asp Leu His Leu Leu Asn His Asp Gly Asn Ile Ile Asp Ala
    50                  55                  60

Ala Ser Ile Ala Ala Ile Val Ala Leu Cys His Phe Arg Arg Pro Asp
65                  70                  75                  80

Val Ser Val Gln Gly Asp Glu Val Thr Leu Tyr Thr Pro Glu Arg
                85                  90                  95

Asp Pro Val Pro Leu Ser Ile His His Met Pro Ile Cys Val Ser Phe
            100                 105                 110

Ala Phe Phe Gln Gln Gly Thr Tyr Leu Leu Val Asp Pro Asn Glu Arg
```

```
                    115                 120                 125
Glu Glu Arg Val Met Asp Gly Leu Leu Val Ile Ala Met Asn Lys His
    130                 135                 140

Arg Glu Ile Cys Thr Ile Gln Ser Ser Gly Gly Ile Met Leu Leu Lys
145                 150                 155                 160

Asp Gln Val Leu Arg Cys Ser Lys Ile Ala Gly Val Lys Val Ala Glu
                165                 170                 175

Ile Thr Glu Leu Ile Leu Lys Ala Leu Glu Asn Asp Gln Lys Val Arg
            180                 185                 190

Lys Glu Gly Gly Lys Phe Gly Phe Ala Glu Ser Ile Ala Asn Gln Arg
        195                 200                 205

Ile Thr Ala Phe Lys Met Glu Lys Ala Pro Ile Asp Thr Ser Asp Val
    210                 215                 220

Glu Glu Lys Ala Glu Glu Ile Ile Ala Glu Ala Glu Pro Pro Ser Glu
225                 230                 235                 240

Val Val Ser Thr Pro Val Leu Trp Thr Pro Gly Thr Ala Gln Ile Gly
                245                 250                 255

Glu Gly Val Glu Asn Ser Trp Gly Asp Leu Glu Asp Ser Glu Lys Glu
            260                 265                 270

Asp Asp Glu Gly Gly Gly Asp Gln Ala Ile Ile Leu Asp Gly Ile Lys
        275                 280                 285

Met Asp Thr Gly Val Glu Val Ser Asp Ile Gly Ser Gln Asp Ala Pro
    290                 295                 300

Ile Ile Leu Ser Asp Ser Glu Glu Glu Met Ile Ile Leu Glu Pro
305                 310                 315                 320

Asp Lys Asn Pro Lys Lys Ile Arg Thr Gln Thr Thr Ser Ala Lys Gln
                325                 330                 335

Glu Lys Ala Pro Ser Lys Lys Pro Val Lys Arg Lys Lys Lys Arg
            340                 345                 350

Ala Ala Asn
        355

<210> SEQ ID NO 21
<211> LENGTH: 1542
<212> TYPE: DNA
<213> ORGANISM: Homo sapiens

<400> SEQUENCE: 21
cgaccggcac gttcacccca tccctcaggc tttatttatt ttttttcgac aggttctttt     60
caaggctcca gtcaccgcag cagttgtcca tgctgtagtt tccactttcc tgtatgggcg    120
ggctggttag gattccactt tcccccaagt gcttagccca gggccagaca aaaagtagtt    180
gcttaagaaa tacttgttga aggaataaat taatgaatga atttgtgctt acagcggctg    240
gatggcagac aaacctatga ttataggaac atcaggatct catttggaac agattacgga    300
tgctgcattg tggaacttgg aaaaacaaga gttcttggac aggtttcctg tgaacttgtg    360
tctccaaaac tcaatcgggc aacagaaggt attcttttt taaccttgaa ctctctcaga    420
tggccgctcc agctttcgaa cctggcaggc agtcagatct cttggtgaag ttgaatcgac    480
tcatggaaag atgtctaaga aattcgaagt gtatagacac tgagtctctc tgtgttgttg    540
ctggtgaaaa ggtttggcaa atacgtgtag acctacattt attaaatcat gatggaaata    600
ttattgatgc tgccagcatt gctgcaatcg tggccttatg tcatttccga agacctgatg    660
tctctgtcca aggagatgaa gtaacactgt atacacctga gagcgtgat cctgtaccat     720
```

-continued

```
taagtatcca ccacatgccc atttgtgtca gttttgcctt tttccagcaa ggaacatatt    780
tattggtgga tcccaatgaa cgagaagaac gtgtgatgga tggcttgctg gtgattgcca    840
tgaacaaaca tcgagagatt tgtactatcc agtccagtgg tgggataatg ctactaaaag    900
atcaagttct gagatgcagt aaaatcgctg gtgtgaaagt agcagaaatt acagagctaa    960
tattgaaagc tttggagaat gaccaaaaag taaggaaaga aggtggaaag tttggttttg   1020
cagagtctat agcaaatcaa aggatcacag catttaaaat ggaaaaggcc cctattgata   1080
cctcggatgt agaagaaaaa gcagaagaaa tcattgctga agcagaacct ccttcagaag   1140
ttgtttctac acctgtgcta tggactcctg gaactgccca aattggagag ggagtagaaa   1200
actcctgggg tgatcttgaa gactctgaga aggaagatga tgaaggcggt ggtgatcaag   1260
ctatcattct tgatggtata aaaatggaca ctggagtaga agtctctgat attggaagcc   1320
aagatgctcc cataatactc tcagatagtg aagaagaaga aatgatcatt ttggaaccag   1380
acaagaatcc aaagaaaata agaacacaga ccaccagtgc aaaacaagaa aaagcaccaa   1440
gtaaaaagcc agtgaaaaga agaaaaaaga agagagctgc caattaaagc taacagttgt   1500
atatctgtat atataactat taaaagggat atttattcca tt                      1542
```

<210> SEQ ID NO 22
<211> LENGTH: 664
<212> TYPE: PRT
<213> ORGANISM: Homo sapiens

<400> SEQUENCE: 22

```
Met Lys Thr Gly Pro Phe Phe Leu Cys Leu Leu Gly Thr Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
```

-continued

```
        225                 230                 235                 240
Asp Asp Ile Leu Glu Glu Ser Asp Gln Pro Thr Gln Val Ser Lys Met
                245                 250                 255
Gln Glu Asp Glu Phe Asp Gln Gly Asn Gln Glu Gln Glu Asp Asn Ser
                260                 265                 270
Asn Ala Glu Met Glu Glu Asn Ala Ser Asn Val Asn Lys His Ile
275                 280                 285
Gln Glu Thr Glu Trp Gln Ser Gln Glu Gly Lys Thr Gly Leu Glu Ala
                290                 295                 300
Ile Ser Asn His Lys Glu Thr Glu Glu Lys Thr Val Ser Glu Ala Leu
305                 310                 315                 320
Leu Met Glu Pro Thr Asp Asp Gly Asn Thr Thr Pro Arg Asn His Gly
                325                 330                 335
Val Asp Asp Asp Gly Asp Asp Gly Asp Asp Gly Gly Thr Asp Gly
                340                 345                 350
Pro Arg His Ser Ala Ser Asp Asp Tyr Phe Ile Pro Ser Gln Ala Phe
                355                 360                 365
Leu Glu Ala Glu Arg Ala Gln Ser Ile Ala Tyr His Leu Lys Ile Glu
                370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
                405                 410                 415
Glu Glu Thr Ser Ser Glu Gly Asn Met Arg Val His Ala Val Asp Ser
                420                 425                 430
Cys Met Ser Phe Gln Cys Lys Arg Gly His Ile Cys Lys Ala Asp Gln
                435                 440                 445
Gln Gly Lys Pro His Cys Val Cys Gln Asp Pro Val Thr Cys Pro Pro
                450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                485                 490                 495
Lys Gly His Gln Leu Gln Leu Asp Tyr Phe Gly Ala Cys Lys Ser Ile
                500                 505                 510
Pro Thr Cys Thr Asp Phe Glu Val Ile Gln Phe Pro Leu Arg Met Arg
                515                 520                 525
Asp Trp Leu Lys Asn Ile Leu Met Gln Leu Tyr Glu Ala Asn Ser Glu
                530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                565                 570                 575
Leu Leu Arg Asp Phe Lys Lys Asn Tyr His Met Tyr Val Tyr Pro Val
                580                 585                 590
His Trp Gln Phe Ser Glu Leu Asp Gln His Pro Met Asp Arg Val Leu
                595                 600                 605
Thr His Ser Glu Leu Ala Pro Leu Arg Ala Ser Leu Val Pro Met Glu
                610                 615                 620
His Cys Ile Thr Arg Phe Phe Glu Glu Cys Asp Pro Asn Lys Asp Lys
625                 630                 635                 640
His Ile Thr Leu Lys Glu Trp Gly His Cys Phe Gly Ile Lys Glu Glu
                645                 650                 655
```

Asp Ile Asp Glu Asn Leu Leu Phe
            660

<210> SEQ ID NO 23
<211> LENGTH: 2808
<212> TYPE: DNA
<213> ORGANISM: Homo sapiens

<400> SEQUENCE: 23

| | | | | | |
|---|---|---|---|---|---|
| cggcatgaga | ggccagcctg | ccagggaaat | ccaggaatct | gcaacaaaaa | cgatgacagt | 60 |
| ctgaaatact | ctctggtgcc | aacctccaaa | ttctcgtctg | tcacttcaga | cccccactag | 120 |
| ttgacagagc | agcagaatat | caactccagt | agacttgaat | gtgcctctgg | caaagaagc | 180 |
| agagctaacg | aggaagggga | tttaaagagt | ttttcttggg | tgtttgtcaa | acttttattc | 240 |
| cctgtctgtg | tgcagagggg | attcaacttc | aattttctgc | agtggctctg | ggtccagccc | 300 |
| cttacttaaa | gatctggaaa | gcatgaagac | tgggcctttt | ttcctatgtc | tcttgggaac | 360 |
| tgcagctgca | atcccgacaa | atgcaagatt | attatctgat | cattccaaac | caactgctga | 420 |
| aacggtagca | cctgacaaca | ctgcaatccc | cagtttatgg | gctgaagctg | aagaaaatga | 480 |
| aaagaaaaca | gcagtatcca | cagaagacga | ttcccaccat | aaggctgaaa | aatcatcagt | 540 |
| actaaagtca | aaagaggaaa | gccatgaaca | gtcagcagaa | cagggcaaga | gttctagcca | 600 |
| agagctggga | ttgaaggatc | aagaggacag | tgatggtcac | ttaagtgtga | atttggagta | 660 |
| tgcaccaact | gaaggtacat | tggacataaa | agaagatatg | attgagcctc | aggagaaaaa | 720 |
| actctcagag | aacactgatt | ttttggctcc | tggtgttagt | tccttcacag | attctaacca | 780 |
| acaagaaagt | atcacaaaga | gagggaaaa | ccaagaacaa | cctagaaatt | attcacatca | 840 |
| tcagttgaac | aggagcagta | acatagcca | aggcctaagg | gatcaaggaa | ccaagagca | 900 |
| ggatccaaat | atttccaatg | gagaagagga | agaagaaaaa | gagccaggtg | aagttggtac | 960 |
| ccacaatgat | aaccaagaaa | gaaagacaga | attgcccagg | gagcatgcta | acagcaagca | 1020 |
| ggaggaagac | aatacccaat | ctgatgatat | tttggaagag | tctgatcaac | caactcaagt | 1080 |
| aagcaagatg | caggaggatg | aatttgatca | gggtaaccaa | gaacaagaag | ataactccaa | 1140 |
| tgcagaaatg | gaagaggaaa | atgcatcgaa | cgtcaataag | cacattcaag | aaactgaatg | 1200 |
| gcagagtcaa | gagggtaaaa | ctggcctaga | agctatcagc | aaccacaaag | agacagaaga | 1260 |
| aaagactgtt | tctgaggctc | tgctcatgga | acctactgat | gatggtaata | ccacgcccag | 1320 |
| aaaatcatgga | gttgatgatg | atggcgatga | tgatggcgat | gatggcggca | ctgatggccc | 1380 |
| caggcacagt | gcaagtgatg | actacttcat | cccaagccag | gcctttctgg | aggccgagag | 1440 |
| agctcaatcc | attgcctatc | acctcaaaat | tgaggagcaa | agaaaaaag | tacatgaaaa | 1500 |
| tgaaaatata | ggtaccactg | agcctggaga | gcaccaagag | gccaagaaag | cagagaactc | 1560 |
| atcaaatgag | gaggaaacgt | caagtgaagg | caacatgagg | gtgcatgctg | tggattcttg | 1620 |
| catgagcttc | cagtgtaaaa | gaggccacat | ctgtaaggca | gaccaacagg | gaaaacctca | 1680 |
| ctgtgtctgc | caggatccag | tgacttgtcc | tccaacaaaa | ccccttgatc | aagtttgtgg | 1740 |
| cactgacaat | cagacctatg | ctagttcctg | tcatctattc | gctactaaat | gcagactgga | 1800 |
| ggggaccaaa | aaggggcatc | aactccagct | ggattatttt | ggagcctgca | aatctattcc | 1860 |
| tacttgtacg | gactttgaag | tgattcagtt | tcctctacgg | atgagagact | ggctcaagaa | 1920 |
| tatcctcatg | cagctttatg | aagccaactc | tgaacatgct | ggttatctaa | atgagaagca | 1980 |
| gagaaataaa | gtcaagaaaa | tttacctgga | tgaaaagagg | cttttggctg | ggaccatcc | 2040 |

-continued

```
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataacccgtt tctttgagga    2220
gtgtgacccc aacaaggata agcacatcac cctgaaggag tggggccact gctttggaat    2280
taaagaagag gacatagatg aaaatctctt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaaatgg aatgctactc ttttgtggtt    2700
tacgtgtatt attttcaata tcttaatacc ctaataaaga gtccataaaa atccaaaaaa    2760
aaaaaaaaaa aaaaaaaaaa aaaaaaaaaa aaaaaaaaa aaaaaaaa                  2808
```

<210> SEQ ID NO 24
<211> LENGTH: 664
<212> TYPE: PRT
<213> ORGANISM: Homo sapiens

<400> SEQUENCE: 24

```
Met Lys Thr Gly Leu Phe Phe Leu Cys Leu Leu Gly Thr Ala Ala Ala
 1               5                  10                  15

Ile Pro Thr Asn Ala Arg Leu Leu Ser Asp His Ser Lys Pro Thr Ala
             20                  25                  30

Glu Thr Val Ala Pro Asp Asn Thr Ala Ile Pro Ser Leu Arg Ala Glu
         35                  40                  45

Asp Glu Asn Glu Lys Glu Thr Ala Val Ser Thr Glu Asp Asp Ser
     50                  55                  60

His His Lys Ala Glu Lys Ser Ser Val Leu Lys Ser Lys Glu Glu Ser
 65                  70                  75                  80

His Glu Gln Ser Ala Glu Gln Gly Lys Ser Ser Gln Glu Leu Gly
                 85                  90                  95

Leu Lys Asp Gln Glu Asp Ser Asp Gly Asp Leu Ser Val Asn Leu Glu
            100                 105                 110

Tyr Ala Pro Ser Glu Gly Thr Leu Asp Ile Lys Glu Asp Met Ser Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240
```

-continued

```
Asp Asp Ile Leu Glu Glu Ser Asp Gln Pro Thr Gln Val Ser Lys Met
            245                 250                 255
Gln Glu Asp Glu Phe Asp Gln Gly Asn Gln Glu Gln Glu Asp Asn Ser
        260                 265                 270
Asn Ala Glu Met Glu Glu Asn Ala Ser Asn Val Asn Lys His Ile
    275                 280                 285
Gln Glu Thr Glu Trp Gln Ser Gln Glu Gly Lys Thr Gly Leu Glu Ala
    290                 295                 300
Ile Ser Asn His Lys Glu Thr Glu Glu Lys Thr Val Ser Glu Ala Leu
305                 310                 315                 320
Leu Met Glu Pro Thr Asp Asp Gly Asn Thr Thr Pro Arg Asn His Gly
                325                 330                 335
Val Asp Asp Asp Gly Asp Asp Asp Asp Gly Gly Thr Asp Gly
                340                 345                 350
Pro Arg His Ser Ala Ser Asp Asp Tyr Phe Ile Pro Ser Gln Ala Phe
            355                 360                 365
Leu Glu Ala Glu Arg Ala Gln Ser Ile Ala Tyr His Leu Lys Ile Glu
    370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
                405                 410                 415
Glu Glu Thr Ser Ser Glu Gly Asn Met Arg Val His Ala Val Asp Ser
            420                 425                 430
Cys Met Ser Phe Gln Cys Lys Arg Gly His Ile Cys Lys Ala Asp Gln
        435                 440                 445
Gln Gly Lys Pro His Cys Val Cys Gln Asp Pro Val Thr Cys Pro Pro
    450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                485                 490                 495
Lys Gly His Gln Leu Gln Leu Asp Tyr Phe Gly Ala Cys Lys Ser Ile
            500                 505                 510
Pro Thr Cys Thr Asp Phe Glu Val Ile Gln Phe Pro Leu Arg Met Arg
        515                 520                 525
Asp Trp Leu Lys Asn Ile Leu Met Gln Leu Tyr Glu Ala Asn Ser Glu
    530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                565                 570                 575
Leu Leu Arg Asp Phe Lys Lys Asn Tyr His Met Tyr Val Tyr Pro Val
            580                 585                 590
His Trp Gln Phe Ser Glu Leu Asp Gln His Pro Met Asp Arg Val Leu
        595                 600                 605
Thr His Ser Glu Leu Ala Pro Leu Arg Ala Ser Leu Val Pro Met Glu
    610                 615                 620
His Cys Ile Thr Arg Phe Phe Glu Glu Cys Asp Pro Asn Lys Asp Lys
625                 630                 635                 640
His Ile Thr Leu Lys Glu Trp Gly His Cys Phe Gly Ile Lys Glu Glu
                645                 650                 655
```

Asp Ile Asp Glu Asn Leu Leu Phe
              660

<210> SEQ ID NO 25
<211> LENGTH: 2645
<212> TYPE: DNA
<213> ORGANISM: Homo sapiens

<400> SEQUENCE: 25

| | | | | |
|---|---|---|---|---|
| gagcagcaga | atttcaactc | cagtagactt | gaatatgcct | ctgggcaaag | aagcagagct | 60 |
| aacgaggaaa | gggatttaaa | gagttttcct | tgggtgtttg | tcaaacttt | attccctgtc | 120 |
| tgtgtgcaga | ggggattcaa | cttcaatttt | tctgcagtgg | ctctgagtcc | agccccttac | 180 |
| ttaaagatct | ggaaagcatg | aagactgggc | ttttttcct | atgtctcttg | ggaactgcag | 240 |
| ctgcaatccc | gacaaatgca | agattattat | ctgatcattc | caaccaact | gctgaaacgg | 300 |
| tagcacccga | caacactgca | atccccagtt | taagggctga | agatgaagaa | atgaaaaag | 360 |
| aaacagcagt | atccacagaa | gacgattccc | accataaggc | tgaaaaatca | tcagtactaa | 420 |
| agtcaaaaga | ggaaagccat | gaacagtcag | cagaacaggg | caagagttct | agccaagagc | 480 |
| tgggattgaa | ggatcaagag | gacagtgatg | gtgacttaag | tgtgaatttg | gagtatgcac | 540 |
| catctgaagg | tacattggac | ataaaagaag | atatgagtga | gcctcaggag | aaaaaactct | 600 |
| cagagaacac | tgatttttg | gctcctggtg | ttagttcctt | cacagattct | aaccaacaag | 660 |
| aaagtatcac | aaagagagag | gaaaaccaag | aacaacctag | aaattattca | catcatcagt | 720 |
| tgaacaggag | cagtaaacat | agccaaggcc | taagggatca | aggaaaccaa | gagcaggatc | 780 |
| caaatattc | caatggagaa | gaggaagaag | aaaagagcc | aggtgaagtt | ggtacccaca | 840 |
| atgataacca | agaagaaag | acagaattgc | ccagggagca | tgctaacagc | aagcaggagg | 900 |
| aagacaatac | ccaatctgat | gatattttgg | aagagtctga | tcaaccaact | caagtaagca | 960 |
| agatgcagga | ggatgaattt | gatcagggta | ccaagaacaa | agaagataac | tccaatgcag | 1020 |
| aaatggaaga | ggaaaatgca | tcgaacgtca | ataagcacat | tcaagaaact | gaatggcaga | 1080 |
| gtcaagaggg | taaaactggc | ctagaagcta | tcagcaacca | caagagaca | gaagaaaaga | 1140 |
| ctgtttctga | ggctctgctc | atggaaccta | ctgatgatgg | taataccacg | cccagaaatc | 1200 |
| atggagttga | tgatgatggc | gatgatgatg | gcgatgatgg | cggcactgat | ggccccaggc | 1260 |
| acagtgcaag | tgatgactac | ttcatcccaa | gccaggcctt | tctggaggcc | gagagagctc | 1320 |
| aatccattgc | ctatcacctc | aaaattgagg | agcaaagaga | aaaagtacat | gaaaatgaaa | 1380 |
| atataggtac | cactgagcct | ggagagcacc | aagaggccaa | gaaagcagag | aactcatcaa | 1440 |
| atgaggagga | aacgtcaagt | gaaggcaaca | tgagggtgca | tgctgtggat | tcttgcatga | 1500 |
| gcttccagtg | taaaagaggc | cacatctgta | aggcagacca | acagggaaaa | cctcactgtg | 1560 |
| tctgccagga | tccagtgact | tgtcctccaa | caaaacccct | tgatcaagtt | tgtggcactg | 1620 |
| acaatcagac | ctatgctagt | tcctgtcatc | tattcgctac | taaatgcaga | ctggagggga | 1680 |
| ccaaaaaggg | gcatcaactc | cagctggatt | attttggagc | ctgcaaatct | attcctactt | 1740 |
| gtacggactt | tgaagtgatt | cagtttcctc | tacggatgag | agactggctc | aagaatatcc | 1800 |
| tcatgcagct | ttatgaagcc | aactctgaac | acgctggtta | tctaaatgag | aagcagagaa | 1860 |
| ataaagtcaa | gaaatttac | ctggatgaaa | agaggctttt | ggctggggac | catcccattg | 1920 |
| accttctctt | aagggacttt | aagaaaaact | accacatgta | tgtgtatcct | gtgcactggc | 1980 |
| agtttagtga | acttgaccaa | cacccctatgg | atagagtctt | gacacattct | gaacttgctc | 2040 |

```
ctctgcgagc atctctggtg cccatggaac actgcataac ccgtttcttt gaggagtgtg    2100 acccccaacaa ggataagcac atcaccctga aggagtgggg ccactgcttt ggaattaaag    2160
aagaggacat agatgaaaat ctcttgtttt gaacgaagat tttaaagaac tcaactttcc    2220
agcatcctcc tctgttctaa ccacttcaga aatatatgca gctgtgatac ttgtagattt    2280
atatttagca aaatgttagc atgtatgaca agacaatgag agtaattgct tgacaacaac    2340
ctatgcacca ggtatttaac attaactttg aaacaaaaa tgtacaatta agtaaagtca    2400
acatatgcaa aatactgtac attgtgaaca gaagtttaat tcatagtaat ttcactctct    2460
gcattgactt atgagataat taatgattaa actattaatg ataaaaataa tgcatttgta    2520
ttgttcataa tatcatgtgc acttcaagaa aatggaatgc tactcttttg tggtttacgt    2580
gtattatttt caatatctta ataccctaat aaagagtcca taaaaatcca aaaaaaaaa    2640 aaaaa                                                                2645
```

<210> SEQ ID NO 26
<211> LENGTH: 664
<212> TYPE: PRT
<213> ORGANISM: Homo sapiens

<400> SEQUENCE: 26

```
Met Lys Thr Gly Pro Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
```

```
                    260                 265                 270
Asn Ala Glu Met Glu Glu Asn Ala Ser Asn Val Asn Lys His Ile
            275                 280                 285
Gln Glu Thr Glu Trp Gln Ser Gln Gly Lys Thr Gly Leu Glu Ala
            290                 295                 300
Ile Ser Asn His Lys Glu Thr Glu Lys Thr Val Ser Glu Ala Leu
305                 310                 315                 320
Leu Met Glu Pro Thr Asp Asp Gly Asn Thr Thr Pro Arg Asn His Gly
            325                 330                 335
Val Asp Asp Asp Gly Asp Asp Gly Asp Gly Gly Thr Asp Gly
            340                 345                 350
Pro Arg His Ser Ala Ser Asp Asp Tyr Phe Ile Pro Ser Gln Ala Phe
            355                 360                 365
Leu Glu Ala Glu Arg Ala Gln Ser Ile Ala Tyr His Leu Lys Ile Glu
            370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
            405                 410                 415
Glu Glu Thr Ser Ser Glu Gly Asn Met Arg Val His Ala Val Asp Ser
            420                 425                 430
Cys Met Ser Phe Gln Cys Lys Arg Gly His Ile Cys Lys Ala Asp Gln
            435                 440                 445
Gln Gly Lys Pro His Cys Val Cys Gln Asp Pro Val Thr Cys Pro Pro
            450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                485                 490                 495
Lys Gly His Gln Leu Gln Leu Asp Tyr Phe Gly Ala Cys Lys Ser Ile
            500                 505                 510
Pro Thr Cys Thr Asp Phe Glu Val Ile Gln Phe Pro Leu Arg Met Arg
            515                 520                 525
Asp Trp Leu Lys Asn Ile Leu Met Gln Leu Tyr Glu Ala Asn Ser Glu
            530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                565                 570                 575
Leu Leu Arg Asp Phe Lys Lys Asn Tyr His Met Tyr Val Tyr Pro Val
            580                 585                 590
His Trp Gln Phe Ser Glu Leu Asp Gln His Pro Met Asp Arg Val Leu
            595                 600                 605
Thr His Ser Glu Leu Ala Pro Leu Arg Ala Ser Leu Val Pro Met Glu
            610                 615                 620
His Cys Ile Thr Arg Phe Phe Glu Glu Cys Asp Pro Asn Lys Asp Lys
625                 630                 635                 640
His Ile Thr Leu Lys Glu Trp Gly His Cys Phe Gly Ile Lys Glu Glu
                645                 650                 655
Asp Ile Asp Glu Asn Leu Leu Phe
            660

<210> SEQ ID NO 27
```

<211> LENGTH: 2808
<212> TYPE: DNA
<213> ORGANISM: Homo sapiens

<400> SEQUENCE: 27

```
cggcatgaga ggccagcctg ccagggaaat ccaggaatct gcaacaaaaa cgatgacagt      60
ctgaaatact ctctggtgcc aacctccaaa ttctcgtctg tcacttcaga cccccactag     120
ttgacagagc agcagaatat caactccagt agacttgaat gtgcctctgg gcaaagaagc     180
agagctaacg aggaaaggga tttaaagagt ttttcttggg tgtttgtcaa acttttattc     240
cctgtctgtg tgcagagggg attcaacttc aattttctgc agtggctctg ggtccagccc     300
cttacttaaa gatctggaaa gcatgaagac tgggccttt t ttcctatgtc tcttgggaac     360
tgcagctgca atcccgacaa atgcaagatt attatctgat cattccaaac caactgctga     420
aacggtagca cctgacaaca ctgcaatccc cagtttatgg gctgaagctg aagaaaatga     480
aaagaaaca gcagtatcca cagaagacga ttcccaccat aaggctgaaa aatcatcagt     540
actaaagtca aagaggaaa gccatgaaca gtcagcagaa cagggcaaga gttctagcca     600
agagctggga ttgaaggatc aagaggacag tgatggtcac ttaagtgtga atttggagta     660
tgcaccaact gaaggtacat tggacataaa agaagatatg attgagcctc aggagaaaaa     720
actctcagag aacactgatt ttttggctcc tggtgttagt tccttcacag attctaacca     780
acaagaaagt atcacaaaga gagaggaaaa ccaagaacaa cctagaaatt attcacatca     840
tcagttgaac aggagcagta acatagcca aggcctaagg gatcaaggaa accaagagca     900
ggatccaaat atttccaatg gagaagagga agaagaaaaa gagccaggtg aagttggtac     960
ccacaatgat aaccaagaaa gaagacaga attgcccagg gagcatgcta acagcaagca    1020
ggaggaagac aatacccaat ctgatgatat tttggaagag tctgatcaac caactcaagt    1080
aagcaagatg caggaggatg aatttgatca gggtaaccaa gaacaagaag ataactccaa    1140
tgcagaaatg gaagaggaaa atgcatcgaa cgtcaataag cacattcaag aaactgaatg    1200
gcagagtcaa gagggtaaaa ctggcctaga agctatcagc aaccacaaag agacagaaga    1260
aaagactgtt tctgaggctc tgctcatgga acctactgat gatggtaata ccacgcccag    1320
aaatcatgga gttgatgatg atggcgatga tgatggcgat gatggcggca ctgatggccc    1380
caggcacagt gcaagtgatg actacttcat cccaagccag gcctttctgg aggccgagag    1440
agctcaatcc attgcctatc acctcaaaat tgaggagcaa agagaaaag tacatgaaaa    1500
tgaaaatata ggtaccactg agcctggaga gcaccaagag gccaagaaag cagagaactc    1560
atcaaatgag gaggaaacgt caagtgaagg caacatgagg gtgcatgctg tggattcttg    1620
catgagcttc cagtgtaaaa gaggccacat ctgtaaggca gaccaacagg gaaaacctca    1680
ctgtgtctgc caggatccag tgacttgtcc tccaacaaaa ccccttgatc aagtttgtgg    1740
cactgacaat cagacctatg ctagttcctg tcatctattc gctactaaat gcagactgga    1800
ggggaccaaa aagggcatc aactccagct ggattatttt ggagcctgca atctattcc     1860
tacttgtacg gactttgaag tgattcagtt tcctctacgg atgagagact ggctcaagaa    1920
tatcctcatg cagctttatg aagccaactc tgaacatgct ggttatctaa atgagaagca    1980
gagaaataaa gtcaagaaaa tttacctgga tgaaaagagg cttttggctg gggaccatcc    2040
cattgatctt ctcttaaggg actttaagaa aaactaccac atgtatgtgt atcctgtgca    2100
ctggcagttt agtgaacttg accaacaccc tatggataga gtcttgacac attctgaact    2160
tgctcctctg cgagcatctc tggtgcccat ggaacactgc ataacccgtt tctttgagga    2220
```

```
gtgtgacccc aacaaggata agcacatcac cctgaaggag tggggccact gctttggaat    2280
taaagaagag gacatagatg aaaatctctt gttttgaacg aagattttaa agaactcaac    2340
tttccagcat cctcctctgt tctaaccact tcagaaatat atgcagctgt gatacttgta    2400
gatttatatt tagcaaaatg ttagcatgta tgacaagaca atgagagtaa ttgcttgaca    2460
acaacctatg caccaggtat ttaacattaa ctttggaaac aaaaatgtac aattaagtaa    2520
agtcaacata tgcaaaatac tgtacattgt gaacagaagt ttaattcata gtaatttcac    2580
tctctgcatt gacttatgag ataattaatg attaaactat taatgataaa aataatgcat    2640
ttgtattgtt cataatatca tgtgcacttc aagaaaatgg aatgctactc ttttgtggtt    2700
tacgtgtatt attttcaata tcttaatacc ctaataaaga gtccataaaa atccaaaaaa    2760
aaaaaaaaaa aaaaaaaaaa aaaaaaaaaa aaaaaaaaaa aaaaaaaa                2808
```

<210> SEQ ID NO 28
<211> LENGTH: 676
<212> TYPE: PRT
<213> ORGANISM: Coturnix coturnix

<400> SEQUENCE: 28

```
Met Lys Thr Val Leu Leu Ile Cys Leu Leu Gly Ser Ala Phe Thr
1               5                   10                  15

Thr Pro Thr Asp Pro Leu Asn Tyr Gln Phe Gly Ala His Gly Gln Lys
            20                  25                  30

Thr Ala Glu Lys His Lys Tyr Thr His Ser Glu Met Pro Glu Glu Glu
        35                  40                  45

Asn Thr Gly Phe Val Asn Lys Gly Asp Val Leu Ser Gly His Arg Thr
    50                  55                  60

Ile Lys Ala Glu Val Pro Val Leu Asp Thr Gln Lys Asp Glu Pro Trp
65                  70                  75                  80

Ala Ser Arg Arg Gln Gly Gln Gly Asp Gly Glu His Gln Thr Lys Asn
                85                  90                  95

Ser Leu Arg Ser Ile Asn Phe Leu Thr Leu His Ser Asn Pro Gly Leu
            100                 105                 110

Ala Ser Asp Asn Gln Glu Ser Asn Ser Gly Ser Ser Arg Glu Gln His
        115                 120                 125

Ser Ser Glu His His Gln Pro Arg Arg His Arg Lys His Gly Asn Met
    130                 135                 140

Ala Gly Gln Trp Ala Leu Arg Gly Glu Ser Pro Val Asp Ala Leu Gly
145                 150                 155                 160

Leu Val Arg Glu Arg Asn Thr Trp Lys Tyr Asn Lys Asn Thr Val Gly
                165                 170                 175

Leu Asp Glu Asn Asn Asn Gly Ser Glu Glu Glu Ala Gly Glu Glu
            180                 185                 190

Glu Asp Glu Glu Trp Gly Glu Glu Thr Asp Tyr Arg Asp Met Lys His
        195                 200                 205

Arg Ala Arg Gly Thr Ser His Gly Arg Glu Tyr Arg Arg Trp Gln Asn
    210                 215                 220

Glu Asn Ser Arg Pro Ser Gly Glu Phe Leu Arg Asp Ser Ser Leu Pro
225                 230                 235                 240

Val Arg Ile Thr Lys Arg His Gly Glu Lys Phe Ser Met Glu Glu Glu
                245                 250                 255

Ser Gln Glu Lys Leu Tyr Lys Glu Gly Lys Leu Pro Leu Ser Lys Lys
            260                 265                 270
```

-continued

```
Asn His Asn Glu Asp Gln Gly Glu Lys Arg Gln Ser Glu Ser Lys
        275                 280                 285
Glu His Phe Gln Val Val Asn Gln Arg Lys His Arg Ala Val Thr Lys
    290                 295                 300
Arg Gln Asp Lys Glu Gly Ser Asn Ala Glu Asp Asp Asn Asp Ser
305                 310                 315                 320
Gly Asp Asp Gly Glu Glu Asp Leu Gly Asn Val Trp Arg Glu Ala Val
                325                 330                 335
Tyr Glu Glu Glu Arg Met Gln Ser Asn Asp Gln Asp Ser Ile Thr
            340                 345                 350
Asn Lys Gln Lys Glu Glu Ile Thr Ala Gly Asp Asp Ser Gly Val Tyr
        355                 360                 365
Arg Glu Met Gln Asp Tyr Lys Gly Asp Lys Ile Lys Asp Val Thr His
    370                 375                 380
Ser Glu Asp Asn His Tyr His His Glu Pro Pro Asn Ser Ser Ser Lys
385                 390                 395                 400
Gln Gln Leu Gln Thr Ser Ser Ser Val Glu Ser Met Asn Ser Thr Glu
            405                 410                 415
His Glu Asp Glu Val Lys Thr Thr Gly Gly Ser Tyr His Glu Glu Ser
        420                 425                 430
Ala Arg Asn Ser Thr Gly Lys Ala Leu Pro Asp Leu Cys Arg Asn Phe
    435                 440                 445
His Cys Lys Arg Gly Lys Val Cys Gln Ala Asp Lys Gln Gly Lys Pro
450                 455                 460
Ser Cys Ile Cys Gln Asp Pro Ala Ala Cys Pro Ser Thr Lys Asp Tyr
465                 470                 475                 480
Lys Arg Val Cys Gly Thr Asp Asn Lys Thr Tyr Asp Gly Thr Cys Gln
                485                 490                 495
Leu Phe Gly Thr Lys Cys Gln Leu Glu Gly Thr Lys Met Gly Arg Gln
            500                 505                 510
Leu His Leu Asp Tyr Met Gly Ala Cys Lys His Ile Pro His Cys Thr
        515                 520                 525
Asp Tyr Glu Val Asn Gln Phe Pro Leu Arg Met Arg Asp Trp Leu Lys
    530                 535                 540
Asn Ile Leu Met Gln Tyr Tyr Glu Arg Asp Gln Asp Thr Ser Ala Phe
545                 550                 555                 560
Leu Thr Glu Lys Gln Arg Asn Lys Val Lys Lys Ile Tyr Leu Asn Glu
                565                 570                 575
Lys Arg Leu Val Ser Gly Glu His Pro Val Glu Leu Leu His Asp
            580                 585                 590
Phe Glu Lys Asn Tyr His Met Tyr Leu Tyr Pro Val His Trp Gln Phe
        595                 600                 605
Tyr Gln Leu Asp Gln His Pro Val Asp Arg Ser Leu Thr His Ser Glu
    610                 615                 620
Leu Ala Pro Leu Arg Ala Ser Leu Val Pro Met Glu His Cys Ile Thr
625                 630                 635                 640
Arg Phe Phe Gln Glu Cys Asp Gly Asp Gln Asp Lys Leu Ile Thr Leu
                645                 650                 655
Lys Glu Trp Cys His Cys Phe Ala Ile Lys Glu Glu Asp Ile Asn Glu
            660                 665                 670
Asn Leu Leu Phe
        675
```

<210> SEQ ID NO 29
<211> LENGTH: 676
<212> TYPE: PRT
<213> ORGANISM: Coturnix coturnix

<400> SEQUENCE: 29

```
Met Lys Thr Val Leu Leu Ile Cys Leu Leu Gly Ser Ala Phe Thr
1               5                   10                  15

Thr Pro Thr Asp Pro Leu Asn Tyr Gln Phe Gly Ala His Gly Gln Lys
            20                  25                  30

Thr Ala Glu Lys His Lys Tyr Thr His Ser Glu Met Pro Glu Glu Glu
        35                  40                  45

Asn Thr Gly Phe Val Asn Lys Gly Asp Val Leu Ser Gly His Arg Thr
    50                  55                  60

Ile Lys Ala Glu Val Pro Val Leu Asp Thr Gln Lys Asp Glu Pro Trp
65                  70                  75                  80

Ala Ser Arg Arg Gln Gly Gln Gly Asp Gly Glu His Gln Thr Lys Asn
                85                  90                  95

Ser Leu Arg Ser Ile Asn Phe Leu Thr Leu His Ser Asn Pro Gly Leu
            100                 105                 110

Ala Ser Asp Asn Gln Glu Ser Asn Ser Gly Ser Ser Arg Glu Gln His
        115                 120                 125

Ser Ser Glu His His Gln Pro Arg Arg His Arg Lys His Gly Asn Met
    130                 135                 140

Ala Gly Gln Trp Ala Leu Arg Gly Glu Ser Pro Val Asp Ala Leu Gly
145                 150                 155                 160

Leu Val Arg Glu Arg Asn Thr Trp Lys Tyr Asn Lys Asn Thr Val Gly
                165                 170                 175

Leu Asp Glu Asn Asn Asn Gly Ser Glu Glu Glu Ala Gly Glu Glu
            180                 185                 190

Glu Asp Glu Glu Trp Gly Glu Glu Thr Asp Tyr Arg Asp Met Lys His
        195                 200                 205

Arg Ala Arg Gly Thr Ser His Gly Arg Glu Tyr Arg Arg Trp Gln Asn
    210                 215                 220

Glu Asn Ser Arg Pro Ser Gly Glu Phe Leu Arg Asp Ser Ser Leu Pro
225                 230                 235                 240

Val Arg Ile Thr Lys Arg His Gly Glu Lys Phe Ser Met Glu Glu Glu
                245                 250                 255

Ser Gln Glu Lys Leu Tyr Lys Glu Gly Lys Leu Pro Leu Ser Lys Lys
            260                 265                 270

Asn His Asn Glu Asp Gln Gly Glu Lys Arg Gln Ser Glu Glu Ser Lys
        275                 280                 285

Glu His Phe Gln Val Val Asn Gln Arg Lys His Arg Ala Val Thr Lys
    290                 295                 300

Arg Gln Asp Lys Glu Gly Ser Asn Ala Glu Glu Asp Asp Asn Asp Ser
305                 310                 315                 320

Gly Asp Asp Gly Glu Glu Asp Leu Gly Asn Val Trp Arg Glu Ala Val
                325                 330                 335

Tyr Glu Glu Glu Arg Met Gln Ser Asn Asp Gln Asp Ser Ile Thr
            340                 345                 350

Asn Lys Gln Lys Glu Glu Ile Thr Ala Gly Asp Asp Ser Gly Val Tyr
        355                 360                 365

Arg Glu Met Gln Asp Tyr Lys Gly Asp Lys Ile Lys Asp Val Thr His
    370                 375                 380
```

```
Ser Glu Asp Asn His Tyr His His Glu Pro Pro Asn Ser Ser Ser Lys
385                 390                 395                 400

Gln Gln Leu Gln Thr Ser Ser Val Glu Ser Met Asn Ser Thr Glu
            405                 410                 415

His Glu Asp Glu Val Lys Thr Thr Gly Gly Ser Tyr His Glu Ser
            420                 425                 430

Ala Arg Asn Ser Thr Gly Lys Ala Leu Pro Asp Leu Cys Arg Asn Phe
            435                 440                 445

His Cys Lys Arg Gly Lys Val Cys Gln Ala Asp Lys Gln Gly Lys Pro
        450                 455                 460

Ser Cys Ile Cys Gln Asp Pro Ala Ala Cys Pro Ser Thr Lys Asp Tyr
465                 470                 475                 480

Lys Arg Val Cys Gly Thr Asp Asn Lys Thr Tyr Asp Gly Thr Cys Gln
            485                 490                 495

Leu Phe Gly Thr Lys Cys Gln Leu Glu Gly Thr Lys Met Gly Arg Gln
            500                 505                 510

Leu His Leu Asp Tyr Met Gly Ala Cys Lys His Ile Pro His Cys Thr
        515                 520                 525

Asp Tyr Glu Val Asn Gln Phe Pro Leu Arg Met Arg Asp Trp Leu Lys
530                 535                 540

Asn Ile Leu Met Gln Tyr Tyr Glu Arg Asp Gly Asp Thr Ser Ala Phe
545                 550                 555                 560

Leu Thr Glu Lys Gln Arg Asn Lys Val Lys Lys Ile Tyr Leu Asn Glu
            565                 570                 575

Lys Arg Leu Val Ser Gly Glu His Pro Val Glu Leu Leu His Asp
            580                 585                 590

Phe Glu Lys Asn Tyr His Met Tyr Leu Tyr Pro Val His Trp Gln Phe
            595                 600                 605

Tyr Gln Leu Asp Gln His Pro Val Asp Arg Ser Leu Thr His Ser Glu
            610                 615                 620

Leu Ala Pro Leu Arg Ala Ser Leu Val Pro Met Glu His Cys Ile Thr
625                 630                 635                 640

Arg Phe Phe Gln Glu Cys Asp Gly Asp Gln Asp Lys Leu Ile Thr Leu
            645                 650                 655

Lys Glu Trp Cys His Cys Phe Ala Ile Lys Glu Glu Asp Ile Asn Glu
            660                 665                 670

Asn Leu Leu Phe
        675

<210> SEQ ID NO 30
<211> LENGTH: 2678
<212> TYPE: DNA
<213> ORGANISM: Coturnix coturnix

<400> SEQUENCE: 30
gtcagacctt cctcctcaga agctcacaga aaaacacgct ttctgaaaga ttccacactc      60
aatgccaaaa ataccacag gaaaattttg caaggctcac ggattccag tgcaccactg       120 gctaaccaag taggagcacc tcttctactg ccatgaaagg aaaccttcaa accctaccac    180
tgagccatta actaccatcc tgtttaagat ctgaaaaaca tgaagactgt attgctcctg    240
atttgtcttc taggatctgc tttcaccact ccaaccgatc cattgaacta ccaatttggg    300
gcccatggac agaaaactgc agagaagcat aaatatactc attctgaaat gccagaggaa    360
gagaacacag ggtttgtaaa caaaggtgat gtgctgtctg gccacaggac cataaaagca    420
```

-continued

```
gaggtaccgg tactggatac acagaaggat gagccctggg cttccagaag acaaggacaa      480
ggtgatggtg agcatcaaac aaaaaacagc ctgaggagca ttaacttcct tactctgcac      540
agtaatccag ggttggcttc tgataaccag gaaagcaact ctggcagcag cagggaacag      600
cacagctctg agcaccacca gcccaggagg cacaggaaac acggcaacat ggctggccag      660
tgggctctga gaggagaaag tccagtggat gctcttggtc tggttcgtga gcgcaacaca      720
tggaaataca ataaaaacac agttggccta gatgaaaaca caatggaagt gaagaagag       780 gaagctgggg aggaagaaga tgaggaatgg ggtgaagaaa ctgattacag ggatatgaaa      840
cacagagccc gtgggacaag ccatggaaga gaatacagaa gatggcaaaa tgaaaacagc      900
cggccatctg gtgaattctt gagagattcc agtctgccag tacgtataac caagagacac      960
ggtgagaaat tcagcatgga ggaggaaagt caggaaaagc tctacaagga aggaaaactc     1020
cctctctcaa agaaaaatca taatgaggat caaggtgaaa aaagacaaag tgaagaaagt     1080
aaagagcatt ttcaagtagt caatcagcgc aaacacagag cagtgacgaa aaggcaggat     1140
aaggagggca gcaatgctga ggaggatgat aatgatagtg gtgatgatgg tgaggaagat     1200
cttggcaatg tctggaggga agcagtctac gaggaagagg aaagaatgca aagcaatgac     1260
caggacagta tcactaacaa gcaaaaagag gaaataactg ctggagatga cagtggagtt     1320
tatagggaga tgcaggatta caaggtgac aaaaattaaag atgttactca ctctgaagac     1380
aatcattacc accatgagcc ccctaattcc agcagcaagc aacaactgca acaagtagc      1440 tctgttgaga gcatgaattc aacagagcat gaggatgagg ttaagaccac aggaggttca     1500
tatcatgagg aaagtgcaag gaacagcact gggaaggctc tcccggatct tgtagaaac     1560 ttccactgca aaagaggaaa agtctgccaa gcagacaagc aaggaaaacc cagctgtatt    1620
tgccaagatc ctgctgcttg cccttccacc aaagattata agcgtgtttg tggcactgat     1680
aataagactt acgatggtac gtgccaactc tttggcacca aatgtcaact tgaagggaca    1740
aaaatgggac gccagctgca cctggactat atgggtgcct gcaaacacat accccactgt    1800
actgattacg aagtgaatca gttccctctc cgtatgagag actggctcaa aaacatccta   1860
atgcaatatt atgaacgtga tcaggatacg tctgcatttc taaccgaaaa gcaaaggaat    1920
aaggtcaaaa agatatacct gaatgagaag cgtctcgtct ctggtgagca cccagttgag    1980
cttctcctgc atgactttga gaaaaactac cacatgtatc tctatcctgt gcactggcaa    2040
ttttatcagc ttgaccagca cccagttgac agatcactga ctcattcaga gctcgctcct    2100
ttgagagcct ccctcgttcc catggaacac tgcataaccc gtttcttcca ggagtgtgat   2160
ggagaccaag acaaacttat cactttgaaa gagtggtgcc actgctttgc gattaaggaa   2220
gaagacataa atgaaaatct cctgttctga gcccacctga gcagaatccc catgcagcgc    2280
tacagcttgt caaacatgca atgcccattt atgactgcaa ttaacagctc tgttaatttt   2340
caggaataag ttggcataag attcttggag gcagaacaag tcgctcttgg ataacacaag    2400
tgcctaattg ttacaaattc attaacagca gtagtgttta agagctctaa gtagctcata   2460
cttaaagagt gtttccctct gcacgtacca ataatctctt agtaagacga ctaacttgat    2520
gactgagttg ttcacaaaac ccttccgtag aattatagga tgtggatttt ataatacacc    2580
gataaaaact actttgaaat aggttttctt ttcctgtcgt ttactgtcag tagctctctg    2640
catagaaatg tcaaataaac agatcttgtt ttggttc                            2678
```

<210> SEQ ID NO 31

<211> LENGTH: 306
<212> TYPE: PRT
<213> ORGANISM: Mus musculus

<400> SEQUENCE: 31

Met Trp Lys Arg Trp Leu Ala Leu Ser Leu Val Thr Ile Ala Leu Val
1               5                   10                  15
His Gly Glu Glu Glu Pro Arg Ser Lys Ser Lys Ile Cys Ala Asn Val
            20                  25                  30
Phe Cys Gly Ala Gly Arg Glu Cys Ala Val Thr Glu Lys Gly Glu Pro
        35                  40                  45
Thr Cys Leu Cys Ile Glu Gln Cys Lys Pro His Lys Arg Pro Val Cys
    50                  55                  60
Gly Ser Asn Gly Lys Thr Tyr Leu Asn His Cys Glu Leu His Arg Asp
65                  70                  75                  80
Ala Cys Leu Thr Gly Ser Lys Ile Gln Val Asp Tyr Asp Gly His Cys
                85                  90                  95
Lys Glu Lys Lys Ser Ala Ser Pro Ser Ala Ser Pro Val Val Cys Tyr
            100                 105                 110
Gln Ala Asn Arg Asp Glu Leu Arg Arg Arg Leu Ile Gln Trp Leu Glu
        115                 120                 125
Ala Glu Ile Ile Pro Asp Gly Trp Phe Ser Lys Gly Ser Asn Tyr Ser
    130                 135                 140
Glu Ile Leu Asp Lys Tyr Phe Lys Ser Phe Asp Asn Gly Asp Ser His
145                 150                 155                 160
Leu Asp Ser Ser Glu Phe Leu Lys Phe Val Glu Gln Asn Glu Thr Ala
                165                 170                 175
Ile Asn Ile Thr Thr Tyr Ala Asp Gln Glu Asn Asn Lys Leu Leu Arg
            180                 185                 190
Ser Leu Cys Val Asp Ala Leu Ile Glu Leu Ser Asp Glu Asn Ala Asp
        195                 200                 205
Trp Lys Leu Ser Phe Gln Glu Phe Leu Lys Cys Leu Asn Pro Ser Phe
    210                 215                 220
Asn Pro Pro Glu Lys Lys Cys Ala Leu Glu Asp Glu Thr Tyr Ala Asp
225                 230                 235                 240
Gly Ala Glu Thr Glu Val Asp Cys Asn Arg Cys Val Cys Ser Cys Gly
                245                 250                 255
His Trp Val Cys Thr Ala Met Thr Cys Asp Gly Lys Asn Gln Lys Gly
            260                 265                 270
Val Gln Thr His Thr Glu Glu Lys Thr Gly Tyr Val Gln Glu Leu
        275                 280                 285
Gln Lys His Gln Gly Thr Ala Leu Lys Thr Lys Val Asn Thr Lys
    290                 295                 300
Glu Ile
305

<210> SEQ ID NO 32
<211> LENGTH: 3610
<212> TYPE: DNA
<213> ORGANISM: Mus musculus

<400> SEQUENCE: 32
gttcctcgga gcctggtgat aagcgacgct cccaccttcg cctctaactc gctgccgcca      60
ccctgcccag tgtcctccgg agtcccggac ccgagcacga tgtggaaacg atggctggcg     120
ctctcgctgg tgaccatcgc cctggtccac ggcgaggagg aacctagaag caaatccaag     180

```
atctgcgcca atgtgttttg tggagctggc agggaatgtg ccgtcacaga aaggggggag      240
cccacgtgcc tctgcattga gcaatgcaaa cctcacaaga ggcctgtgtg tggcagtaat      300
ggcaagacct acctcaacca ctgtgaactt catagagatg cctgcctcac tggatccaag      360
atccaggttg attatgatgg gcactgcaaa gaaaagaagt ctgcgagtcc atctgccagc      420
ccagttgtct gctatcaagc taaccgcgat gagctccgac ggcgcctcat ccagtggctg      480
gaagctgaga tcattccaga tggctggttc tctaaaggca gtaactacag tgagatccta      540
gacaagtact ttaagagctt tgataatggc gactctcacc tggactccag tgaattcctg      600
aaattcgtgg agcagaatga aacagccatc aacatcacca cttatgcaga tcaggagaac      660
aacaaactgc tcagaagcct ctgtgttgac gccctcattg aactgtctga tgagaacgct      720
gactggaaac tcagcttcca agagttcctc aagtgcctca cccatccctt caaccctcct      780
gagaagaagt gtgccctgga ggacgaaacc tatgcagatg agctgagac tgaggtggac       840 tgcaatcgct gtgtctgttc ctgtggccac tgggtctgca cagcaatgac ctgtgatgga      900
aagaatcaga aggggtccga cccacacaga aggaggaga agacaggata tgtccaggaa        960
ctccagaagc accagggcac agcagaaaag accaagaagg tgaacaccaa agagatctaa     1020
gaagaggcac agagcaccgt gtccggagcc cagcgcctcc tcttcagcgc tgagcccagt     1080
acacacagag tctgcagcaa tcaccaaatc actagtattt gcttgtatgg cagcgaatct     1140
tattttgttt gtttttgcaat aaaggaaatg agggtggcca gcctagcgag gaaggccac     1200 aaccttcacc tgtaggaatg ctttaagaga aactaaagga caccttggga cgagaggcaa     1260
ctaaggaaac agcatcgggt tggcagagga gcagaggcag gtttgaatga agcctttctg     1320
gggtcacagc agctgcgagg agaatacagg aaaagcatag agaaacattg aactagccct     1380
gctggaggaa gtgggggag ctttgtaggg aggaaccctg ctgctttgac ccttgtcacc      1440
actgtcagca tgacagacct gcagcaagtc tgcttctcct tttggtccca acaatcacct     1500
gaacacacag ccgcccaact agttacctgt gtccctcagc cttgcatgga gtttcctgga     1560
ggaggtgttt aaatgatgca gacacttatg tacttcaagc gccatggaga cctaaccaaa     1620 ttttttaaaat acattttttct ttttttttttt ttttgttaac caaaggtgct atttctctgt   1680
aaaagacttt tttccaagct gacttcattc ctcagttatt accgttatat tattgttgtt     1740
ttttaatatt tcatttttttg actagatatt aagcttttgt aattatttttt tcattagtcc   1800 tactatttca gaagtgaagg tgaagggggt ttgggcattt ttccaggtac agggaactct     1860
gtaacacaaa cagcccatac cctgtcacat attagaccgg ttgcagttcg gagctgcacc     1920
ccaacccaga gcttctagaa aatcagctcc atgccacgaa gcacaagagg cccctcagac     1980
agaagccaca ggacaaagca tcttcataga cagctgttga gatccaaaca gttaatttgc     2040 ttttgttttct tgtaagaagt tccaaggatg gacgctcagg ctatcccagc ctgccagcct    2100
gctgtgatct gtggctaact ggcagagtca gccactgtgg tccttagctg ctcctgtttc     2160
taggtgtcag tttacttagt aaactggtaa gaatgaatct tggaatttaa taaatggtag     2220
tttgtggttt agccaactgg tccagaggga gctaccttct ccttaggata gatgaatcta     2280
caccataaga aaaccagcc aggaatagca tggatgggtt ttgctttggt tgaaatgatc      2340
ctagcaggtg actgggtatg aggacttcat ggtcactctg cccaggaaga gagcgtgaag     2400
gacaactagc agcttcctta gggatggtac acatgagtgt gatctctgga gtcagaggtt     2460
tccccacaca catgatgata aaacttttca gatttagagc ggttaaaact ggagatcgaa     2520
```

-continued

```
tctggattga gaatcagcac tgggggagaa actgttattg aaagtcaatc ctttctttga    2580
gcctccgaat aaactatgga gattttcctg cataggaaag tgtggaatgt tgagctattg    2640
agatgggagt ggaattcgtc ctaaatagtt tttcctggtc tcatctgaac aagacaattt    2700
ggctctgcct agtgttctgt gccctccctt tcaaaagctc tgagcccgc tcatgcagtc    2760
cagatttcat cccctctcc aagtgccttg gagagctcac agcagcaatg ccatcatcaa    2820
aagttttgct gctgggaaga aaaaaaaaa aaaaaagaa aaaaaaagt tttgctggtt       2880
cttggaggtg atgggagagg gcaggagtat caatttgttc aagtagctgc agtgtctgtt   2940
ggccaatcat ctttagaacc ctgtaacact gagtaccaga gggcaagccc acattcctct   3000
tctgctactt cagtgtaact agggcagctg ttgtctgaag caccatagat tcaggtgatc   3060
ctccatagat tcaggtgatc ctccatagat tcaggtgatc cttgaaccgt tcatgaaaag   3120
ctgctaagta gcctggtttg ggagacttgg gttgagattt gcatgggacc aacacgcagg   3180
attacatctt cttcagttcc tagagtcctc tagaagccta tagaacaaga cggcaagctc   3240
tctgggcttg ctctggggtt ttgttctgtg gttttatgtt gttcttgttg ttttattaac   3300
atcagtgtct cttaagatcc aggacccagg gaggtctttt cacatacata taccaggact   3360
cttgggtact actgtcagtc ttggggaagc aggctcctcc atcggcaacc aaatccatgt   3420
gagcactccg aatgccttgg ttagtcctat gacctaaata gttaaacttc agaaaatggt   3480
ttcaacagat ttctgtgccg agtggttttg aaattgcatt tgtatttgct gtgcttctgt    3540
attccattta actgggtttt ttgttacttc tgattttgt tactattaat aaataaaaat   3600
aaaataaagt                                                         3610
```

<210> SEQ ID NO 33
<211> LENGTH: 439
<212> TYPE: PRT
<213> ORGANISM: Homo sapiens

<400> SEQUENCE: 33

```
Met Pro Ala Ile Ala Val Leu Ala Ala Ala Ala Ala Trp Cys Phe
1               5                   10                  15

Leu Gln Val Glu Ser Arg His Leu Asp Ala Leu Ala Gly Gly Ala Gly
            20                  25                  30

Pro Asn His Gly Asn Phe Leu Asp Asn Asp Gln Trp Leu Ser Thr Val
        35                  40                  45

Ser Gln Tyr Asp Arg Asp Lys Tyr Trp Asn Arg Phe Arg Asp Asp
    50                  55                  60

Tyr Phe Arg Asn Trp Asn Pro Asn Lys Pro Phe Asp Gln Ala Leu Asp
65                  70                  75                  80

Pro Ser Lys Asp Pro Cys Leu Lys Val Lys Cys Ser Pro His Lys Val
                85                  90                  95

Cys Val Thr Gln Asp Tyr Gln Thr Ala Leu Cys Val Ser Arg Lys His
                100                 105                 110

Leu Leu Pro Arg Gln Lys Lys Gly Asn Val Ala Gln Lys His Trp Val
            115                 120                 125

Gly Pro Ser Asn Leu Val Lys Cys Lys Pro Cys Pro Val Ala Gln Ser
        130                 135                 140

Ala Met Val Cys Gly Ser Asp Gly His Ser Tyr Thr Ser Lys Cys Lys
145                 150                 155                 160

Leu Glu Phe His Ala Cys Ser Thr Gly Lys Ser Leu Ala Thr Leu Cys
                165                 170                 175
```

```
Asp Gly Pro Cys Pro Cys Leu Pro Glu Pro Glu Pro Lys His Lys
            180                 185                 190

Ala Glu Arg Ser Ala Cys Thr Asp Lys Glu Leu Arg Asn Leu Ala Ser
        195                 200                 205

Arg Leu Lys Asp Trp Phe Gly Ala Leu His Glu Asp Ala Asn Arg Val
    210                 215                 220

Ile Lys Pro Thr Ser Ser Asn Thr Ala Gln Gly Arg Phe Asp Thr Ser
225                 230                 235                 240

Ile Leu Pro Ile Cys Lys Asp Ser Leu Gly Trp Met Phe Asn Lys Leu
                245                 250                 255

Asp Met Asn Tyr Asp Leu Leu Leu Asp Pro Ser Glu Ile Asn Ala Ile
            260                 265                 270

Tyr Leu Asp Lys Tyr Glu Pro Cys Ile Lys Pro Leu Phe Asn Ser Cys
        275                 280                 285

Asp Ser Phe Lys Asp Gly Lys Leu Ser Asn Asn Glu Trp Cys Tyr Cys
    290                 295                 300

Phe Gln Lys Pro Gly Gly Leu Pro Cys Gln Asn Glu Met Asn Arg Ile
305                 310                 315                 320

Gln Lys Leu Ser Lys Gly Lys Ser Leu Leu Gly Ala Phe Ile Pro Arg
                325                 330                 335

Cys Asn Glu Glu Gly Tyr Tyr Lys Ala Thr Gln Cys His Gly Ser Thr
            340                 345                 350

Gly Gln Cys Trp Cys Val Asp Lys Tyr Gly Asn Glu Leu Ala Gly Ser
        355                 360                 365

Arg Lys Gln Gly Ala Val Ser Cys Glu Glu Glu Gln Glu Thr Ser Gly
    370                 375                 380

Asp Phe Gly Ser Gly Gly Ser Val Val Leu Leu Asp Asp Leu Glu Tyr
385                 390                 395                 400

Glu Arg Glu Leu Gly Pro Lys Asp Lys Glu Gly Lys Leu Arg Val His
                405                 410                 415

Thr Arg Ala Val Thr Glu Asp Asp Glu Asp Glu Asp Asp Lys Glu
            420                 425                 430

Asp Glu Val Gly Tyr Ile Trp
        435
```

<210> SEQ ID NO 34
<211> LENGTH: 3484
<212> TYPE: DNA
<213> ORGANISM: Homo sapiens

<400> SEQUENCE: 34

```
cactctctgt tgtccaatgg acacacctgt cgtgttttga gccagcgaga gatgcagtgg      60
aagtgaaaag catggttaca gactccccat gcgacagtac actcttctga agtagcggac     120
gcctggttag cttgacattc tatgcaaaga tccataatgt ggttcctgca gatggcacag     180
ttatcaacca caatatccca ggcccagagg ctactgcat  tccactttt cacttcaaag     240
cgcttcttgc ccgcgccgct gttggtgccg ctcggggtat ccacatccat cgctgcgggc     300
tcacaaagcg gccagacgct cggcggcggc gtgtggcagg agcgcagggg cgcgagccgg     360
cgatcagcct tcccggcgac cgtgccgcgg gagctcgagc aactcggact aggggacccg     420
ggccggcccc caagatgccg gcgatcgcgg tgttggcggg gccgccgcg  gcgtggtgct     480
tcctccaagt cgagagccgg cacctggacg cgctcgccgg aggcgcgggc cccaaccacg     540
gcaatttcct agacaatgac cagtggctga gcaccgtctc ccagtacgac cgggacaagt     600
```

```
actggaaccg ctttcgagac gatgattatt tcagaaactg gaatcccaac aagcccttTg      660
accaagccct ggacccatcc aaggacccct gcctgaaggt aaaatgcagc cctcacaaag      720
tgtgtgtgac ccaggactac cagaccgccc tgtgtgtcag ccgcaagcac ctgctcccca      780
ggcaaaagaa ggggaacgtg gcccagaaac actgggttgg accttcgaat ttggtcaagt      840
gcaagccctg tcccgtggca cagtcagcca tggtctgcgg ctcagatggc cactcctaca      900
catccaagtg caaattggag ttccatgctt gttctactgg caaaagcctc gccaccctct      960
gtgatgggcc ctgtccctgt ctcccagagc ctgagccacc aaagcacaag gcagaaagga     1020
gtgcctgcac agacaaggag ttgcggaacc ttgcctcccg gctgaaggat tggtttggag     1080
ctctccacga ggatgcgaac agagtcatca agcccaccag ctccaacaca gcccaaggca     1140
ggtttgacac tagcatcctg cccatctgca aggactccct gggctggatg ttcaacaagt     1200
tggacatgaa ctatgacctc ctgcttgacc cttcagagat caatgccatc tacctggata     1260
agtacgagcc ctgtatcaag cctctttTca actcgtgtga ctccttcaag gatggcaagc     1320
tttctaacaa tgagtggtgc tactgcttcc agaagcctgg aggtctccct gccagaatg      1380 aaatgaacag aattcagaag ctgagtaagg ggaaaagcct gttgggggcc ttcatacctc     1440
ggtgtaatga ggagggctat tacaaagcca cacagtgcca cggcagcacg gggcagtgct     1500
ggtgtgtgga caaatatggg aatgagttgg ctggctccag gaaacagggt gctgtgagct     1560
gtgaagagga gcaggaaacc tcaggggatt ttggcagtgg tgggtccgtg gtcctgctgg     1620
atgacctaga atatgaacgg gagctgggac caaaggacaa agaggggaag ctgagggtgc     1680
acacccgagc cgtgacagag gatgatgagg atgaggatga tgacaaagag gatgaggtcg     1740
ggtacatatg gtagtgccca caagaaagag gacacaagtt ttgcacaaaa ttgcaagtca     1800
cttcctattc ctgcatttgt atctaagact ccaaggcacc aaggtctctt ctccattgtt     1860
gctctctata cccgacctaa ggtttggaag acaactgctt gttcccagag gattctgatt     1920
ttgcatatgt ttgtatggga gaagggtgt tgtgtttttt tttttgttgt tgtttatttt      1980
ttggataggg aagtcattgg cttaattaga gcctccttcc tttctgtgag atttttccaa     2040
caagcatgtg atttacgtgg aattctgaca gtgcagggag ccccccaccct cttaaatgtc    2100 aaagacccct tttgattacc cacactggtg gttattacag catggttccc agccttacag     2160
tgtctaagtg cttctcttgt gtcctgtaga tgttgtgaaa agaaaaaaa caaaaaatac      2220 accacactgt actttttccc cctgcccccg ttactgccgg tgattattat taaaaattag     2280 ttttttttcac atcattctat ctggcttcct ataaacaaca gccttaattc agtcaagact    2340
cccttTggga attcatttta ttaaaaattg gtgtctggat acttccctgt acatgcataa     2400
atatgcatgc atgtacagaa agactgtatg tgtgtgcctt gcacacacac ccataccTct    2460 cagaaaagt gtttgggtat cttaaaaact cgaaaaacaa tgataaattt ctcagcttgt     2520
ccagacctgg aacaaaattt ctggaataag aaatttgtat taaagtcctt ttttgcacta    2580
acagttggct cttgtagcct gcaggctgag gaagtctctt ctctgtgcat cagcagagtt    2640
actgaaagcc tctgattgag aaaaaacctc cgtctgccta aatcacttTt ctcgcagaag    2700
ccatgcgact cccacacgac acgggcagct tcacaagcca tctctttcat ttctgcttga    2760 agcccccttgg ctgcagcaat cctgtctgcc ataggtttct tccttcctta cctactcaag   2820
ggcttttTct aaggcatgca cacatatctc ctgttctctg agagtaccat ggtgttcctt    2880
aaaagaagaa aatttctaat tctgaactca atgttttgct tttactccct ttctactgac    2940
aaatcatgat aagggcacaa aagctgtaca gatttttTtt tttaaccact caatcccaaa   3000
```

-continued

```
tggaggccta caaagaacat cgtaataaca catggaagca aacccgggt ttttaagagc    3060 aaattctgtc ccccctcac tcccccaagt gacaagatac taatgaagaa agttcttcac    3120
catagtgttt gttttaacta aactcattgg agtctagttc caaatttggt agggtcatca    3180
tctctacatt ccttaggatt tctctcccta tcaagctggc ccagatacaa gtaccaaaca    3240
gtagtctctg aagttcccat ttccttcagt accagtctat aagctactgt ccgccactga    3300
ttttcatcta tcagggtgtc ctaatcagaa tcagccaccc aagcaagcct ctctggccca    3360
catatctatc tcttgccttc ccccatgaac ttcagcctgt ccacacaaaa gccacataaa    3420
ctcaagcaag aaatatgttc agccaaaaca tgattatagt ggcagctgac caatacccca    3480
cccc                                                                3484
```

<210> SEQ ID NO 35
<211> LENGTH: 434
<212> TYPE: PRT
<213> ORGANISM: Homo sapiens

<400> SEQUENCE: 35

```
Met Leu Pro Ala Arg Cys Ala Arg Leu Leu Thr Pro His Leu Leu Leu
1               5                   10                  15

Val Leu Val Gln Leu Ser Pro Ala Arg Gly His Arg Thr Thr Gly Pro
                20                  25                  30

Arg Phe Leu Ile Ser Asp Arg Asp Pro Gln Cys Asn Leu His Cys Ser
            35                  40                  45

Arg Thr Gln Pro Lys Pro Ile Cys Ala Ser Asp Gly Arg Ser Tyr Glu
        50                  55                  60

Ser Met Cys Glu Tyr Gln Arg Ala Lys Cys Arg Asp Pro Thr Leu Gly
65                  70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
                165                 170                 175

Asp Gly Ser Lys Pro Thr Pro Thr Met Glu Thr Gln Pro Val Phe Asp
            180                 185                 190

Gly Asp Glu Ile Thr Ala Pro Thr Leu Trp Ile Lys His Leu Val Ile
        195                 200                 205

Lys Asp Ser Lys Leu Asn Asn Thr Asn Ile Arg Asn Ser Glu Lys Val
    210                 215                 220

Tyr Ser Cys Asp Gln Glu Arg Gln Ser Ala Leu Glu Glu Ala Gln Gln
225                 230                 235                 240

Asn Pro Arg Glu Gly Ile Val Ile Pro Glu Cys Ala Pro Gly Gly Leu
                245                 250                 255

Tyr Lys Pro Val Gln Cys His Gln Ser Thr Gly Tyr Cys Trp Cys Val
            260                 265                 270

Leu Val Asp Thr Gly Arg Pro Leu Pro Gly Thr Ser Thr Arg Tyr Val
```

-continued

```
                275                 280                 285
Met Pro Ser Cys Glu Ser Asp Ala Arg Ala Lys Thr Thr Glu Ala Asp
        290                 295                 300

Asp Pro Phe Lys Asp Arg Glu Leu Pro Gly Cys Pro Glu Gly Lys Lys
305                 310                 315                 320

Met Glu Phe Ile Thr Ser Leu Leu Asp Ala Leu Thr Thr Asp Met Val
                325                 330                 335

Gln Ala Ile Asn Ser Ala Ala Pro Thr Gly Gly Arg Phe Ser Glu
            340                 345                 350

Pro Asp Pro Ser His Thr Leu Glu Glu Arg Val Val His Trp Tyr Phe
            355                 360                 365

Ser Gln Leu Asp Ser Asn Ser Ser Asn Asp Ile Asn Lys Arg Glu Met
        370                 375                 380

Lys Pro Phe Lys Arg Tyr Val Lys Lys Ala Lys Pro Lys Lys Cys
385                 390                 395                 400

Ala Arg Arg Phe Thr Asp Tyr Cys Asp Leu Asn Lys Asp Lys Val Ile
                405                 410                 415

Ser Leu Pro Glu Leu Lys Gly Cys Leu Gly Val Ser Lys Glu Gly Arg
            420                 425                 430

Leu Val
```

<210> SEQ ID NO 36
<211> LENGTH: 3669
<212> TYPE: DNA
<213> ORGANISM: Homo sapiens

<400> SEQUENCE: 36

| | | | | | |
|---|---|---|---|---|---|
| gcctgctgcc | gcctgggccc | cgccgagcgg | agctagcgcc | gcgcgcagag | cacacgctcg | 60 |
| cgctccagct | cccctcctgc | gcggttcatg | actgtgtccc | ctgaccgcag | cctctgcgag | 120 |
| ccccgccgc | aggaccacgg | cccgctcccc | gccgccgcga | gggcccccgag | cgaaggaagg | 180 |
| aagggaggcg | cgctgtgcgc | cccgcggagc | ccgcgaaccc | cgctcgctgc | cggctgccca | 240 |
| gcctggctgg | caccatgctg | cccgcgcgct | gcgcccgcct | gctcacgccc | cacttgctgc | 300 |
| tggtgttggt | gcagctgtcc | cctgctcgcg | gccaccgcac | cacaggcccc | aggtttctaa | 360 |
| taagtgaccg | tgacccacag | tgcaacctcc | actgctccag | gactcaaccc | aaacccatct | 420 |
| gtgcctctga | tggcaggtcc | tacgagtcca | tgtgtgagta | ccagcgagcc | aagtgccgag | 480 |
| acccgacccct | gggcgtggtg | catcgaggta | gatgcaaaga | tgctggccag | agcaagtgtc | 540 |
| gcctggagcg | ggctcaagcc | ctggagcaag | ccaagaagcc | tcaggaagct | gtgtttgtcc | 600 |
| cagagtgtgg | cgaggatggc | tcctttaccc | aggtgcagtg | ccatacttac | actgggtact | 660 |
| gctggtgtgt | caccccggat | gggaagccca | tcagtggctc | ttctgtgcag | aataaaactc | 720 |
| ctgtatgttc | aggttcagtc | accgacaagc | ccttgagcca | gggtaactca | ggaaggaaag | 780 |
| atgacgggtc | taagccgaca | cccacgatgg | agacccagcc | ggtgttcgat | ggagatgaaa | 840 |
| tcacagcccc | aactctatgg | attaaacact | tggtgatcaa | ggactccaaa | ctgaacaaca | 900 |
| ccaacataag | aaattcagag | aaagtctatt | cgtgtgacca | ggagaggcag | agtgccctgg | 960 |
| aagaggccca | gcagaatccc | cgtgagggta | ttgtcatccc | tgaatgtgcc | cctgggggac | 1020 |
| tctataagcc | agtgcaatgc | caccagtcca | ctggctactg | ctggtgtgtg | ctggtggaca | 1080 |
| cagggcgccc | gctgcctggg | acctccacac | gctacgtgat | gcccagttgt | gagagcgacg | 1140 |
| ccagggccaa | gactacagag | gcggatgacc | ccttcaagga | cagggagcta | ccaggctgtc | 1200 |

-continued

```
cagaagggaa gaaaatggag tttatcacca gcctactgga tgctctcacc actgacatgg    1260
ttcaggccat taactcagca gcgcccactg gaggtgggag gttctcagag ccagacccca    1320
gccacaccct ggaggagcgg gtagtgcact ggtatttcag ccagctggac agcaatagca    1380
gcaacgacat taacaagcgg gagatgaagc ccttcaagcg ctacgtgaag aagaaagcca    1440
agcccaagaa atgtgcccgg cgtttcaccg actactgtga cctgaacaaa gacaaggtca    1500
tttcactgcc tgagctgaag ggctgcctgg gtgttagcaa agaaggacgc ctcgtctaag    1560
gagcagaaaa cccaagggca ggtggagagt ccagggaggc aggatggatc accagacacc    1620
taaccttcag cgttgcccat ggccctgcca catcccgtgt aacataagtg gtgcccacca    1680
tgtttgcact tttaataact cttacttgcg tgttttgttt ttggtttcat tttaaaacac    1740
caatatctaa taccacagtg ggaaaaggaa agggaagaaa gactttattc tctctcttat    1800
tgtaagtttt tggatctgct actgacaact tttagagggt tttggggggg tggggagggg    1860
tgttgttggg gcctgagaag aaagagattt atatgctgta tataaatata tatgtaaatt    1920
gtatagttct tttgtacagg cattggcatt gctgtttgtt tatttctctc cctctgcctg    1980
ctgtgggtgg tgggcactct ggacacatag tccagctttc taaaatccag gactctatcc    2040
tgggcctact aaacttctgt ttggagactg acccttgtgt ataaagacgg gagtcctgca    2100
attgtactgc ggactccacg agttcttttc tggtgggagg actatattgc cccatgccat    2160
tagttgtcaa aattgataag tcacttggct ctcggccttg tccagggagg ttgggctaag    2220
gagagatgga aactgccctg ggagaggaag ggagtccaga tcccatgaat agcccacaca    2280
ggtaccggct ctcagagggt ccgtgcattc ctgctctccg gacccccaaa gggcccagca    2340
ttggtgggtg caccagtatc ttagtgaccc tcggagcaaa ttatccacaa aggatttgca    2400
ttacgtcact cgaaacgttt tcatccatgc ttagcatcta ctctgtataa cgcatgagag    2460
gggaggcaaa gaagaaaagg acacacggaa gggcctttaa aaaagtagat atttaatatc    2520
taagcagggg aggggacagg acagaaagcc tgcactgagg ggtgcggtgc aacagggaa    2580 actcttcacc tccctgcaaa cctaccagtg aggctcccag agacgcagct gtctcagtgc    2640
ccaggggcag attgggtgtg acctctccac tcctccatct cctgctgttg tcctagtggc    2700
tatcacaggc ctgggtgggt gggttggggg aagtgtcagt caccttgttg gtaacactaa    2760
agttgttttg ttggtttttt aaaaacccaa tactgaggtt cttcctgttc cctcaagttt    2820
tcttatgggc ttccaggctt taagctaatt ccagaagtaa aactgatctt gggtttccta    2880
ttctgcctcc cctagaaggg caggggtgat aacccagcta cagggaaatc ccggcccagc    2940
tttccacagg catcacaggc atcttccgcg gattctaggg tgggctgccc agccttctgg    3000
tctgaggcgc agctccctct gcccaggtgc tgtgcctatt caagtggcct tcaggcagag    3060
cagcaagtgg cccttagcgc cccttcccat aagcagctgt ggtggcagtg agggaggttg    3120
ggtagccctg gactggtccc ctcctcagat caccccttgca aatctggcct catcttgtat    3180
tccaacccga catccctaaa agtacctcca cccgttccgg gtctggaagg cgttggcacc    3240
acaagcactg tccctgtggg aggagcacaa ccttctcggg acaggatctg atggggtctt    3300
gggctaaagg aggtccctgc tgtcctggag aaagtcctag aggttatctc aggaatgact    3360
ggtggccctg ccccaacgtg gaaggtggg aaggaagcct tctcccatta gcccaatga    3420 gagaactcaa cgtgccggag ctgagtgggc cttgcacgag acactggccc cactttcagg    3480
cctggaggaa gcatgcacac atggagacgg cgcctgcctg tagatgtttg gatcttcgag    3540
atctccccag gcatcttgtc tcccacagga tcgtgtgtgt aggtggtgtt gtgtggtttt    3600
```

```
cctttgtgaa ggagagaggg aaactatttg tagcttgttt tataaaaaat aaaaaatggg    3660
taaatcttg                                                            3669
```

<210> SEQ ID NO 37
<211> LENGTH: 263
<212> TYPE: PRT
<213> ORGANISM: Mus musculus

<400> SEQUENCE: 37

```
Met Leu Pro Cys Phe Gln Leu Leu Arg Ile Gly Gly Arg Gly Gly
1               5                   10                  15

Asp Leu Tyr Thr Phe His Pro Pro Ser Lys Ser Gly Cys Thr Tyr Gly
            20                  25                  30

Leu Gly Cys Arg Ala Asp Leu Cys Asp Val Ala Leu Arg Pro Gln Gln
        35                  40                  45

Glu Pro Gly Leu Ile Ser Gly Val His Ala Glu Leu His Ala Glu Leu
    50                  55                  60

Gln Gly Asp Asp Trp Arg Val Ser Leu Glu Asp His Ser Ser Gln Gly
65                  70                  75                  80

Thr Leu Val Asn Asn Val Arg Leu Pro Arg Gly His Arg Leu Glu Leu
                85                  90                  95

Ser Asp Gly Asp Leu Leu Thr Phe Gly Pro Gln Gly Gln Ala Gly Thr
            100                 105                 110

Ser Ser Ser Ser Glu Phe Tyr Phe Met Phe Gln Gln Val Arg Val Lys
        115                 120                 125

Pro Gln Asp Phe Ala Ala Ile Thr Val Pro Arg Ser Lys Gly Glu Ala
    130                 135                 140

Gly Gly Gly Phe Gln Pro Met Leu Pro Pro Gln Gly Ala Pro Gln Arg
145                 150                 155                 160

Pro Leu Ser Thr Leu Ser Ser Ala Pro Lys Ala Thr Leu Ile Leu Asn
                165                 170                 175

Ser Ile Gly Ser Leu Ser Lys Leu Gln Ala Gln Pro Leu Thr Phe Ser
            180                 185                 190

Arg Gly Gly Gly Arg Pro Gln Gly Leu Ala Ile Pro Ser Gln His Gly
        195                 200                 205

Glu Ala Gln Val Ser Pro Ala Pro Pro Thr Arg Asn Arg Arg Lys Ser
    210                 215                 220

Ala His Lys Val Leu Ala Glu Leu Asp Asp Glu Val Ser Pro Gly Pro
225                 230                 235                 240

Leu Ser Val Leu Thr Glu Pro Arg Lys Arg Leu Arg Val Glu Lys Ala
                245                 250                 255

Ala Leu Ile Ala Ser Gly Glu
            260
```

<210> SEQ ID NO 38
<211> LENGTH: 1611
<212> TYPE: DNA
<213> ORGANISM: Mus musculus

<400> SEQUENCE: 38

```
ggaatccctt cctcagttta ccccgcgagc gaaaaaaaga aaggattgtc ggaggctccc    60
ggatgttgag ccgcctgagg atccggcttc actgaggtgc acaagacgt  cttcctggtt   120 ttgcatcgca tcaggacttt actggaattg ctttttaaac ctcatcttga cagcctctgt   180
cttggtgcat atccaggcct ctggcgctct gaatctgcac tgcttaagtt ggcattaggc   240
```

```
acaatactta gctgttgaca tcagagagaa ctgaattgaa gcccacggtg catgacccag      300
gagtaggaga gggaatggac ttctgaggtg ggcgaagtgg tgcagagggg gcaccccca       360
tgctgccctg tttccagctg ctgcgtatag ggggcggcag gggcggtgac ctctacacct      420
tccaccccc gtccaagtct ggctgcacct atggattggg ctgcagggcc gacctgtgtg       480
atgtggccct gcggcccag caggagcccg gcctcatctc tggagtccat gcggaattgc       540
atgctgaact ccaaggggac gactggaggg tcagcctgga ggatcacagc agccaaggga      600
cttggtcaa taatgtccga cttccaagag gccacagact ggagttgagt gatggtgacc       660
ttctgacctt tggcccccaa ggtcaagcag gaaccagctc ctcctcagag ttctacttca      720
tgtttcaaca gtccgggtt aaacctcagg actttgcagc cataaccgtc cctcggtcta       780
agggagaagc tgggggcggt ttccaaccta tgctgccccc caagggggca cctcagaggc      840
cactcagcac tctctcctct gcccccaagg ccacactgat tctcaattcc atcggcagcc      900
tcagcaaact ccaggcccag cctctcacct tctcccgtgg tggtggcagg ccacagggcc      960
tggctattcc ctctcagcat ggggaagcgc aagtttcgcc tgctccaccc acaagaaacc     1020
ggaggaaatc agctcataaa gtgttggcag agctagatga cgaggtctcc ccaggccccc     1080
tgtccgtcct gacggagccc aggaagaggc tccgggtgga gaaagctgct ctgatagcca     1140
gtgggaatg accacaggga aaggtccatt gctaaagact gactcaaggc tggagaatgc      1200
ttgcaaatga agtgacagaa aagatggttt cctgccaaag atgttgcagc ctccaagttt     1260
ccagtgagct acaagcccag tcacaaggaa taaagccttg cctccatgga tgccaggata     1320
cctgcagtta gagcaccggt cccagaaacc attcctagaa ggtatggttt tattttgctg     1380
aagccagcat ataccaggca agtgctctgc cacaataccc taaccctact catgttcttg     1440
aatggcatcg gctaaagcac cctgaaggac ccagagcaca ttcccaaggc atcctcatgc     1500
caccgctagc tagtatcacc accagctgag tctctgggac tagcttttca gagcttagtc     1560
tttattccca aataaagaat aaactgtttc atccaaaaaa aaaaaaaaa a               1611
```

<210> SEQ ID NO 39
<211> LENGTH: 2133
<212> TYPE: DNA
<213> ORGANISM: Homo sapiens

<400> SEQUENCE: 39

```
cgggagagcg cgctctgcct gccgcctgcc tgcctgccac tgagggttcc cagcaccatg       60
agggcctgga tcttctttct cctttgcctg gccgggaggg ccttggcagc ccctcagcaa      120
gaagccctgc ctgatgagac agaggtggtg gaagaaactg tggcagaggt gactgaggta      180
tctgtgggag ctaatcctgt ccaggtggaa gtaggagaat ttgatgatgg tgcagaggaa      240
accgaagagg aggtggtggc ggaaaatccc tgccagaacc accactgcaa acacggcaag      300
gtgtgcgagc tggatgagaa caacaccccc atgtgcgtgt gccaggaccc caccagctgc      360
ccagccccca ttggcgagtt tgagaaggtg tgcagcaatg acaacaagac cttcgactct      420
tcctgccact tctttgccac aaagtgcacc ctggagggca ccaagaaggg ccacaagctc      480
cacctggact acatcgggcc ttgcaaatac atccccccctt gcctggactc tgagctgacc      540
gaattccccc tgcgcatgcg ggactggctc aagaacgtcc tggtcaccct gtatgagagg      600
gatgaggaca caacccttct gactgagaag cagaagctgc gggtgaagaa gatccatgag      660
aatgagaagc gcctggagg aggagaccac cccgtggagc tgctggcccg ggacttcgag       720
```

-continued

```
aagaactata acatgtacat cttccctgta cactggcagt tcggccagct ggaccagcac    780
cccattgacg ggtacctctc ccacaccgag ctggctccac tgcgtgctcc cctcatcccc    840
atggagcatt gcaccacccg cttttttcgag acctgtgacc tggacaatga caagtacatc    900
gccctggatg agtgggccgg ctgcttcggc atcaagcaga aggatatcga caaggatctt    960
gtgatctaaa tccactcctt ccacagtacc ggattctctc tttaaccctc cccttcgtgt   1020
ttcccccaat gtttaaaatg tttggatggt ttgttgttct gcctggagac aaggtgctaa   1080
catagattta agtgaataca ttaacggtgc taaaaatgaa aattctaacc caagacatga   1140
cattcttagc tgtaacttaa ctattaaggc ttttccaca cgcattaata gtcccatttt   1200
tctcttgcca tttgtagctt tgcccattgt cttattggca catgggtgga cacggatctg   1260
ctgggctctg ccttaaacac acattgcagc ttcaactttt ctctttagtg ttctgtttga   1320
aactaatact taccgagtca gactttgtgt tcatttcatt tcagggtctt ggctgcctgt   1380
gggcttcccc aggtggcctg gaggtgggca aagggaagta acagacacac gatgttgtca   1440
aggatggttt tgggactaga ggctcagtgg tgggagagat ccctgcagaa tccaccaacc   1500
agaacgtggt ttgcctgagg ctgtaactga gagaaagatt ctggggctgt cttatgaaaa   1560
tatagacatt ctcacataag cccagttcat caccatttcc tcctttacct ttcagtgcag   1620
tttcttttca cattaggctg ttggttcaaa cttttgggag cacggactgt cagttctctg   1680
ggaagtggtc agcgcatcct gcagggcttc tcctcctctg tcttttggag aaccagggct   1740
cttctcaggg gctctaggga ctgccaggct gtttcagcca ggaaggccaa aatcaagagt   1800
gagatgtaga aagttgtaaa atagaaaaag tggagttggt gaatcggttg ttcttccctc   1860
acatttggat gattgtcata aggtttttag catgttcctc cttttcttca ccctcccctt   1920
tgttcttcta ttaatcaaga gaaacttcaa agttaatggg atggtcggat ctcacaggct   1980
gagaactcgt tcacctccaa gcatttcatg aaaaagctgc ttcttattaa tcatacaaac   2040
tctcaccatg atgtgaagag tttcacaaat cttttcaaaat aaaaagtaat gacttagaaa   2100
ctgaaaaaaa aaaaaaaaaa aaaaaaaaaa aaa                                 2133
```

<210> SEQ ID NO 40
<211> LENGTH: 2678
<212> TYPE: DNA
<213> ORGANISM: Coturnix coturnix

<400> SEQUENCE: 40

```
gtcagacctt cctcctcaga agctcacaga aaaacacgct ttctgaaaga ttccacactc     60
aatgccaaaa tataccacag gaaaatttttg caaggctcac ggatttccag tgcaccactg    120
gctaaccaag taggagcacc tcttctactg ccatgaaagg aaaccttcaa accctaccac    180
tgagccatta actaccatcc tgtttaagat ctgaaaaaca tgaagactgt attgctcctg    240
atttgtcttc taggatctgc tttcaccact ccaaccgatc cattgaacta ccaatttggg    300
gcccatggac agaaaactgc agagaagcat aaatatactc attctgaaat gccagaggaa    360
gagaacacag ggtttgtaaa caaggtgat gtgctgtctg ccacaggac cataaaagca     420
gaggtaccgg tactggatac acagaaggat gagccctggg cttccagaag acaaggacaa    480
ggtgatggtg agcatcaaac aaaaaacagc ctgaggagca ttaacttcct tactctgcac    540
agtaatccag ggttggcttc tgataaccag gaaagcaact ctggcagcag cagggaacag    600
cacagctctg agcaccacca gcccaggagg cacaggaaac acggcaacat ggctggccag    660
tgggctctga gaggagaaag tccagtggat gctcttggtc tggttcgtga gcgcaacaca    720
```

| | |
|---|---|
| tggaaataca ataaaaacac agttggccta gatgaaaaca acaatggaag tgaagaagag | 780 |
| gaagctgggg aggaagaaga tgaggaatgg ggtgaagaaa ctgattacag ggatatgaaa | 840 |
| cacagagccc gtgggacaag ccatggaaga gaatacagaa gatggcaaaa tgaaaacagc | 900 |
| cggccatctg gtgaattctt gagagattcc agtctgccag tacgtataac caagagacac | 960 |
| ggtgagaaat tcagcatgga ggaggaaagt caggaaaagc tctacaagga aggaaaactc | 1020 |
| cctctctcaa agaaaaatca taatgaggat caaggtgaaa aaagacaaag tgaagaaagt | 1080 |
| aaagagcatt ttcaagtagt caatcagcgc aaacacagag cagtgacgaa aaggcaggat | 1140 |
| aaggagggca gcaatgctga ggaggatgat aatgatagtg gtgatgatgg tgaggaagat | 1200 |
| cttggcaatg tctggaggga agcagtctac gaggaagagg aaagaatgca agcaatgac | 1260 |
| caggacagta tcactaacaa gcaaaaagag gaaataactg ctggagatga cagtggagtt | 1320 |
| tatagggaga tgcaggatta caaggtgac aaaattaaag atgttactca ctctgaagac | 1380 |
| aatcattacc accatgagcc ccctaattcc agcagcaagc aacaactgca acaagtagc | 1440 |
| tctgttgaga gcatgaattc aacagagcat gaggatgagg ttaagaccac aggaggttca | 1500 |
| tatcatgagg aaagtgcaag gaacagcact gggaaggctc tcccggatct ttgtagaaac | 1560 |
| ttccactgca aaagaggaaa agtctgccaa gcagacaagc aaggaaaacc cagctgtatt | 1620 |
| tgccaagatc ctgctgcttg cccttccacc aaagattata gcgtgtttg tggcactgat | 1680 |
| aataagactt acgatggtac gtgccaactc tttggcacca aatgtcaact tgaagggaca | 1740 |
| aaaatgggac gccagctgca cctggactat atgggtgcct gcaaacacat accccactgt | 1800 |
| actgattacg aagtgaatca gttccctctc cgtatgagag actggctcaa aaacatccta | 1860 |
| atgcaatatt atgaacgtga tcaggatacg tctgcatttc taaccgaaaa gcaaaggaat | 1920 |
| aaggtcaaaa agatataccct gaatgagaag cgtctcgtct ctggtgagca cccagttgag | 1980 |
| cttctcctgc atgactttga gaaaaactac cacatgtatc tctatcctgt gcactggcaa | 2040 |
| ttttatcagc ttgaccagca cccagttgac agatcactga ctcattcaga gctcgctcct | 2100 |
| ttgagagcct ccctcgttcc catggaacac tgcataaccc gtttcttcca ggagtgtgat | 2160 |
| ggagaccaag acaaacttat cactttgaaa gagtggtgcc actgctttgc gattaaggaa | 2220 |
| gaagacataa atgaaaatct cctgttctga gcccacctga gcagaatccc catgcagcgc | 2280 |
| tacagcttgt caaacatgca atgcccattt atgactgcaa ttaacagctc tgttaatttt | 2340 |
| caggaataag ttggcataag attcttggag gcagaacaag tcgctcttgg ataacacaag | 2400 |
| tgcctaattg ttacaaattc attaacagca gtagtgttta agagctctaa gtagctcata | 2460 |
| cttaaagagt gtttccctct gcacgtacca ataatctctt agtaagacga ctaacttgat | 2520 |
| gactgagttg ttcacaaaac ccttccgtag aattatagga tgtggatttt ataatacacc | 2580 |
| gataaaaact actttgaaat aggttttctt ttcctgtcgt ttactgtcag tagctctctg | 2640 |
| catagaaatg tcaaataaac agatcttgtt ttggtttc | 2678 |

<210> SEQ ID NO 41
<211> LENGTH: 2808
<212> TYPE: DNA
<213> ORGANISM: Homo sapiens

<400> SEQUENCE: 41

| | |
|---|---|
| cggcatgaga ggccagcctg ccagggaaat ccaggaatct gcaacaaaaa cgatgacagt | 60 |
| ctgaaatact ctctggtgcc aacctccaaa ttctcgtctg tcacttcaga cccccactag | 120 |

```
ttgacagagc agcagaatat caactccagt agacttgaat gtgcctctgg gcaaagaagc      180
agagctaacg aggaaaggga tttaaagagt ttttcttggg tgtttgtcaa acttttattc      240
cctgtctgtg tgcagagggg attcaacttc aattttctgc agtggctctg ggtccagccc      300
cttacttaaa gatctggaaa gcatgaagac tgggcctttt ttcctatgtc tcttgggaac      360
tgcagctgca atcccgacaa atgcaagatt attatctgat cattccaaac caactgctga      420
aacggtagca cctgacaaca ctgcaatccc cagtttatgg gctgaagctg aagaaaatga      480
aaaagaaaca gcagtatcca cagaagacga ttcccaccat aaggctgaaa atcatcagt      540 actaaagtca aaagaggaaa gccatgaaca gtcagcagaa cagggcaaga gttctagcca      600
agagctggga ttgaaggatc aagaggacag tgatggtcac ttaagtgtga atttggagta      660
tgcaccaact gaaggtacat tggacataaa agaagatatg attgagcctc aggagaaaaa      720
actctcagag aacactgatt ttttggctcc tggtgttagt tccttcacag attctaacca      780
acaagaaagt atcacaaaga gagaggaaaa ccaagaacaa cctagaaatt attcacatca      840
tcagttgaac aggagcagta acatagcca aggcctaagg gatcaaggaa accaagagca      900
ggatccaaat atttccaatg gagaagagga agaagaaaaa gagccaggtg aagttggtac      960
ccacaatgat aaccaagaaa gaaagacaga attgcccagg gagcatgcta acagcaagca     1020
ggaggaagac aatacccaat ctgatgatat tttggaagag tctgatcaac caactcaagt     1080
aagcaagatg caggaggatg aatttgatca gggtaaccaa gaacaagaag ataactccaa     1140
tgcagaaatg gaagaggaaa atgcatcgaa cgtcaataag cacattcaag aaactgaatg     1200
gcagagtcaa gagggtaaaa ctggcctaga agctatcagc aaccacaaag agacagaaga     1260
aaagactgtt tctgaggctc tgctcatgga acctactgat gatggtaata ccacgcccag     1320
aaatcatgga gttgatgatg atggcgatga tgatggcgat gatggcggca ctgatggccc     1380
caggcacagt gcaagtgatg actacttcat cccaagccag gccttttctgg aggccgagag     1440 agctcaatcc attgcctatc acctcaaaat tgaggagcaa agagaaaaag tacatgaaaa     1500
tgaaaatata ggtaccactg agcctggaga gcaccaagag gccaagaaag cagagaactc     1560
atcaaatgag gaggaaacgt caagtgaagg caacatgagg gtgcatgctg tggattcttg     1620
catgagcttc cagtgtaaaa gaggccacat ctgtaaggca gaccaacagg aaaaacctca     1680
ctgtgtctgc caggatccag tgacttgtcc tccaacaaaa ccccttgatc aagtttgtgg     1740
cactgacaat cagacctatg ctagttcctg tcatctattc gctactaaat gcagactgga     1800
ggggaccaaa aaggggcatc aactccagct ggattatttt ggagcctgca aatctattcc     1860
tacttgtacg gactttgaag tgattcagtt tcctctacgg atgagagact ggctcaagaa     1920
tatcctcatg cagctttatg aagccaactc tgaacatgct ggttatctaa atgagaagca     1980
gagaaataaa gtcaagaaaa tttacctgga tgaaaagagg cttttggctg gggaccatcc     2040
cattgatctt ctcttaaggg actttaagaa aaactaccac atgtatgtgt atcctgtgca     2100
ctggcagttt agtgaacttg accaacaccc tatggataga gtcttgacac attctgaact     2160
tgctcctctg cgagcatctc tggtgcccat ggaacactgc ataacccgtt tctttgagga     2220
gtgtgacccc aacaaggata agcacatcac cctgaaggag tggggccact gctttggaat     2280
taaagaagag gacatagatg aaaatctctt gttttgaacg aagattttaa agaactcaac     2340
tttccagcat cctcctctgt tctaaccact tcagaaatat atgcagctgt gatacttgta     2400
gatttatatt tagcaaaatg ttagcatgta tgacaagaca atgagagtaa ttgcttgaca     2460
acaacctatg caccaggtat ttaacattaa ctttggaaac aaaaatgtac aattaagtaa     2520
```

| | | | | |
|---|---|---|---|---|
| agtcaacata | tgcaaaatac | tgtacattgt | gaacagaagt | ttaattcata gtaatttcac | 2580 |
| tctctgcatt | gacttatgag | ataattaatg | attaaactat | taatgataaa aataatgcat | 2640 |
| ttgtattgtt | cataatatca | tgtgcacttc | aagaaaatgg | aatgctactc ttttgtggtt | 2700 |
| tacgtgtatt | attttcaata | tcttaatacc | ctaataaaga | gtccataaaa atccaaaaaa | 2760 |
| aaaaaaaaaa | aaaaaaaaaa | aaaaaaaaaa | aaaaaaaaaa | aaaaaaaa | 2808 |

<210> SEQ ID NO 42
<211> LENGTH: 4804
<212> TYPE: DNA
<213> ORGANISM: Homo sapiens

<400> SEQUENCE: 42

| | | | | |
|---|---|---|---|---|
| agcggccaga | cgctcggcgg | cggcgtgtgg | caggagcgca | ggggcgcgag ccggcgatca | 60 |
| gccttcccgg | cgaccgtgcc | gcgggagctc | gagcaactcg | gactagggga cccgggccgg | 120 |
| cccccaagat | gccggcgatc | gcggtattgg | cggcggccgc | cgcggcgtgg tgcttcctcc | 180 |
| aagtcgagag | ccggcacctg | gacgcgctcg | ccggaggcgc | gggccccaac cacggcaatt | 240 |
| tcctagacaa | tgaccagtgg | ctgagcaccg | tctcccagta | cgaccgggac aagtactgga | 300 |
| accgctttcg | agacgatgat | tatttcagaa | actggaatcc | caacaagccc tttgaccaag | 360 |
| ccctggaccc | atccaaggac | ccctgcctga | aggtaaaatg | cagccctcac aaagtgtgtg | 420 |
| tgacccagga | ctaccagacc | gccctgtgtg | tcagccgcaa | gcacctgctc cccaggcaaa | 480 |
| agaaggggaa | cgtggcccag | aaaacactgg | gttggacctt | cgaatttggt c aagtgcaagc | 540 |
| cctgtcccgt | ggcacagtca | gccatggtct | gcggctcaga | tggccactcc tacacatcca | 600 |
| agtgcaaatt | ggagttccat | gcttgttcta | ctggcaaaag | cctcgccacc ctctgtgatg | 660 |
| ggccctgtcc | ctgtctccca | gagcctgagc | caccaaagca | aaggcagaa aggagtgcct | 720 |
| gcacagacaa | ggagttgcgg | aaccttgcct | cccggctgaa | ggattggttt ggagctctcc | 780 |
| acgaggatgc | gaacagagtc | atcaagccca | ccagctccaa | cacagcccaa ggcaggtttg | 840 |
| acactagcat | cctgcccatc | tgcaaggact | ccctgggctg | gatgttcaac aagttggaca | 900 |
| tgaactatga | cctcctgctt | gacccttcag | agatcaatgc | catctacctg gataagtacg | 960 |
| agccctgtat | caagcctctt | ttcaactcgt | gtgactcctt | caaggatggc aagctttcta | 1020 |
| acaatgagtg | gtgctactgc | ttccagaagc | ctggaggtct | cccttgccag aatgaaatga | 1080 |
| acagaattca | gaagctgagt | aaggggaaaa | gccgtgttggg | ggccttcata cctcggtgta | 1140 |
| atgaggaggg | ctattacaaa | gccacacagt | gccacggcag | cacggggcag tgctggtgtg | 1200 |
| tggacaaata | tgggaatgag | ttggctggct | ccaggaaaca | gggtgctgtg agctgtgaag | 1260 |
| aggagcagga | aacctcaggg | gattttggca | gtggtgggtc | cgtggtcctg ctggatgacc | 1320 |
| tagaatatga | acgggagctg | ggaccaaagg | acaaagaggg | gaagctgagg gtgcacaccc | 1380 |
| gagccgtgac | agaggatgat | gaggatgagg | atgatgacaa | agaggatgag gtcgggtaca | 1440 |
| tatggtagtg | cccacaagaa | agaggacaca | agttttgcac | aaaattgcaa gtcacttcct | 1500 |
| attcctgcat | ttgtatctaa | gactccaagg | caccaaggtc | tcttctccat tgttgctctc | 1560 |
| tatacccgac | ctaaggtttg | gaagacaact | gcttgttccc | agaggattct gattttgcat | 1620 |
| atgtttgtat | gggagaaagg | gtgttgtgtt | ttttttttg | ttgttgttta tttttttggat | 1680 |
| agggaagtca | ttggcttaat | tagagcctcc | ttcctttctg | tgagattttt ccaacaagca | 1740 |
| tgtgatttac | gtggaattct | gacagtgcag | ggagccccca | ccctcttaaa tgtcaaagac | 1800 |

```
cctttttgat tacccacact ggtggttatt acagcatggt tcccagcctt acagtgtcta    1860
agtgcttctc ttgtgtcctg tagatgttgt gaaaaagaaa aaacaaaaa atacaccaca     1920 ctgtactttt tccccctgcc cccgctactg ccggtgatta ttattaaaaa ttagtttttt    1980
tcacatcatt atatctggct tcctataaac aacagcctta attcagtcaa gactcccttt    2040
gggaattcat tttattaaaa attggtgtct ggatacttcc ctgtacatgc ataaatatgc    2100
atgcatgtac aggaagactg tatgtgtgtg ccttgcacac acaccatac ctctcagaaa     2160 aagtgggtat attaaaaact cgaaaaacaa tgataaattt ctcagcttgt ccagacctgg    2220
aacaaaattt ctggaataag aaatttgtat taaagtcctt ttttgcacta acagttggct    2280
cttgtagcct gcaggctgag gaagtctctt ctctgtgcat cagcagagtt actgaaagcc    2340
tctgattgag aaaaaacctc cgtctgccta atcactttt ctcgcagaag ccatgcgact     2400
cccacacgac acgggcagct tcacaagcca tctctttcat ttctgcttga agccccttg     2460 gctgcagcaa tcctgtctgc cataggtttc ttccttcctt acctactcaa ggcttttc     2520 taaggcatgc acacatatct cctgttctct gagagtacca tggtgttcct taaaagaaga    2580
aaatttctaa ttctgaactc aatgttttgc ttttactccc tttctactga caaatcatga    2640
taagggcaca aaagctgtac agattttttt ttttaaccac tcaatcccaa atggaggcct    2700
acaaagaaca tcgtaataac acatggaagc aaaccctggg tttttaagag caaattctgt    2760
ccccccctca ctcccccaag tgacaagata ctaatgaaga aagttcttca ccatagtgtt    2820
tgttttaact aaactcattg gagtctagtt ccaaatttgg tagggtcatc atctctacat    2880
tccttaggat ttctctccct atcaagctgg cccagataca agtaccaaac agtagtctct    2940
gaagttcccc catttccttc agtaccagtc tataagctac tgtccgccac tgattttcat    3000
ctatcagggt gtcctaatca gaatcagcca cccaagcaag cctctctggc ccacatatct    3060
atctcttgcc ttcccccatg aacttcagcc tgtccacaca aaagccacat aaactcaagc    3120
aagaaatatg ttcagccaaa acatgattat agtggcagct gaccaatccc ccatcccaaa    3180
ttgaccattt agatgtacca actcaccttaa aattagcatg ttccaatcca gtcggcattg    3240
cctgaataca gtagcatcat acctatagtt ggtcttagat aagaaatgaa ctacttgata    3300
tagcaaagtc ctttggcttc gtaaataacc ctgaggtttt gtacttactt tccccatagg    3360
aagacagacc ataggcaaac tctgttttgg gatctcaact ccatcacctt tgtttcaata    3420
ttttttttct ctcttgaaca aaactgagat aatttagaaa acaggtgctt aattgcaata    3480
aaattactat gaagtatatt aaaaatcacg acattgtaaa atctcacttt agatcatcaa    3540
agaaaaccat tgttactatc tcctttgagc ttaggaaaat gtacaagaga acaaattaaa    3600
attgaaaaat tgatttcact tagaaaaact tctaggaaca gggtgaacca ctgattttaa    3660
tttgcctaat tatcttatga caagtatcaa attaagatga cacttaaaga tccttagcat    3720
taacttaatg atggagaaga gtgctcaaca gacagttccc agtaaggtaa tgagatgcca    3780
ttttccgaga cattctaaga agatattttg attcattaaa acattaaata aaaagccctc    3840
ctcagattgg aaccccaaa tcgatggagt cacattaata atacttttca tgcctcactt     3900
tgacatgaca gcattcgatt ttttttaaga tctttaatac tttccatgag tactaaagat    3960
tgtaatgagt taccttatcc ttagaagtag aatgtttgct ttcttcttct tggaaatagt    4020
cctccaaaaa gtccacttgt accagtgaca agaagtcact tgtatagtga ccaagtacac    4080
ataaaatacc gattataaaa atattgtaat aaaccacttc ctcatttgat actggtatta    4140
agctgaatcc tcactaattc acttttgaaa agttcttaat gaacagtttt attcttatac    4200
```

```
catgaacagc tctttaata caatttcctt ggtatccaac ttaaatccca gaattttgtt    4260
ccaccatggt tagttatttg ccatatgaat gtattcttgt ttctaccaat attctaggca    4320
tgagaatacc ttaatactga gttggagatt ttgtatctgt ttctcctcct ttacgcccat    4380
tttcctaccc acagcagcaa atgacaacgt gtctgtccag gtctgtcccc ctgctcatcc    4440
caggatgcca ctcacatttt tttcttcttt gttacccttg acccacgctg tacaagtaac    4500
atccaagagc ccattctaca agtgggtggt tttggtcttt ttataacttt ttctcaaagt    4560
cactgatgtt tgttcctgtt aaatgtatag cattgtaatg agagcccatc aaatcctgag    4620
tgtcagtttg ttgtccctat tgtagatgaa atagtgatgt agcaaaaacc tagtaaattc    4680
tgaatgcttt tccacgtaga cttatctgga atgtgaacac aactctttgg ttaatagtaa    4740
atgcttaact gtagtcctga gtaggtgcat ttctgtctgt ctcaataaat tttactttgt    4800
ctgc                                                                 4804

<210> SEQ ID NO 43
<211> LENGTH: 1370
<212> TYPE: DNA
<213> ORGANISM: Rattus norvegicus

<400> SEQUENCE: 43
ctggcctcca actcactgct tccatcctgc ccagtgtcct ctcgagtccc ggacccgagc      60
acgatgtgga aacgctggct ggcgctcgcg ctggtgacca tcgccctggt ccacggcgag     120
gaggaacaaa gaagcaaatc caagatctgc gccaatgtgt tttgtggagc tggccgggaa     180
tgcgccgtca cggagaaggg ggagccaacg tgcctctgca ttgagcaatg caaacctcac     240
aagaggcctg tgtgtggcag taatggcaag acctacctca accattgtga acttcacaga     300
gacgcctgcc tcactggatc caagatccag gttgattatg atgggcactg caaagaaaag     360
aagtctgtga gtccatccgc cagccccgtt gtctgctatc aggctaaccg tgatgagctg     420
cggcgccgga tcatccagtg gctggaagcc gagatcattc cagatggctg gttctctaaa     480
ggcagtaact acagtgagat cctagacaag tactttaaga gctttgataa tggtgactct     540
cacctggact ccagcgaatt cctgaaattc gtggagcaga atgaaacagc cgtcaacatc     600
accgcttacc ccaatcagga gaacaacaaa ctgctcagag gcctctgtgt tgatgccctc     660
attgaactgt ccgatgagaa cgctgactgg aaactcagct ccaagagttt cctcaagtgc     720
ctcaacccat ccttcaaccc tcctgagaag aagtgcgccc tggaggacga aacctatgca     780
gatggagctg agaccgaggt ggactgcaat cgctgtgtct gttcctgtgg acactgggtc     840
tgcacagcga tgacctgtga tggaaagaat cagaaggggg tccagaccca cacagaggag     900
gagatgacga gatatgccca ggaactccag aagcaccagg aacagcagaa aagaccaag      960 aaggtgaaca ccaaagagat ctaagaagag gcacgtagca cctcatctgg aacccagcac    1020
ctcctcttca gcgctaagcc cagtatacag cgtctgtggc aatcaccgaa tcaccagtat    1080
ttgcttgtac ggcagcaaat cttatctgtt tgttttgcaa taaggaagt gagggtggct    1140 ggctagccag ggcaggcagg ccacaacttt cacttctagg aatgctttaa gagacactaa    1200
agggcacctt ggggcaggag gcgagtatcc ggttggcaga ggagcagagg caggtctgaa    1260
tgaaaccttt ctggggtcag ctgtgaggat acaacaggaa aagcatgtga tgttaggggg    1320
aacactgagc tggccctgct ggaggaaata gggggagctt ggtggggagg               1370

<210> SEQ ID NO 44
```

<211> LENGTH: 303
<212> TYPE: PRT
<213> ORGANISM: Homo sapiens

<400> SEQUENCE: 44

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 45
<211> LENGTH: 439
<212> TYPE: PRT
<213> ORGANISM: Homo sapiens

<400> SEQUENCE: 45

Met Pro Ala Ile Ala Val Leu Ala Ala Ala Ala Ala Trp Cys Phe
1               5                   10                  15

Leu Gln Val Glu Ser Arg His Leu Asp Ala Leu Ala Gly Gly Ala Gly
            20                  25                  30

Pro Asn His Gly Asn Phe Leu Asp Asn Asp Gln Trp Leu Ser Thr Val
        35                  40                  45

-continued

```
Ser Gln Tyr Asp Arg Asp Lys Tyr Trp Asn Arg Phe Arg Asp Asp
 50                  55                  60

Tyr Phe Arg Asn Trp Asn Pro Asn Lys Pro Phe Asp Gln Ala Leu Asp
 65                  70                  75                  80

Pro Ser Lys Asp Pro Cys Leu Lys Val Lys Cys Ser Pro His Lys Val
                 85                  90                  95

Cys Val Thr Gln Asp Tyr Gln Thr Ala Leu Cys Val Ser Arg Lys His
            100                 105                 110

Leu Leu Pro Arg Gln Lys Lys Gly Asn Val Ala Gln Lys His Trp Val
        115                 120                 125

Gly Pro Ser Asn Leu Val Lys Cys Lys Pro Cys Pro Val Ala Gln Ser
130                 135                 140

Ala Met Val Cys Gly Ser Asp Gly His Ser Tyr Thr Ser Lys Cys Lys
145                 150                 155                 160

Leu Glu Phe His Ala Cys Ser Thr Gly Lys Ser Leu Ala Thr Leu Cys
                165                 170                 175

Asp Gly Pro Cys Pro Cys Leu Pro Glu Pro Glu Pro Pro Lys His Lys
            180                 185                 190

Ala Glu Arg Ser Ala Cys Thr Asp Lys Glu Leu Arg Asn Leu Ala Ser
        195                 200                 205

Arg Leu Lys Asp Trp Phe Gly Ala Leu His Glu Asp Ala Asn Arg Val
210                 215                 220

Ile Lys Pro Thr Ser Ser Asn Thr Ala Gln Gly Arg Phe Asp Thr Ser
225                 230                 235                 240

Ile Leu Pro Ile Cys Lys Asp Ser Leu Gly Trp Met Phe Asn Lys Leu
                245                 250                 255

Asp Met Asn Tyr Asp Leu Leu Leu Asp Pro Ser Glu Ile Asn Ala Ile
            260                 265                 270

Tyr Leu Asp Lys Tyr Glu Pro Cys Ile Lys Pro Leu Phe Asn Ser Cys
        275                 280                 285

Asp Ser Phe Lys Asp Gly Lys Leu Ser Asn Asn Glu Trp Cys Tyr Cys
290                 295                 300

Phe Gln Lys Pro Gly Gly Leu Pro Cys Gln Asn Glu Met Asn Arg Ile
305                 310                 315                 320

Gln Lys Leu Ser Lys Gly Lys Ser Leu Leu Gly Ala Phe Ile Pro Arg
                325                 330                 335

Cys Asn Glu Glu Gly Tyr Tyr Lys Ala Thr Gln Cys His Gly Ser Thr
            340                 345                 350

Gly Gln Cys Trp Cys Val Asp Lys Tyr Gly Asn Glu Leu Ala Gly Ser
        355                 360                 365

Arg Lys Gln Gly Ala Val Ser Cys Glu Glu Glu Gln Glu Thr Ser Gly
370                 375                 380

Asp Phe Gly Ser Gly Gly Ser Val Val Leu Leu Asp Asp Leu Glu Tyr
385                 390                 395                 400

Glu Arg Glu Leu Gly Pro Lys Asp Lys Glu Gly Lys Leu Arg Val His
                405                 410                 415

Thr Arg Ala Val Thr Glu Asp Asp Glu Asp Glu Asp Asp Lys Glu
            420                 425                 430

Asp Glu Val Gly Tyr Ile Trp
        435
```

<210> SEQ ID NO 46
<211> LENGTH: 664

```
<212> TYPE: PRT
<213> ORGANISM: Homo sapiens

<400> SEQUENCE: 46

Met Lys Thr Gly Pro Phe Phe Leu Cys Leu Leu Gly Thr Ala Ala Ala
1               5                   10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
            260                 265                 270

Asn Ala Glu Met Glu Glu Glu Asn Ala Ser Asn Val Asn Lys His Ile
        275                 280                 285

Gln Glu Thr Glu Trp Gln Ser Gln Glu Gly Lys Thr Gly Leu Glu Ala
    290                 295                 300

Ile Ser Asn His Lys Glu Thr Glu Glu Lys Thr Val Ser Glu Ala Leu
305                 310                 315                 320

Leu Met Glu Pro Thr Asp Asp Gly Asn Thr Thr Pro Arg Asn His Gly
                325                 330                 335

Val Asp Asp Asp Gly Asp Asp Gly Asp Asp Gly Gly Thr Asp Gly
            340                 345                 350

Pro Arg His Ser Ala Ser Asp Asp Tyr Phe Ile Pro Ser Gln Ala Phe
        355                 360                 365

Leu Glu Ala Glu Arg Ala Gln Ser Ile Ala Tyr His Leu Lys Ile Glu
    370                 375                 380

Glu Gln Arg Glu Lys Val His Glu Asn Glu Asn Ile Gly Thr Thr Glu
385                 390                 395                 400
```

-continued

Pro Gly Glu His Gln Glu Ala Lys Lys Ala Glu Asn Ser Ser Asn Glu
            405                 410                 415

Glu Glu Thr Ser Ser Glu Gly Asn Met Arg Val His Ala Val Asp Ser
        420                 425                 430

Cys Met Ser Phe Gln Cys Lys Arg Gly His Ile Cys Lys Ala Asp Gln
            435                 440                 445

Gln Gly Lys Pro His Cys Val Cys Gln Asp Pro Val Thr Cys Pro Pro
        450                 455                 460

Thr Lys Pro Leu Asp Gln Val Cys Gly Thr Asp Asn Gln Thr Tyr Ala
465                 470                 475                 480

Ser Ser Cys His Leu Phe Ala Thr Lys Cys Arg Leu Glu Gly Thr Lys
            485                 490                 495

Lys Gly His Gln Leu Gln Leu Asp Tyr Phe Gly Ala Cys Lys Ser Ile
            500                 505                 510

Pro Thr Cys Thr Asp Phe Glu Val Ile Gln Phe Pro Leu Arg Met Arg
        515                 520                 525

Asp Trp Leu Lys Asn Ile Leu Met Gln Leu Tyr Glu Ala Asn Ser Glu
530                 535                 540

His Ala Gly Tyr Leu Asn Glu Lys Gln Arg Asn Lys Val Lys Lys Ile
545                 550                 555                 560

Tyr Leu Asp Glu Lys Arg Leu Leu Ala Gly Asp His Pro Ile Asp Leu
            565                 570                 575

Leu Leu Arg Asp Phe Lys Lys Asn Tyr His Met Tyr Val Tyr Pro Val
        580                 585                 590

His Trp Gln Phe Ser Glu Leu Asp Gln His Pro Met Asp Arg Val Leu
            595                 600                 605

Thr His Ser Glu Leu Ala Pro Leu Arg Ala Ser Leu Val Pro Met Glu
        610                 615                 620

His Cys Ile Thr Arg Phe Phe Glu Glu Cys Asp Pro Asn Lys Asp Lys
625                 630                 635                 640

His Ile Thr Leu Lys Glu Trp Gly His Cys Phe Gly Ile Lys Glu Glu
            645                 650                 655

Asp Ile Asp Glu Asn Leu Leu Phe
            660

<210> SEQ ID NO 47
<211> LENGTH: 306
<212> TYPE: PRT
<213> ORGANISM: Rattus norvegicus

<400> SEQUENCE: 47

Met Trp Lys Arg Trp Leu Ala Leu Ala Leu Val Thr Ile Ala Leu Val
1               5                   10                  15

His Gly Glu Glu Glu Gln Arg Ser Lys Ser Lys Ile Cys Ala Asn Val
            20                  25                  30

Phe Cys Gly Ala Gly Arg Glu Cys Ala Val Thr Glu Lys Gly Glu Pro
        35                  40                  45

Thr Cys Leu Cys Ile Glu Gln Cys Lys Pro His Lys Arg Pro Val Cys
    50                  55                  60

Gly Ser Asn Gly Lys Thr Tyr Leu Asn His Cys Glu Leu His Arg Asp
65                  70                  75                  80

Ala Cys Leu Thr Gly Ser Lys Ile Gln Val Asp Tyr Asp Gly His Cys
            85                  90                  95

Lys Glu Lys Lys Ser Val Ser Pro Ser Ala Ser Pro Val Val Cys Tyr

```
                    100                 105                 110
Gln Ala Asn Arg Asp Glu Leu Arg Arg Ile Ile Gln Trp Leu Glu
            115                 120                 125
Ala Glu Ile Ile Pro Asp Gly Trp Phe Ser Lys Gly Ser Asn Tyr Ser
        130                 135                 140
Glu Ile Leu Asp Lys Tyr Phe Lys Ser Phe Asp Asn Gly Asp Ser His
145                 150                 155                 160
Leu Asp Ser Ser Glu Phe Leu Lys Phe Val Glu Gln Asn Glu Thr Ala
                165                 170                 175
Val Asn Ile Thr Ala Tyr Pro Asn Gln Glu Asn Asn Lys Leu Leu Arg
            180                 185                 190
Gly Leu Cys Val Asp Ala Leu Ile Glu Leu Ser Asp Glu Asn Ala Asp
                195                 200                 205
Trp Lys Leu Ser Phe Gln Glu Phe Leu Lys Cys Leu Asn Pro Ser Phe
            210                 215                 220
Asn Pro Pro Glu Lys Lys Cys Ala Leu Glu Asp Glu Thr Tyr Ala Asp
225                 230                 235                 240
Gly Ala Glu Thr Glu Val Asp Cys Asn Arg Cys Val Cys Ser Cys Gly
                245                 250                 255
His Trp Val Cys Thr Ala Met Thr Cys Asp Gly Lys Asn Gln Lys Gly
            260                 265                 270
Val Gln Thr His Thr Glu Glu Met Thr Arg Tyr Ala Gln Glu Leu
            275                 280                 285
Gln Lys His Gln Gly Thr Ala Leu Lys Thr Lys Val Asn Thr Lys
        290                 295                 300
Glu Ile
305

<210> SEQ ID NO 48
<211> LENGTH: 676
<212> TYPE: PRT
<213> ORGANISM: Coturnix coturnix

<400> SEQUENCE: 48

Met Lys Thr Val Leu Leu Ile Cys Leu Leu Gly Ser Ala Phe Thr
1                   5                   10                  15

Thr Pro Thr Asp Pro Leu Asn Tyr Gln Phe Gly Ala His Gly Gln Lys
            20                  25                  30

Thr Ala Glu Lys His Lys Tyr Thr His Ser Glu Met Pro Glu Glu Glu
        35                  40                  45

Asn Thr Gly Phe Val Asn Lys Gly Asp Val Leu Ser Gly His Arg Thr
    50                  55                  60

Ile Lys Ala Glu Val Pro Val Leu Asp Thr Gln Lys Asp Glu Pro Trp
65                  70                  75                  80

Ala Ser Arg Arg Gln Gly Gln Gly Asp Gly Glu His Gln Thr Lys Asn
                85                  90                  95

Ser Leu Arg Ser Ile Asn Phe Leu Thr Leu His Ser Asn Pro Gly Leu
            100                 105                 110

Ala Ser Asp Asn Gln Glu Ser Asn Ser Gly Ser Ser Arg Glu Gln His
        115                 120                 125

Ser Ser Glu His His Gln Pro Arg Arg His Arg Lys His Gly Asn Met
    130                 135                 140

Ala Gly Gln Trp Ala Leu Arg Gly Glu Ser Pro Val Asp Ala Leu Gly
145                 150                 155                 160
```

-continued

```
Leu Val Arg Glu Arg Asn Thr Trp Lys Tyr Asn Lys Asn Thr Val Gly
            165                 170                 175

Leu Asp Glu Asn Asn Gly Ser Glu Glu Glu Ala Gly Glu Glu
        180                 185                 190

Glu Asp Glu Glu Trp Gly Glu Glu Thr Asp Tyr Arg Asp Met Lys His
        195                 200                 205

Arg Ala Arg Gly Thr Ser His Gly Arg Glu Tyr Arg Arg Trp Gln Asn
    210                 215                 220

Glu Asn Ser Arg Pro Ser Gly Glu Phe Leu Arg Asp Ser Ser Leu Pro
225                 230                 235                 240

Val Arg Ile Thr Lys Arg His Gly Glu Lys Phe Ser Met Glu Glu Glu
                245                 250                 255

Ser Gln Glu Lys Leu Tyr Lys Glu Gly Lys Leu Pro Leu Ser Lys Lys
            260                 265                 270

Asn His Asn Glu Asp Gln Gly Glu Lys Arg Gln Ser Glu Glu Ser Lys
        275                 280                 285

Glu His Phe Gln Val Val Asn Gln Arg Lys His Arg Ala Val Thr Lys
        290                 295                 300

Arg Gln Asp Lys Glu Gly Ser Asn Ala Glu Glu Asp Asp Asn Asp Ser
305                 310                 315                 320

Gly Asp Asp Gly Glu Glu Asp Leu Gly Asn Val Trp Arg Glu Ala Val
                325                 330                 335

Tyr Glu Glu Glu Glu Arg Met Gln Ser Asn Asp Gln Asp Ser Ile Thr
            340                 345                 350

Asn Lys Gln Lys Glu Glu Ile Thr Ala Gly Asp Asp Ser Gly Val Tyr
        355                 360                 365

Arg Glu Met Gln Asp Tyr Lys Gly Asp Lys Ile Lys Asp Val Thr His
    370                 375                 380

Ser Glu Asp Asn His Tyr His His Glu Pro Pro Asn Ser Ser Ser Lys
385                 390                 395                 400

Gln Gln Leu Gln Thr Ser Ser Ser Val Glu Ser Met Asn Ser Thr Glu
                405                 410                 415

His Glu Asp Glu Val Lys Thr Thr Gly Gly Ser Tyr His Glu Glu Ser
            420                 425                 430

Ala Arg Asn Ser Thr Gly Lys Ala Leu Pro Asp Leu Cys Arg Asn Phe
        435                 440                 445

His Cys Lys Arg Gly Lys Val Cys Gln Ala Asp Lys Gln Gly Lys Pro
    450                 455                 460

Ser Cys Ile Cys Gln Asp Pro Ala Ala Cys Pro Ser Thr Lys Asp Tyr
465                 470                 475                 480

Lys Arg Val Cys Gly Thr Asp Asn Lys Thr Tyr Asp Gly Thr Cys Gln
                485                 490                 495

Leu Phe Gly Thr Lys Cys Gln Leu Glu Gly Thr Lys Met Gly Arg Gln
            500                 505                 510

Leu His Leu Asp Tyr Met Gly Ala Cys Lys His Ile Pro His Cys Thr
        515                 520                 525

Asp Tyr Glu Val Asn Gln Phe Pro Leu Arg Met Arg Asp Trp Leu Lys
    530                 535                 540

Asn Ile Leu Met Gln Tyr Tyr Glu Arg Asp Gln Asp Thr Ser Ala Phe
545                 550                 555                 560

Leu Thr Glu Lys Gln Arg Asn Lys Val Lys Lys Ile Tyr Leu Asn Glu
                565                 570                 575

Lys Arg Leu Val Ser Gly Glu His Pro Val Glu Leu Leu Leu His Asp
```

580                 585                 590
Phe Glu Lys Asn Tyr His Met Tyr Leu Tyr Pro Val His Trp Gln Phe
            595                 600                 605

Tyr Gln Leu Asp Gln His Pro Val Asp Arg Ser Leu Thr His Ser Glu
        610                 615                 620

Leu Ala Pro Leu Arg Ala Ser Leu Val Pro Met Glu His Cys Ile Thr
625                 630                 635                 640

Arg Phe Phe Gln Glu Cys Asp Gly Asp Gln Asp Lys Leu Ile Thr Leu
                645                 650                 655

Lys Glu Trp Cys His Cys Phe Ala Ile Lys Glu Glu Asp Ile Asn Glu
            660                 665                 670

Asn Leu Leu Phe
        675

<210> SEQ ID NO 49
<211> LENGTH: 4
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(4)
<223> OTHER INFORMATION: Conserved domain.
      X at position 2 can be any amino acid.
<220> FEATURE:
<221> NAME/KEY: misc_feature
<222> LOCATION: (2)..(2)
<223> OTHER INFORMATION: Xaa can be any naturally occurring amino acid

<400> SEQUENCE: 49

Arg Xaa Lys Arg
1

<210> SEQ ID NO 50
<211> LENGTH: 12
<212> TYPE: DNA
<213> ORGANISM: Unknown
<220> FEATURE:
<223> OTHER INFORMATION: Nucleotide sequence for conserved domain
<220> FEATURE:
<221> NAME/KEY: misc_feature
<222> LOCATION: (1)..(12)
<223> OTHER INFORMATION: Nucleotide sequence for conserved domain.
      n at 4-6 is any of a, t, g, and c.

<400> SEQUENCE: 50
cgcnnnaagc gc                                                          12

<210> SEQ ID NO 51
<211> LENGTH: 6
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(6)
<223> OTHER INFORMATION: Conserved domain

<400> SEQUENCE: 51

Pro Leu Gly Leu Trp Ala
1               5

<210> SEQ ID NO 52
<211> LENGTH: 18

```
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(18)

<400> SEQUENCE: 52
cccctgggcc tgtgggcc                                                   18

<210> SEQ ID NO 53
<211> LENGTH: 6
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(6)
<223> OTHER INFORMATION: conserved domain

<400> SEQUENCE: 53

Tyr Glu Val Asp Gly Trp
1               5

<210> SEQ ID NO 54
<211> LENGTH: 18
<212> TYPE: DNA
<213> ORGANISM: Unknown
<220> FEATURE:
<223> OTHER INFORMATION: nucleotide sequence for conserved domain
<220> FEATURE:
<221> NAME/KEY: misc_feature
<222> LOCATION: (1)..(18)
<223> OTHER INFORMATION: nucleotide sequence for conserved domain

<400> SEQUENCE: 54
tacgaggtgg acggctgg                                                   18

<210> SEQ ID NO 55
<211> LENGTH: 7
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(7)
<223> OTHER INFORMATION: Conserved domain

<400> SEQUENCE: 55

Val Asp Val Ala Asp Gly Trp
1               5

<210> SEQ ID NO 56
<211> LENGTH: 21
<212> TYPE: DNA
<213> ORGANISM: Unknown
<220> FEATURE:
<223> OTHER INFORMATION: Nucleotide sequence for conserved domain
<220> FEATURE:
<221> NAME/KEY: misc_feature
<222> LOCATION: (1)..(21)
<223> OTHER INFORMATION: Nucleotide sequence for conserved domain

<400> SEQUENCE: 56
gtggacgtgg ccgacggctg g                                               21
```

```
<210> SEQ ID NO 57
<211> LENGTH: 7
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(7)
<223> OTHER INFORMATION: Conserved domain

<400> SEQUENCE: 57

Val Asp Gln Met Asp Gly Trp
1               5

<210> SEQ ID NO 58
<211> LENGTH: 21
<212> TYPE: DNA
<213> ORGANISM: Unknown
<220> FEATURE:
<223> OTHER INFORMATION: Nucleotide sequence for conserved domain
<220> FEATURE:
<221> NAME/KEY: misc_feature
<222> LOCATION: (1)..(21)
<223> OTHER INFORMATION: Nucleotide sequence for conserved domain.

<400> SEQUENCE: 58
gtggaccaga tggacggctg g                                            21

<210> SEQ ID NO 59
<211> LENGTH: 6
<212> TYPE: PRT
<213> ORGANISM: Unknown
<220> FEATURE:
<223> OTHER INFORMATION: Conserved sequence
<220> FEATURE:
<221> NAME/KEY: DOMAIN
<222> LOCATION: (1)..(6)
<223> OTHER INFORMATION: Conserved domain

<400> SEQUENCE: 59

Leu Glu Val Asp Gly Trp
1               5

<210> SEQ ID NO 60
<211> LENGTH: 18
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(18)
<223> OTHER INFORMATION: Nucleotide sequence for conserved domain.

<400> SEQUENCE: 60
ctggaggtgg acggctgg                                                18

<210> SEQ ID NO 61
<211> LENGTH: 6
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(6)
<223> OTHER INFORMATION: Conserved domain

<400> SEQUENCE: 61
```

```
Val Gln Val Asp Gly Trp
1               5
```

<210> SEQ ID NO 62
<211> LENGTH: 18
<212> TYPE: DNA
<213> ORGANISM: Unknown
<220> FEATURE:
<223> OTHER INFORMATION: Nucleotide sequence for conserved domain
<220> FEATURE:
<221> NAME/KEY: misc_feature
<222> LOCATION: (1)..(18)
<223> OTHER INFORMATION: Nucleotide sequence for conserved domain.

<400> SEQUENCE: 62
gtgcaggtgg acggctgg                                                       18

<210> SEQ ID NO 63
<211> LENGTH: 7
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(7)
<223> OTHER INFORMATION: Conserved domain

<400> SEQUENCE: 63

```
Val Asp Gln Val Asp Gly Trp
1               5
```

<210> SEQ ID NO 64
<211> LENGTH: 21
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(21)
<223> OTHER INFORMATION: Nucleotide sequence for conserved domain.

<400> SEQUENCE: 64
gtggaccagg tggacggctg g                                                   21

<210> SEQ ID NO 65
<211> LENGTH: 4
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(4)
<223> OTHER INFORMATION: Conserved domain.
      X at positions 2-3 can be any amino acid.
<220> FEATURE:
<221> NAME/KEY: misc_feature
<222> LOCATION: (2)..(3)
<223> OTHER INFORMATION: Xaa can be any naturally occurring amino acid

<400> SEQUENCE: 65

```
Asp Xaa Xaa Asp
1
```

<210> SEQ ID NO 66
<211> LENGTH: 12
<212> TYPE: DNA
<213> ORGANISM: Unknown

```
<220> FEATURE:
<223> OTHER INFORMATION: Nucleotide sequence for conserved domain.
<220> FEATURE:
<221> NAME/KEY: misc_feature
<222> LOCATION: (1)..(12)
<223> OTHER INFORMATION: Nucleotide sequence for conserved domain.
      n at positions 4-9 cna be any of a, t, g, and c.

<400> SEQUENCE: 66
gacnnnnnng ac                                                              12

<210> SEQ ID NO 67
<211> LENGTH: 4
<212> TYPE: PRT
<213> ORGANISM: Unknown
<220> FEATURE:
<223> OTHER INFORMATION: Conserved domain.
<220> FEATURE:
<221> NAME/KEY: DOMAIN
<222> LOCATION: (1)..(4)
<223> OTHER INFORMATION: Conserved domain.

<400> SEQUENCE: 67

Arg Gly Leu Thr
1

<210> SEQ ID NO 68
<211> LENGTH: 12
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(12)
<223> OTHER INFORMATION: Nucleotide sequence for conserved domain.

<400> SEQUENCE: 68
cgcggcctga cc                                                              12

<210> SEQ ID NO 69
<211> LENGTH: 17
<212> TYPE: PRT
<213> ORGANISM: Unknown
<220> FEATURE:
<223> OTHER INFORMATION: Conserved domain.
<220> FEATURE:
<221> NAME/KEY: DOMAIN
<222> LOCATION: (1)..(17)
<223> OTHER INFORMATION: Conserved domain.

<400> SEQUENCE: 69

Asn Phe Asp Leu Leu Lys Leu Ala Gly Asp Val Glu Ser Asn Pro Gly
1               5                   10                  15

Pro

<210> SEQ ID NO 70
<211> LENGTH: 51
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(51)
<223> OTHER INFORMATION: Nucleotide sequence for conserved domain.

<400> SEQUENCE: 70
aacttcgacc tgctgaagct ggccggcgac gtggagagca accccggccc c                   51
```

```
<210> SEQ ID NO 71
<211> LENGTH: 4
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(4)
<223> OTHER INFORMATION: Conserved domain.
      X at positions 2 and 4 can be any amino acid.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 71

Ala Xaa Ala Xaa
1

<210> SEQ ID NO 72
<211> LENGTH: 12
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(12)
<223> OTHER INFORMATION: Nucleotide sequence for conserved domain.
      n at positions 4-6, 10-12 can be any of a, t, g, and c.

<400> SEQUENCE: 72
gccnnngccn nn                                                            12

<210> SEQ ID NO 73
<211> LENGTH: 3
<212> TYPE: PRT
<213> ORGANISM: Unknown
<220> FEATURE:
<223> OTHER INFORMATION: Conserved domain.
<220> FEATURE:
<221> NAME/KEY: DOMAIN
<222> LOCATION: (1)..(3)
<223> OTHER INFORMATION: Conserved domain.

<400> SEQUENCE: 73

Leu Thr Lys
1

<210> SEQ ID NO 74
<211> LENGTH: 9
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(9)
<223> OTHER INFORMATION: Nucleotide sequence for conserved domain.

<400> SEQUENCE: 74 ctgaccaag                                                                 9

<210> SEQ ID NO 75
```

```
<211> LENGTH: 9
<212> TYPE: PRT
<213> ORGANISM: Unknown
<220> FEATURE:
<223> OTHER INFORMATION: Conserved sequence
<220> FEATURE:
<221> NAME/KEY: DOMAIN
<222> LOCATION: (1)..(9)
<223> OTHER INFORMATION: Conserved domain.

<400> SEQUENCE: 75

Gly Gly Phe Leu Arg Lys Val Gly Gln
1               5

<210> SEQ ID NO 76
<211> LENGTH: 27
<212> TYPE: DNA
<213> ORGANISM: Unknown
<220> FEATURE:
<223> OTHER INFORMATION: Nucleotide sequence for conserved domain.
<220> FEATURE:
<221> NAME/KEY: misc_feature
<222> LOCATION: (1)..(27)
<223> OTHER INFORMATION: Nucleotide sequence for conserved domain.

<400> SEQUENCE: 76
ggcggcttcc tgcgcaaggt gggccag                                         27

<210> SEQ ID NO 77
<211> LENGTH: 17
<212> TYPE: PRT
<213> ORGANISM: Unknown
<220> FEATURE:
<223> OTHER INFORMATION: Conserved domain
<220> FEATURE:
<221> NAME/KEY: DOMAIN
<222> LOCATION: (1)..(17)
<223> OTHER INFORMATION: Conserved domain.

<400> SEQUENCE: 77

Asn Phe Asp Leu Leu Lys Leu Ala Gly Asp Val Glu Ser Asn Pro Gly
1               5                   10                  15

Pro

<210> SEQ ID NO 78
<211> LENGTH: 23
<212> TYPE: DNA
<213> ORGANISM: Artificial Sequence
<220> FEATURE:
<223> OTHER INFORMATION: Synthetis primer
<220> FEATURE:
<221> NAME/KEY: misc_feature
<222> LOCATION: (1)..(23)
<223> OTHER INFORMATION: Synthetis primer

<400> SEQUENCE: 78
cgaagaggag gtggtggcgg aaa                                             23

<210> SEQ ID NO 79
<211> LENGTH: 26
<212> TYPE: DNA
<213> ORGANISM: Artificial sequence
<220> FEATURE:
<223> OTHER INFORMATION: Synthetis primer
<220> FEATURE:
<221> NAME/KEY: misc_feature
<222> LOCATION: (1)..(26)
<223> OTHER INFORMATION: Synthetic primer

<400> SEQUENCE: 79
```

```
ggttgttgtc ctcatccctc tcatac                                        26

<210> SEQ ID NO 80
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: Synthetic primer

<400> SEQUENCE: 80
ctctctgctc ctcctgttcg acag                                          24

<210> SEQ ID NO 81
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: Synthetic primer

<400> SEQUENCE: 81
aggggtctta ctccttggag gcca                                          24
```

What is claimed is:

1. A method for sensitizing cancer cells of a mammal to a therapeutic treatment comprising:
   contacting the cancer cells in vitro with a polypeptide comprising SEQ ID NO: 1;
   determining whether the cancer cells are sensitized in vitro to a therapeutic treatment by the polypeptide comprising SEQ ID NO: 1, and, if so;
   administering the polypeptide to the cancer cells of the mammal in vivo in an amount effective to sensitize the cancer cells to the therapeutic treatment.

2. The method of claim 1, wherein the therapeutic treatment is chemotherapy, radiation therapy, biological therapy, photodynamic therapy, hyperthermic therapy or combinations thereof.

3. The method of claim 2, wherein the therapeutic treatment is immunotherapy and comprises the administration of an effective amount of an antibody to the mammal.

4. A method for treating a mammal diagnosed with cancer comprising:
   (a) determining in cells from a first cancer sample from the mammal the expression level of a polypeptide comprising SEQ ID NO: 1;
   (b) comparing the expression level determined in step (a) with the expression level of the polypeptide in cells from a second cancer sample, wherein the cells in the second cancer sample are diagnosed as the same type of cancer as the cells in the first cancer sample and do not exhibit resistance to a therapeutic treatment, and
   (c) if the expression level of the polypeptide comprising SEQ ID NO: 1 is lower in the first cancer sample compared to the expression level in the second sample, administering to the mammal the therapeutic treatment and an amount of a polypeptide comprising SEQ ID NO: 1 effective to sensitize the cancer cells in the mammal to the therapeutic treatment.

5. The method of claim 4, wherein the level of the polypeptide comprising SEQ ID NO: 1 is determined by immunohistochemistry, Western Blot or immunoassay.

6. The method of claim 4, wherein the therapeutic treatment is chemotherapy, radiation therapy, biological therapy, photodynamic therapy, hyperthermic therapy, immunotherapy or combinations thereof.

7. The method of claim 5, wherein the therapeutic treatment is chemotherapy and comprises the administration of an effective amount of a chemotherapeutic agent to the mammal.

8. The method of claim 6, wherein the therapeutic treatment is immunotherapy and comprises the administration of an effective amount of an antibody to the mammal.

9. The method of claim 4, wherein the first and second cancer samples are from the same mammal.

10. The method of claim 4, wherein the first and second cancer samples are from different mammals diagnosed with the same cancer.

11. A method for treating a mammal diagnosed with cancer comprising:
   (a) determining in a first cancer sample of cancer cells from the mammal the expression level of an RNA transcript encoding a polypeptide of SEQ ID NO: 1;
   (b) comparing the expression level determined in step (a) with the expression level of the RNA transcript encoding a polypeptide of SEQ ID NO: 1 in cancer cells from a second cancer sample, wherein the cancer cells from the second cancer sample are diagnosed as the same type of cancer as the cells in the first cancer sample and do not exhibit resistance to a therapeutic treatment, and (c) if the comparison in step(b) indicates that the expression level of mRNA encoding polypeptides comprising SEQ ID NO:1 of cancer cells of the first cancer sample is lower compared to the expression level of the second sample, administering to the mammal the therapeutic treatment and an amount of a polypeptide comprising SEQ ID NO: 1 effective to sensitize the cancer cells to the therapeutic treatment.

12. The method of claim 11, wherein the expression level of the RNA transcript encoding a polypeptide of SEQ ID NO: 1 is determined by PCR, Northern Blot or Microarray.

13. The method of claim 12, wherein the expression level of the RNA transcript encoding a polypeptide of SEQ ID NO: 1 is determined by Microarray, and said Microarray is a DNA Microarray or an oligonucleotide Microarray.

14. The method of claim 11, wherein the therapeutic treatment is chemotherapy, radiation therapy, biological therapy, photodynamic therapy, hyperthermic therapy, immunotherapy or combinations thereof.

15. The method of claim 14, wherein the therapeutic treatment is chemotherapy and comprises the administration of an effective amount of a chemotherapeutic agent to the mammal.

16. The method of claim 14, wherein the therapeutic treatment is immunotherapy and comprises the administration of an effective amount of an antibody to the mammal.

17. The method of claim 11, wherein the first and second cancer samples are from the same mammal.

18. The method of claim 11, wherein the first and second cancer samples are from different mammals diagnosed with the same cancer.

* * * * *